US011883381B2

United States Patent
Grembecka et al.

(10) Patent No.: US 11,883,381 B2
(45) Date of Patent: *Jan. 30, 2024

(54) ASH1L INHIBITORS AND METHODS OF TREATMENT THEREWITH

(71) Applicant: The Regents of the University of Michigan, Ann Arbor, MI (US)

(72) Inventors: Jolanta Grembecka, Ann Arbor, MI (US); Tomasz Cierpicki, Ann Arbor, MI (US); David Rogawski, Ann Arbor, MI (US); Dmitry Borkin, Ann Arbor, MI (US); Szymon Klossowski, Ann Arbor, MI (US); Zhuang Jin, Ann Arbor, MI (US); Deanna Montgomery, Ann Arbor, MI (US); Jing Deng, Ann Arbor, MI (US); Marta Krotoska, Ann Arbor, MI (US); Hao Li, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/300,421

(22) PCT Filed: May 12, 2017

(86) PCT No.: PCT/US2017/032365
§ 371 (c)(1),
(2) Date: Nov. 9, 2018

(87) PCT Pub. No.: WO2017/197240
PCT Pub. Date: Nov. 16, 2017

(65) Prior Publication Data
US 2019/0142799 A1 May 16, 2019

Related U.S. Application Data

(60) Provisional application No. 62/335,160, filed on May 12, 2016.

(51) Int. Cl.
*A61K 31/404* (2006.01)
*A61K 45/06* (2006.01)
*C07D 209/18* (2006.01)
*C07D 209/08* (2006.01)
*A61P 35/02* (2006.01)

(52) U.S. Cl.
CPC ............ *A61K 31/404* (2013.01); *A61K 45/06* (2013.01); *A61P 35/02* (2018.01); *C07D 209/08* (2013.01); *C07D 209/18* (2013.01)

(58) Field of Classification Search
CPC ....... A61K 31/404; A61K 45/06; A61P 35/02; C07D 209/08; C07D 209/18
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,112,095 A * | 9/1978 | Allen, Jr. ............. C07D 237/04 514/248 |
| 4,151,273 A | 4/1979 | Riegelman et al. |
| 4,201,211 A | 5/1980 | Chandrasekaran et al. |
| 4,229,447 A | 10/1980 | Porter |
| 4,230,105 A | 10/1980 | Harwood |
| 4,292,299 A | 9/1981 | Suzuki et al. |
| 4,292,303 A | 9/1981 | Keith et al. |
| 4,343,789 A | 8/1982 | Kawata et al. |
| 4,476,116 A | 10/1984 | Anik |
| 4,596,795 A | 6/1986 | Pitha |
| 4,755,386 A | 7/1988 | Hsiao et al. |
| 4,755,389 A | 7/1988 | Jones et al. |
| 5,033,252 A | 7/1991 | Carter |
| 5,052,558 A | 10/1991 | Carter |
| 5,116,817 A | 5/1992 | Anik |

(Continued)

FOREIGN PATENT DOCUMENTS

| | | |
|---|---|---|
| EP | 0606046 | 7/1994 |
| EP | 0780386 | 6/1997 |

(Continued)

OTHER PUBLICATIONS

Dumaitre; J. Med. Chem. 1996, 39, 8, 1635-1644. (Year: 1996).*
National Center for Biotechnology Information. PubChem Substance Record for SID 292557486, SID 292557486, Source: Aurora Fine Chemicals LLC. https://pubchem.ncbi.nlm.nih.gov/substance/292557486. Deposit Date Jan. 20, 2016. (Year: 2016).*
STN Registry Database, Record for RN 1175821-79-0, "2'-Methoxy[1,1'-biphenyl]-3-carbothioamide", Entered Aug. 26, 2009. (Year: 2009).*

(Continued)

*Primary Examiner* — Daniel R Carcanague
(74) *Attorney, Agent, or Firm* — David W. Staple

(57) ABSTRACT

Provided herein are small molecule inhibitors of ASH1L activity and small molecules that facilitate ASH1L degradation and methods of use thereof for the treatment of disease, including acute leukemia, solid cancers and other diseases dependent on activity of ASH1L.

13 Claims, 6 Drawing Sheets

(56) References Cited

U.S. PATENT DOCUMENTS

| | | | |
|---|---|---|---|
| 5,124,342 A * | 6/1992 | Kerdesky | A61P 37/08 |
| | | | 514/369 |
| 5,281,420 A | 1/1994 | Kelm et al. | |
| 5,323,907 A | 6/1994 | Kalvelage | |
| 5,336,168 A | 8/1994 | Sibalis | |
| 5,340,591 A | 8/1994 | Nakano et al. | |
| 5,391,452 A | 2/1995 | Sacripante et al. | |
| 5,456,923 A | 10/1995 | Nakamichi et al. | |
| 5,665,378 A | 9/1997 | Davis et al. | |
| 5,700,485 A | 12/1997 | Berde et al. | |
| 5,723,269 A | 3/1998 | Akagi et al. | |
| 5,739,136 A | 4/1998 | Ellinwood, Jr. et al. | |
| 5,837,280 A | 11/1998 | Kenealy et al. | |
| 5,858,401 A | 1/1999 | Bhalani et al. | |
| 5,861,510 A | 1/1999 | Piscopio et al. | |
| 5,863,949 A | 1/1999 | Robinson et al. | |
| 5,869,090 A | 2/1999 | Rosenbaum | |
| 6,083,518 A | 7/2000 | Lindahl | |
| 6,337,344 B1 | 1/2002 | Defossa et al. | |
| 6,391,452 B1 | 5/2002 | Antonsen et al. | |
| 6,511,993 B1 | 1/2003 | Dack et al. | |
| 6,667,048 B1 | 12/2003 | Lambert et al. | |
| 6,923,983 B2 | 8/2005 | Morgan et al. | |
| 6,929,801 B2 | 8/2005 | Klose et al. | |
| 6,946,144 B1 | 9/2005 | Jordan | |
| 6,960,563 B2 | 11/2005 | Egbaria et al. | |
| 7,030,242 B2 | 4/2006 | Noe et al. | |
| 7,998,966 B2 | 8/2011 | Bearss et al. | |
| 8,314,140 B2 | 11/2012 | Wallace et al. | |
| 10,632,209 B2 * | 4/2020 | Grembecka | C07D 471/04 |
| 11,110,177 B2 * | 9/2021 | Grembecka | A61K 38/45 |
| 11,147,885 B2 * | 10/2021 | Grembecka | C12Y 203/02 |
| 2004/0013734 A1 | 1/2004 | Babcock et al. | |
| 2008/0167371 A1 * | 7/2008 | Ruggeri | A61P 3/10 |
| | | | 549/426 |
| 2009/0069400 A1 * | 3/2009 | Bleisch | C07D 209/14 |
| | | | 514/415 |
| 2010/0041891 A1 * | 2/2010 | Setoh | A61P 43/00 |
| | | | 546/281.1 |
| 2010/0311811 A1 | 12/2010 | Sauer | |
| 2010/0317863 A1 | 12/2010 | Kuzmich et al. | |
| 2012/0028831 A1 | 2/2012 | Croce | |
| 2012/0053345 A1 * | 3/2012 | Ericson | C07D 403/12 |
| | | | 544/280 |
| 2019/0142961 A1 | 5/2019 | Grembecka et al. | |
| 2019/0144442 A1 | 5/2019 | Grembecka et al. | |
| 2020/0246474 A1 * | 8/2020 | Grembecka | A61K 38/45 |
| 2022/0072142 A1 * | 3/2022 | Grembecka | A61K 47/64 |
| 2022/0288217 A1 * | 9/2022 | Grembecka | A61P 35/02 |

FOREIGN PATENT DOCUMENTS

| | | | |
|---|---|---|---|
| EP | 0818442 | | 1/1998 |
| EP | 0931788 | | 7/1999 |
| EP | 1004578 | | 5/2000 |
| GB | 1080246 A * | | 8/1967 |
| WO | WO 1990/05719 | | 5/1990 |
| WO | WO 1996/27583 | | 9/1996 |
| WO | WO 1996/33172 | | 10/1996 |
| WO | WO 1998/03516 | | 1/1998 |
| WO | WO 1998/07697 | | 2/1998 |
| WO | WO 1998/30566 | | 7/1998 |
| WO | WO 1998/33768 | | 8/1998 |
| WO | WO 1998/34915 | | 8/1998 |
| WO | WO 1998/34918 | | 8/1998 |
| WO | WO 1999/07675 | | 2/1999 |
| WO | WO 1999/29667 | | 6/1999 |
| WO | WO 1999/52889 | | 10/1999 |
| WO | WO 1999/52910 | | 10/1999 |
| WO | WO 2008/128072 | | 10/2008 |
| WO | WO 2009051956 | | 4/2009 |
| WO | WO 2011018415 | | 2/2011 |
| WO | WO-2011145669 A1 * | 11/2011 | C07D 207/27 |
| WO | WO 2014/077784 | | 5/2014 |
| WO | WO 2017/025868 | | 2/2017 |
| WO | WO-2017025868 A1 * | 2/2017 | A61P 25/16 |
| WO | WO 2017/185023 | | 10/2017 |
| WO | WO 2017/197240 | | 11/2017 |
| WO | WO 2019/094772 | | 5/2019 |
| WO | WO 2019/094773 | | 5/2019 |

OTHER PUBLICATIONS

STN Registry Database, Record for RN 1175743-53-9, "4'-Methoxy[1,1'-biphenyl]-3-carbothioamide", Entered Aug. 26, 2009. (Year: 2009).*

STN Registry Database, Record for RN 1174708-56-5, "5-Phenyl-2-thiophenecarbothioamide", Entered Aug. 20, 2009. (Year: 2009).*

Irwin; J. Chem. Inf. Model. 2005, 45, 1, 177-182. (Year: 2005).*

Kutsunugi; New J. Chem., 2009, 33, 1368-1373. (Year: 2009).*

Chemical Abstracts STN Registry Database, record for RN 1256483-33-6, "3-(3H-Imidazo[4,5-b]pyridin-2-yl) benzenecarbothioamide", Entered STN Dec. 14, 2010. (Year: 2010).*

National Center for Biotechnology Information. "PubChem Compound Summary for CID 39247168, 3-(2-Methylphenyl)benzenecarbothioamide" PubChem, https://pubchem.ncbi.nlm.nih.gov/compound/3-_2-Methylphenyl_benzenecarbothioamide. Create Date May 29, 2009. (Year: 2009).*

National Center for Biotechnology Information. "PubChem Compound Summary for CID 39247169, 3-(3-Methylphenyl)benzenecarbothioamide" PubChem, https://pubchem.ncbi.nlm.nih.gov/compound/3-_3-Methylphenyl_benzenecarbothioamide. Create Date May 29, 2009. (Year: 2009).*

National Center for Biotechnology Information. "PubChem Compound Summary for CID 39247170, 3-(4-Methylphenyl)benzenecarbothioamide" PubChem, https://pubchem.ncbi.nlm.nih.gov/compound/3-_4-Methylphenyl_benzenecarbothioamide. Create Date May 29, 2009. (Year: 2009).*

Laufer; Bioorg. Med. Chem. 2014, 22, 4968-4997. (Year: 2014).*

Chemical Abstracts Stn Registry Database, Record for RN 1125442-24-1, "2-(5-Methyl-1H-indol-3-yl)-4-pyridinecarboxamide", entered STN Mar. 23, 2009. (Year: 2009).*

Kusakabe; J. Med. Chem. 2013, 56, 11, 4343-4356. https://doi.org/10.1021/jm4000215 (Year: 2013).*

Chemical Abstracts STN Registry Database, record for RN 1622517-57-0, Entered into STN on Sep. 12, 2014. (Year: 2014).*

Chemical Abstracts STN Registry Database, record for RN 1394597-13-7, Entered into STN on Sep. 18, 2012. (Year: 2012).*

Chemical Abstracts STN Registry Database, record for RN 1394583-46-0, Entered into STN on Sep. 18, 2012. (Year: 2012).*

Chemical Abstracts STN Registry Database, record for RN 1360395-54-5, Entered into STN on Mar. 7, 2012. (Year: 2012).*

Chemical Abstracts STN Registry Database, record for RN 1360322-05-9, Entered into STN on Mar. 7, 2012. (Year: 2012).*

Chemical Abstracts STN Registry Database, record for RN 1360305-07-2, Entered into STN on Mar. 7, 2012. (Year: 2012).*

Chemical Abstracts STN Registry Database, record for RN 1309317-71-2, Entered into STN on Jun. 14, 2011. (Year: 2011).*

Chemical Abstracts STN Registry Database, record for RN 1309109-66-7, Entered into STN on Jun. 13, 2011. (Year: 2011).*

Andreeff et al., HOX expression patterns identify a common signature for favorable AML. Leukemia. Nov. 2008;22(11):2041-7.

Cabianca et al., A long ncRNA links number variation to a polycomb/trithorax epigenetic switch in FSHD muscular dystrophy. Cell. May 11, 2012;149(4):819-31.

Colamaio et al., miR-142-3p down-regulation contributes to thyroid follicular tumorigenesis by targeting ASH1L and MLL1. J Clin Endocrinol Metab. Jan. 2015;100(1):E59-69.

Faber et al., HOXA9 is required for survival in human MLL-rearranged acute leukemias. Blood. Mar. 12, 2009;113(11):2375-85.

Fujimoto et al., Whole-genome mutational landscape and characterization of noncoding and structural mutations in liver cancer. Nat Genet. May 2016;48(5):500-9.

Jones et al., Ash1l controls quiescence and self-renewal potential in hematopoietic stem cells. J Clin Invest. May 2015;125(5):2007-20.

(56) References Cited

OTHER PUBLICATIONS

Kanellopoulou et al., Reprogramming of Polycomb-Mediated Gene Silencing in Embryonic Stem Cells by the miR-290 Family and the Methyltransferase Ash1l. Stem Cell Reports. Dec. 8, 2015;5(6):971-978.
Kroon et al., Hoxa9 transforms primary bone marrow cells through specific collaboration with Meis1a but not Pbx1b. EMBO J. Jul. 1, 1998;17(13):3714-25.
Liu et al., Genetic alterations of histone lysine methyltransferases and their significance in breast cancer. Oncotarget. Feb. 2015; 6(4): 2466-2482.
Miyazaki et al., Ash1l methylates Ly536 of histone H3 independently of transcriptional elongation to counteract polycomb silencing. PLoS Genet. Nov. 2013;9(11):e1003897
Perugorria et al., Histone methyltransferase ASH1 orchestrates fibrogenic gene transcription during myofibroblast transdifferentiation. Hepatology. Sep. 2012;56(3):1129-39.
Rogawski et al., Two Loops Undergoing Concerted Dynamics Regulate the Activity of the ASH1L Histone Methyltransferase. Biochemistry. Sep. 8, 2015;54(35):5401-13
Shah et al., The Hox genes and their roles in oncogenesis. Nat Rev Cancer. May 2010;10(5):361-71.
Tanaka et al., Dual function of histone H3 lysine 36 methyltransferase ASH1 in regulation of Hox gene expression. PLoS One. 2011;6(11):e28171
Wang et al., Small molecule epigenetic inhibitors targeted to histone lysine methyltransferases and demethylases. Q Rev Biophys. Nov. 2013;46(4):349-73.
Zhu et al., ASH1L Links Histone H3 Lysine 36 Dimethylation to MLL Leukemia. Cancer Discov. Jul. 2016;6(7):770-83
International Search Report and Written Opinion for PCT/US2017/032365, dated Sep. 12, 2017, 10 pages.
International Search Report and Written Opinion for PCT/US2018/060101, dated Jan. 16, 2019, 8 pages.
International Search Report and Written Opinion for PCT/US2018/060102, dated Jan. 29, 2019, 9 pages.
Chemical Abstract Service, Accession No. 2013:1474439, 2013, 1 page.
Chemical Abstract Service, Accession No. 2013:273371, 2013, 1 page.
Chemical Abstract Service, Accession No. 2012:485967, 2012, 1 page.
Chemical Abstract Service, Accession No. 2011:1243461, 2011, 1 page.
Chemical Abstract Service, Accession No. 1993:38871, 1993, 1 page.
Chemical Abstract Service, Accession No. 2006:600185, 2006, 1 page.
Chemical Abstract Service, Accession No. 2004:819180, 2004, 1 page.
Chemical Abstract Service, Accession No. 2004:559860, 2004, 1 page.
Chemical Abstract Service, Accession No. 2000:675083, 2000, 1 page.
Chemical Abstract Service, Accession No. 1999:797879, 1999, 1 page.
Chemical Abstract Service, Accession No. 1999:661868, 1999, 1 page.
Chemical Abstract Service, Accession No. 1996:175895, 1996, 1 page.
Chemical Abstract Service, Accession No. 1996:132307, 1996, 1 page.
Chemical Abstract Service, Accession No. 1930:37386, 1930, 1 page.
Eram et al., Kinetic characterization of human histone H3 lysine 36 methyltrasferases, ASH1L and SETD2. Biochimica et Biophysica Acta 2015;1850:1842-8.
Von der Saal et al., Syntheses and Selective Inhibitory Activities or Terphenyl-Bisamidines for Serine Proteases. Arch Pharm Pharm Med Chem 1996;329(2):73-82.
Yao et al., Selective Inhibitors of Histone Methyltransferase DOT1L: Design, Synthesis, and Crystallographic Studies. J Am Chem Soc. 2015;133(42):16746-9.
Extended European Search Report for EP 17796920.1, dated Nov. 15, 2019, 24 pages.
Adams et al., Application of fragment-based screening to the design of inhibitors of *Escherichia coli* DsbA. Angew Chem Int Ed Engl. Feb. 9, 2015;54(7):2179-84.
Antonini et al., N*-N*-S* tridentate ligand system as potential antitumor agents. J Med Chem. Oct. 1981;24(10):1181-4.
Dumaitre et al., "Synthesis and Cyclic GMP Phosphodiesterase Inhibitory Activity of a Series of 6-Phenylpyrazolo [3,4-d] Pyrimidines," J. Med. Chem. 1996; 39:1635-1644.
Office Action for Japanese Application No. 2022-106297, dated Sep. 19, 2023, 3 pages.

\* cited by examiner

ASH1L INHIBITORS AND METHODS OF TREATMENT THEREWITH

CROSS-REFERENCE TO RELATED APPLICATIONS

The present application claims the priority benefit of U.S. Provisional Patent Application 62/335,160, filed May 12, 2016, which is incorporated by reference in its entirety.

FIELD

Provided herein are small molecule inhibitors of ASH1L activity and small molecules that facilitate ASH1L degradation and methods of use thereof for the treatment of disease, including acute leukemia, solid cancers and other diseases dependent on activity of ASH1L.

BACKGROUND

ASH1L (Absent small and homeotic disks protein 1 homolog; EC:2.1.1.43) is a histone-lysine N-mnethyltransferase (KMTase), which methylates histone 3, lysine 36 (H3K36). ASH1L is required for chromatin association of MLL fusion proteins at crucial leukemia target genes and for MLL fusion protein mediated oncogenic transformation, implying that ASH1L represents a therapeutic target in MLL leukemias and possibly other leukemias with high HOX expression (ref. 1; incorporated by reference in their entireties). ASH1L is also overexpressed in a variety of solid tumors, including thyroid and breast cancer (refs. 2, 3; incorporated by reference in their entireties). In thyroid cancer, ASH1L is overexpressed in tumor-specific truncated forms. The tumor suppressor microRNA miR-142-3p inhibits ASH1L protein expression by binding to the ASH1L 3'UTR, an effect correlated with inhibition of colony formation and slowing of thyroid cancer cell growth (ref. 2; incorporated by reference in its entirety). In addition, the ASH1L gene frequently undergoes copy number amplification in aggressive basal-like breast cancer, and high expression of ASH1L mRNA is associated with shorter survival of breast cancer patients (ref. 3; incorporated by reference in its entirety). Finally, in hepatocellular carcinoma (HCC), structural variations are found near the ASH1L gene, and knockdown of ASH1L in HCC cells slows proliferation (ref. 4; incorporated by reference in its entirety).

In multiple developmental and oncogenic contexts, ASH1L activates HOXA-B, -C, and -D genes and MEIS1 (refs. 5-8; incorporated by reference in their entireties). ASH1L's KMTase activity is required for at least some of its gene activating function, as deletion of the ASH1L SET domain in differentiating mouse embryonic stem cells leads to loss of expression of 152 genes, including members of the Hox and Wnt familes (ref. 8; incorporated by reference in its entirety). These findings are highly relevant because HOX genes are oncogenic drivers in many different blood and solid tumors (ref. 9; incorporated by reference in its entirety). For example, overexpression of HOXA9 is highly associated with a poor prognosis in AML (ref. 10; incorporated by reference in its entirety), and HOXA9 and its collaborator MEIS1 are required for survival of MLL-rearranged leukemia cells (refs. 11, 12; incorporated by reference in their entireties). ASH1L deficiency causes a major reduction in long-term hematopoietic stem cells (HSC) in mouse bone marrow, but has very modest effects on peripheral blood counts due to increased proliferation of progenitors downstream of HSCs (ref. 5; incorporated by reference in its entirety). ASH1L-deficient HSCs are also unable to reconstitute bone marrow output when transplanted into lethally irradiated mice (ref. 5; incorporated by reference in its entirety). These findings indicate that ASH1L maintains quiescence and self-renewal potential of long-term HSCs.

ASH1L also plays important roles in diseases beyond cancer. For example, in facioscapulohumeral muscular dystrophy, ASH1L is recruited by a noncoding RNA to chromosome region 4q35, where it causes H3K36 dimethylation, chromatin remodeling, and abnormal transcription of 4q35 genes (ref. 13; incorporated by reference in its entirety). In liver fibrosis, during the transdifferentiation of hepatic stellate cells to fibrogenic myofibroblasts, ASH1L is upregulated and binds to and activates profibrogenic genes (ref. 14; incorporated by reference in its entirety).

SUMMARY

Provided herein are small molecule inhibitors of ASH1L activity and small molecules that facilitate ASH1L degradation and methods of use thereof for the treatment of disease, including acute leukemia, solid cancers and other diseases dependent on activity of ASH1L.

In some embodiments, provided herein are compounds comprising a structure of Formula (I):

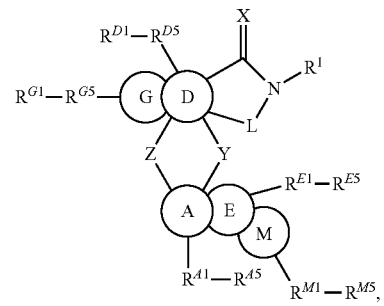

or a salt thereof;

wherein X is S, O, NH or $CH_2$;

wherein $R^1$ is selected from H, alkyl, substituted alkyl, hydroxy, alkoxy, amine, thioalkyl, halogen, ketone, amide, cyano, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

wherein L is 0-3 C, S, O, and/or N members, and wherein if L is 0 members there is no bond at L;

wherein Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by $R^{D1}$-$R^{D5}$ substituents;

wherein $R^{D1}$-$R^{D5}$, when present, are independently selected from H, alkyl, substituted alkyl, hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

wherein Ⓖ is an optionally present 4-7 member carbocyclic, heterocyclic, aryl, or heteroaryl ring which forms a ring system with Ⓓ, and is optionally substituted at 0-5 positions by $R^{G1}$-$R^{G5}$ substituents;

wherein $R^{G1}$-$R^{G5}$, when present, are independently selected from H, alkyl, substituted alkyl, hydroxy, alkoxy, amine, substituted amine, thioalkyl, halogen, ketone, amide, cyano, sulfonyl, carboxy, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

wherein Y is linker of 0-3 C, S, O, and/or N members, wherein any C or N members of Y may be optionally substituted, wherein if Y is 0 members, there is covalent bond at Y between Ⓓ and Ⓐ;

wherein Z is linker of 0-3 C, S, O, and/or N members, wherein any C or N members of Z may be optionally substituted, and wherein if Z is 0 members, there is no bond at Z between Ⓓ and Ⓐ;

wherein Ⓐ is a 5-7 member aryl, heteroaryl, carbocyclic ring, or heterocyclic ring, optionally substituted at 0-5 positions by $R^{A1}$-$R^{A5}$ substituents, wherein $R^{A1}$-$R^{A5}$, when present, are independently selected from H, alkyl, substituted alkyl, branched alkyl, a substituted branched alkyl (e.g. halogen substituted branched alkyl) hydroxy, alkoxy, amine, substitutes amine, thioalkyl, halogen, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, tetrahydropyran, alkylsulfonyl substituted piperidine (see compound 263), sulfonamide substituted piperidine (see compound 268)), carbocyclic or heterocyclic aromatic ring fused to another aromatic ring, a hydrogen bond donor, a hydrogen bond acceptor, and combinations thereof;

wherein Ⓔ is an optionally present 5-7 member carbocyclic ring, heterocyclic ring, aryl, or heteroaryl which forms a ring system with Ⓐ and is optionally substituted at 0-5 positions by $R^{E1}$-$R^{E5}$ substituents;

wherein $R^{E1}$-$R^{E5}$, when present, are independently selected from H, alkyl, substituted alkyl, hydroxy, alkoxy, amine, substituted amine, alkylamine, substituted alkylamine (e.g. comp. 290), thioalkyl, halogen, ketone, amide, substituted amide, alkylamide, substituted alkylamide (e.g. comp. 289) cyano, sulfonyl, carboxy, dialkylphosphine oxide, a carbocyclic ring, a substituted carbocyclic ring an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

wherein Ⓜ is an optionally present 4-7 member carbocyclic ring, heterocyclic ring, aryl, or heteroaryl which forms a ring system with Ⓔ and Ⓐ and is optionally substituted at 0-5 positions by $R^{M1}$-$R^{M5}$ substituents; and wherein $R^{M1}R^{M5}$, when present, are independently selected from H, alkyl, substituted alkyl, hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In some embodiments, the compound is of one or more of:

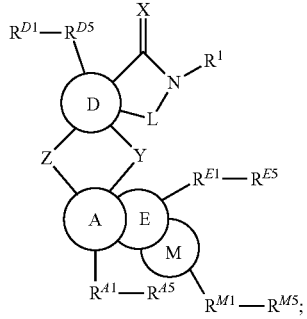

Formula (I-A)

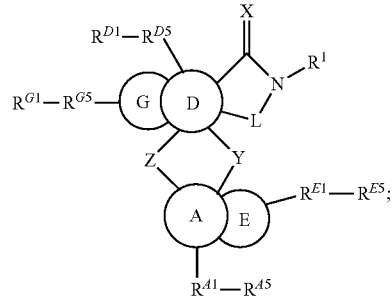

Formula (I-B)

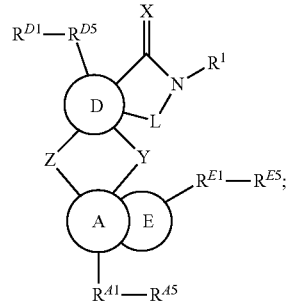

Formula (I-C)

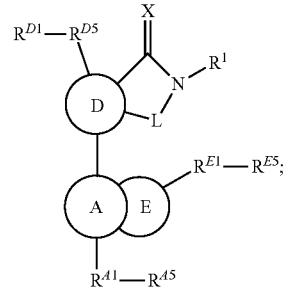

Formula (I-D)

-continued

Formula (I-E)

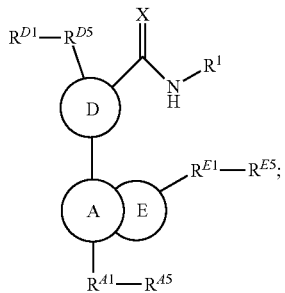

Formula (I-F)

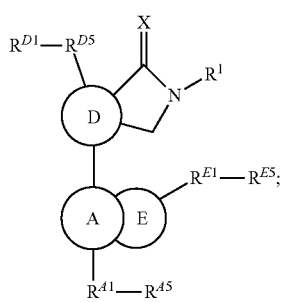

Formula (I-G)

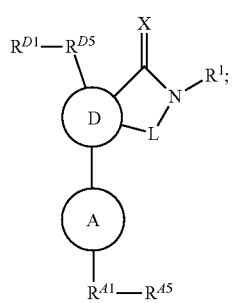

Formula (I-H)

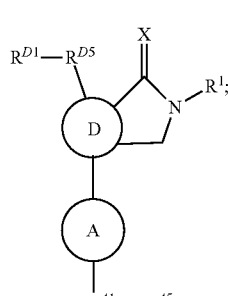

Formula (I-I)

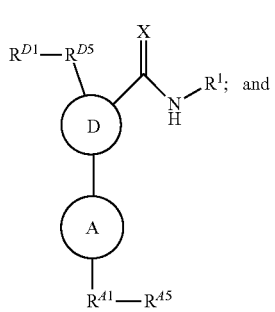

-continued

Formula (I-J)

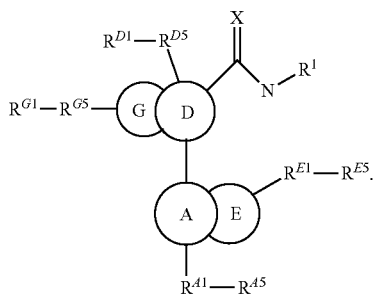

In some embodiments, R1, $R^{D1\text{-}5}$, $R^{G1\text{-}5}$, $R^{A1\text{-}5}$, $R^{E1\text{-}5}$, and $R^{M1\text{-}5}$ substituents, when present in a compound of any one of Formulas (I), (I-A), (I-B), (I-C), (I-D), (I-E), (I-F), (I-G), (I-H), (I-I), and (I-J) may be of any suitable chemical functional group selected from or comprising: H, alkyl, alkenyl, alkynyl, cycloalkyl, aromatic carbocycle, amine, alkyl amine, ether, alcohol, thioether, thiol, sulfonamide, sulfonyl, thioamide, carbamate, carbamide, amide, cyano, halogen, haloalkyl, dihaloalkyl, trihaloalkyl, alkyl group with halo substitutions at multiple positions, heterocycle, heteroaryl, a ring system comprising 2-3 rings selected from cycloalkyl, aromatic carbocycle, heterocycle and/or heteroaryl rings; wherein any of the aforementioned functional groups may be combined and/or further substituted (e.g., multiple times) to yield suitable substituents, including but not limited to those of compound 1-324.

In some embodiments, any of the R1, $R^{D1\text{-}5}$, $R^{G1\text{-}5}$, $R^{A1\text{-}5}$, $R^{E1\text{-}5}$, and $R^{M1\text{-}5}$ substituents, when present in a compound of any one of Formulas (I), (I-A), (I-B), (I-C), (I-D), (I-E), (I-F), (I-G), (I-H), (I-I), and (I-J) are of one of Formulas (IIa-IIq):

—J;  Formula (IIa)

—J—Q;  Formula (IIb)

—J¹—Q—J²;  Formula (IIc)

—J¹—Q¹—J²—Q²;  Formula (IId)

—J¹—Q¹—J²—Q²—J³;  Formula (IIe)

—J¹—J²;  Formula (IIf)

—J¹—J²—J³;  Formula (IIg)

—J¹—J²—Q¹;  Formula (IIh)

—J¹—J²—Q¹—J³;  Formula (IIi)

—J¹—J²—Q¹—J³—J⁴; and  Formula (IIj)

-continued

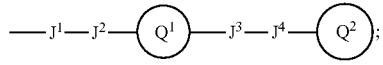
Formula (IIk)

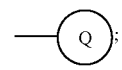
Formula (III)

Formula (IIm)

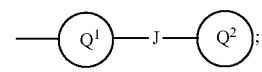
Formula (IIn)

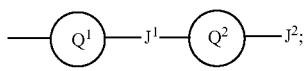
Formula (IIo)

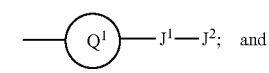
Formula (IIp) and

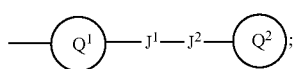
Formula (IIq)

wherein one of J, $Q^1$, or $J^1$, when present, is linked to one of the D, G, A, E, or M rings;

wherein each J, $J^1$, $J^2$, $J^3$, and $J^4$, when present, are independently selected from the group consisting of: a covalent bond, H, alkyl$_{1-15}$, alkenyl$_{1-6}$, alkynyl$_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}(CH_2)_{1-6}$ (See, e.g., Compound 80), $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}CH_2F$, $(CH_2)_{0-3}CHF(CH_2)_{0-2}CH_3$, or similar with Br, Cl, or I), dihaloalkyl (e.g., $(CH_2)_{0-6}CF_2H$, $(CH_2)_{0-3}CF_2(CH_2)_{0-2}CH_3$, or similar with Br, Cl, or I), trihaloalkyl (e.g., $(CH_2)_{0-6}CF_3$, or similar with Br, Cl, or I), alkyl with 1-3 halogens at two or more positions along its length (See, e.g., Compounds 126, 144, 194, 195, 200, 207, 245, 251, etc.), $(CH_2)_{1-4}SP(Ph)_2=S$ (See, e.g., Compound 52), $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, $(CH_2)_{0-6}NH(CH_2)_{1-6}NH(CH_2)_{1-5}OH$, $(CH_2)_{0-6}NH(CH_2)_{1-6}NH(CH_2)_{1-5}NH_2$, $(CH_2)_{0-6}NH(CH_2)_{1-6}NH$ $(CH_2)_{1-5}SH$, $(CH_2)_{0-6}NH(CH_2)_{1-6}O(CH_2)_{1-5}OH$, $(CH_2)_{0-6}NH(CH_2)_{1-6}O(CH_2)_{1-5}NH_2$, $(CH_2)_{0-6}NH(CH_2)_{1-6}O(CH_2)_{1-5}SH$, $(CH_2)_{0-6}NH(CH_2)_{1-6}S(CH_2)_{1-5}OH$, $(CH_2)_{0-6}NH(CH_2)_{1-6}S(CH_2)_{1-5}NH_2$, $(CH_2)_{0-6}NH(CH_2)_{1-6}S(CH_2)_{1-5}SH$, $(CH_2)_{0-3}C(O)O$ $(CH_2)_{0-3}$, $(CH_2)_{0-3}C(S)O(CH_2)_{0-3}$, $(CH_2)_{0-3}C(O)S$ $(CH_2)_{0-3}$, $(CH_2)_{0-3}C(S)S(CH_2)_{0-3}$, $(CH_2)_{0-3}C(O)NH$ $(CH_2)_{0-3}$, $(CH_2)_{0-3}C(S)NH(CH_2)_{0-3}$, $(CH_2)_{0-3}NHC(O)$ $(CH_2)_{0-3}$, $(CH_2)_{0-3}NHC(S)(CH_2)_{0-3}$, $(CH_2)_{0-3}OC(O)$ $(CH_2)_{0-3}$, $(CH_2)_{0-3}OC(S)(CH_2)_{0-3}$, $(CH_2)_{0-3}SC(O)$ $(CH_2)_{0-3}$, $(CH_2)_{0-3}SC(S)(CH_2)_{0-3}$, $(CH_2)_{0-3}NHC(O)$ $NH(CH_2)_{0-3}$, $(CH_2)_{0-3}NHC(S)NH(CH_2)_{0-3}$, $(CH_2)_{0-3}OC(O)NH(CH_2)_{0-3}$, $(CH_2)_{0-3}OC(S)NH$ $(CH_2)_{0-3}$, $(CH_2)_{0-3}SC(O)NH(CH_2)_{0-3}$, $(CH_2)_{0-3}SC(S)$ $NH(CH_2)_{0-3}$, $(CH_2)_{0-3}NHC(O)O(CH_2)_{0-3}$, $(CH_2)_{0-3}NHC(S)O(CH_2)_{0-3}$, $(CH_2)_{0-3}OC(O)O$ $(CH_2)_{0-3}$, $(CH_2)_{0-3}OC(S)O(CH_2)_{0-3}$, $(CH_2)_{0-3}SC(O)O$ $(CH_2)_{0-3}$, $(CH_2)_{0-3}SC(S)O(CH_2)_{0-3}$, $(CH_2)_{0-3}NHC(O)$ $S(CH_2)_{0-3}$, $(CH_2)_{0-3}NHC(S)S(CH_2)_{0-3}$, $(CH_2)_{0-3}OC$ $(O)S(CH_2)_{0-3}$, $(CH_2)_{0-3}OC(S)S(CH_2)_{0-3}$, $(CH_2)_{0-3}SC$ $(O)S(CH_2)_{0-3}$, $(CH_2)_{0-3}SC(S)S(CH_2)_{0-3}$, $(CH_2O)_{1-6}$, and trimethyl methane;

wherein each Q, $Q^1$, and $Q^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, pepierazine, morpholine, thiomorpholine, dioxane, dithiane, trioxane, thithiane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable $C^3$-$C^7$ cycloalkyl group, and any of the ring structures depicted in Table 1a, 1b, 2, 3, 4 or 5;

wherein each Q, $Q^1$, and $Q^2$, when present, may display one or more additional J groups at any position on the Q ring;

wherein any alkyl or $(CH_2)_{x-y}$ groups above may be straight or branched (See, e.g., Compounds 103, 104, 138, 245, etc.);

wherein any alkyl or $(CH_2)_{x-y}$ groups above may additionally comprise OH, =O, $NH_2$, CN, dihaloalkyl (e.g., $CF_2H$), trihaloalkyl (e.g., $CF_3$), or halogen (e.g., F) substituents at one or more carbons;

wherein the number of hydrogens on terminal positions of the groups above may be adjusted if the group is linked to an additional group (e.g., $CH_3$ adjusted to $CH_2$, OH adjusted to O, etc.) or if the group is terminal (e.g., $CH_2$ adjusted to $CH_3$, O adjusted to OH, etc.); and wherein any of formulas (IIa-q) may additionally comprise a terminal fluorophore (e.g. fluoresceine), solid surface, enzyme ligand (e.g. thalidomide, e.g., Compounds 198, 199, 301, 286, 291) or VHL ligand (e.g., (2S,4R)-1-((S)-2-amino-3,3-dimethylbutanoyl)-4-hydroxy-N-(4-(4-methylthiazol-5-yl)benzyl)pyrrolidine-2-carboxamide (e.g. compound 302), etc.), or affinity tag.

In some embodiments, any of formulas (IIa-q) may represent bifunctional compounds composed of ASH1L inhibitor and an E3 ubiquitin ligase ligand connected with a linker, which function to bind to ASH1L and recruit E3 ubiquiting ligase (Cereblon, VHL ligase, etc.) complex to ubiquitinate and induce proteosome-mediated degradation of ASH1L (e.g., Compounds 198, 199, 301,302, 286, 291). Exemplary compounds which induce degradation of the target protein by engaging the ubiquitin ligase are described, for example, in U.S. Pub. 2015/0291562; U.S. Pub. 2016/0235731; both of which are incorporated by reference in their entireties.

In some embodiments, R1, $R^{D1-5}$, $R^{G1-5}$, $R^{A1-5}$, $R^{E1-5}$, and $R^{M1-5}$ substituents, when present in a compound of any one of Formulas (I), (I-A), (I-B), (I-C), (I-D), (I-E), (I-F), (I-G), (I-H), (I-I), and (I-J), are independently any of the substituent groups present on Compounds 1-324, as depicted in Table 6 or Table 7, without being limited to the positions of the substituents on Compounds 1-324.

In some embodiments, the compound is selected from the compounds depicted in Table 6 or Table 7 (e.g., Compounds 1-324).

In some embodiments, provided herein are pharmaceutical compositions comprising a compound of any one of the preceding claims and a pharmaceutically acceptable carrier. In some embodiments, the pharmaceutical composition is formulated for oral administration. In some embodiments, the pharmaceutical composition is formulated for injection.

In some embodiments, provided herein are methods of inhibiting the activity of ASH1L, comprising contacting ASH1L with an effective amount of a compound described herein. In some embodiments, contacting comprises contacting a cell that expresses ASH1L.

In some embodiments, provided herein are methods of degrading ASH1L by bifunctional compounds, which function to recruit both ASH1L and proteins of E3 Ubiquitine Ligase Complex (e.g. Cereblon, VHL ligase, etc.) for ubiquitination and proteasome-mediated degradation of ASH1L.

In some embodiments, provided herein are methods of treating a disease, comprising administering to a subject a pharmaceutical composition described herein in an amount effective to inhibit the activity of ASH1L or degrade ASH1L. In some embodiments, the disease is a cancer. In some embodiments, the disease is a proliferative disorder. In some embodiments, the pharmaceutical composition is co-administered with an additional cancer therapeutic. In some embodiments, the subject is a human.

In some embodiments, provided herein is the use of a compound described herein. In some embodiments, provided herein is the use of a compound described herein for inhibiting ASH1L activity or degradation of ASH1L. In some embodiments, provided herein is the use of a compound described herein for the treatment of a disease (e.g., cancer).

DEFINITIONS

Figure 1:
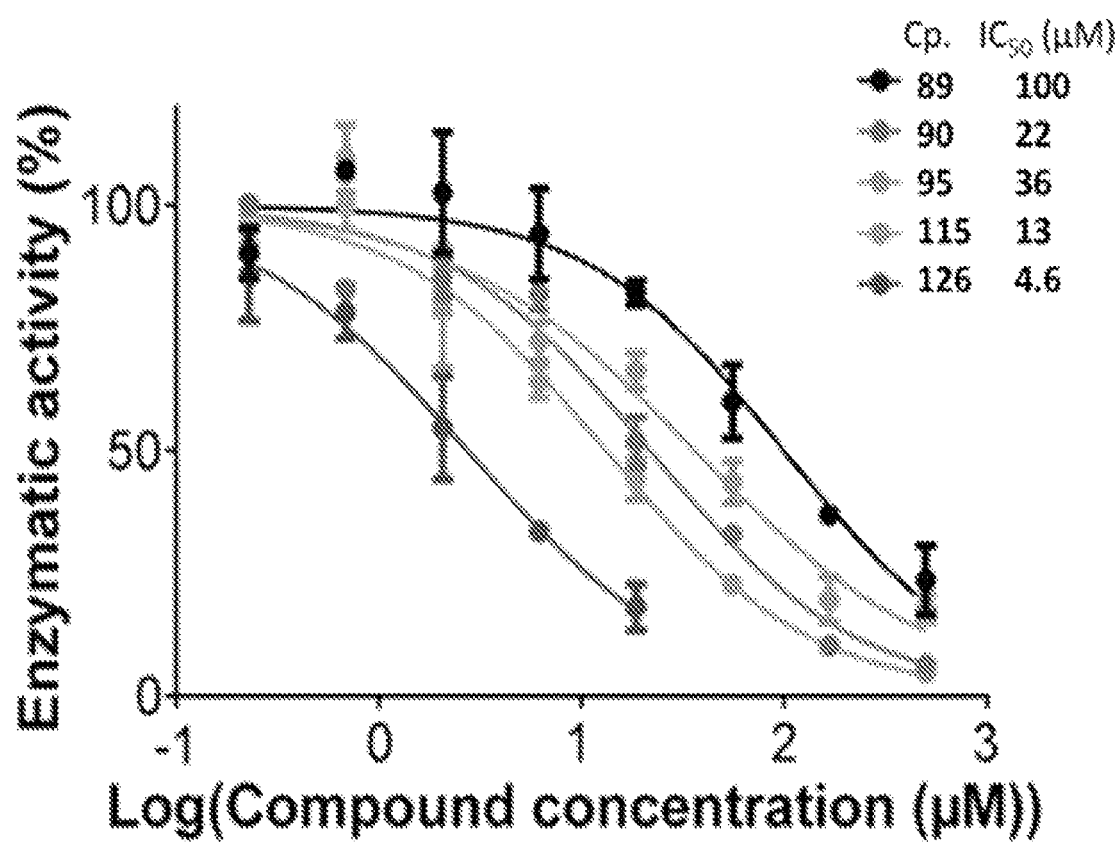
FIG. 1. Biochemical characterization of ASH1L inhibitors. Comparison of the activity of ASH1L inhibitors (compounds: 89, 90, 95, 115, 126) in in vitro KMTase assay for ASH1L. $IC_{50}$ values are provided.
Figure 2:
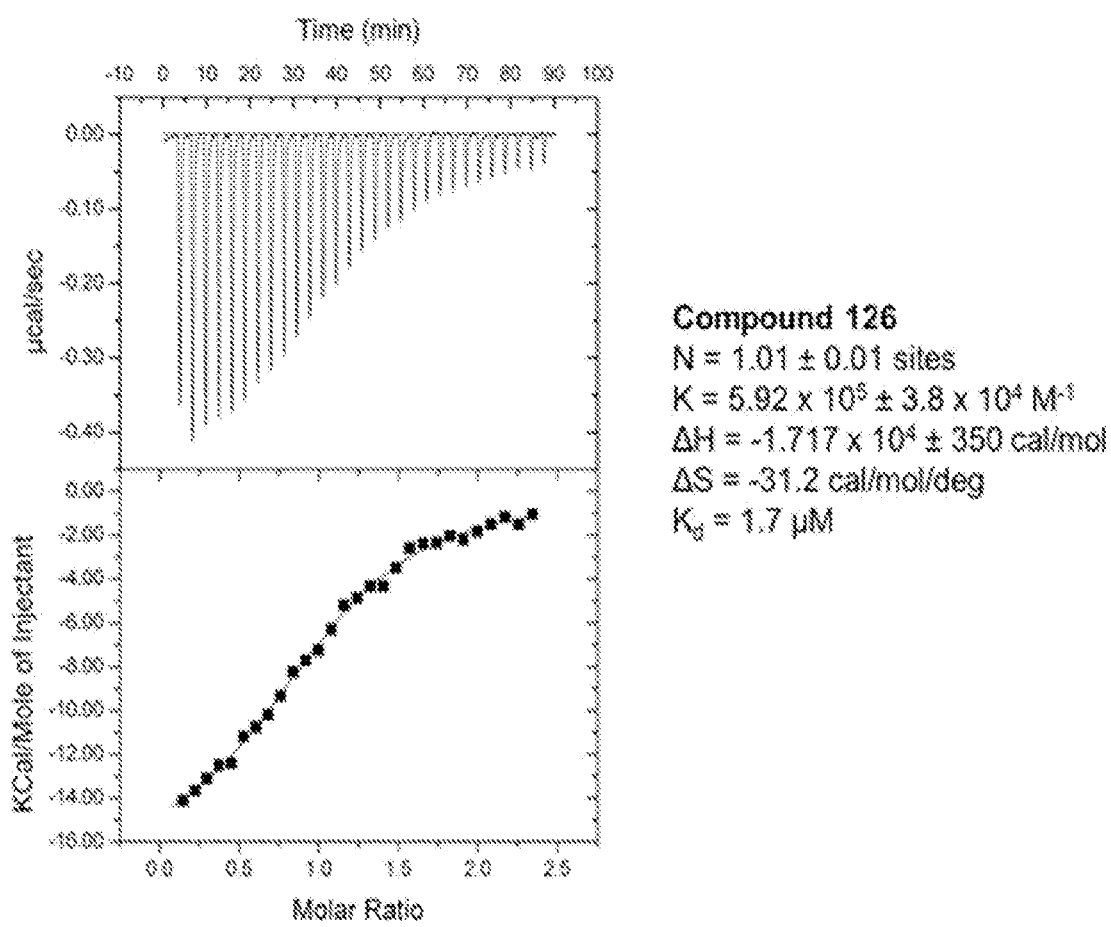
FIG. 2. Binding of compound 126 to ASH1L SET domain measured by Isothermal Titration Calorimetry (ITC).
Figure 3:
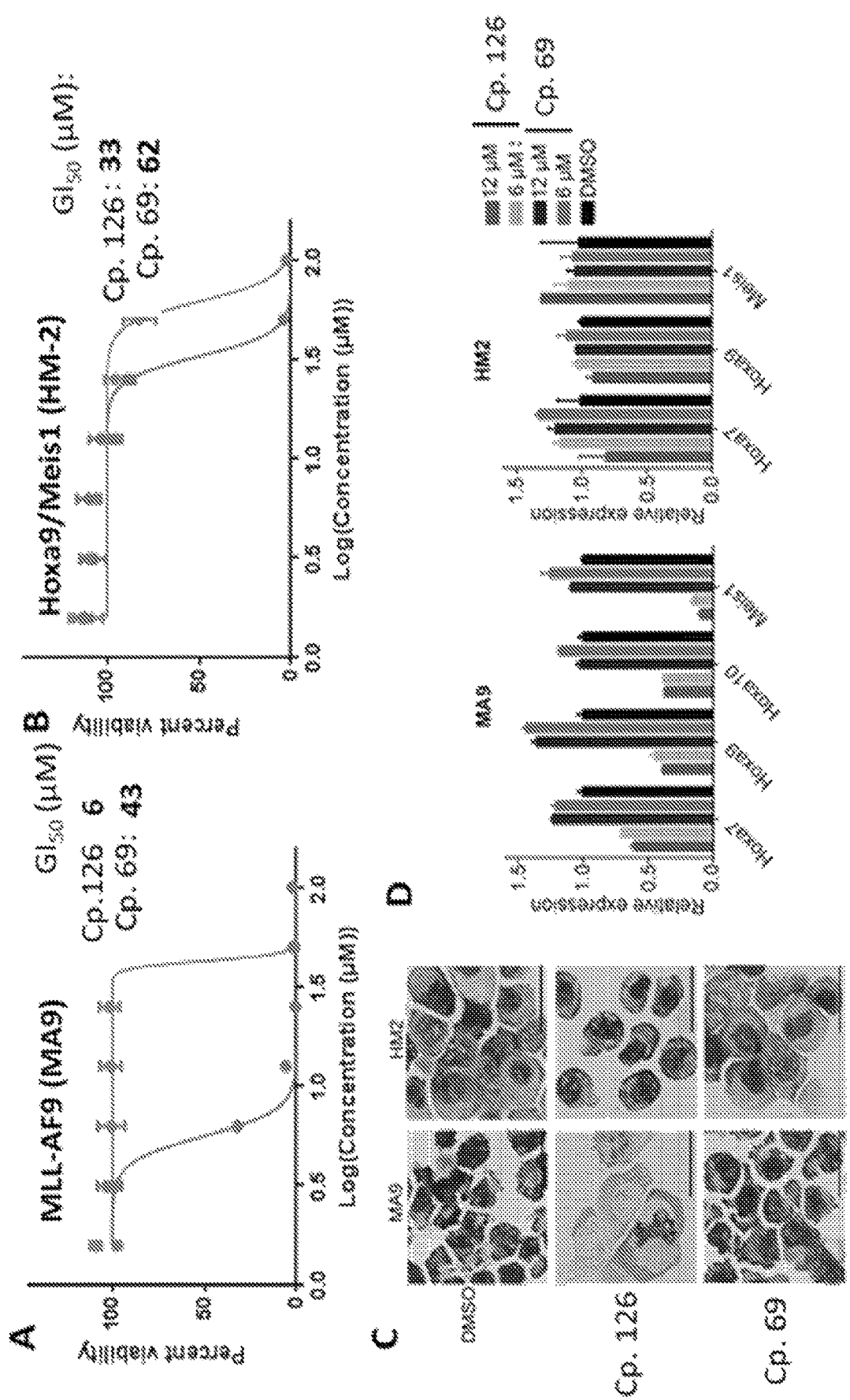
FIG. 3. Cellular activity of compounds 126 and 69 (negative control compound). A,B) Inhibition of cell proliferation in murine bone marrow cells transformed with A) MLL-AF9 (MA9) and B) Hoxa9/Meis1 (HM-2, negative control cell line) induced by compound 126 after 8 days of treatment. C) Compound 126 induces differentiation of MLL-AF9 cells but not in negative control cell line HM-2. D) Compound 126 downregulates expression of MLL fusion target genes (Hoxa cluster, Meis1) but has no effect on expression of these genes in control cell line HM-2. Negative control compound, 69, does not affect gene expression in both cell lines. Gene expression data are normalized to β-actin.
Figure 4:
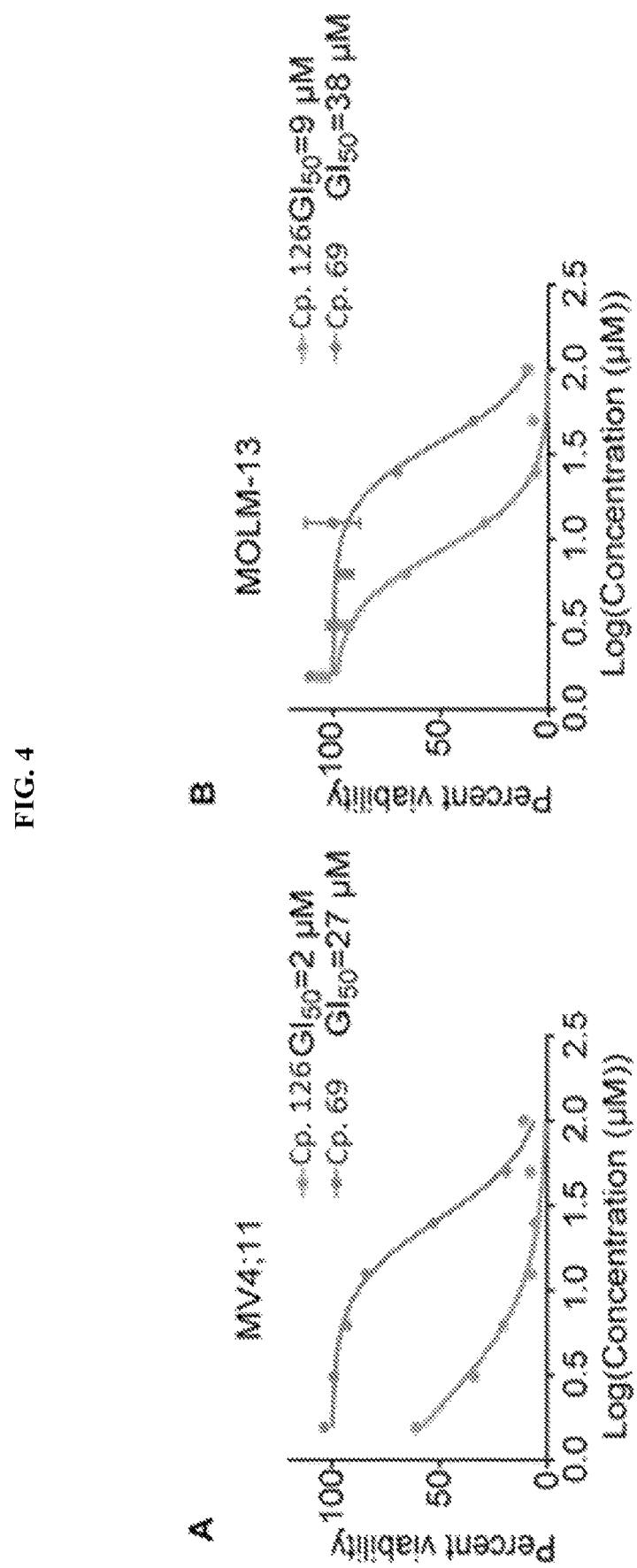
FIG. 4. Activity of 126 in human leukemia cell lines. A) Inhibition of cell proliferation in MV4;11 cells (expressing MLL-AF4) and in B) MOLM13 cells expressing MLL-AF9, after 4 days of treatment with compounds 126 and 69. $GI_{50}$ values for 126 and negative control compound 69 are provided.
Figure 5:
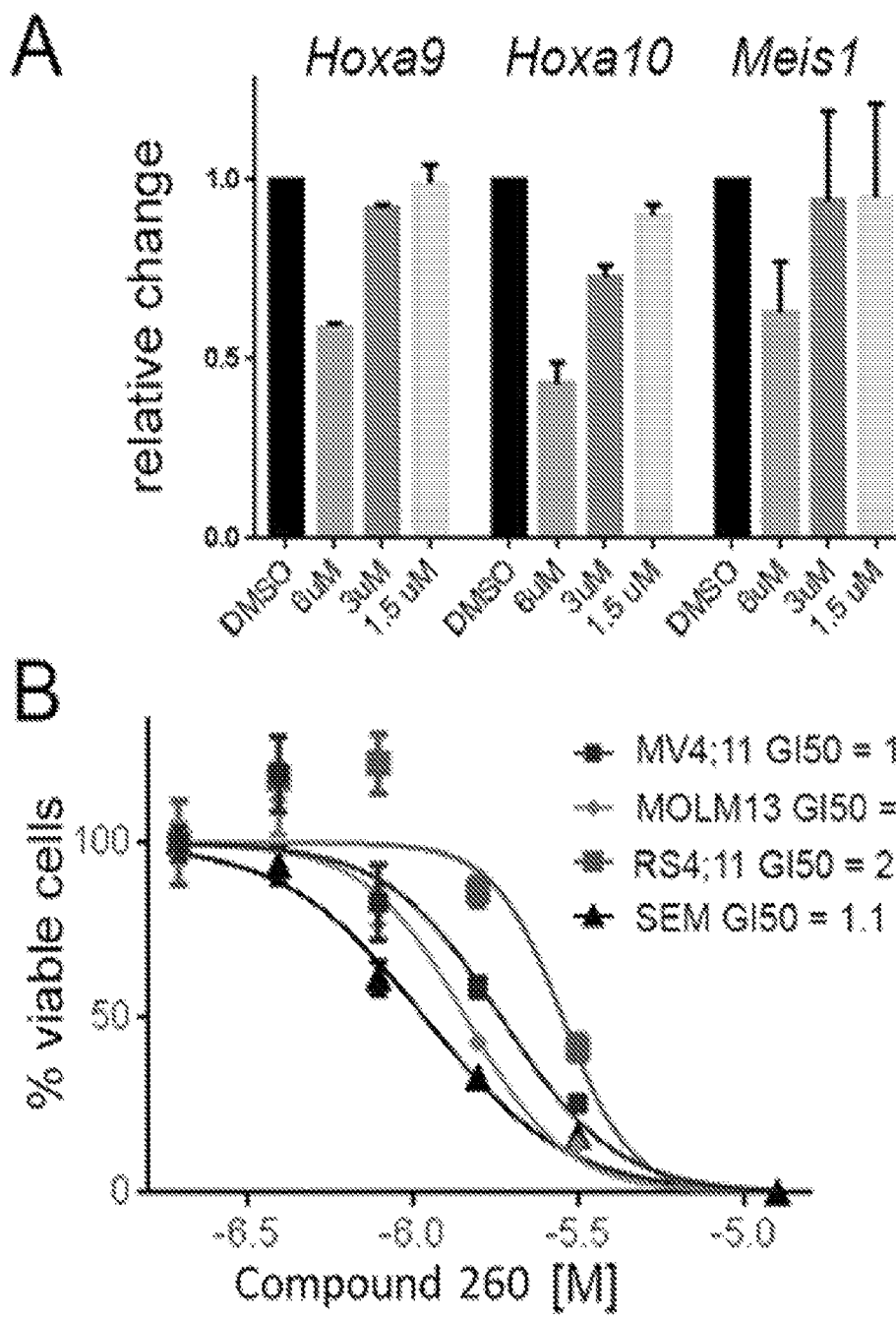
FIG. 5. Activity of 260 in leukemia cells. A) Compound 260 downregulates expression of MLL fusion target genes (Hoxa9, Hoxa10 and Meis1) in MLL-AF9 transformed murine leukemia cells. B) Compound 260 inhibits cell proliferation in a panel of human acute leukemia cells with various MLL translocations.
Figure 6:
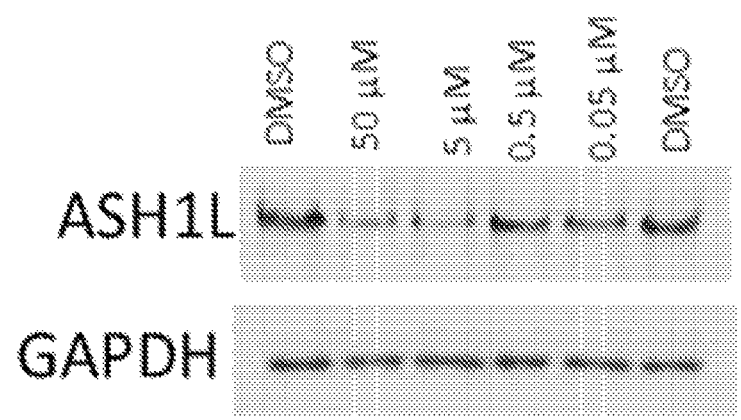
FIG. 6. Degradation of ASH1L induced by 301 in HeLa cells. Concentrations of 301 are shown (0.05-50 µM).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a ASH1L inhibitor" is a reference to one or more ASH1L inhibitors and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

All chemical names of substituents should be interpreted in light of IUPAC and/or a modified format in which functional groups within a substituent are read in the order in which they branch from the scaffold or main structure. For example, in the modified nomenclature, methyl-sulfonyl-propanol refers to CH$_2$SO$_2$CH$_2$CH$_2$CH$_2$OH or:

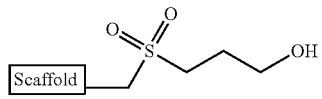

As another example, according to the modified nomenclature, a methyl-amine substituent is:

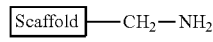

while an amino-methyl substituent is:

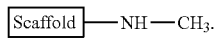

All chemical names of substituents should be interpreted in light of IUPAC and/or the modified nomenclature and with reference to the chemical structures depicted and/or described herein.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "subject at risk for a disease," for example, "a subject at risk for cancer" refers to a subject with one or more risk factors for developing the disease (e.g., cancer). Depending upon the specific disease, risk factors may include, but are not limited to, gender, age, genetic predisposition, environmental exposures, infections, and previous incidents of diseases, lifestyle, etc.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., ASH1L inhibitor and one or more additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula NW$_4^+$, wherein W is C$_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds herein are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

"Amino" refers to the —$NH_2$ moiety.

"Carbonyl" refers to a moiety of the formula —C(═O)—.

"Carboxy" or "carboxyl" refers to the —$CO_2H$ moiety.

"Cyano" refers to the —CN moiety.

Hydroxy" or "hydroxyl" refers to the —OH moiety.

Imino" refers to the ═NH moiety. Unless stated otherwise specifically in the specification, an imino group is optionally substituted.

"Nitro" refers to the —$NO_2$ moiety.

"Oxo" refers to the ═O moiety.

"Thioxo" refers to the ═S moiety.

"Acyl" refers to the group —C(═O)$R_a$, where $R_a$ is selected from the group consisting of alkyl, cycloalkyl, aryl, heteroaryl (bonded through a ring carbon), heteroalkyl, and heterocyclylalkyl. Unless stated otherwise specifically in the specification, an acyl group is optionally substituted.

"Alkyl" refers to a straight or branched hydrocarbon chain moiety consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds). Unless stated otherwise specifically in the specification, an alkyl group is optionally substituted.

"Alkoxy" refers to a moiety of the formula —$OR_a$ where $R_a$ is an alkyl group as defined herein containing one to twelve carbon atoms. Unless stated otherwise specifically in the specification, an alkoxy group is optionally substituted.

"Alkylamino" refers to a moiety of the formula —$NHR_a$ or —$NR_aR_b$ where $R_a$ and $R_b$ are each independently an alkyl group as defined herein containing one to twelve carbon atoms. Unless stated otherwise specifically in the specification, an alkylamino group is optionally substituted.

"Alkylaminoalkyl" refers to an alkyl moiety comprising at least one alkylamino substituent. The alkylamino substituent can be on a tertiary, secondary or primary carbon. Unless stated otherwise specifically in the specification, an alkylaminoalkyl group is optionally substituted.

"Amide" or "amido" refers to a moiety with formula —C(═O)$NR_aR_b$ or —$NR_aC$(═O) $R_b$, where $R_a$ and $R_b$ are each independently selected from the group consisting of hydrogen, alkyl, cycloalkyl, aryl, heteroaryl (bonded through a ring carbon), heteroalkyl, and heterocyclylalkyl, each of which moiety may itself be optionally substituted. In some embodiments, it is a $C_1$-$C_4$ amido or amide group, which includes the amide carbonyl in the total number of carbons in the group. The $R_aR_b$ of —$NR_aR_b$ of the amide may optionally be taken together with the nitrogen to which it is attached to form a 4-, 5-, 6-, or 7-membered ring. Unless stated otherwise specifically in the specification, an amido group is optionally substituted.

"Aminoalkyl" refers to an alkyl moiety comprising at least one amino substituent. The amino substituent can be on a tertiary, secondary or primary carbon. Unless stated otherwise specifically in the specification, an aminoalkyl group is optionally substituted.

"Aminocarbonyl" refers to an amide moiety of the formula —C(═O)$NR_aR_b$, where $R_a$ and $R_b$ are each independently H or alkyl. Unless stated otherwise specifically in the specification, an aminocarbonyl group is optionally substituted.

"Aryl" refers to a hydrocarbon ring system moiety comprising 6 to 18 carbon atoms and at least one aromatic ring. For purposes of this invention, the aryl moiety is a monocyclic, bicyclic, tricyclic, or tetracyclic ring system, which may include fused or bridged ring systems. Aryl moieties include, but are not limited to, aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted.

"Aralkyl" refers to a moiety of the formula —$R_b$—$R_c$ where $R_b$ is an alkylene chain as defined herein and $R_c$ is one or more aryl moieties as defined herein, for example, benzyl, diphenylmethyl, and the like. Unless stated otherwise specifically in the specification, an aralkyl group is optionally substituted.

"Aralkylamino" refers to a aralkyl-$NR_a$— moiety, where $R_a$ is H or alkyl. Unless stated otherwise specifically in the specification, an aralkylamino is optionally substituted.

"Aralkyloxy" refers to an aralkyl-O— moiety. Unless stated otherwise specifically in the specification, an aralkyloxy is optionally substituted.

"Arylamino" refers to a —$NR_a$-aryl moiety, where $R_a$ is H or alkyl. Unless stated otherwise specifically in the specification, an arylamino is optionally substituted.

"Aryloxy" refers to an —O-aryl moiety. Unless stated otherwise specifically in the specification, an aryloxy is optionally substituted.

"Bicycloalkyl" refers to a moiety with two cycloalkyl moieties, that have two or more atoms in common. If the cycloalkyl moieties have exactly two adjacent atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, adamantyl, bicyclo[3.2.1]

heptyl ("norbornyl"), bicyclo[2.2.2]octyl, and the like. Unless stated otherwise specifically in the specification, a bicycloalkyl is optionally substituted.

"Carboxyalkyl" refers to a moiety of the formula —$R_b$—$R_c$ where $R_b$ is an alkylene chain as defined herein and $R_c$ is a carboxy group as defined herein. Unless stated otherwise specifically in the specification, carboxyalkyl group is optionally substituted.

"Cyanoalkyl" refers to a moiety of the formula —$R_b$—$R_c$ where $R_b$ is an alkylene chain as defined herein and $R_c$ is a cyano group as defined herein. Unless stated otherwise specifically in the specification, a cyanoalkyl group is optionally substituted.

"Carbocycle" or "carbocyclic ring" refers to a saturated or unsaturated, non-aromatic, monocyclic or polycyclic hydrocarbon moiety, which may include fused or bridged ring systems, having from three to fifteen carbon atoms, preferably having from three to ten carbon atoms, including cycloalkyls, cycloalkenyls, etc. "Cycloalkyl" refers to a saturated, non-aromatic, monocyclic or polycyclic hydrocarbon moiety, which may include fused or bridged ring systems, having from three to fifteen carbon atoms, preferably having from three to ten carbon atoms. Monocyclic cycloalkyl moieties include, for example, cyclopropyl, cyclobutyl, cyclopentyl, cyclopentenyl, cyclohexyl, cyclohexenyl, cycloheptyl, and cyclooctyl. Polycyclic cycloalkyl moieties include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring, such as cyclopentenyl and cyclohexenyl. Unless otherwise stated specifically in the specification, a cycloalkyl group is optionally substituted.

"Cycloalkylalkyl" refers to a moiety of the formula —$R_bR_d$ where $R_b$ is an alkylene chain as defined herein and $R_d$ is a cycloalkyl moiety as defined herein. Unless stated otherwise specifically in the specification, a cycloalkylalkyl group is optionally substituted.

"Cycloalkylalkylamino" refers to a cycloalkylalkyl-$NR_a$— moiety, where $R_a$ is H or alkyl and where the cycloalkylalkyl moiety is attached via a carbon atom to nitrogen, wherein the nitrogen functions as a linker to attach the moiety to the remainder of the molecule. Unless stated otherwise specifically in the specification, a cycloalkylalkylamino is optionally substituted.

"Cycloalkylalkyloxy" refers to a —O-cycloalkylalkyl moiety, where the cycloalkylalkyl moiety is attached via a carbon atom to oxygen, wherein the oxygen functions as a linker to attach the moiety to the remainder of the molecule. Unless stated otherwise specifically in the specification, a cycloalkylalkyloxy is optionally substituted.

"Cycloalkylamino" refers to a —$NR_a$-cycloalkyl moiety, where $R_a$ is H or alkyl. Unless stated otherwise specifically in the specification, a cycloalkylamino is optionally substituted.

"Cycloalkyloxy" refers to an —O-cycloalkyl moiety. Unless stated otherwise specifically in the specification, a cycloalkyloxy is optionally substituted.

"Halo" or "halogen" refers to fluoro, chloro, bromo, or iodo.

"Haloalkyl" refers to an alkyl group, as defined herein, that is substituted by one or more halo atoms, as defined herein, e.g., trifluoromethyl, difluoromethyl, fluoromethyl, trichloromethyl, —$CH_2CF_3$, —$CH_2CHF_2$, —$CH_2CH_2F$, —$CHFCF_3$, —$CHFCHF_2$, —$CHFCH_2F$, —$CHFCH_3$, —$CF_2CF_3$, —$CF_2CHF_2$, —$CF_2CH_2F$, —$CF_2CH_3$, —$CH_2CF_2CH_3$, —$CH_2CHFCH_3$, 3-bromo-2-fluoropropyl, 1,2-dibromoethyl, and the like. Unless stated otherwise specifically in the specification, a haloalkyl group is optionally substituted.

As used herein, the term "heteroatom" or "ring heteroatom" is meant to include any element other than carbon or hydrogen. Preferred heteroatoms are oxygen (O), nitrogen (N), sulfur (S), and phosphorus (P).

"Heteroalkyl," by itself or in combination with another term, means, unless otherwise stated, a straight or branched chain; monocyclic or polycyclic moiety, which may include fused or bridged ring systems; or any combination thereof, comprising at least one carbon atom and at least one heteroatom, such as O, N, P, Si and S, wherein one or more heteroatoms may be oxidized. Heteroatom(s) may be positioned within the alkyl moiety, e.g., —$CH_2$—O—$CH_2$—; at a point of connectivity with the remainder of the molecule, e.g., —$SO_2CH(CH_3)CH_2$—; or a combination thereof, e.g., —$NH_2CH_2CH_2SO_2CH_2$—. Unless stated otherwise specifically in the specification, a heteroalkyl group is optionally substituted.

"Heteroaryl" refers to a 5- to 14-membered ring system moiety comprising one to thirteen carbon atoms; one to six heteroatoms such as nitrogen, oxygen, and sulfur; and one or multiple rings wherein at least one ring is aromatic. For purposes of this invention, the heteroaryl group may be a monocyclic, bicyclic, tricyclic, or tetracyclic ring system, which may include fused or bridged ring systems and one or more heteroatoms may be oxidized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

"Heteroarylalkyl" refers to a moiety of the formula —$R_bR_f$ where $R_b$ is an alkylene chain as defined herein and $R_f$ is a heteroaryl group as defined herein. Unless stated otherwise specifically in the specification, a heteroarylalkyl group is optionally substituted.

"Heteroarylalkylamino" refers to a heteroarylalkyl-$NR_a$— moiety, where $R_a$ is H or alkyl. Unless stated otherwise specifically in the specification, an heteroarylalkylamino is optionally substituted.

"Heteroarylalkyloxy" refers to an heteroarylalkyl-O— moiety. Unless stated otherwise specifically in the specification, a heteroarylalkyloxy is optionally substituted.

"Heteroarylamino" refers to a —$NR_a$-heteroaryl moiety, where $R_a$ is H or alkyl. Unless stated otherwise specifically in the specification, a heteroarylamino is optionally substituted.

"Heteroaryloxy" refers to an —O-heteroaryl moiety. Unless stated otherwise specifically in the specification, an heteroaryloxy is optionally substituted.

"Heterobicycloalkyl" refers to a bicycloalkyl structure in which at least one carbon ring atom is replaced with a heteroatom such as oxygen, nitrogen, and sulfur. Unless stated otherwise specifically in the specification, a heterobicycloalkyl is optionally substituted.

"Heterocyclyl" or "heterocyclic ring" refers to a 3- to 18-membered non-aromatic ring which consists of two to twelve carbon atoms and from one to six heteroatoms such as nitrogen, oxygen, and sulfur. Unless stated otherwise specifically in the specification, the heterocyclyl group is a monocyclic, bicyclic, tricyclic, or tetracyclic ring system, which may include fused or bridged ring systems; the heteroatoms may be optionally oxidized; and the heterocyclyl may be unsaturated or saturated. Examples of such heterocyclyl moieties include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group is optionally substituted.

"Heterocyclylalkyl" or "heterocycloalkyl" refers to a moiety of the formula —$R_b R_c$ where $R_b$ is an alkylene chain as defined herein and $R_c$ is a heterocyclyl moiety as defined herein, and if the heterocyclyl is a nitrogen-containing heterocyclyl, the heterocyclyl is optionally attached to the alkyl moiety at the nitrogen atom. Unless stated otherwise specifically in the specification, a heterocyclylalkyl group is optionally substituted.

"Heterocyclylalkylamino" refers to a heterocyclylalkyl-$NR_a$— moiety, where $R_a$ is H or alkyl and where the heterocyclylalkyl moiety is attached via a carbon atom to nitrogen, wherein the nitrogen functions as a linker to attach the moiety to the remainder of the molecule. Unless stated otherwise specifically in the specification, a heterocyclylalkylamino is optionally substituted.

"Heterocyclylalkyloxy" refers to a —O-heterocycloalkyl moiety, where the heterocyclylalkyl moiety is attached via a carbon atom to oxygen, wherein the oxygen functions as a linker to attach the moiety to the remainder of the molecule. Unless stated otherwise specifically in the specification, a heterocyclylalkyloxy is optionally substituted.

"Heterocyclylamino" refers to a —$NR_a$-heterocyclyl moiety, where $R_a$ is H or alkyl and where the heterocyclyl moiety is attached via a carbon atom to nitrogen, wherein the nitrogen functions as a linker to attach the moiety to the remainder of the molecule. Unless stated otherwise specifically in the specification, a heterocyclylamino is optionally substituted.

"Heterocyclyloxy" refers to an —O-heterocyclyl moiety, where the heterocyclyl moiety is attached via a carbon atom to oxygen, wherein the oxygen functions as a linker to attach the moiety to the remainder of the molecule. Unless stated otherwise specifically in the specification, a heterocyclyloxy is optionally substituted.

"Hydroxyalkyl" or "hydroxylalkyl" refers to an alkyl group comprising at least one hydroxyl substituent. The —OH substituent may be on a primary, secondary, or tertiary carbon. Unless stated otherwise specifically in the specification, a hydroxyalkyl group is optionally substituted.

"N-heteroaryl" refers to a heteroaryl moiety as defined herein containing at least one nitrogen and where the point of attachment of the heteroaryl moiety to the rest of the molecule is through a nitrogen atom in the heteroaryl ring. Unless stated otherwise specifically in the specification, an N-heteroaryl group is optionally substituted.

"N-heterocyclyl" refers to a heterocyclyl moiety as defined herein containing at least one nitrogen and where the point of attachment of the heterocyclyl moiety to the rest of the molecule is through a nitrogen atom in the heterocyclyl ring. Unless stated otherwise specifically in the specification, a N-heterocyclyl group is optionally substituted.

"Thioalkyl" refers to a moiety of the formula —$SR_a$ where $R_a$ is an alkyl moiety as defined herein containing one to twelve carbon atoms. Unless stated otherwise specifically in the specification, a thioalkyl group is optionally substituted.

"Alkylene" or "alkylene chain" refers to a straight or branched divalent hydrocarbon chain linking two groups in a molecule, which may be saturated or unsaturated (i.e., contains one or more double and/or triple bonds), and have from one to twelve carbon atoms, preferably one to eight carbon atoms ($C_1$-$C_8$ alkylene) or one to six carbon atoms ($C_1$-$C_6$ alkylene), e.g., methylene, ethylene, propylene, n-butylene, ethenylene, propenylene, n-butenylene, propynylene, n-butynylene, and the like. The alkylene chain is attached to the rest of the molecule through a single or double bond. The points of attachment of the alkylene chain to the rest of the molecule may be through one carbon, e.g., methylene, or any two carbons within the chain, e.g., —$CH_2CH(CH_3)CH_2CH_2$—. Unless stated otherwise specifically in the specification, an alkylene chain is optionally substituted.

"Alkylenecarbonyl" refers to a moiety of the formula —C(=O)$R_a$—, where $R_a$ is an alkylene chain as defined herein. Unless stated otherwise specifically in the specification, an alkylenecarbonyl is optionally substituted.

"Alkenylene" is an unsaturated alkylene, as defined herein, which comprises one or more carbon-carbon double bonds. Unless stated otherwise specifically in the specification, an alkenylene is optionally substituted.

"Alkenylenecarbonyl" refers to an unsaturated alkylenecarbonyl, as defined herein, which comprises one or more carbon-carbon double bonds. Unless stated otherwise specifically in the specification, an alkenylenecarbonyl is optionally substituted.

"Arylene" refers to a divalent aryl group which links one part of the molecule to another part of the molecule. Unless stated specifically otherwise, an arylene is optionally substituted.

"Heteroalkylene" refers to an alkylene group comprising at least one heteroatom (e.g., N, O or S). In some embodiments, the heteroatom is within the alkylene chain (i.e., the heteroalkylene comprises at least one carbon-heteroatom-carbon bond). In other embodiments, the heteroatom is at a terminus of the alkylene and joins the alkylene to the remainder of the molecule (e.g., M1-H-A-M2, where M1 and M2 are portions of a molecule, H is a heteroatom and A is an alkylene). A heteroalkylene may have both internal and terminal heteroatoms, e.g., —$OCH_2CH_2OCH_2CH_2O$—. Unless stated otherwise specifically in the specification, a heteroalkylene is optionally substituted.

"Heteroalkylenecarbonyl" refers to a moiety of the formula —C(=O)$R_a$—, where $R_a$ is a heteroalkylene chain as defined herein. Unless stated otherwise specifically in the specification, a heteroalkylenecarbonyl is optionally substituted.

"Heteroarylene" refers to a divalent heteroaryl group which links one part of the molecule to another part of the molecule. Unless stated specifically otherwise, a heteroarylene is optionally substituted.

"Heteroarylenecarbonyl" refers to a moiety of the formula —C(=O)R$_a$—, wherein R$_a$ is a heteroarylene as defined herein. Unless stated specifically otherwise, a heteroarylenecarbonyl is optionally substituted.

"Heterocyclylalkylene" refers to a divalent heterocyclyl group which links one part of the molecule to another part of the molecule. Unless stated specifically otherwise, a heterocycloalkylene is optionally substituted.

"Heterocyclylalkylenecarbonyl" refers to a moiety of the formula —C(=O)R$_a$—, wherein R$_a$ is a heterocycloalkylene as defined herein. Unless stated specifically otherwise, a heterocycloalkylenecarbonyl is optionally substituted.

The term "substituted" used herein refers to replacement of at least one hydrogen atom with any of the above groups (e.g., amino, carboxy, hydroxyl, imino, acyl, alkyl, alkoxy, alkylamino, alkylaminoalkyl, amide, aminoalkyl, aminocarbonyl, aryl, aralkyl, aralkylamino, aralkyloxy, arylamino, aryloxy, bicycloalkyl, carboxyalkyl, cyanoalkyl, cycloalkyl, cycloalkylalkyl, cycloalkylalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, and/or heterocyclylalkylenecarbonyl), wherein the at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups such as alkyl sulfone groups, sulfonyl groups such as sulfonamide groups and sulfonylalkyl groups such as sulfonylmethane, and sulfoxide groups such as alkyl sulfoxide groups; a nitrogen atom in groups such as amino, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; a phosphorus atom in groups such as dialkylphosphine oxide groups; and other heteroatoms in various other groups. "Substituted" also means any of the above groups in which one or more hydrogen atoms are replaced by a higher-order bond (e.g., a double- or triple-bond) to a carbon atom or a heteroatom such as oxygen in oxo, carbonyl, carboxyl, and ester groups; and nitrogen in groups such as imines, oximes, hydrazones, and nitriles. "Substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, —SO$_2$NR$_g$R$_h$, —C(=O)R$_g$, —C(=O)OR$_g$, —C(=O)NR$_g$R$_h$, —CH$_2$SO$_2$R$_g$, or —CH$_2$SO$_2$NR$_g$R$_h$, where R$_g$ and R$_h$ are independently hydrogen, alkyl, alkoxy, alkylamino, thioalkyl, aryl, aralkyl, cycloalkyl, cycloalkylalkyl, haloalkyl, heteroalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, carbonyl, carboxy, cyano, hydroxyl, imino, nitro, oxo, thioxo, acyl, alkyl, alkoxy, alkylamino, alkylaminoalkyl, amide, aminoalkyl, aminocarbonyl, aryl, aralkyl, aralkylamino, aralkyloxy, arylamino, aryloxy, bicycloalkyl, carboxyalkyl, cyanoalkyl, cycloalkyl, cycloalkylalkyl, cycloalkylalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, heterocyclylalkylenecarbonyl, trimethylsilanyl, dialkylphosphine oxide, —OR$^a$, —SR$^a$, —OC(O)—R$^a$, —N(R$^a$)$^2$, —C(O)R$^a$, —C(O)OR$^a$, —C(O)N(R$^a$)$^2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$^2$ (where t is 1 or 2), —PO(R$^a$)$^2$, or —PO(OR$^a$)$^2$ group, where each R$^a$ is independently hydrogen, alkyl, haloalkyl, cycloalkyl, cycloalkylalkyl, aryl, aralkyl, heterocyclyl, heterocyclylalkyl, heteroaryl or heteroarylalkyl group. In addition, each of the foregoing substituents is optionally substituted with one or more of the above substituents.

The term "optionally substituted", as used herein, means that the referenced group (e.g., alkyl, cycloalkyl, etc.) may or may not be substituted with one or more additional group(s).

As used herein, the term "absent" when used in reference to functional group or substituent, particularly in reference to the chemical structure of a compound, means that the particular functional group or substituent is not present in the compound being described. When used in reference to a substituent (e.g., a pendant group, not a linking group), the absence of the substituent typically means that the bond to the substituent is absent and that absence of the bond is compensated for with a H atom. When used in reference to a position within a chain or ring (e.g., a linking group, not a pendant group), the absence of the position typically means that the two positions otherwise connected by the absent position are either (1) directly connected by a covalent bond, or (2) not connected, as will either be apparent from the structure or explicitly indicated.

As used herein, the terms "ring system" and "multiring system" refer to a chemical structure or moiety comprising two or more rings that share at least one bond (and two or more atomic positions). For example, a multiring system comprising a cyclohexane and cyclopentane is:

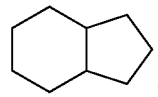

If an aryl or heteroaryl ring is included in a multiring system, the aromaticity of the ring is maintained, unless described otherwise, for example, a multiring system comprising a benzene and cyclohexane is:

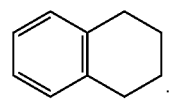

DETAILED DESCRIPTION

Provided herein are small molecule inhibitors of ASH1L activity and small molecules that facilitate ASH1L degradation and methods of use thereof for the treatment of disease, including acute leukemia, solid cancers and other diseases dependent on activity of ASH1L.

In some embodiments, provided herein are small molecule inhibitors directly targeting the SET domain of ASH1L and blocking its catalytic activity. In experiments conducted during development of embodiments herein, small molecule inhibitors of ASH1L demonstrated anti-proliferative effect in MLL leukemia cells, and ASH1L knockdown inhibits growth of breast cancer cells with ASH1L overexpression and downregulate expression of target genes, including Hoxa9 and Meis1 in MLL leukemia models.

In some embodiments, the compounds described herein find use in the treatment or prevention of disease (e.g., cancer (e.g., leukemia, breast cancer, ovarian cancer, melanoma, prostate cancer, thyroid cancer, or metastasis thereof), muscular dystrophy, liver fibrosis, etc.) and/or the alleviation of symptoms associated therewith. In some embodiments, provided herein are pharmaceutical compositions comprising a compound described and/or within the scope herein. In some embodiments, pharmaceutical compositions comprising a compound described and/or within the scope herein are administered to a subject to treat a disease of condition (e.g., cancer (e.g., leukemia, breast cancer, ovarian cancer, melanoma, prostate cancer, thyroid cancer, or metastasis thereof), muscular dystrophy, liver fibrosis, etc.).

In certain embodiments, provided herein is a compound having a structure of Formula (I):

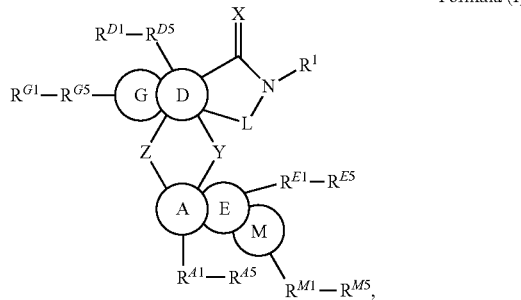

Formula (I)

or a salt thereof;
wherein:
X=S, O, NH or CH$_2$;
R$^1$ is any suitable substituent (e.g., pendant groups) described herein;
L is 0-3 C, S, O, and/or N members, and wherein if L is 0 members there is no bond at L (e.g., no bond directly connecting N and Ⓓ);
Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein;
Ⓖ is an optionally present 4-7 member carbocyclic (e.g., cycloalkyl ring or unsaturated non-aromatic carbocyclic ring), heterocyclic, aryl, or heteroaryl ring which forms a ring system with Ⓓ, and is optionally substituted at 0-5 positions by R$^{G1}$-R$^{G5}$ substituents, and wherein R$^{G1}$-R$^{G5}$ are selected from any suitable substituents (e.g., pendant groups) described herein;
Y is linker of 0-3 C, S, O, and/or N members, wherein any C or N members of Y may be optionally substituted with any suitable substituents (e.g., pendant groups) described herein, wherein if Y is 0 members, there is covalent bond at Y (i.e., between Ⓓ s and Ⓐ);
Z is linker of 0-3 C, S, O, and/or N members, wherein any C or N members of Z may be optionally substituted with any suitable substituents (e.g., pendant groups) described herein, wherein if Z is 0 members, there is no bond at Z (i.e., between Ⓓ and Ⓐ);
Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein;
Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by R$^{E1}$-R$^{E5}$ substituents, and wherein R$^{E1}$-R$^{E5}$ are selected from any suitable substituents (e.g., pendant groups) described herein; and
Ⓜ is an optionally present 4-7 member carbocyclic (e.g., cycloalkyl ring or unsaturated non-aromatic carbocyclic ring), heterocyclic, aryl, or heteroaryl ring which forms a ring system with Ⓔ and Ⓐ, and is optionally substituted at 0-5 positions by R$^{M1}$-R$^{M5}$ substituents, and wherein R$^{M1}$-R$^{M5}$ are selected from any suitable substituents (e.g., pendant groups) described herein.

In some embodiments, suitable substituents, as described herein (e.g., R$^{D1}$-R$^{D5}$, R$^{G1}$-R$^{G5}$, R$^{A1}$-R$^{A5}$, R$^{E1}$-R$^{E5}$, R$^{M1}$-R$^{M5}$, R$^1$, etc.), are each independently selected from H, alkyl, substituted alkyl (e.g. halogen substituted alkyl), branched alkyl, substituted branched alkyl (e.g. halogen substituted branched alkyl) hydroxy, alkoxy, amine, substituted amine, thioalkyl, halogen, ketone, amide, substituted amide, cyano, sulfonyl, carboxy, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R$^{D1}$-R$^{D5}$, R$^{G1}$-R$^{G5}$, R$^{A1}$-R$^{A5}$, R$^{E1}$-R$^{E5}$, R$^{M1}$-R$^{M5}$ may be present at any suitable positions of the Ⓓ, Ⓖ, Ⓐ, Ⓔ, and Ⓜ rings, respectively.

In some embodiments, provided herein is a compound having a structure of Formula (I-A):

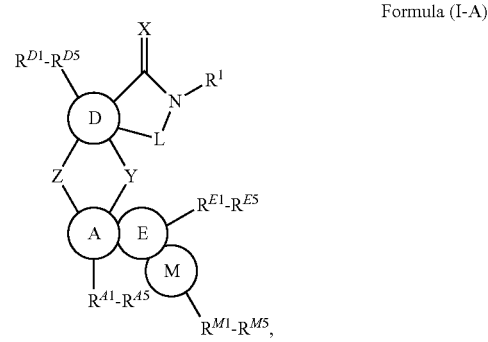

Formula (I-A)

23 or a salt thereof;
wherein:
X=S, O, NH or CH$_2$;
R$^1$ is any suitable substituent (e.g., pendant groups) described herein;
L is 0-3 C, S, O, and/or N members, and wherein if L is 0 members there is no bond at L (e.g., no bond directly connecting N and Ⓓ);
Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein;
Y is linker of 0-3 C, S, O, and/or N members, wherein any C or N members of Y may be optionally substituted with any suitable substituents (e.g., pendant groups) described herein, wherein if Y is 0 members, there is covalent bond at Y (i.e., between Ⓓ and Ⓐ);
Z is linker of 0-3 C, S, O, and/or N members, wherein any C or N members of Z may be optionally substituted with any suitable substituents (e.g., pendant groups) described herein, wherein if Z is 0 members, there is no bond at Z (i.e., between Ⓓ and Ⓐ);
Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein;
Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by R$^{E1}$-R$^{E5}$ substituents, and wherein R$^{E1}$-R$^{E5}$ are selected from any suitable substituents (e.g., pendant groups) described herein; and
Ⓜ is an optionally present 4-7 member carbocyclic (e.g., cycloalkyl ring or unsaturated non-aromatic carbocyclic ring), heterocyclic, aryl, or heteroaryl ring which forms a ring system with Ⓔ and Ⓐ, and is optionally substituted at 0-5 positions by R$^{M1}$-R$^{M5}$ substituents, and wherein R$^{M1}$-R$^{M5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^{E1}$-R$^{E5}$, R$^{M1}$-R$^{M5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

24

In some embodiments, provided herein is a compound having a structure of Formula (I-B):

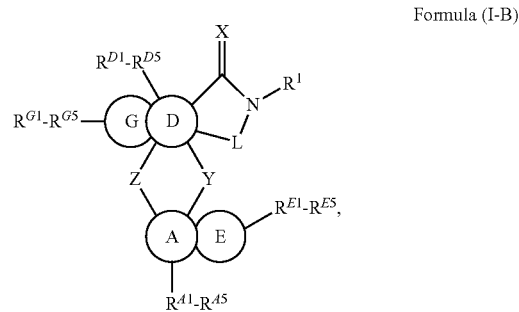

Formula (I-B)

or a salt thereof;
wherein:
X=S, O, NH or CH$_2$;
R$^1$ is any suitable substituent (e.g., pendant groups) described herein;
L is 0-3 C, S, O, and/or N members, and wherein if L is 0 members there is no bond at L (e.g., no bond directly connecting N and Ⓓ);
Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein;
Ⓖ is an optionally present 4-7 member carbocyclic (e.g., cycloalkyl ring or unsaturated non-aromatic carbocyclic ring), heterocyclic, aryl, or heteroaryl ring which forms a ring system with Ⓓ, and is optionally substituted at 0-5 positions by R$^{G1}$-R$^{G5}$ substituents, and wherein R$^{G1}$-R$^{G5}$ are selected from any suitable substituents (e.g., pendant groups) described herein;
Y is linker of 0-3 C, S, O, and/or N members, wherein any C or N members of Y may be optionally substituted with any suitable substituents (e.g., pendant groups) described herein, wherein if Y is 0 members, there is covalent bond at Y (i.e., between Ⓓ and Ⓐ);
Z is linker of 0-3 C, S, O, and/or N members, wherein any C or N members of Z may be optionally substituted with any suitable substituents (e.g., pendant groups) described herein, wherein if Z is 0 members, there is no bond at Z (i.e., between Ⓓ and Ⓐ);
Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein; and
Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by R$^{E1}$-R$^{E5}$ substituents, and wherein R$^{E1}$-R$^{E5}$ are selected from any suitable substituents (e.g., pendant groups) described herein.

In some embodiments, suitable substituents, as described herein (e.g., R$^{D1}$-R$^{D5}$, R$^{G1}$-R$^{G5}$, R$^{A1}$-R$^{A5}$, R$^{E1}$-R$^{E5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R6 can and may be present at any suitable positions, for example, one or more of the positions of the Ⓓ, Ⓖ, Ⓐ, and Ⓔ rings.

In certain embodiments, provided herein is a compound having a structure of Formula (I-C):

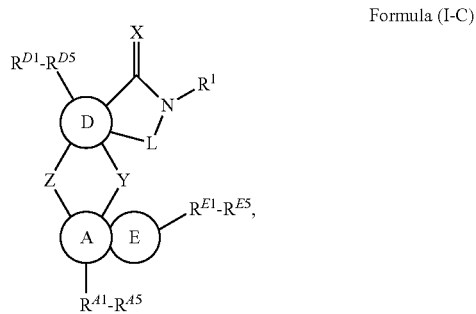

Formula (I-C)

or a salt thereof;
wherein:
  X=S, O, NH or $CH_2$;
  $R^1$ is any suitable substituent (e.g., pendant groups) described herein;
  L is 0-3 C, S, O, and/or N members, and wherein if L is 0 members there is no bond at L (e.g., no bond directly connecting N and Ⓓ);
  Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by $R^{D1}$-$R^{D5}$ substituents, and wherein $R^{D1}$-$R^{D5}$ are selected from any suitable substituents (e.g., pendant groups) described herein;
  Y is linker of 0-3 C, S, O, and/or N members, wherein any C or N members of Y may be optionally substituted with any suitable substituents (e.g., pendant groups) described herein, wherein if Y is 0 members, there is covalent bond at Y (i.e., between Ⓓ and Ⓐ);
  Z is linker of 0-3 C, S, O, and/or N members, wherein any C or N members of Z may be optionally substituted with any suitable substituents (e.g., pendant groups) described herein, wherein if Z is 0 members, there is no bond at Z (i.e., between Ⓓ and Ⓐ);
  Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by $R^{A1}$-$R^{A5}$ substituents, and wherein $R^{A1}$-$R^{A5}$ are selected from any suitable substituents (e.g., pendant groups) described herein; and
  Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by $R^{E1}$-$R^{E5}$ substituents, and wherein $R^{E1}$-$R^{E5}$ are selected from any suitable substituents (e.g., pendant groups) described herein.

In some embodiments, suitable substituents, as described herein (e.g., $R^{D1}$-$R^{D5}$, $R^{A1}$-$R^{A5}$, $R^{E1}$-$R^{E5}$, $R^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R6 can and may be present at any suitable positions, for example, one or more of the positions of the Ⓓ, Ⓐ, and Ⓔ rings.

In certain embodiments, provided herein is a compound having a structure of Formula (I-D):

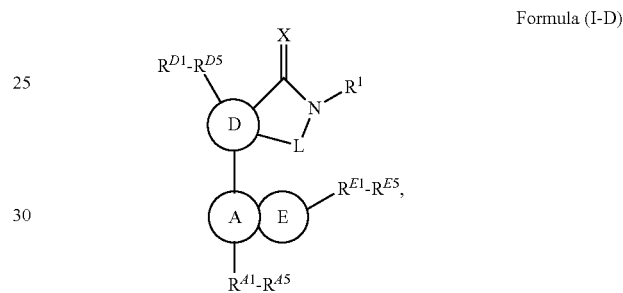

Formula (I-D)

or a salt thereof;
wherein:
  X=S, O, NH or $CH_2$;
  $R^1$ is any suitable substituent (e.g., pendant groups) described herein;
  L is 0-3 C, S, O, and/or N members, and wherein if L is 0 members there is no bond at L (e.g., no bond directly connecting N and Ⓓ);
  Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by $R^{D1}$-$R^{D5}$ substituents, and wherein $R^{D1}$-$R^{D5}$ are selected from any suitable substituents (e.g., pendant groups) described herein;
  Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by $R^{A1}$-$R^{A5}$ substituents, and wherein $R^{A1}$-$R^{A5}$ are selected from any suitable substituents (e.g., pendant groups) described herein; and
  Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by $R^{E1}$-$R^{E5}$ substituents, and wherein $R^{E1}$-$R^{E5}$ are selected from any suitable substituents (e.g., pendant groups) described herein.

In some embodiments, suitable substituents, as described herein (e.g., $R^{D1}$-$R^{D5}$, $R^{A1}$-$R^{A5}$, $R^{E1}$-$R^{E5}$, $R^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R6 can and may be present at any suitable positions, for example, one or more of the positions of the Ⓓ, Ⓐ, and Ⓔ rings.

In certain embodiments, provided herein is a compound having a structure of Formula (E):

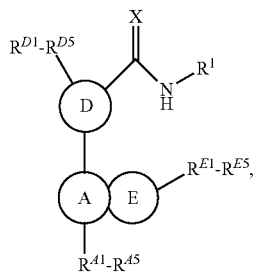

Formula (E)

or a salt thereof;
wherein:
X=S, O, NH or CH$_2$;
R$^1$ is any suitable substituent (e.g., pendant groups) described herein;
Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein;
Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein; and
Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by R$^{E1}$-R$^{E5}$ substituents, and wherein R$^{E1}$-R$^{E5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^{E1}$-R$^{E5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, provided herein is a compound having a structure of Formula (I-F):

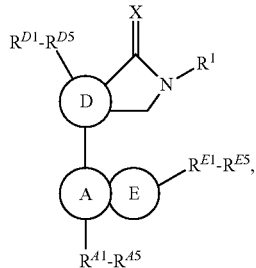

Formula (I-F)

or a salt thereof;
wherein:
X=S, O, NH or CH$_2$;
R is any suitable substituent (e.g., pendant groups) described herein;
Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D55}$ substituents, and wherein R$^{D1}$-R$^{D5}$ are selected from any suitable substituents (e.g., pendant groups) described herein;
Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein; and
Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by R$^{E1}$-R$^{E5}$ substituents, and wherein R$^{E1}$-R$^{E5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^{E1}$-R$^{E5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof; wherein R6 can and may be present at any suitable positions, for example, one or more of the positions of the Ⓓ, Ⓐ, and Ⓔ rings.

In certain embodiments, provided herein is a compound having a structure of Formula (I-G):

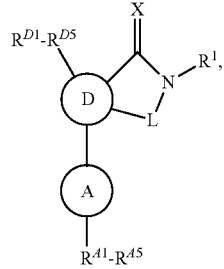

Formula (I-G)

or a salt thereof,
wherein:
  X=S, O, NH or CH$_2$;
  R$^1$ is any suitable substituent (e.g., pendant groups) described herein;
  L is 0-3 C, S, O, and/or N members, and wherein if L is 0 members there is no bond at L (e.g., no bond directly connecting N and Ⓓ);
  Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein; and
  Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, provided herein is a compound having a structure of Formula (I-H):

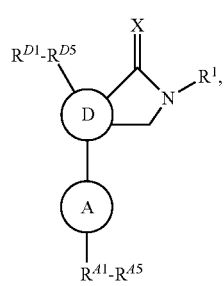

Formula (I-H)

or a salt thereof;
wherein:
  X=S, O, NH or CH$_2$;
  R$^1$ is any suitable substituent (e.g., pendant groups) described herein;
  Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein; and
  Ⓖ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In certain embodiments, provided herein is a compound having a structure of Formula (I-I):

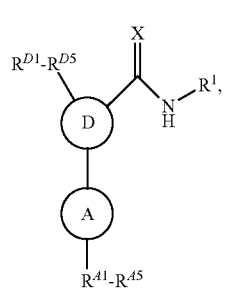

Formula (I-I)

or a salt thereof;
wherein:
  X=S, O NH, or CH$_2$;
  R$^1$ is any suitable substituent (e.g., pendant groups) described herein;
  Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein; and
  Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

In certain embodiments, provided herein is a compound having a structure of Formula (I-J):

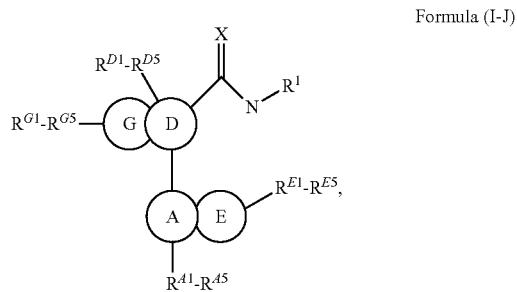

Formula (I-J)

or a salt thereof;
wherein:
- X=S, O NH, or CH$_2$;
- R$^1$ is any suitable substituent (e.g., pendant groups) described herein;
- Ⓓ is a 4-7 member aryl, heteroaryl, carbocyclic (e.g., cycloalkyl ring or unsaturated non-aromatic carbocyclic ring) or heterocyclic ring, optionally substituted at 0-5 positions by R$^{D1}$-R$^{D5}$ substituents, and wherein R$^{D1}$-R$^{D5}$ are selected from any suitable substituents (e.g., pendant groups) described herein;
- Ⓖ is an optionally present 4-7 member carbocyclic (e.g., cycloalkyl ring or unsaturated non-aromatic carbocyclic ring), heterocyclic, aryl, or heteroaryl ring which forms a ring system with Ⓓ, and is optionally substituted at 0-5 positions by R$^{G1}$-R$^{G5}$ substituents, and wherein R$^{G1}$-R$^{G5}$ are selected from any suitable substituents (e.g., pendant groups) described herein;
- Ⓐ is a 5-7 member aryl, heteroaryl, carbocyclic (e.g., cycloalkyl ring or unsaturated non-aromatic carbocyclic ring), or heterocyclic ring, optionally substituted at 0-5 positions by R$^{A1}$-R$^{A5}$ substituents, and wherein R$^{A1}$-R$^{A5}$ are selected from any suitable substituents (e.g., pendant groups) described herein; and
- Ⓔ is an optionally present 5-7 member carbocyclic (e.g., cycloalkyl ring or unsaturated non-aromatic carbocyclic ring), heterocyclic, aryl, or heteroaryl ring which forms a ring system with Ⓐ, and is optionally substituted at 0-5 positions by R$^{E1}$-R$^{E5}$ substituents, and wherein R$^{E1}$-R$^{E5}$ are selected from any suitable substituents (e.g., pendant groups) described herein.

In some embodiments, suitable substituents, as described herein (e.g., R$^{D1}$-R$^{D5}$, R$^{A1}$-R$^{A5}$, R$^1$, etc.), are each independently selected from H, alkyl, substituted alkyl (e.g. halogen substituted alkyl), branched alkyl, substituted branched alkyl (e.g. halogen substituted branched alkyl), hydroxy, alkoxy, amine, substituted amine, thioalkyl, halogen, ketone, amide, substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In some embodiments, Ⓓ of any of Formulas (I), (I-A), (I-B), (I-C), (I-D), (I-E), (I-F), (I-G), (I-H), (I-I) and/or (I-J) is a 4-7 member aryl, heteroaryl, carbocyclic (e.g., cycloalkyl ring or unsaturated non-aromatic carbocyclic ring), or heterocyclic ring. In some embodiments, Q is selected from an optionally substituted 5-membered heteroaryl, an optionally substituted 6-membered aryl, an optionally substituted 6-membered heteroaryl, an optionally substituted 5-membered cycloalkyl, an optionally substituted 6-membered cycloalkyl, an optionally substituted 5-membered carbocycle, an optionally substituted 6-membered carbocycle, an optionally substituted 5-membered non-aromatic heterocycle, or an optionally substituted 6-membered non-aromatic heterocycle.

In some embodiments, of any of Formulas (I), (I-A), (I-B), (I-C), (I-D), (I-E), (I-F), (I-G), (I-H), (I-I) and/or (I-J) is has the structure of

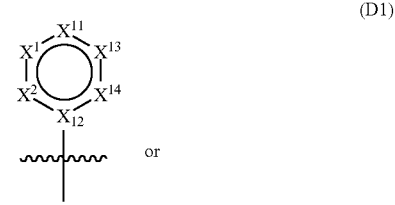

(D1)

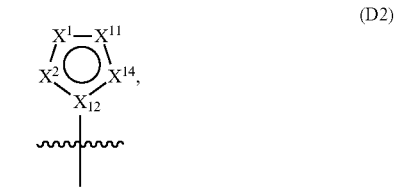

(D2)

wherein

indicates the connection through Y to Ⓐ. In some embodiments, each of X$^1$, X$^2$, X$^{11}$, X$^{12}$, X$^{13}$ (when present), and X$^{14}$ of Ⓓ are independently selected from C, N, O, and S. In other embodiments, X$^1$, X$^2$, X$^{11}$, X$^{12}$, X$^{13}$ (when present), and X$^{14}$ are C, unless specified as O, N, or S. In other embodiments, X$^1$, X$^2$, X$^{11}$, X$^{12}$, X$^{13}$ (when present), and X$^{14}$ are each independently C, N, O, or S, even if another position is specified as O, N, or S. In some embodiments, Ⓓ is selected from a structure listed in Table 1a. In some cases, Ⓓ is not one or more structures listed in Table 1a.

TABLE 1a
Non-limiting examples of ⓡ structures
| ⓡ Number | ⓡ Structure |
|---|---|
| D | 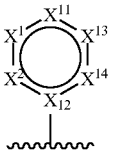 |
| D-A | 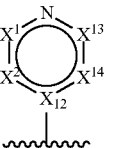 |
| D1-B | 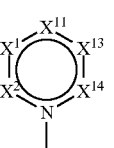 |
| D1-C | 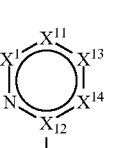 |
| D1-D | 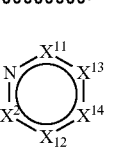 |
| D1-E | 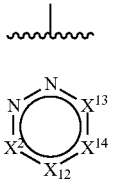 |
| D1-F | 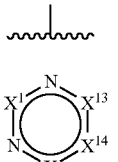 |
| D1-G | 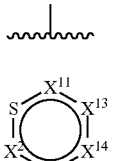 |
| D1-H | 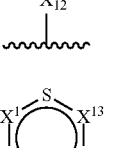 |
| D2 | 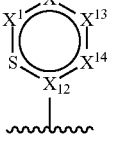 |
| D1-J | 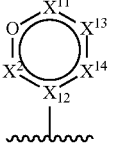 |
| D1-K | 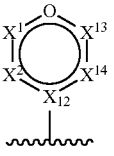 |
| D1-L | 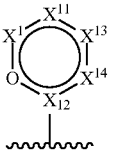 |
| D2- | 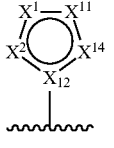 |
| D2-A | 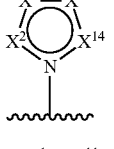 |
| D2-B | 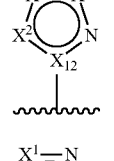 |
| D2-C | 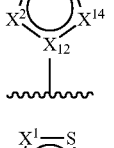 |
| D2-D | 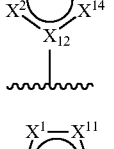 |
| D2-E | 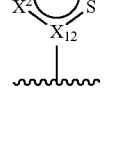 |

TABLE 1a-continued
Non-limiting examples of Ⓓ structures
| Ⓓ Number | Ⓓ Structure |
|---|---|
| D2-F | 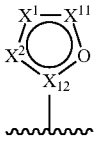 |
| D2-G | 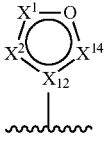 |
In some embodiments, Ⓓ is selected from a structure listed in Table 1b. In some cases, Ⓓ is not one or more structures listed in Table 1b.
TABLE 1b
Non-limiting examples of Ⓓ structures
| Ⓓ Number | Ⓓ Structure |
|---|---|
| D-1 | 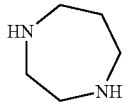 |
| D-2 |  |
| D-3 |  |
| D-4 |  |
| D-5 |  |
| D-6 |  |
| D-7 |  |
| D-8 |  |
| D-9 |  |
| D-10 |  |
| D-11 | |
| D-12 | |
| D-13 | |
| D-14 | |
| D-15 | |
| D-16 | |
| D-17 | |
| D-18 | |
| D-19 | |
| D-20 | |
| D-21 | |
| D-22 | |
| D-23 |  |

TABLE 1b-continued

Non-limiting examples of Ⓓ structures

| Ⓓ Number | Ⓓ Structure |
|---|---|
| D-24 | isoxazolidine (O-NH saturated 5-ring) |
| D-25 | 1,3-dithiolene |
| D-26 | 1,3-dioxole |
| D-27 | 1H-pyrrole |
| D-28 | cyclopentadiene |
| D-29 | thiophene |
| D-30 | furan |
| D-31 | 1H-pyrazole |
| D-32 | 1H-imidazole |
| D-33 | isoxazole |
| D-34 | oxazole |
| D-35 | isothiazole |
| D-36 | thiazole |
| D-37 | pyridine |
| D-38 | benzene |
| D-39 | 2H-thiopyran |
| D-40 | 2H-pyran |
| D-41 | pyrazine |
| D-42 | pyrimidine |
| D-43 | 1,4-dioxine |
| D-44 | pyridazine |
| D-45 | 1,3,5-triazine |
| D-46 | 1,2,4-triazine |
| D-47 | thiomorpholine-like (S, NH 6-ring) |
| D-48 | 2H-1,2-oxazine |
| D-49 | 1,2-oxazinane (O-NH 6-ring) |
| D-50 | 4H-1,2-oxazine |

TABLE 1b-continued

Non-limiting examples of ⓓ structures

| ⓓ Number | ⓓ Structure |
|---|---|
| D-51 | 1,3-oxazine (isomer) |
| D-52 | 1,3-oxazine (isomer) |
| D-53 | 1,3-oxazine (isomer) |
| D-54 | 1,4-oxazine (NH) |
| D-55 | 1,4-oxazine |
| D-56 | cycloheptatriene |
| D-57 | azepine (NH) |
| D-58 | oxepine |
| D-59 | thiepine |
| D-60 | 1,4-diazepine |
| D-61 | 1,3-diazepine |
| D-62 | 1,2-diazepine |
| D-63 | 1,4-thiazepine |
| D-64 | bicyclic amine |
| D-65 | bicyclic amine |
| D-66 | bicyclic amine |
| D-67 | bicyclic amine |
| D-68 | bicyclic amine |
| D-69 | bicyclic amine |
| D-70 | cyclohexene |
| D-71 | 1,3-cyclohexadiene |
| D-72 | 1,4-cyclohexadiene |
| D-73 | dihydropyridine |
| D-74 | dihydropyridine |
| D-75 | dihydropyran |

TABLE 1b-continued

Non-limiting examples of Ⓓ structures

| Ⓓ Number | Ⓓ Structure |
|---|---|
| D-76 | thiopyran (S-containing 6-membered ring with two double bonds) |
| D-77 | 1,4-dihydropyrazine (NH, NH) |
| D-78 | δ-valerolactam (6-membered ring, NH, C=O) |
| D-79 | γ-butyrolactam / pyrrolidinone (5-membered ring, NH, C=O) |
| D-80 | ε-caprolactam (7-membered ring, NH, C=O) |
| D-81 | β-lactam (4-membered ring, NH, C=O) |
| D-82 | 2-pyridone (6-membered ring, NH, C=O, with double bonds) |
| D-83 | 3-pyrrolin-2-one (5-membered ring, NH, C=O, with double bond) |
| D-84 | 2-azetinone (4-membered ring, NH, C=O, with double bond) |
| D-85 | cyclobutane (square) |

As depicted in Tables 1a and 1b, Ⓓ of a compound of one of Formulas (I), (I-A), (I-B), (I-C), (I-D), (I-E), (I-F), (I-G), (I-H), (I-I) and/or (I-J) may contain one or more heteroatoms. In some cases, Ⓓ contains 0, 1, 2, 3, or 4 ring heteroatoms. In some cases, Ⓓ contains 2, 3, 4, 5, or 6 ring carbon atoms.

In some embodiments, $R^{D1}$, $R^{D2}$, $R^{D3}$, $R^{D4}$, and/or $R^{D5}$ (when present, depending upon the ring size of Ⓓ) are independently selected from: H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^{D1-5}$ group may be connected to any ring atom of Ⓓ. In some cases, an $R^{D1-5}$ group is connected to a ring carbon of Ⓓ. In some cases, an $R^{D1-5}$ group is connected to a ring heteroatom of Ⓓ. In some cases, an $R^{D1-5}$ group is connected to the ring atom in position 1, 2, 3, 4, 5, 6, or 7 of Ⓓ. In some cases, two $R^{D1-5}$ groups may be connected to the same ring atom of Ⓓ. In some cases, only one $R^{D1-5}$ group may be connected to each ring atom of Ⓓ.

In some embodiments, X is $CH_2$, O, NH, or S.

In some embodiments, $R^1$ is H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino.

In some embodiments, L is 0-3 (e.g., 0, 1, 2, 3) linearly-linked members (e.g., C, S, O, and/or N) in length. In some embodiments, when L is absent, there is no direct bond or connection between Ⓓ and N. In some embodiments, L is a direct bond between Ⓓ and N. In some embodiments, L is selected from: O, NH, S, $CH_2$, $(CH_2)_2$, $(CH_2)_3$, $OCH_2$, $SCH_2$, $NHCH_2$, $CH_2OCH_2$, $CH_2SCH_2$, $CH_2NHCH_2$, $O(CH_2)_2$, $S(CH_2)_2$, $NH(CH_2)_2$, CH=CH, NCH, and $CH_2CH$=CH, and in either suitable orientation. In some embodiments, L is a linker of any suitable combination of S-, C-, O-, and N-containing moieties. In some embodiments, any C or N members of the L linkage are optionally substituted with a group selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino.

In some embodiments, Ⓖ of any of Formulas (I), (I-A), (I-B), (I-C), (I-D), (I-E), (I-F), (I-G), (I-H), (I-I) and/or (I-J) is an optionally present 3-7 member carbocyclic (e.g., cycloalkyl ring or unsaturated non-aromatic carbocyclic ring), heterocyclic, aryl, or heteroaryl ring which forms a ring system with Ⓓ. In some embodiments, Ⓖ is absent. In some embodiments, Ⓖ is selected from an optionally substituted 5-membered heteroaryl, an optionally substituted 6-membered aryl, an optionally substituted 6-membered heteroaryl, an optionally substituted 5-membered cycloalkyl, an optionally substituted 6-membered cycloalkyl, an optionally substituted 5-membered carbocycle, an optionally substituted 6-membered carbocycle, an optionally substituted 5-membered non-aromatic heterocycle, or an optionally substituted 6-membered non-aromatic heterocycle. In some embodiments, Ⓖ is selected from a structure listed in Table 2. In some cases, Ⓖ is not one or more structures listed in Table 2.
TABLE 2
Non-limiting examples of Ⓖ structures
| Ⓖ Number | Ⓖ Structure |
|---|---|
| G-1 |  |
| G-2 |  |
| G-3 |  |
| G-4 |  |
| G-5 |  |
| G-6 |  |
| G-7 |  |
| G-8 |  |
| G-9 |  |
| G-10 |  |
| G-11 |  |
| G-12 |  |
| G-13 |  |
TABLE 2-continued
Non-limiting examples of Ⓖ structures
| Ⓖ Number | Ⓖ Structure |
|---|---|
| G-14 | 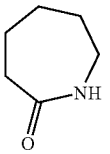 |
| G-15 |  |
| G-16 | 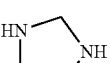 |
| G-17 | 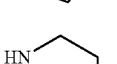 |
| G-18 | 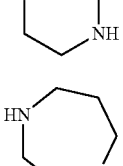 |
| G-19 | 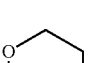 |
| G-20 | 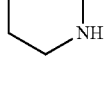 |
| G-21 | 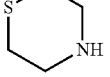 |
| G-22 | 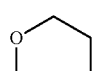 |
| G-23 | 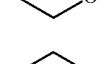 |
| G-24 | 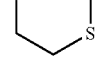 |
| G-25 |  |
| G-26 | 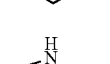 |
| G-27 | 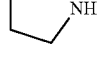 |

TABLE 2-continued
Non-limiting examples of Ⓖ structures
| Ⓖ Number | Ⓖ Structure |
|---|---|
| G-28 |  |
| G-29 |  |
| G-30 |  |
| G-31 |  |
| G-32 |  |
| G-33 |  |
| G-34 |  |
| G-35 |  |
| G-36 |  |
| G-37 |  |
| G-38 |  |
| G-39 |  |
| G-40 |  |
| G-41 |  |
| G-42 |  |
| G-43 |  |
| G-44 |  |
| G-45 |  |
| G-46 |  |
| G-47 |  |
| G-48 |  |
| G-49 |  |
| G-50 |  |
| G-51 |  |
| G-52 |  |
| G-53 |  |
| G-54 |  |
| G-55 |  |
| G-56 |  |

TABLE 2-continued
Non-limiting examples of Ⓖ structures
| Ⓖ Number | Ⓖ Structure |
|---|---|
| G-57 | 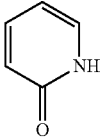 |
| G-58 |  |
| G-59 |  |
| G-60 |  |
| G-61 | 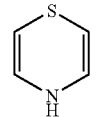 |
| G-62 |  |
| G-63 |  |
| G-64 |  |
| G-65 |  |
| G-66 |  |
| G-67 |  |
| G-68 |  |
| G-69 |  |
| G-70 |  |
| G-71 |  |
| G-72 |  |
| G-73 | 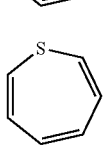 |
| G-74 |  |
| G-75 |  |
| G-76 |  |
| G-77 |  |
| G-78 |  |
| G-79 |  |

TABLE 2-continued

Non-limiting examples of Ⓖ structures

| Ⓖ Number | Ⓖ Structure |
|---|---|
| G-80 | (piperidine with gem-difluoro) |
| G-81 | (piperidine with gem-difluoro) |
| G-82 | (bicyclic amine) |
| G-83 | (bicyclic amine) |
| G-84 | (bicyclic amine) |
| G-85 | (bicyclic amine) |
| G-86 | (bicyclic amine) |
| G-87 | (bicyclic amine) |
| G-88 | (cyclohexene) |
| G-89 | (cyclohexadiene) |
| G-90 | (cyclohexadiene) |
| G-91 | (dihydropyridine) |
| G-92 | (dihydropyridine) |
| G-93 | (dihydropyran) |
| G-94 | (dihydrothiopyran) |
| G-95 | (dihydropyrazine) |
| G-96 | (benzoquinone) |

As depicted in Table 1a, Ⓖ of a compound of one of Formulas (I), (I-A), (I-B), (I-C), (I-D), (I-E), (I-F), (I-G), (I-H), (I-I) and/or (I-J) may contain one or more heteroatoms. In some cases, Ⓖ contains 0, 1, 2, 3, or 4 ring heteroatoms. In some cases, Ⓖ contains 2, 3, 4, 5, or 6 ring carbon atoms.

In some embodiments, Ⓖ forms a multiring system with Ⓓ. In some embodiments, Ⓖ and Ⓓ share a bond and a pair of atoms. In some embodiments, any suitable bond and pair of atoms may be shared between Ⓖ and Ⓓ to produce a multiring system.

In some embodiments, $R^{G1}$, $R^{G2}$, $R^{G3}$, $R^{G4}$, and/or $R^{G5}$ (when present, depending upon the ring size of Ⓖ) are independently selected from: H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^{G1-5}$ group may be connected to any ring atom of Ⓖ. In some cases, an $R^{G1-5}$ group is connected to a ring carbon of Ⓖ. In some cases, an $R^{G1-5}$ group is connected to a ring heteroatom of Ⓖ. In some cases, an $R^{G1-5}$ group is connected to the ring atom in position 1, 2, 3, 4, 5, 6, or 7 of Ⓖ. In some cases, two $R^{G1-5}$ groups may be connected to the same ring atom of Ⓖ. In some cases, only one $R^{G}$-5 group may be connected to each ring atom of Ⓖ.

In some embodiments, Z is present or absent in a compound of one of Formulas (I), (I-A), (I-B), (I-C), (I-D), (I-E), (I-F), (I-G), (I-H), (I-I) and/or (I-J). When Z is absent, there is no bond or atom at Z. In some embodiments, Z is 0-3 linearly-linked members (when Z=0, there is no bond, atom, or connection between, Ⓐ and Ⓓ at Z). In some embodiments, Z is 0-3 linearly-linked O, C, N, and/or S members. In some embodiments, Z is selected from: a direct bond between Ⓐ and Ⓓ, O, NH, S, $CH_2$, $(CH_2)_2$, $(CH_2)_3$, $OCH_2$, $SCH_2$, $NHCH_2$, $CH_2OCH_2$, $CH_2SCH_2$, $CH_2NHCH_2$, $O(CH_2)_2$, $S(CH_2)_2$, $NH(CH_2)_2$, CH=CH, NCH, and $CH_2CH$=CH, and in either suitable orientation. In some embodiments, Z is a linker of any suitable combination of S-, C-, O-, and N-containing moieties. In some embodiments, any C or N members of the Z linkage are optionally substituted with a group selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino.

In some embodiments, Y is present or absent in a compound of one of Formulas (I), (I-A), (I-B), (I-C), (I-D), (I-E), (I-F), (I-G), (I-H), (I-I) and/or (I-J). When Y is absent, there is a direct bond between Ⓐ and Ⓓ at Y. In some embodiments, Y is 0-3 linearly-linked members (when Y=0, there is a direct covalent bond between Ⓐ and Ⓓ at Y). In some embodiments, Y is 0-3 linearly-linked O, C, N, and/or S members. In some embodiments, Y is selected from: a direct bond between Ⓐ and Ⓓ, O, NH, S, $CH_2$, $(CH_2)_2$, $(CH_2)_3$, $OCH_2$, $SCH_2$, $NHCH_2$, $CH_2OCH_2$, $CH_2SCH_2$, $CH_2NHCH_2$, $O(CH_2)_2$, $S(CH_2)_2$, $NH(CH_2)_2$, CH=CH, NCH, and $CH_2CH$=CH, and in either suitable orientation. In some embodiments, Y is a linker of any suitable combination of S-, C-, O-, and N-containing moieties. In some embodiments, any C or N members of the Y linkage are optionally substituted with a group selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino.

In some embodiments, Ⓐ of any of Formulas (I), (I-A), (I-B), (I-C), (I-D), (I-E), (I-F), (I-G), (I-H), (I-I) and/or (I-J) is a 5-7 member aryl, heteroaryl, carbocyclic (e.g., cycloalkyl ring or unsaturated non-aromatic carbocyclic ring), or heterocyclic ring. In some embodiments, Ⓐ is selected from an optionally substituted 5-membered heteroaryl, an optionally substituted 6-membered aryl, an optionally substituted 6-membered heteroaryl, an optionally substituted 5-membered cycloalkyl, an optionally substituted 6-membered cycloalkyl, an optionally substituted 5-membered carbocycle, an optionally substituted 6-membered carbocycle, an optionally substituted 5-membered non-aromatic heterocycle, or an optionally substituted 6-membered non-aromatic heterocycle.

In some embodiments, Ⓐ of any of Formulas (I), (I-A), (I-B), (I-C), (I-D), (I-E), (I-F), (I-G), (I-H), (I-I) and/or (I-J) is has the structure of L

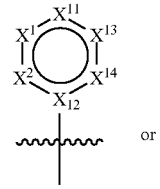

(A1)

or

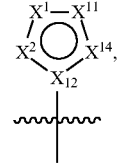

(A2)

wherein

indicates the connection through Y to Ⓓ. In some embodiments, each of $X^1$, $X^2$, $X^1$, $X^{12}$, $X^{13}$ (when present), and $X^{14}$ of Ⓐ are independently selected from C, N, O, and S. In other embodiments, $X^1$, $X^2$, $X^{11}$, $X^{12}$, $X^{13}$ (when present), and $X^{14}$ are C, unless specified as O, N, or S. In other embodiments, $X^1$, $X^2$, $X^{11}$, $X^{12}$, $X^{13}$ (when present), and $X^{14}$ are each independently C, N, O, or S, even if another position is specified as O, N, or S. In some embodiments, Ⓐ is selected from a structure listed in Table 3a. In some cases, Ⓐ is not one or more structures listed in Table 3a.

TABLE 3a

Non-limiting examples of Ⓐ structures

| Ⓐ Number | Ⓐ Structure |
| --- | --- |
| A1 | ![structure] |
| A1-A | ![structure] |
| A1-B | ![structure] |

TABLE 3a-continued

Non-limiting examples of Ⓐ structures

| Ⓐ Number | Ⓐ Structure |
|---|---|
| A1-C | pyridine ring with N, $X^{11}$, $X^{13}$, $X^{14}$, $X_{12}$ |
| A1-D | ring with $X^1$, $X^{11}$, $X^2$, $X^{13}$, $X^{14}$, $X_{12}$, N |
| A1-E | ring with N, N, $X^{13}$, $X^2$, $X^{14}$, $X_{12}$ |
| A1-F | ring with $X^1$, N, $X^{13}$, N, $X^{14}$, $X_{12}$ |
| A1-G | ring with S, $X^{11}$, $X^2$, $X^{13}$, $X^{14}$, $X_{12}$ |
| A1-H | ring with $X^1$, S, $X^{13}$, $X^2$, $X^{14}$, $X_{12}$ |
| A1-I | ring with $X^1$, $X^{11}$, S, $X^{13}$, $X^{14}$, $X_{12}$ |
| A1-J | ring with O, $X^{11}$, $X^2$, $X^{13}$, $X^{14}$, $X_{12}$ |
| A1-K | ring with $X^1$, O, $X^{13}$, $X^2$, $X^{14}$, $X_{12}$ |

TABLE 3a-continued

Non-limiting examples of Ⓐ structures

| Ⓐ Number | Ⓐ Structure |
|---|---|
| A1-L | ring with $X^1$, $X^{11}$, O, $X^{13}$, $X^{14}$, $X_{12}$ |
| A1-M | ring with $X^1$, $X_{11}$, N, N, $X^{14}$, $X_{12}$ |
| A2 | 5-membered ring with $X^1$, $X^{11}$, $X^2$, $X^{14}$, $X_{12}$ |
| A2-A | 5-membered ring with $X^1$, $X^{11}$, $X^2$, $X^{14}$, N |
| A2-B | 5-membered ring with $X^1$, $X^{11}$, $X^2$, N, $X_{12}$ |
| A2-C | 5-membered ring with $X^1$, N, $X^2$, $X^{14}$, $X_{12}$ |
| A2-D | 5-membered ring with $X^1$, S, $X^2$, $X^{14}$, $X_{12}$ |
| A2-E | 5-membered ring with $X^1$, $X^{11}$, $X^2$, S, $X_{12}$ |
| A2-F | 5-membered ring with $X^1$, $X^{11}$, $X^2$, O, $X_{12}$ |
| A2-G | 5-membered ring with $X^1$, O, $X^2$, $X^{14}$, $X_{12}$ |

TABLE 3a-continued

Non-limiting examples of Ⓐ structures

| Ⓐ Number | Ⓐ Structure |
|---|---|
| A2-H | tetrazole with $X_1$–$X_{11}$, $X_2$, N, N |
| A2-I | $X_1$=N, $X_2$, NH, $X_{12}$ |
| A2-J | N=$X_{14}$, $X_2$, NH, $X_{12}$ |
| A2-K | $X_1$=$X_{14}$, N, NH, $X_{12}$ |
| A2-L | $X_1$–N, $X_2$, N, $X_{14}$ |

In some embodiments, Ⓐ is selected from a structure listed in Table 3b. In some cases, Ⓐ is not one or more structures listed in Table 3b.

TABLE 3b

Non-limiting examples of Ⓐ structures

| Ⓐ Number | Ⓐ Structure |
|---|---|
| A-1 | cyclopentane |
| A-2 | cyclohexane |
| A-3 | cycloheptane |
| A-4 | pyrrolidine (NH) |
| A-5 | piperidine (NH) |
| A-6 | azepane (NH) |
| A-7 | piperazine (HN, NH) |
| A-8 | imidazolidine (HN, NH) |
| A-9 | morpholine (O, NH) |
| A-10 | 1,4-diazepane (HN, NH) |
| A-11 | 1,4-dioxane (O, O) |
| A-12 | thiomorpholine (S, NH) |
| A-13 | 1,3,5-trithiane (S, S, S) |
| A-14 | 1,4-dithiane (S, S) |
| A-15 | tetrahydrofuran (O) |
| A-16 | pyrazolidine (HN, NH) |
| A-17 | oxepane (O) |
| A-18 | tetrahydropyran (O) |
| A-19 | thiane (S) |

TABLE 3b-continued
Non-limiting examples of Ⓐ structures
| Ⓐ Number | Ⓐ Structure |
|---|---|
| A-20 |  |
| A-21 |  |
| A-22 |  |
| A-23 |  |
| A-24 |  |
| A-25 |  |
| A-26 |  |
| A-27 |  |
| A-28 |  |
| A-29 |  |
| A-30 |  |
| A-31 |  |
| A-32 |  |
| A-33 |  |
| A-34 |  |
| A-35 |  |
| A-36 |  |
| A-37 |  |
| A-38 |  |
| A-39 |  |
| A-40 |  |
| A-41 |  |
| A-42 |  |
| A-43 |  |
| A-44 |  |
| A-45 |  |
| A-46 |  |

TABLE 3b-continued

Non-limiting examples of Ⓐ structures

| Ⓐ Number | Ⓐ Structure |
|---|---|
| A-47 | (thiomorpholine-like ring with S and NH) |
| A-48 | (6-membered ring with O–N) |
| A-49 | (6-membered ring with O–NH) |
| A-50 | (6-membered ring with O–N) |
| A-51 | (6-membered ring with O and N) |
| A-52 | (6-membered ring with O and N) |
| A-53 | (6-membered ring with O and N) |
| A-54 | (morpholine-like ring with O and NH) |
| A-55 | (6-membered ring with O and N) |
| A-56 | (cycloheptatriene) |
| A-57 | (azepine with NH) |
| A-58 | (oxepine with O) |

TABLE 3b-continued

Non-limiting examples of Ⓐ structures

| Ⓐ Number | Ⓐ Structure |
|---|---|
| A-59 | (thiepine with S) |
| A-60 | (diazepine with NH and N) |
| A-61 | (diazepine with NH and N) |
| A-62 | (diazepine with NH–N) |
| A-63 | (thiazepine with S and N) |
| A-64 | (bicyclic amine with NH) |
| A-65 | (bicyclic amine with NH) |
| A-66 | (bicyclic amine with NH) |
| A-67 | (bicyclic amine with NH) |
| A-68 | (bicyclic amine with NH) |
| A-69 | (bicyclic amine with NH) |
| A-70 | (cyclohexene) |
| A-71 | (cyclohexadiene) |

TABLE 3b-continued

Non-limiting examples of Ⓐ structures

| Ⓐ Number | Ⓐ Structure |
|---|---|
| A-72 |  |
| A-73 |  |
| A-74 |  |
| A-75 |  |
| A-76 |  |
| A-77 | 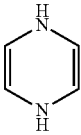 |

As depicted in Tables 3a and 3b, Ⓐ of a compound of one of Formulas (I), (I-A), (I-B), (I-C), (I-D), (I-E), (I-F), (I-G), (I-H), (I-I) and/or (I-J) may contain one or more heteroatoms. In some cases, Ⓐ contains 0, 1, 2, 3, or 4 ring heteroatoms. In some cases, Ⓐ contains 2, 3, 4, 5, or 6 ring carbon atoms.

In some embodiments, $R^{41}$, $R^{42}$, $R^{43}$, $R^{44}$, and/or $R^{45}$ (when present, depending upon the ring size of Ⓐ) are independently selected from: H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^{41-5}$ group may be connected to any ring atom of Ⓐ. In some cases, an $R^{41-5}$ group is connected to a ring carbon of Ⓐ. In some cases, an $R^{41-5}$ group is connected to a ring heteroatom of Ⓐ. In some cases, an $R^{41-5}$ group is connected to the ring atom in position 1, 2, 3, 4, 5, 6, or 7 of Ⓐ. In some cases, two $R^{41-5}$ groups may be connected to the same ring atom of Ⓐ. In some cases, only one $R^{41-5}$ group may be connected to each ring atom of Ⓐ.

In some embodiments, Ⓔ of any of Formulas (I), (I-A), (I-B), (I-C), (I-D), (I-E), (I-F), (I-G), (I-H), (I-I) and/or (I-J) is an optionally present 3-7 member carbocyclic (e.g., cycloalkyl ring or unsaturated non-aromatic carbocyclic ring), heterocyclic, aryl, or heteroaryl ring which forms a ring system with Ⓐ. In some embodiments, Ⓔ is absent. In some embodiments, Ⓔ is selected from an optionally substituted 5-membered heteroaryl, an optionally substituted 6-membered aryl, an optionally substituted 6-membered heteroaryl, an optionally substituted 5-membered cycloalkyl, an optionally substituted 6-membered cycloalkyl, an optionally substituted 5-membered carbocycle, an optionally substituted 6-membered carbocycle, an optionally substituted 5-membered non-aromatic heterocycle, or an optionally substituted 6-membered non-aromatic heterocycle. In some embodiments, Ⓔ is selected from a structure listed in Table 4. In some cases, Ⓔ is not one or more structures listed in Table 4.

TABLE 4

Non-limiting examples of Ⓔ structures

| Ⓔ Number | Ⓔ Structure |
|---|---|
| E-1 |  |
| E-2 |  |
| E-3 |  |
| E-4 |  |
| E-5 |  |
| E-6 |  |
| E-7 |  |
| E-8 |  |
| E-9 |  |
| E-10 |  |
| E-11 |  |

TABLE 4-continued
Non-limiting examples of ⓔ structures
| ⓔ Number | ⓔ Structure |
|---|---|
| E-12 | 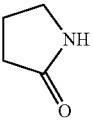 |
| E-13 | 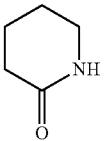 |
| E-14 | 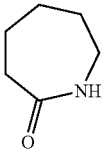 |
| E-15 |  |
| E-16 |  |
| E-17 |  |
| E-18 |  |
| E-19 | 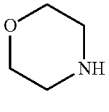 |
| E-20 |  |
| E-21 |  |
| E-22 |  |
| E-23 |  |
| E-24 |  |
| E-25 |  |
| E-26 |  |
| E-27 |  |
| E-28 |  |
| E-29 |  |
| E-30 |  |
| E-31 |  |
| E-32 |  |
| E-33 |  |
| E-34 |  |
| E-35 |  |
| E-36 |  |
| E-37 |  |
| E-38 |  |
| E-39 |  |
| E-40 |  |

TABLE 4-continued
Non-limiting examples of ⓔ structures
| ⓔ Number | ⓔ Structure |
|---|---|
| E-41 |  |
| E-42 |  |
| E-43 |  |
| E-44 |  |
| E-45 |  |
| E-46 |  |
| E-47 |  |
| E-48 |  |
| E-49 |  |
| E-50 |  |
| E-51 |  |
| E-52 |  |
| E-53 |  |
| E-54 |  |
| E-55 |  |
| E-56 |  |
| E-57 | 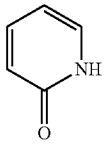 |
| E-58 |  |
| E-59 |  |
| E-60 |  |
| E-61 |  |
| E-62 |  |
| E-63 |  |
| E-64 |  |
| E-65 |  |

TABLE 4-continued

Non-limiting examples of ⒺStructures

| ⒺNumber | ⒺStructure |
|---|---|
| E-66 | oxazine |
| E-67 | oxazine isomer |
| E-68 | 1,4-oxazine (NH) |
| E-69 | oxazine isomer |
| E-70 | cycloheptatriene |
| E-71 | azepine (NH) |
| E-72 | oxepine |
| E-73 | thiepine |
| E-74 | 1,4-diazepine |
| E-75 | 1,3-diazepine |
| E-76 | 1,2-diazepine |
| E-77 | thiazine |
| E-78 | 3-fluoropiperidine |
| E-79 | 2-fluoropiperidine |
| E-80 | 3,3-difluoropiperidine |
| E-81 | 3,3-difluoropiperidine isomer |
| E-82 | azabicyclo[2.1.1] |
| E-83 | azabicyclo[2.2.1] |
| E-84 | azabicyclo[2.2.1] isomer |
| E-85 | azabicyclo[2.2.1] isomer |
| E-86 | azabicyclo[2.2.2] |
| E-87 | azabicyclo |
| E-88 | cyclohexene |
| E-89 | cyclohexadiene |

TABLE 4-continued

Non-limiting examples of Ⓔ structures

| Ⓔ Number | Ⓔ Structure |
|---|---|
| E-90 |  |
| E-91 |  |
| E-92 |  |
| E-93 |  |
| E-94 |  |
| E-95 | 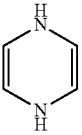 |
| E-96 | 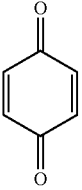 |

As depicted in Table 4, Ⓔ of a compound of one of Formulas (I), (I-A), (I-B), (I-C), (I-D), (I-E), (I-F), (I-G), (I-H), (I-I) and/or (I-J) may contain one or more heteroatoms. In some cases, Ⓔ contains 0, 1, 2, 3, or 4 ring heteroatoms. In some cases, Ê contains 2, 3, 4, 5, or 6 ring carbon atoms.

In some embodiments, Ⓔ forms a multiring system with Ⓐ. In some embodiments, Ⓔ and Ⓐ share a bond and a pair of atoms. In some embodiments, any suitable bond and pair of atoms may be shared between Ⓔ and Ⓐ to produce a multiring system.

In some embodiments, $R^{E1}$, $R^{E2}$, $R^{E3}$, $R^{E4}$, and/or $R^{E5}$ (when present, depending upon the ring size of Ⓔ) are independently selected from: H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^{E1-5}$ group may be connected to any ring atom of Ⓔ. In some cases, an $R^{E1-5}$ group is connected to a ring carbon of Ⓔ. In some cases, an $R^{E1-5}$ group is connected to a ring heteroatom of Ⓔ. In some cases, an $R^{E1-5}$ group is connected to the ring atom in position 1, 2, 3, 4, 5, 6, or 7 of Ⓔ. In some cases, two $R^{E1-5}$ groups may be connected to the same ring atom of Ⓔ. In some cases, only one $R^{E1-5}$ group may be connected to each ring atom of Ⓔ.

In some embodiments, Ⓜ of any of Formulas (I), (I-A), (I-B), (I-C), (I-D), (I-E), (I-F), (I-G), (I-H), (I-I) and/or (I-J) is an optionally present 3-7 member carbocyclic (e.g., cycloalkyl ring or unsaturated non-aromatic carbocyclic ring), heterocyclic, aryl, or heteroaryl ring which forms a ring system with Ⓔ and Ⓐ. In some embodiments, Ⓜ is absent. In some embodiments, Ⓜ is selected from an optionally substituted 5-membered heteroaryl, an optionally substituted 6-membered aryl, an optionally substituted 6-membered heteroaryl, an optionally substituted 5-membered cycloalkyl, an optionally substituted 6-membered cycloalkyl, an optionally substituted 5-membered carbocycle, an optionally substituted 6-membered carbocycle, an optionally substituted 5-membered non-aromatic heterocycle, or an optionally substituted 6-membered non-aromatic heterocycle. In some embodiments, Ⓜ is selected from a structure listed in Table 5. In some cases, Ⓜ is not one or more structures listed in Table 5.

TABLE 5

Non-limiting examples of Ⓜ structures

| Ⓜ Number | Ⓜ Structure |
|---|---|
| M-1 |  |
| M-2 |  |
| M-3 |  |
| M-4 |  |
| M-5 |  |
| M-6 |  |
| M-7 |  |
| M-8 |  |
| M-9 |  |

TABLE 5-continued

Non-limiting examples of Ⓜ structures

| Ⓜ Number | Ⓜ Structure |
|---|---|
| M-10 | azepane (7-membered ring with NH) |
| M-11 | β-propiolactam (azetidinone) |
| M-12 | 2-pyrrolidinone |
| M-13 | δ-valerolactam (piperidinone) |
| M-14 | ε-caprolactam (azepanone) |
| M-15 | 1,3-diazetidine |
| M-16 | imidazolidine |
| M-17 | piperazine |
| M-18 | 1,4-diazepane |
| M-19 | morpholine |
| M-20 | thiomorpholine |
| M-21 | 1,4-dioxane |
| M-22 | 1,4-dithiane |
| M-23 | 1,3-dithiane |
| M-24 | pyrazolidine |
| M-25 | ethylene oxide (oxirane) |
| M-26 | oxetane |
| M-27 | tetrahydrofuran |
| M-28 | tetrahydropyran |
| M-29 | oxepane |
| M-30 | thiirane |
| M-31 | thietane |
| M-32 | tetrahydrothiophene |
| M-33 | tetrahydrothiopyran |
| M-34 | thiepane |
| M-35 | 1,2-oxazolidine |
| M-36 | isoxazolidine |
| M-37 | thiazolidine |

TABLE 5-continued
Non-limiting examples of ⓜ structures
| ⓜ Number | ⓜ Structure |
|---|---|
| M-38 |  |
| M-39 |  |
| M-40 |  |
| M-41 |  |
| M-42 |  |
| M-43 |  |
| M-44 |  |
| M-45 |  |
| M-46 |  |
| M-47 |  |
| M-48 |  |
| M-49 |  |
| M-50 |  |
| M-51 |  |
TABLE 5-continued
Non-limiting examples of ⓜ structures
| ⓜ Number | ⓜ Structure |
|---|---|
| M-52 |  |
| M-53 |  |
| M-54 |  |
| M-55 |  |
| M-56 |  |
| M-57 |  |
| M-58 |  |
| M-59 |  |
| M-60 |  |
| M-61 |  |
| M-62 |  |
| M-63 |  |

TABLE 5-continued

Non-limiting examples of ⓜ structures

| ⓜ Number | ⓜ Structure |
|---|---|
| M-64 | 6-membered ring with O-N (oxazine isomer) |
| M-65 | 6-membered ring with O and N (oxazine) |
| M-66 | 6-membered ring with O and N (oxazine) |
| M-67 | 6-membered ring with O and N (oxazine) |
| M-68 | 6-membered ring with O and NH (morpholine-like) |
| M-69 | 6-membered ring with O and N |
| M-70 | cycloheptatriene |
| M-71 | azepine (NH) |
| M-72 | oxepine (O) |
| M-73 | thiepine (S) |
| M-74 | 1,4-diazepine |
| M-75 | 1,3-diazepine |
| M-76 | 1,2-diazepine (NH-N) |
| M-77 | thiazepine (S, N) |
| M-78 | 3-fluoropiperidine |
| M-79 | 2-fluoropiperidine |
| M-80 | 3,3-difluoropiperidine |
| M-81 | 2,2-difluoropiperidine |
| M-82 | bicyclic amine |
| M-83 | bicyclic amine |
| M-84 | bicyclic amine |
| M-85 | bicyclic amine |
| M-86 | bicyclic amine |
| M-87 | bicyclic amine |

TABLE 5-continued

Non-limiting examples of Ⓜ structures

| Ⓦ Number | Ⓜ Structure |
|---|---|
| M-88 | cyclohexene |
| M-89 | cyclohexadiene |
| M-90 | benzene |
| M-91 | dihydropyridine (NH) |
| M-92 | tetrahydropyridine (NH) |
| M-93 | dihydropyran (O) |
| M-94 | dihydrothiopyran (S) |
| M-95 | piperazine (NH, NH) |
| M-96 | 1,4-benzoquinone (O, O) |

As depicted in Table 5, Ⓜ of a compound of one of Formulas (I), (I-A), (I-B), (I-C), (I-D), (I-E), (I-F), (I-G), (I-H), (I-I) and/or (I-J) may contain one or more heteroatoms. In some cases, Ⓜ contains 0, 1, 2, 3, or 4 ring heteroatoms. In some cases, Ⓜ contains 2, 3, 4, 5, or 6 ring carbon atoms.

In some embodiments, Ⓜ forms a multiring system with Ⓔ and Ⓐ. In some embodiments Ⓜ and Ⓔ share a bond and a pair of atoms. In some embodiments, any suitable bond and pair of atoms may be shared between Ⓜ and Ⓔ to produce a multiring system.

In some embodiments, $R^{M1}$, $R^{M2}$, $R^{M3}$, $R^{M4}$, and/or $R^{M5}$ (when present, depending upon the ring size of Ⓜ) are independently selected from: H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^{M1-5}$ group may be connected to any ring atom of Ⓜ. In some cases, an $R^{M1-5}$ group is connected to a ring carbon of Ⓜ. In some cases, an $R^{M1-5}$ group is connected to a ring heteroatom of Ⓜ. In some cases, an $R^{M1-5}$ group is connected to the ring atom in position 1, 2, 3, 4, 5, 6, or 7 of Ⓜ. In some cases, two $R^{M1-5}$ groups may be connected to the same ring atom of Ⓜ. In some cases, only one $R^{M1-5}$ group may be connected to each ring atom of Ⓜ.

As noted above, the R1, $R^{D1-5}$, $R^{G1-5}$, $R^{A1-5}$, $R^{E1-5}$, and $R^{M1-5}$ substituents, when present in a compound of any one of Formulas (I), (I-A), (I-B), (I-C), (I-D), (I-E), (I-F), (I-G), (I-H), (I-I), and (I-J) may be of any suitable chemical functional group, such as:

single atoms: H, Cl, Br, F, or I;
alkyl groups: methyl, ethyl, propyl, butyl, pentyl, hexyl, or any suitable straight chain or branched $C^1$-$C^{10}$ alkyl group;
alkenyl: ethenyl, propenyl, butenyl, pentenyl, hexenyl, or any suitable $C^1$-$C^{10}$ alkenyl group;
alkynyl: ethynyl, propynyl, butynyl, pentynyl, hexynyl, or any suitable $C^1$-$C^{10}$ alkenyl group;
cycloalkyl: cyclopropyl, cyclobutyl, cyclopentyl, cyclohexyl, or any suitable $C^3$-$C^7$ cycloalkyl group; optionally further substituted (e.g. compounds 186-190);
cycloalkenyl: cyclopropene, cyclobutene, cyclopentene, cyclohexene, cycloheptene, 1,3-cyclohexadiene, 1,4-cyclohexadiene, 1,5-cyclooctadiene; optionally further substituted;
aryl or heteroaryl: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), thiadiazole, etc.; optionally further substituted;
non-aromatic heterocyclic rings: aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, pepierazine, morpholine, thiomorpholine, dioxane, dithiane, trioxane, thithiane, azepane, oxepane, thiepane, homopiperazine, azocane, tetrahydropyran, etc.;
haloalkanes: halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.), and branched haloalkanes (e.g. compounds 195-200);

alcohols: OH, methanol, ethanol, propanol, butanol, pentanol, hexanol, cyclic alcohols (e.g., cyclohexanol), aromatic alcohols (e.g., phenol), or any other suitable combination of an OH moiety with a second moiety, branched alcohols (e.g., compounds 123 and 151);

ketones: methyl ketone (acetone), methyl ethyl ketone (butanone), propyl ethyl ketone (pentanone), or any other suitable combination of alkyl chains with =O;

aldehydes: methanal, ethanal, propanal, butanal, pentanal, hexanal, or any other suitable combination of alkyl chain with =O;

carboxylates: methanoate, ethanoate, propanote, butanoate, pentanoate, hexanoate, or any other suitable combination of alkyl chain with $OO^-$;

carboxylic acids: methanoic acid, ethanoic acid, propanoic acid, butanoic acid, pentanoic acid, hexanoic acid, or any other suitable combination of alkyl chain with OOH;

ethers: methoxy, ethoxy, methylmethoxy, ethylmethoxy, or any other suitable combination of alkyl chains surrounding an O;

amides: methanamide ($CONH_2$), ethanamide ($CH_2CONH_2$), propanamide (($CH_2)_2CONH_2$), alkanamide (($CH_2)_nCONH_2$), n-methyl alkanamide (($CH_2)_nCONHCH_3$), c-methyl alkan″amide (($CH_2)_nNHCOCH_3$), n-alkyl alkan″amide (($CH_2)_nCONH(CH_2)_mCH_3$), c-methyl alkan″amide (($CH_2)_nNHCO(CH_2)_mCH_3$), etc.;

primary amines: $NH_2$, methylamine, ethylamine, cyclopropylamine, etc.;

secondary amines: aminomethyl ($NHCH_3$), aminoethyl ($NHCH_2CH_3$), methyl-aminomethyl ($CH_2NHCH_3$; aka methylamine-methane), alkyl″-aminomethane (($CH_2)_nNHCH_3$), etc.;

tertiary amines: dimethylamine ($N(CH_3)_2$), dimethylamine ($N(CH_3)_2$), methyl-ethylamine ($NCH_3CH_2CH_3$), methane-diethylamine ($CH_2N(CH_2CH_3)_2$; aka methylamine-diethane), etc.;

azides: methyl azide ($CH_2NNN$), ethyl azide (($CH_2)_2NNN$), alkyl″ azide (($CH_2)NNN$), etc.;

cyanates: methyl cyanate ($CH_2OCN$), ethyl cyanate (($CH_2)_2OCN$), alkyl″ cyanate (($CH_2)_nOCN$), etc.;

Cyanos: cyano (—CN), methyl carbonitrile ($CH_2CN$), ethyl carbonitrile (($CH_2)_2CN$), alkyl″ carbonitrile (($CH_2)_nCN$), etc.

thiols: methanethiol ($CH_2SH$), ethanethiol (($CH_2)_2SH$), alkan″ethiol (($CH_2)_nSH$), etc. sulfides: dimethyl sulfide ($CH_2SCH_3$), methyl-ethyl sulfide ($CH_2SCH_2CH_3$), alkyl″-alkyl‴ sulfide (($CH_2)_nS(CH_2)_{m-1}CH_3$), etc.;

sulfoxides: dimethyl sulfoxide ($CH_2SOCH_3$), methyl-ethyl sulfoxide ($CH_2SOCH_2CH_3$), alkyl-alkyl‴ sulfoxide (($CH_2)_nSO(CH_2)_{m-1}CH_3$), etc.;

sulfone: dimethyl sulfone ($CH_2SO_2CH_3$; aka methyl-sulfone-methyl), methyl-ethyl sulfone ($CH_2SO_2CH_2CH_3$; aka methyl-sulfone-ethyl), alkyl″-alkyl‴ sulfone (($CH_2)_nSO_2(CH_2)_{m-1}CH_3$; aka alkyl″-sulfone-alkyl‴), $R^XSO_2R^y$ (wherein Rx and Ry are independently selected from any of the moieties provided in this list or combinations thereof), etc.;

sulfonamides: $SO_2NH_2$, methyl sulfonamide ($CH_2SO_2NH_2$), ethyl sulfonamide (($CH_2)_2SO_2NH_2$), alkyl″ sulfonamide (($CH_2)_nSO_2NH_2$), methyl methyl-sulfonamide ($CH_2SO_2NHCH_3$), alkyl″ alkyl‴sulfonamide (($CH_2)_nSO_2NH(CH_2)_mCH_3$), etc.;

sulfinic acids: $SO_2H$, methyl sulfinic acid ($CH_2SO_2H$), ethyl sulfinic acid (($CH_2)_2SO_2H$), alkyl″ sulfinic acid (($CH_2)_nSO_2H$), etc.;

thiocyanate: SCN, methyl thiocyanate ($CH_2SCN$), ethyl thiocyanate (($CH_2)_2SCN$), alkyl″ thiocyanate (($CH_2)_nSCN$), etc.;

phosphates: $OP(=O)(OH)_2$, methyl phosphate ($CH_2OP(=O)(OH)_2$), ethyl phosphate (($CH_2)_2OP(=O)(OH)_2$), alkyl″ phosphate (($CH_2)_nOP(=O)(OH)_2$), etc.;

and suitable combinations thereof. For example, in some embodiments, $R^1$, $R^{D1-5}$, $R^{G1-5}$, $R^{A1-5}$, $R^{E1-5}$, and $R^{M1-5}$ substituents (when present) are independently selected from: H, alkyl group (e.g., straight-chain alkyl (e.g., methyl, ethyl, propyl, butyl, pentyl, hexyl, etc.), branched alkyl group (e.g., iso-propyl, 2-methyl-hexyl, 3-methyl, 2-propyl-octyl, etc.), cycloalkyl (e.g., cyclopropyl, cyclobutyl, cyclopentyl, cyclohexyl, cycloheptyl, cyclooctyl, etc.), branched cyclic alkyl (e.g., methylcyclohexyl, ethylcyclobutyl, propylcyclohexyl, etc.)), a substituted alkyl group (e.g., halogen-substituted alkyl group (e.g., trihalobutane (e.g. trifluorobutane), dihalobutane (e.g. difluorobutane), monohalobutane (e.g. monofluorobutane), trihalopropane (e.g. trifluoropropane), dihalopropane (e.g. difluoropropane), monohalopropane (monofluoropropane), trihaloethane (e.g., trifluoroethane), dihaloethane (e.g. difluroethane), haloethane (e.g. fluoroethane), halomethane (e.g., fluoromethane), dihalomethane (e.g., difluoromethane), trihalomethane (e.g., trifluoromethane), an alkyl group substituted by halogens at multiple carbons (e.g., 3-fluoro, 4-trifluoroisobutane (e.g., See $R^A$ substituent of Compound 245), 2-difluoro, 3-fluoropropane, etc.), etc.), alkene (e.g., $CH=CH_2$, $CH_2CH=CH_2$, $CH=CHCH_3$, etc.), alkyne (e.g., $C≡CH$, $C≡CCH_3$, $CH_2C≡CH$, etc.), alkoxy group (e.g., hydroxyl (e.g., $(CH_2)_{0-6}OH$, ether (($CH_2)_{0-6}O(CH_2)_{0-6}$)), halogen substituted alkoxy (4-trifluoro, 3-isobutanol (See, e.g., Compound 252), 3-difluoro, 2-propanol, etc.), amine (e.g., $NH_2$), alkylamine (e.g., primary amine (e.g., ethylamine, isobutylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl (e.g., thiol (e.g., $(CH_2)_{0-6}$—SH), thioether (e.g., $(CH_2)_{0-6}$—S—$(CH_2)_{0-6}$), etc.), substituted ethers and thioethers (See, e.g., Compound 266), combinations thereof, etc.), a substituted cycloalkyl group (e.g., halogen-substituted cycloalkyl group, cycloalkoxy group, cycloalkylamine, etc.), a halogen substituted alkyl amine (e.g., trifluromethylamine, trifluoroethylamine (e.g., See Compound 248), trifluorobutylamine, etc.), a halogen (e.g., F, Cl, Br, I, and At), a ketone, an amide, an alkylamide, a cyano group, methyl carbonitrile (e.g. $CH_2CN$), —$SO_2CH_3$ group, —$SO_2NH_2$ group, sulfonyl group (e.g., methyl sulfonyl, ethyl sulfonyl, propyl sulfonyl), substituted alkyl sulfonyl (e.g., trifluoroethyl sulfonyl), etc.), sulfonamine (e.g., $(CH_2)_{0-6}SO_2NH_2$ (See e.g., Compound 268), $(CH_2)_{0-6}NHSO_2$, $(CH_2)_{0-6}NHSO_2(CH_2)_{0-6}$ (See e.g., Compound 309), $(CH_2)_{0-6}SO_2NH(CH_2)_{0-6}$, etc.), dialkylphosphine oxide (e.g., —$PO(CH_3)_2$), a carbocyclic ring (substituted or non-substituted), a heterocyclic ring (substituted (See, e.g., compound 274) or non-substituted), an aromatic ring, a substituted aromatic ring (e.g., branched aromatic ring (e.g., ethylbenzene, methyl benzene, etc.), halobenzene (e.g., chlorobenzene, fluorobenzene, etc.)), a carbocyclic (substituted or non-substituted), aryl carbocyclic (substituted or non-substituted), heteroaryl (substituted (e.g., sulfonyl substituted (See, e.g., Compound 263), halo-substituted, etc.) or non-substituted), an alkyl-linked carbocyclic ring (substituted or non-substituted), an alkyl-linked heterocyclic ring (substituted or non-substituted), an alkyl-linked aromatic ring (substituted or non-substituted), an alkyl-linked substituted aromatic ring, alkyl-linked halobenzene (e.g., chlorobenzene, fluorobenzene, etc.)), an alkyl-linked carbocyclic (substituted (e.g., halo substituted (See, e.g., Compound 258), trihalo-alkyl substituted (See, e.g., Compound 257), etc.) or non-substituted), an alkyl-linked aryl carbocyclic (substituted or non-substituted), an alkyl-linked heteroaryl (substituted or non-substituted), an amine-linked carbocyclic ring (substituted or non-substituted), an amine-linked heterocyclic ring (substituted or non-substituted), an amine-linked aromatic ring(substituted or non-substituted), an amine-linked substituted aromatic ring, amine-linked halobenzene, an amine-linked carbocyclic (substituted or non-substituted), an amine-linked aryl carbocyclic (substituted or non-substituted), an amine-linked heteroaryl (substituted (See e.g., Compound 271) or non-substituted), an alkylamine-linked carbocyclic ring (substituted or non-substituted), an alkylamine-linked heterocyclic ring (substituted or non-substituted), an alkylamine-linked aromatic ring(substituted or non-substituted), an alkylamine-linked substituted aromatic ring, alkylamine-linked halobenzene, an alkylamine-linked carbocyclic (substituted or non-substituted), an alkylamine-linked aryl carbocyclic (substituted or non-substituted), an alkylamine-linked heteroaryl (substituted or non-substituted), an ether-linked carbocyclic ring (substituted or non-substituted), an ether-linked heterocyclic ring (substituted or non-substituted), an ether-linked aromatic ring (substituted or non-substituted), an ether-linked substituted aromatic ring, ether-linked halobenzene, an ether-linked carbocyclic (substituted or non-substituted), an ether-linked aryl carbocyclic (substituted or non-substituted), an ether-linked heteroaryl (substituted or non-substituted), a thioether-linked carbocyclic ring (substituted or non-substituted), a thioether-linked heterocyclic ring (substituted or non-substituted), a thioether-linked aromatic ring (substituted or non-substituted), a thioether-linked substituted aromatic ring, a thioether-linked halobenzene, a thioether-linked carbocyclic (substituted or non-substituted), a thioether-linked aryl carbocyclic (substituted or non-substituted), a thioether-linked heteroaryl (substituted or non-substituted), a sulfonyl-linked carbocyclic ring (substituted or non-substituted), a sulfonyl-linked heterocyclic ring (substituted or non-substituted), a sulfonyl-linked aromatic ring (substituted or non-substituted), a sulfonyl-linked substituted aromatic ring, a sulfonyl-linked halobenzene, a sulfonyl-linked carbocyclic (substituted or non-substituted), a sulfonyl-linked aryl carbocyclic (substituted or non-substituted), a sulfonyl-linked heteroaryl (substituted or non-substituted), a sulfonamide-linked carbocyclic ring (substituted or non-substituted), a sulfonamide-linked heterocyclic ring (substituted or non-substituted), a sulfonamide-linked aromatic ring (substituted or non-substituted), a sulfonamide-linked substituted aromatic ring, a sulfonamide-linked halobenzene, a sulfonamide-linked carbocyclic (substituted or non-substituted), a sulfonamide-linked aryl carbocyclic (substituted or non-substituted), a sulfonamide-linked heteroaryl (substituted or non-substituted), an amide-linked carbocyclic ring (substituted or non-substituted), an amide-linked heterocyclic ring (substituted or non-substituted), an amide-linked aromatic ring (substituted or non-substituted), an amide-linked substituted aromatic ring, amide-linked halobenzene, an amide-linked carbocyclic (substituted or non-substituted), an amide-linked aryl carbocyclic (substituted or non-substituted), an amide-linked heteroaryl (substituted (e.g., alkyl pyrrole (See, e.g., Compound 293), pyrrole amine (See, e.g., Compound 296), pyrrole ether (See, e.g., Compound 297), etc.) or non-substituted (e.g., imidazole (See, e.g., compound 273), indole (See, e.g., compounds 293 and 294), etc.)), an alkylamide-linked carbocyclic ring (substituted or non-substituted), an alkylamide-linked heterocyclic ring (substituted or non-substituted), an alkylamide-linked aromatic ring (substituted or non-substituted), an alkylamide-linked substituted aromatic ring, alkylamide-linked halobenzene, an alkylamide-linked carbocyclic (substituted or non-substituted), an alkylamide-linked aryl carbocyclic (substituted or non-substituted), an alkylamide-linked heteroaryl (substituted or non-substituted), a carbamide-linked carbocyclic ring (substituted or non-substituted), a carbamide-linked heterocyclic ring (substituted or non-substituted), a carbamide-linked aromatic ring (substituted or non-substituted), a carbamide-linked substituted aromatic ring, a carbamide-linked halobenzene, a carbamide-linked carbocyclic (substituted or non-substituted), a carbamide-linked aryl carbocyclic (substituted or non-substituted), a carbamide-linked heteroaryl (substituted or non-substituted (e.g., See, e.g., Compound 314)), a bridged carbocyclic ring (substituted or non-substituted), a bridged heterocyclic ring (substituted (See e.g., Compound 272) or non-substituted), a bridged aromatic ring (substituted or non-substituted), a bridged substituted aromatic ring, a bridged halobenzene, a bridged carbocyclic (substituted or non-substituted), a bridged aryl carbocyclic (substituted or non-substituted), a bridged heteroaryl (substituted or non-substituted), and/or combinations thereof.

In some embodiments, any of the R1, $R^{D1-5}$, $R^{G1-5}$, $R^{A1-5}$, $R^{E1-5}$, and $R^{M1-5}$ substituents, when present in a compound of any one of Formulas (I), (I-A), (I-B), (I-C), (I-D), (I-E), (I-F), (I-G), (I-H), (I-I), and (I-J) are of one of Formulas (IIa-IIq):

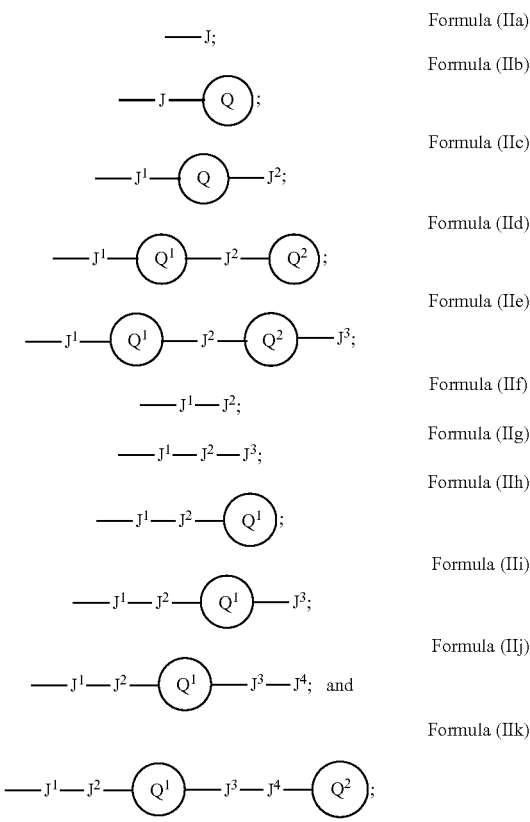

Formula (IIl)

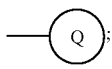

Formula (IIm)

Formula (IIn)

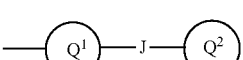

Formula (IIo)

Formula (IIp)

and

Formula (IIq)

wherein one of J, $Q^1$, or $J^1$, when present, is linked to one of the D, G, A, E, or M rings;

wherein each J, $J^1$, $J^2$, $J^3$, and $J^4$, when present, are independently selected from the group consisting of: a covalent bond, H, $alkyl_{1-15}$, $alkenyl_{1-6}$, $alkynyl_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NHC(O)(CH_2)_{1-6}$, alkylsulfonyl, sulfonamide, alkylsulfonamide, $(CH_2)_{0-6}NH(CH_2)_{1-6}$, $(CH_2)_{0-6}N(CH_2)_{1-6}(CH_2)_{1-6}$ (See, e.g., Compound 80), $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}CH_2F$, $(CH_2)_{0-3}CHF(CH_2)_{0-2}CH_3$, or similar with Br, Cl, or I), dihaloalkyl (e.g., $(CH_2)_{0-6}CF_2H$, $(CH_2)_{0-3}CF_2(CH_2)_{0-2}CH_3$, or similar with Br, Cl, or I), trihaloalkyl (e.g., $(CH_2)_{0-6}CF_3$, or similar with Br, Cl, or I), alkyl with 1-3 halogens at two or more positions along its length (See, e.g., Compounds 126, 144, 194, 195, 200, 207, 245, 251, etc.), $(CH_2)_{1-4}SP(Ph)_2=S$ (See, e.g., Compound 52), $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{16}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, $(CH_2)_{0-6}NH(CH_2)_{16}NH(CH_2)_{1-5}OH$, $(CH_2)_{0-6}NH(CH_2)_{1-6}NH(CH_2)_{1-5}NH_2$, $(CH_2)_{0-6}NH(CH_2)_{1-6}NH(CH_2)_{1-5}SH$, $(CH_2)_{0-6}NH(CH_2)_{1-6}O(CH_2)_{1-5}OH$, $(CH_2)_{0-6}NH(CH_2)_{1-6}O(CH_2)_{1-5}NH_2$, $(CH_2)_{0-6}NH(CH_2)_{1-6}O(CH_2)_{1-5}SH$, $(CH_2)_{0-6}NH(CH_2)_{1-6}S(CH_2)_{1-5}OH$, $(CH_2)_{0-6}NH(CH_2)_{1-6}S(CH_2)_{1-5}NH_2$, $(CH_2)_{0-6}NH(CH_2)_{1-6}S(CH_2)_{1-5}SH$, $(CH_2)_{0-3}C(O)O(CH_2)_{0-3}$, $(CH_2)_{0-3}C(S)O(CH_2)_{0-3}$, $(CH_2)_{0-3}C(O)S(CH_2)_{0-3}$, $(CH_2)_{0-3}C(S)S(CH_2)_{0-3}$, $(CH_2)_{0-3}C(O)NH(CH_2)_{0-3}$, $(CH_2)_{0-3}C(S)NH(CH_2)_{0-3}$, $(CH_2)_{0-3}NHC(O)(CH_2)_{0-3}$, $(CH_2)_{0-3}NHC(S)(CH_2)_{0-3}$, $(CH_2)_{0-3}OC(O)(CH_2)_{0-3}$, $(CH_2)_{0-3}OC(S)(CH_2)_{0-3}$, $(CH_2)_{0-3}SC(O)(CH_2)_{0-3}$, $(CH_2)_{0-3}SC(S)(CH_2)_{0-3}$, $(CH_2)_{0-3}NHC(O)NH(CH_2)_{0-3}$, $(CH_2)_{0-3}NHC(S)NH(CH_2)_{0-3}$, $(CH_2)_{0-3}OC(O)NH(CH_2)_{0-3}$, $(CH_2)_{0-3}OC(S)NH(CH_2)_{0-3}$, $(CH_2)_{0-3}SC(O)NH(CH_2)_{0-3}$, $(CH_2)_{0-3}SC(S)NH(CH_2)_{0-3}$, $(CH_2)_{0-3}NHC(O)O(CH_2)_{0-3}$, $(CH_2)_{0-3}NHC(S)O(CH_2)_{0-3}$, $(CH_2)_{0-3}OC(O)O(CH_2)_{0-3}$, $(CH_2)_{0-3}OC(S)O(CH_2)_{0-3}$, $(CH_2)_{0-3}SC(O)O(CH_2)_{0-3}$, $(CH_2)_{0-3}SC(S)O(CH_2)_{0-3}$, $(CH_2)_{0-3}NHC(O)S(CH_2)_{0-3}$, $(CH_2)_{0-3}NHC(S)S(CH_2)_{0-3}$, $(CH_2)_{0-3}OC(O)S(CH_2)_{0-3}$, $(CH_2)_{0-3}OC(S)S(CH_2)_{0-3}$, $(CH_2)_{0-3}SC(O)S(CH_2)_{0-3}$, $(CH_2)_{0-3}SC(S)S(CH_2)_{0-3}$, $(CH_2O)_{1-6}$, and trimethyl methane;

wherein each Q, $Q^1$, and $Q^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, pepierazine, morpholine, thiomorpholine, dioxane, dithiane, trioxane, thithiane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable $C^3$-$C^7$ cycloalkyl group, and any of the ring structures depicted in Table 1a, 1b, 2, 3, 4 or 5;

wherein each Q, $Q^1$, and $Q^2$, when present, may display one or more additional J groups at any position on the Q ring;

wherein any alkyl or $(CH_2)_{x-y}$ groups above may be straight or branched (See, e.g., Compounds 103, 104, 138, 245, etc.);

wherein any alkyl or $(CH_2)_{x-y}$ groups above may additionally comprise OH, =O, $NH_2$, CN, dihaloalkyl (e.g., $CF_2H$), trihaloalkyl (e.g., $CF_3$), or halogen (e.g., F) substituents at one or more carbons;

wherein the number of hydrogens on terminal positions of the groups above may be adjusted if the group is linked to an additional group (e.g., $CH_3$ adjusted to $CH_2$, OH adjusted to O, etc.) or if the group is terminal (e.g., $CH_2$ adjusted to $CH_3$, O adjusted to OH, etc.); and wherein any of formulas (IIa-q) may additionally comprise a terminal fluorophore (e.g. fluoresceine), solid surface, enzyme ligand (e.g. thalidomide (e.g., Compounds 198, 199, 301, 286, 291) or VHL ligand (e.g., (2S,4R)-1-((S)-2-amino-3,3-dimethylbutanoyl)-4-hydroxy-N-(4-(4-methylthiazol-5-yl)benzyl)pyrrolidine-2-carboxamide (e.g. compound 302), etc.), or affinity tag.

In some embodiments, any of formulas (IIa-q) may represent bifunctional compounds composed of ASH1L inhibitor and an E3 ubiquitin ligase ligand connected with a linker, which function to bind to ASH1L and recruit E3 ubiquiting ligase (Cereblon, VHL ligase, etc.) complex to ubiquitinate and induce proteosome-mediated degradation of ASH1L (e.g., Compounds 198, 199, 301,302, 286, 291). Exemplary compounds which induce degradation of the target protein by engaging the ubiquitin ligase are described, for example, in U.S. Pub. 2015/0291562; U.S. Pub. 2016/0235731; both of which are incorporated by reference in their entireties.

In some embodiments, a compound is of one of Formulas (I-A) through (I-G) or (I-J), wherein rings Ⓐ and Ⓔ together form an indole ring, wherein the indole nitrogen (1-position) is substituted with a heterocyclic ring (e.g., piperidine, bridged piperidine, alkyl substituted piperidine, etc.) which is further substituted by an alkylsulfonyl (See, e.g., compound 318) or sulfonamide (See, e.g., compound 268); wherein the 6-position of the indole ring is substituted by an alkylamine (e.g., $(CH_2)_{0-3}NH(CH_2)_{0-3}$)-linked heteroaryl group (See, e.g., Compound 319) or an alkylamide (e.g., $(CH_2)_{0-3}NHC(O)(CH_2)_{0-3}$)-linked heteroaryl group (See, e.g., Compound 318). In particular embodiments, a compound is of Formulas (I-E), X is S, $R^1$ is H, rings Ⓐ and Ⓔ together form an indole ring, wherein the indole nitrogen (1-position) is substituted with a piperidine (bridged or unbridged) which is further substituted by an alkylsulfonyl (See, e.g., compound 318) or sulfonamide (See, e.g., compound 268); wherein the 6-position of the indole ring is substituted by an alkylamine (e.g., $(CH_2)_{0-3}NH(CH_2)_{03}$)-linked heteroaryl group (See, e.g., Compound 319) or an alkylamide (e.g., $(CH_2)_{0-3}NHC(O)(CH_2)_{0-3}$)-linked heteroaryl group (See, e.g., Compound 318).

In some embodiments, the R1, $R^{D1-5}$, $R^{G1-5}$, $R^{41-5}$, $R^{E1-5}$, and $R^{M1-5}$ substituents, when present in a compound of any one of Formulas (I), (I-A), (I-B), (I-C), (I-D), (I-E), (I-F), (I-G), (I-H), (I-I), and (I-J) may display on any of the aforementioned substituent groups (or combinations thereof) a bioactive or functional small molecule moiety, such as: a fluorophore (See, e.g., Compounds 287 and 288), a drug or druglike moiety (e.g., thalidomide (See, e.g., Compounds 198, 199, 286, 291, etc.)), an affinity moiety (e.g., biotin), etc. In some embodiments, a substituent displays a ligand for an enzyme of interest (e.g., a ubiquitin ligase ligand (e.g., thalidomide), a von Hippel-Lindau tumor suppressor ligand (See, e.g., Compound 302, etc.).

In some embodiments, the R1, $R^{D1-5}$, $R^{G1-5}$, $R^{41-5}$, $R^{E1-5}$, and $R^{M1-5}$ substituents, when present in a compound of any one of Formulas (I), (I-A), (I-B), (I-C), (I-D), (I-E), (I-F), (I-G), (I-H), (I-I), and (I-J) may be linked to a solid surface.

A compound of any one of Formulas (I), (I-A), (I-B), (I-C), (I-D), (I-E), (I-F), (I-G), (I-H), (I-I), and (I-J) may be selected from compounds 1 to 324 listed in Table 6. Compounds of Formulas (I), (I-A), (I-B), (I-C), (I-D), (I-E), (I-F), (I-G), (I-H), (I-I) and/or (I-J) that are not listed in Table 6 are also within the scope herein.

TABLE 6

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| | $IC_{50} > 100$ μM | | |
| 1 | 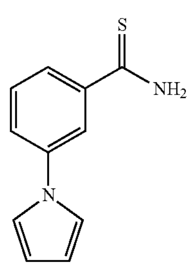 [SMILES: NC(=S)c1cccc(-n2cccc2)c1] | 202.06 | 203.0638 |
| 2 | 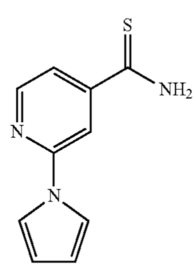 [SMILES: NC(=S)c1ccnc(-n2cccc2)c1] | 203.05 | 204.0589 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 3 | biphenyl-3-carbothioamide | 213.06 | 214.0685 |
| 4 | 2'-methoxybiphenyl-3-carbothioamide | 243.07 | 244.0793 |
| 5 | 4'-methoxybiphenyl-3-carbothioamide | 243.07 | 244.0790 |
| 6 | 2'-hydroxybiphenyl-3-carbothioamide | 229.06 | 230.0632 |
| 7 | 4'-hydroxybiphenyl-3-carbothioamide | 229.06 | 230.0635 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 8 | 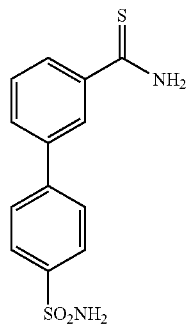 [SMILES: NC(=S)c1cccc(-c2ccc(S(N)(=O)=O)cc2)c1] | 292.03 | 293.0432 |
| 9 | 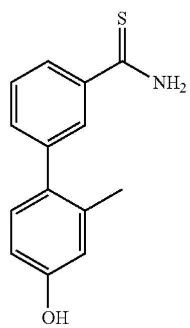 [SMILES: Cc1cc(O)ccc1-c1cccc(C(N)=S)c1] | 243.07 | 244.0793 |
| 10 | 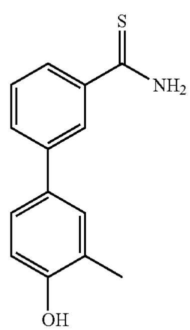 [SMILES: Cc1cc(-c2cccc(C(N)=S)c2)ccc1O] | 243.07 | 244.0792 |
| 11 | 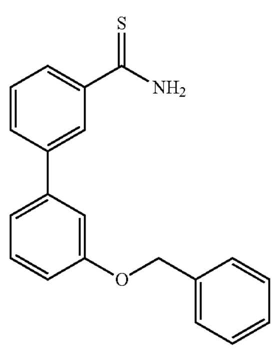 [SMILES: NC(=S)c1cccc(-c2cccc(OCc3ccccc3)c2)c1] | 319.10 | 320.1105 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 12 | 3'-hydroxy-[1,1'-biphenyl]-3-carbothioamide | 229.06 | 230.0631 |
| 13 | 5-(4-hydroxyphenyl)pyridine-3-carbothioamide | 230.05 | 231.0589 |
| 14 | 6-(4-hydroxyphenyl)pyridine-2-carbothioamide | 230.05 | 231.0588 |
| 15 | 4-(4-hydroxyphenyl)pyridine-2-carbothioamide | 230.05 | 231.0588 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 16 | 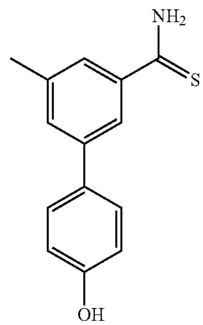 [SMILES: Cc1cc(C(N)=S)cc(-c2ccc(O)cc2)c1] | 243.07 | 244.0790 |
| 17 | 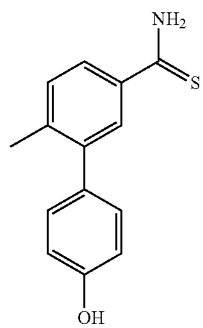 [SMILES: Cc1ccc(C(N)=S)cc1-c1ccc(O)cc1] | 243.07 | 244.0791 |
| 18 | 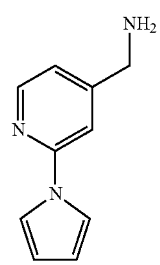 [SMILES: NCc1ccnc(-n2cccc2)c1] | 173.22 | 174.1026 |
| 19 | 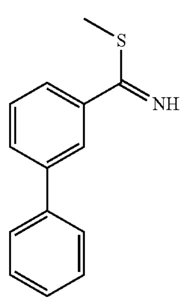 [SMILES: CSC(=N)c1cccc(-c2ccccc2)c1] | 227.08 | 228.0842 |
| 20 | 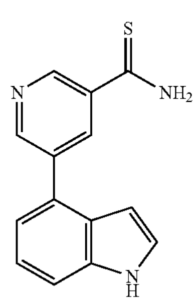 [SMILES: NC(=S)c1cncc(-c2cccc3[nH]ccc23)c1] | 253.07 | 254.0745 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 21 | 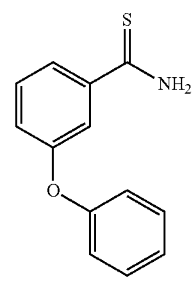 [SMILES: NC(=S)c1cccc(Oc2ccccc2)c1] | 229.06 | 230.0635 |
| 22 | 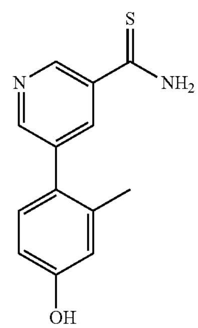 [SMILES: Cc1cc(O)ccc1-c1cncc(C(N)=S)c1] | 244.07 | 245.0745 |
| 23 | 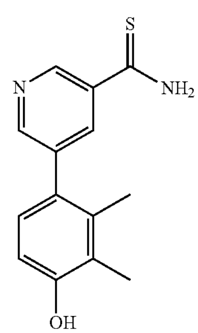 [SMILES: Cc1c(O)ccc(-c2cncc(C(N)=S)c2)c1C] | 258.08 | 259.0901 |
| 24 | 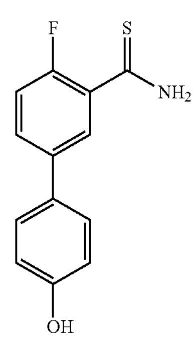 [SMILES: NC(=S)c1cc(-c2ccc(O)cc2)ccc1F] | 247.05 | 248.0538 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 25 | 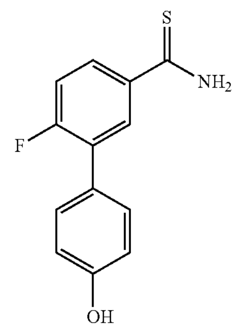 [SMILES: NC(=S)c1ccc(F)c(-c2ccc(O)cc2)c1] | 247.05 | 248.0540 |
| 26 | 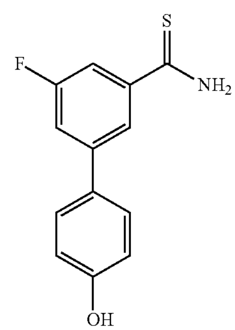 [SMILES: NC(=S)c1cc(F)cc(-c2ccc(O)cc2)c1] | 247.05 | 248.0539 |
| 27 | 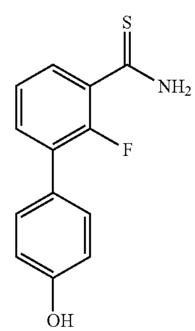 [SMILES: NC(=S)c1cccc(-c2ccc(O)cc2)c1F] | 247.05 | 248.0541 |
| 28 | 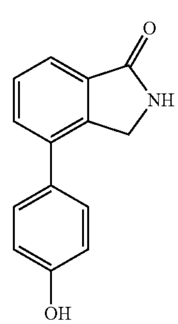 [SMILES: O=C1NCc2c1cccc2-c1ccc(O)cc1] | 225.08 | 226.0864 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 29 | 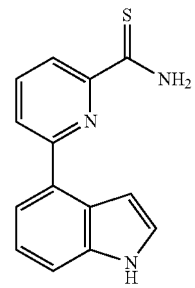 [SMILES: NC(=S)c1cccc(-c2cccc3[nH]ccc23)n1] | 253.07 | 254.0747 |
| 30 | 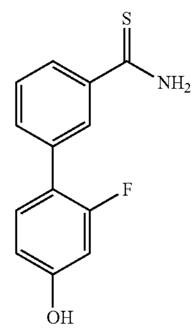 | 247.05 | 248.0541 |
| 31 | 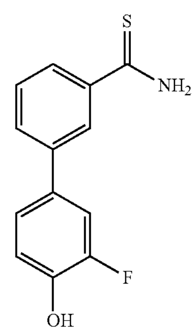 | 247.05 | 248.0540 |
| 32 | 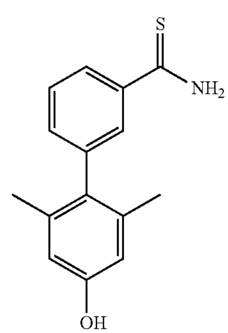 [SMILES: Cc1cc(O)cc(C)c1-c1cccc(C(N)=S)c1] | 257.09 | 258.0946 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M_w calc. (Da) | [MH]+ found (Da) |
|---|---|---|---|
| 33 | 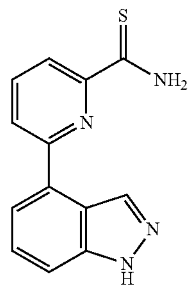 [SMILES: NC(=S)c1cccc(-c2cccc3[nH]ncc23)n1] | 254.05 | 255.0700 |
| 34 | 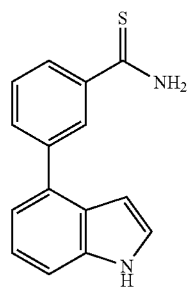 [SMILES: NC(=S)c1cccc(-c2cccc3[nH]ccc23)c1] | 253.07 | 254.0748 |
| 35 | 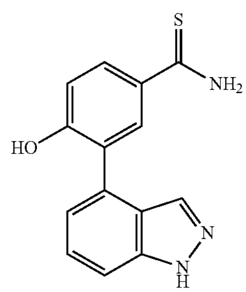 [SMILES: NC(=S)c1ccc(O)c(-c2cccc3[nH]ncc23)c1] | 268.07 | 269.0745 |
| 36 | 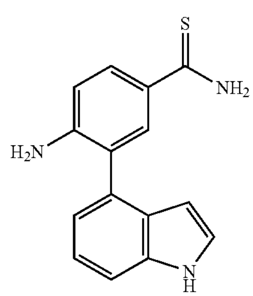 [SMILES: NC(=S)c1ccc(N)c(-c2cccc3[nH]ccc23)c1] | 267.08 | 268.0904 |
| 37 | 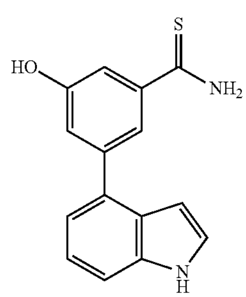 [SMILES: NC(=S)c1cc(O)cc(-c2cccc3[nH]ccc23)c1] | 268.07 | 269.0744 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]⁺ found (Da) |
|---|---|---|---|
| 38 | 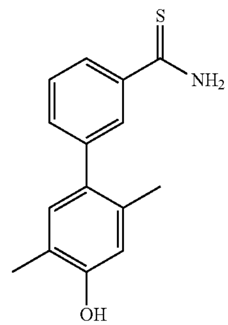 [SMILES: Cc1cc(-c2cccc(C(N)=S)c2)c(C)cc1O] | 257.09 | 258.0948 |
| 39 | 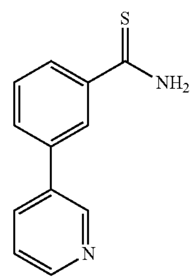 [SMILES: NC(=S)c1cccc(-c2cccnc2)c1] | 214.06 | 215.0639 |
| 40 | 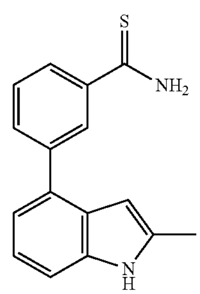 [SMILES: Cc1cc2c(-c3cccc(C(N)=S)c3)cccc2[nH]1] | 266.09 | 267.0950 |
| 41 | 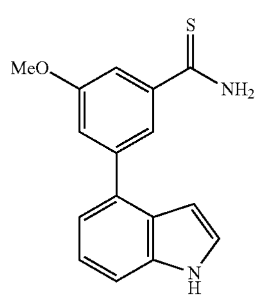 [SMILES: COc1cc(C(N)=S)cc(-c2cccc3[nH]ccc23)c1] | 282.08 | 283.0901 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 42 | 3-(1-ethyl-1H-indol-4-yl)benzothioamide | 280.10 | 281.1109 |
| 43 | 5-phenylthiophene-2-carbothioamide | 219.02 | 220.0250 |
| 44 | 4-phenylthiophene-2-carbothioamide | 219.02 | 220.0249 |
| 45 | 5-(4-hydroxyphenyl)thiophene-2-carbothioamide | 235.01 | 236.0199 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 46 | (4-(4-hydroxyphenyl)thiophene-2-carbothioamide) | 235.01 | 236.0198 |
| 47 | (4'-(aminomethyl)-[1,1'-biphenyl]-3-carbothioamide) | 242.09 | 243.0951 |
| 48 | (3-(1-(2-hydroxyethyl)-1H-indol-4-yl)benzothioamide) | 296.10 | 297.1057 |
| 49 | (3-(3-methyl-1H-indol-4-yl)benzothioamide) | 266.09 | 267.0948 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 50 | 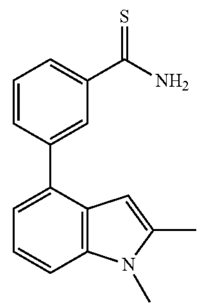 [SMILES: Cc1cc2c(-c3cccc(C(N)=S)c3)cccc2n1C] | 280.10 | 281.1107 |
| 51 | 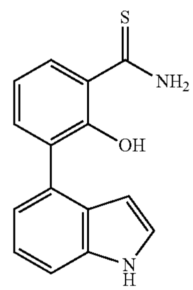 [SMILES: NC(=S)c1cccc(-c2cccc3[nH]ccc23)c1O] | 268.07 | 269.0744 |
| 52 | 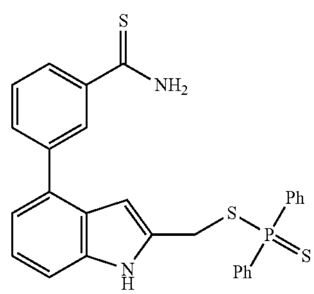 [SMILES: NC(=S)c1cccc(-c2cccc3[nH]c(CSP(=S)(c4ccccc4)c4ccccc4)cc23)c1] | 514.08 | 515.0832 |
| 53 | 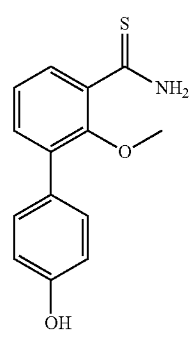 [SMILES: COc1c(C(N)=S)cccc1-c1ccc(O)cc1] | 259.07 | 260.0741 |
| 54 | 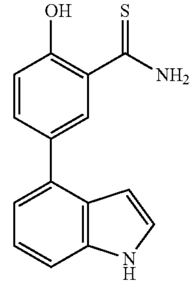 [SMILES: NC(=S)c1cc(-c2cccc3[nH]ccc23)ccc1O] | 268.07 | 269.0742 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 55 | 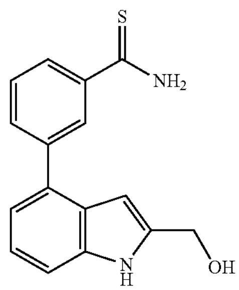 [SMILES: NC(=S)c1cccc(-c2cccc3[nH]c(CO)cc23)c1] | 282.08 | 283.0900 |
| 56 | 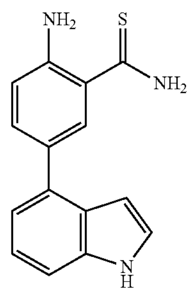 [SMILES: NC(=S)c1cc(-c2cccc3[nH]ccc23)ccc1N] | 267.08 | 268.0904 |
| 57 | 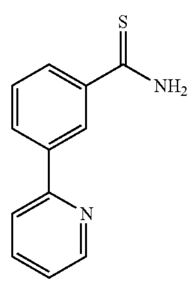 [SMILES: NC(=S)c1cccc(-c2ccccn2)c1] | 214.06 | 215.0638 |
| 58 | 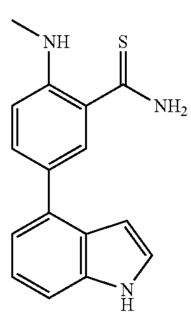 [SMILES: CNc1ccc(-c2cccc3[nH]ccc23)cc1C(N)=S] | 281.10 | 282.1061 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 59 | 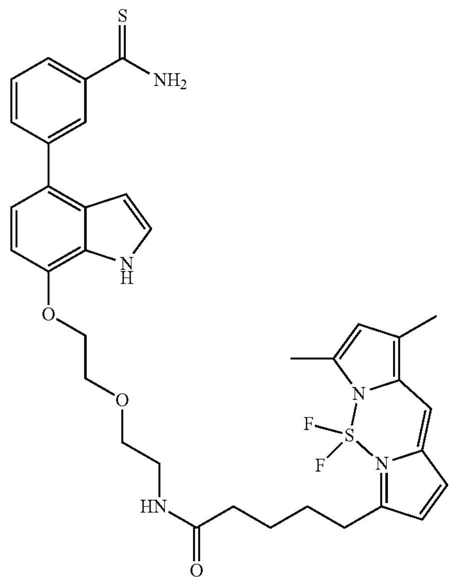 | 657.28 | 658.2830 |
| 60 | 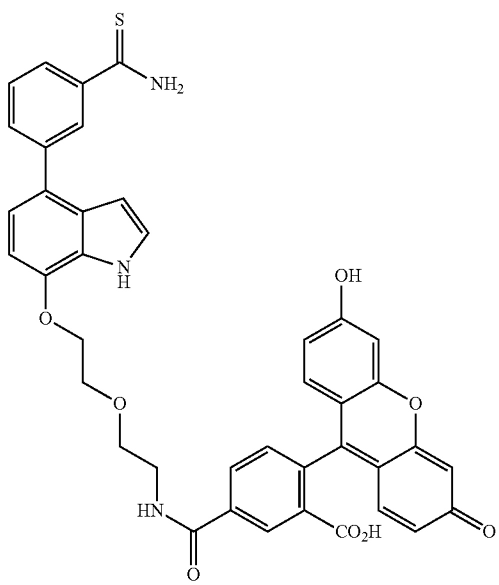 [SMILES: NC(=S)c1cccc(-c2ccc(OCCOCCNC(=O)c3ccc(-c4c5ccc(=O)cc-5oc5cc(O)ccc45)c(C(=O)O)c3)c3[nH]ccc23)c1] | 713.18 | 714.1906 |
| 61 | 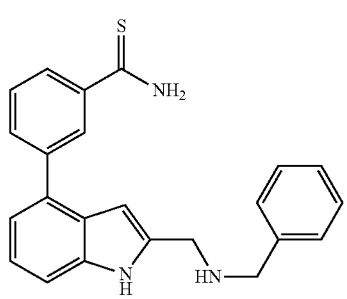 [SMILES: NC(=S)c1cccc(-c2cccc3[nH]c(CNCc4ccccc4)cc23)c1] | 371.10 | 372.1530 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 62 | 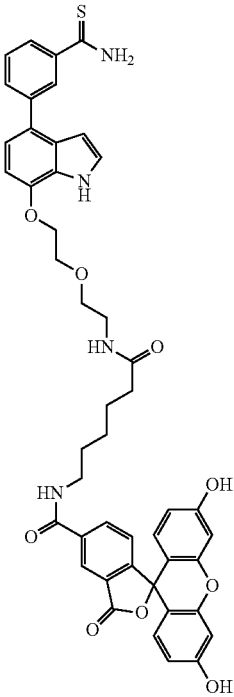 [SMILES: NC(=S)c1cccc(-c2ccc(OCCOCCNC(=O)CCCCCNC(=O)c3ccc4c(c3)C(=O)OC43c4ccc(O)cc4Oc4cc(O)ccc43)c3[nH]ccc23)c1] | 826.27 | 827.2747 |
| 63 | 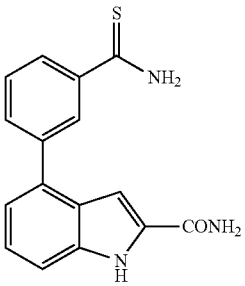 [SMILES: NC(=O)c1cc2c(-c3cccc(C(N)=S)c3)cccc2[nH]1] | 295.08 | 296.0851 |
| 64 | 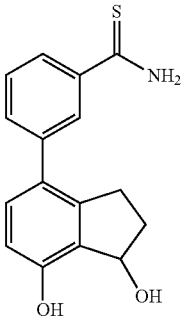 [SMILES: NC(=S)c1cccc(-c2ccc(O)c3c2CCC3O)c1] | 285.08 | 286.0894 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 65 | 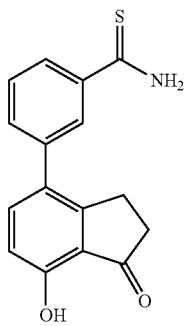 [SMILES: NC(=S)c1cccc(-c2ccc(O)c3c2CCC3=O)c1] | 283.07 | 284.0741 |
| 66 | 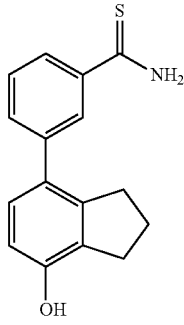 [SMILES: NC(=S)c1cccc(-c2ccc(O)c3c2CCC3)c1] | 269.09 | 270.0948 |
| 67 | 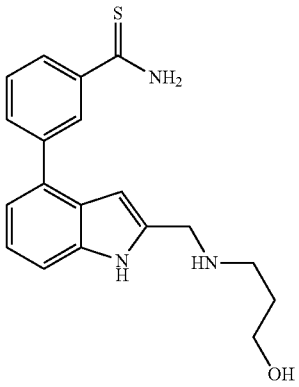 [SMILES: NC(=S)c1cccc(-c2cccc3[nH]c(CNCCCO)cc23)c1] | 339.14 | 340.1476 |
| 68 | 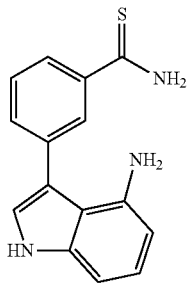 | 267.08 | 268.0905 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 69 | 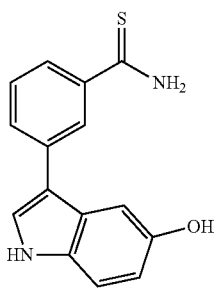 [SMILES: NC(=S)c1cccc(-c2c[nH]c3ccc(O)cc23)c1] | 268.07 | 269.0743 |
| 70 | 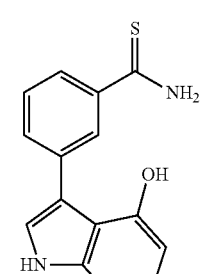 | 268.07 | 269.0745 |
| 71 | 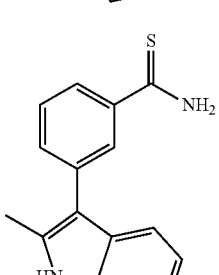 | 266.09 | 267.0951 |
| 72 | 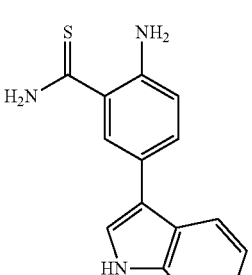 | 267.08 | 268.0899 |
| 73 | 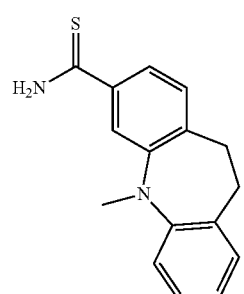 | 268.10 | 269.1105 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 74 | 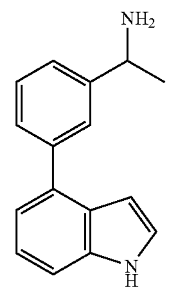 [SMILES: CC(N)c1cccc(-c2cccc3[nH]ccc23)c1] | 236.13 | 237.1384 |
| 75 | 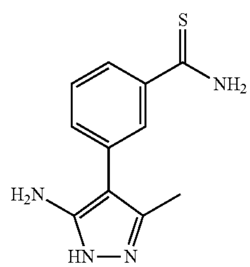 [SMILES: Cc1n[nH]c(N)c1-c1cccc(C(N)=S)c1] | 323.18 | |
| 76 | 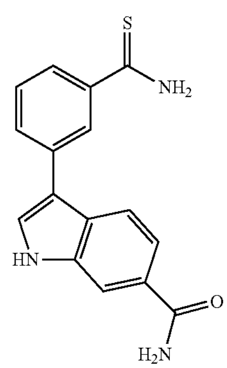 | 295.08 | 296.0851 |
| 77 | 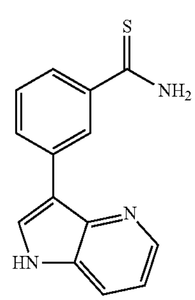 [SMILES: NC(=S)c1cccc(-c2c[nH]c3cccnc23)c1] | 253.07 | 254.0746 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 78 | 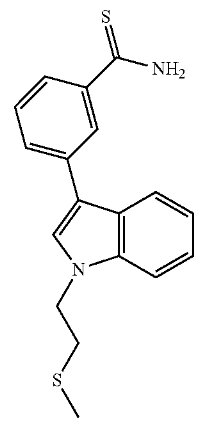 [SMILES: CSCCn1cc(-c2cccc(C(N)=S)c2)c2ccccc21] | 326.09 | 327.0985 |
| 79 | 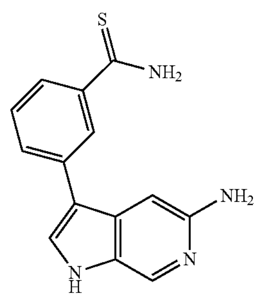 [SMILES: NC(=S)c1cccc(-c2c[nH]c3cnc(N)cc23)c1] | 268.08 | 269.0854 |
| 80 | 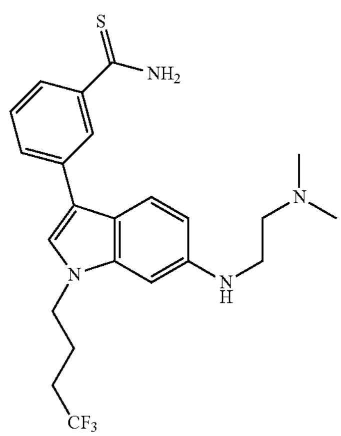 [SMILES: CN(C)CCNc1ccc2c(-c3cccc(C(N)=S)c3)cn(CCCC(F)(F)F)c2c1] | 448.19 | |
| 132 | 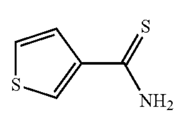 | 143.22 | |
| 133 | 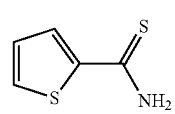 | 143.22 | |
| 134 | 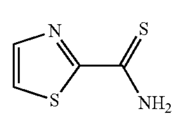 | 144.21 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 135 | 1H-indole-6-carbothioamide  20 μM < IC$_{50}$ < 100 μM | 176.24 | |
| 247 | 3-(6-(trifluoromethyl)-1H-indol-4-yl)benzothioamide | 320.33 | 321.0668 |
| 249 | 3-(1-(2-hydroxyethyl)-6-(trifluoromethyl)-1H-indol-4-yl)benzothioamide | 364.39 | 365.0931 |
| 250 | 3-(6-(trifluoromethyl)-1-(2,2,2-trifluoroethyl)-1H-indol-4-yl)benzothioamide | 402.36 | 403.0698 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]$^+$ found (Da) |
|---|---|---|---|
| 254 | 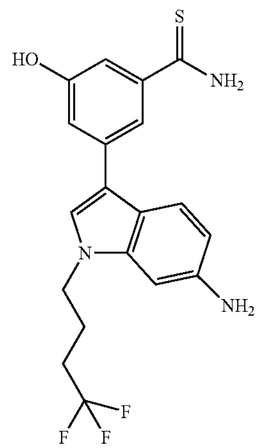 [SMILES: NC(=S)c1cc(O)cc(-c2cn(CCCC(F)(F)F)c3cc(N)ccc23)c1] | 393.43 | 394.1161 |
| 255 | 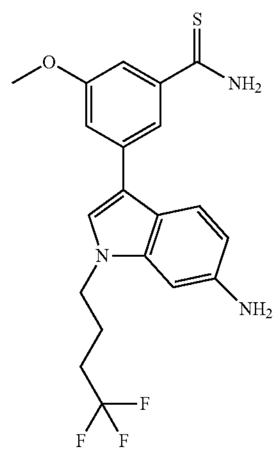 [SMILES: COc1cc(C(N)=S)cc(-c2cn(CCCC(F)(F)F)c3cc(N)ccc23)c1] | 407.46 | 408.1353 |
| 264 | 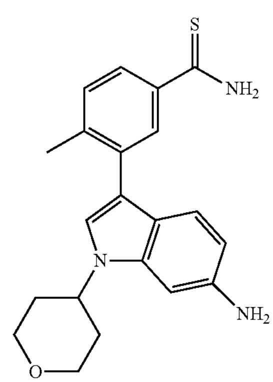 [SMILES: Cc1ccc(C(N)=S)cc1-c1cn(C2CCOCC2)c2cc(N)ccc12] | 365.50 | 366.1633 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 269 | 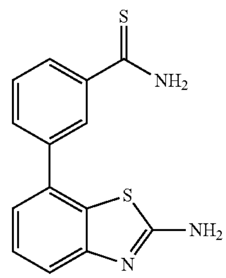 [SMILES: NC(=S)c1cccc(-c2cccc3nc(N)sc23)c1] | 285.38 | 286.0468 |
| 275 | 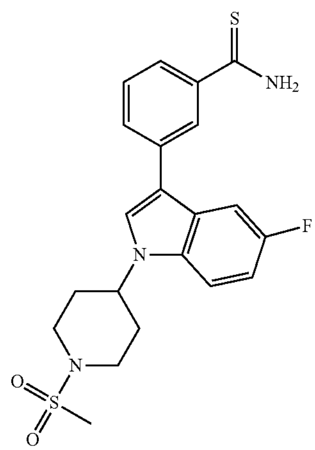 [SMILES: CS(=O)(=O)N1CCC(n2cc(-c3cccc(C(N)=S)c3)c3cc(F)ccc32)CC1] | 431.54 | 432.1212 |
| 81 | 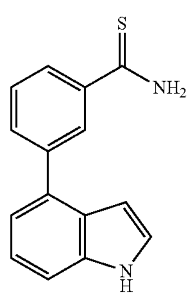 [SMILES: NC(=S)c1cccc(-c2cccc3[nH]ccc23)c1] | 252.07 | 253.0795 |
| 82 | 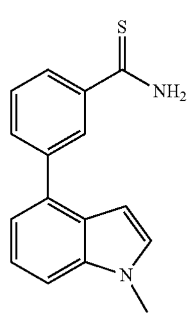 [SMILES: Cn1ccc2c(-c3cccc(C(N)=S)c3)cccc21] | 266.09 | 267.0949 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 83 | 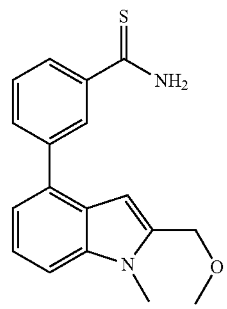 [SMILES: COCc1cc2c(-c3cccc(C(N)=S)c3)cccc2n1C] | 310.11 | 311.1215 |
| 84 | 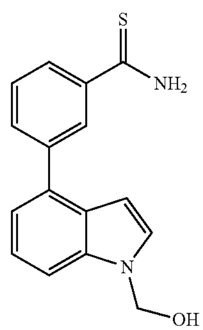 [SMILES: NC(=S)c1cccc(-c2cccc3c2ccn3CO)c1] | 282.08 | 283.0899 |
| 85 | 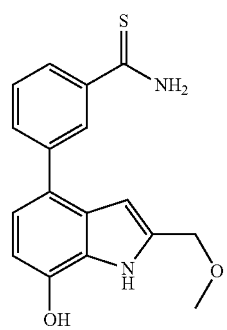 [SMILES: COCc1cc2c(-c3cccc(C(N)=S)c3)ccc(O)c2[nH]1] | 312.09 | 313.1006 |
| 86 | 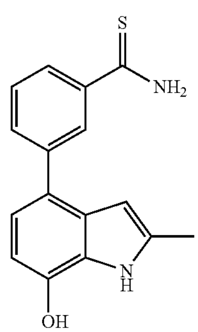 [SMILES: Cc1cc2c(-c3cccc(C(N)=S)c3)ccc(O)c2[nH]1] | 282.08 | 283.0901 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 87 | 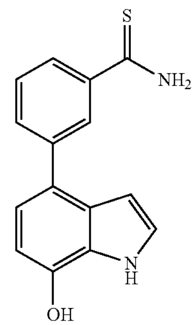 [SMILES: NC(=S)c1cccc(-c2ccc(O)c3[nH]ccc23)c1] | 268.07 | 269.0742 |
| 88 | 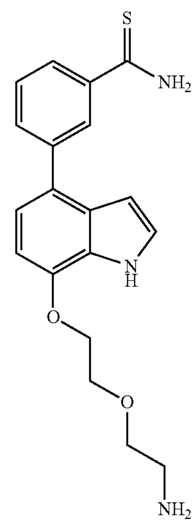 [SMILES: NCCOCCOc1ccc(-c2cccc(C(N)=S)c2)c2cc[nH]c12] | 355.14 | 356.1428 |
| 89 | 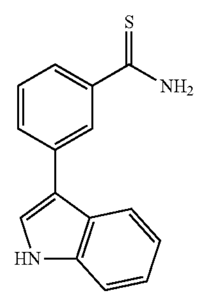 [SMILES: NC(=S)c1cccc(-c2c[nH]c3ccccc23)c1] | 252.07 | 253.0795 |
| 90 | 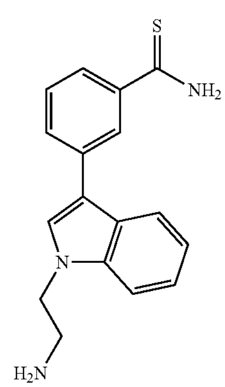 [SMILES: NCCn1cc(-c2cccc(C(N)=S)c2)c2ccccc21] | 295.11 | 296.1218 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 91 | 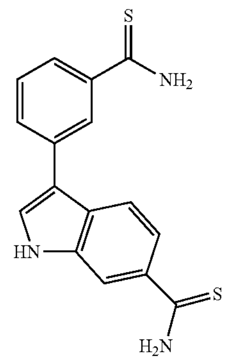 | 311.06 | 312.0625 |
| 92 | 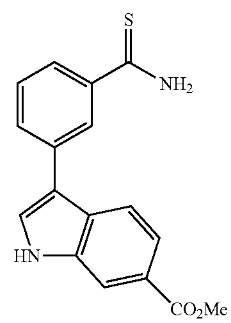 [SMILES: COC(=O)c1ccc2c(-c3cccc(C(N)=S)c3)c[nH]c2c1] | 310.08 | 311.0850 |
| 93 | 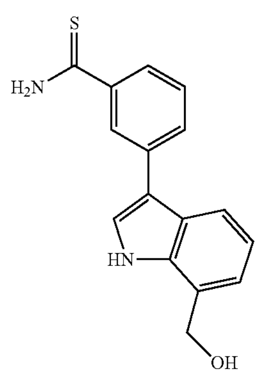 [SMILES: NC(=S)c1cccc(-c2c[nH]c3c(CO)cccc23)c1] | 282.08 | 283.0899 |
| 94 | 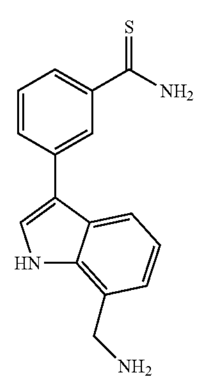 [SMILES: NCc1cccc2c(-c3cccc(C(N)=S)c3)c[nH]c12] | 281.10 | 282.1057 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 95 | 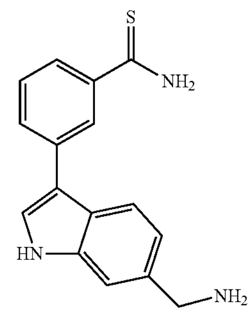 [SMILES: NCc1ccc2c(-c3cccc(C(N)=S)c3)c[nH]c2c1] | 281.10 | 282.1060 |
| 96 | 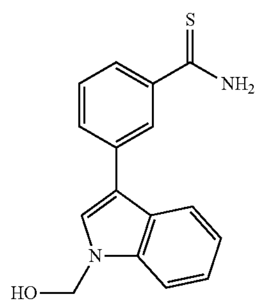 [SMILES: NC(=S)c1cccc(-c2cn(CO)c3ccccc23)c1] | 282.08 | 283.0900 |
| 97 | 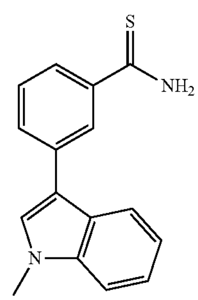 [SMILES: Cn1cc(-c2cccc(C(N)=S)c2)c2ccccc21] | 266.09 | 267.0950 |
| 98 | 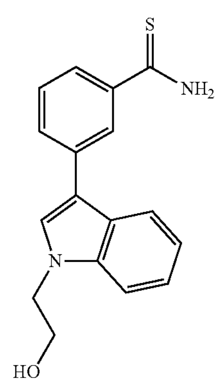 [SMILES: NC(=S)c1cccc(-c2cn(CCO)c3ccccc23)c1] | 296.10 | 297.1058 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 99 | 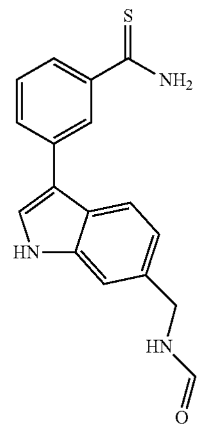 [SMILES: NC(=S)c1cccc(-c2c[nH]c3cc(CNC=O)ccc23)c1] | 309.09 | 310.1067 |
| 100 | 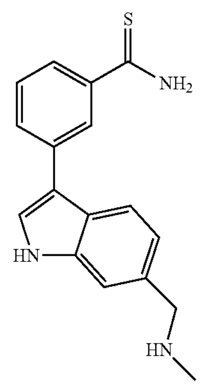 [SMILES: CNCc1ccc2c(-c3cccc(C(N)=S)c3)c[nH]c2c1] | 295.11 | 296.1217 |
| 101 | 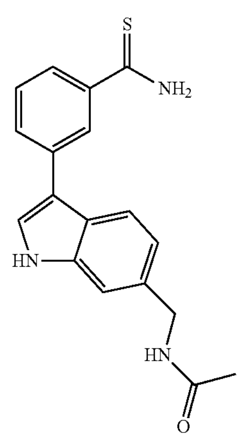 [SMILES: CC(=O)NCc1ccc2c(-c3cccc(C(N)=S)c3)c[nH]c2c1] | 323.11 | 324.1165 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 102 | 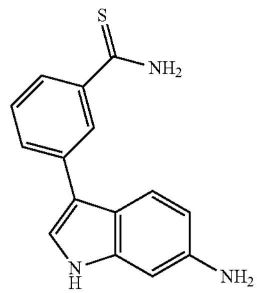 [SMILES: NC(=S)c1cccc(-c2c[nH]c3cc(N)ccc23)c1] | 267.08 | 268.0905 |
| 103 | 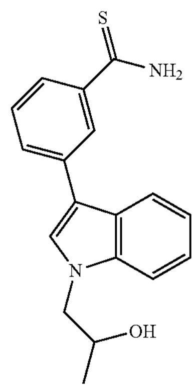 [SMILES: CC(O)Cn1cc(-c2cccc(C(N)=S)c2)c2ccccc21] | 310.11 | 311.1210 |
| 104 | 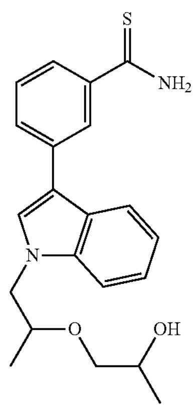 [SMILES: CC(O)COC(C)Cn1cc(-c2cccc(C(N)=S)c2)c2ccccc21] | 368.16 | 369.1624 |
| 105 | 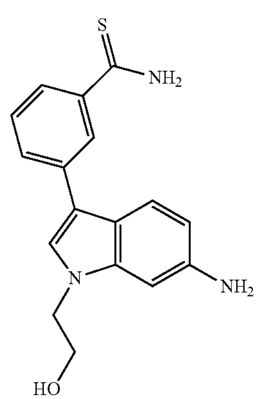 [SMILES: NC(=S)c1cccc(-c2cn(CCO)c3cc(N)ccc23)c1] | 311.11 | 312.1162 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 106 | 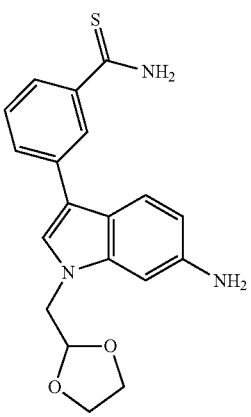 [SMILES: NC(=S)c1cccc(-c2cn(CC3OCCO3)c3cc(N)ccc23)c1] | 353.12 | |
| 107 | 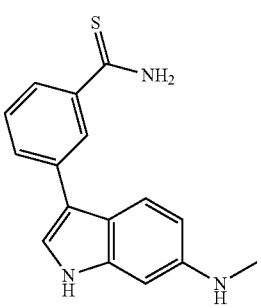 [SMILES: CNc1ccc2c(-c3cccc(C(N)=S)c3)c[nH]c2c1] | 281.10 | |
| 108 | 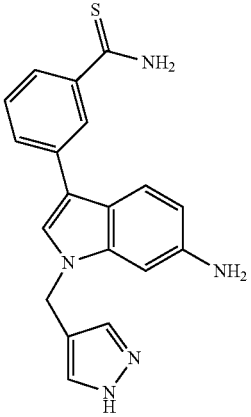 [SMILES: NC(=S)c1cccc(-c2cn(Cc3cn[nH]c3)c3cc(N)ccc23)c1] | 347.12 | 348.1277 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 109 | 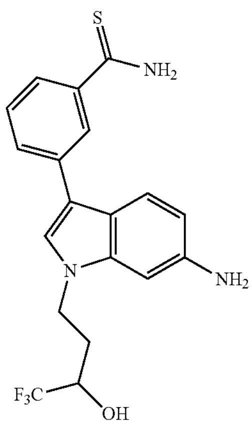 [SMILES: NC(=S)c1cccc(-c2cn(CCC(O)C(F)(F)F)c3cc(N)ccc23)c1] | 393.12 | 394.1196 |
| 110 | 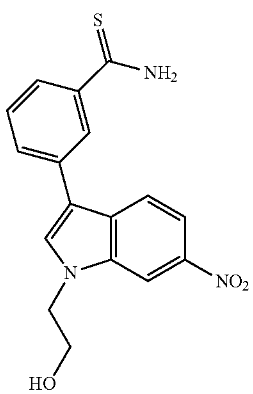 [SMILES: NC(=S)c1cccc(-c2cn(CCO)c3cc([N+](=O)[O-])ccc23)c1] | 341.08 | 342.0905 |
| 111 | 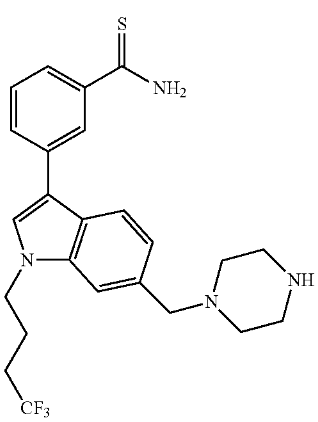 [SMILES: NC(=S)c1cccc(-c2cn(CCCC(F)(F)F)c3cc(CN4CCNCC4)ccc23)c1] | 460.19 | 461.1981 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 112 | 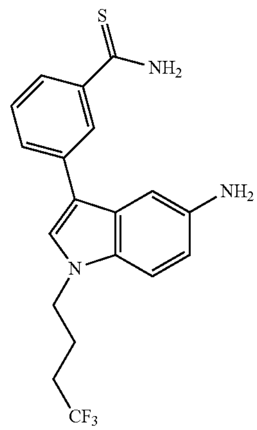 [SMILES: NC(=S)c1cccc(-c2cn(CCCC(F)(F)F)c3ccc(N)cc23)c1] | 377.11 | 378.1249 |
| 113 | 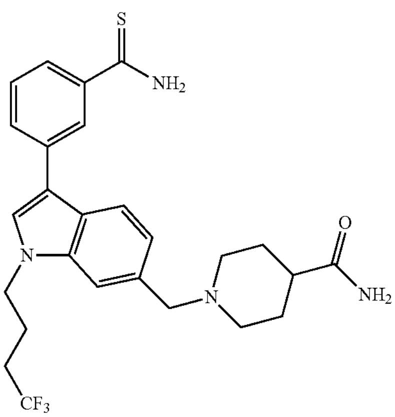 [SMILES: NC(=O)C1CCN(Cc2ccc3c(-c4cccc(C(N)=S)c4)cn(CCCC(F)(F)F)c3c2)CC1] | 502.20 | 503.2085 |
| 114 | 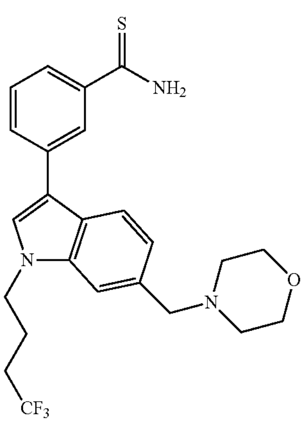 [SMILES: NC(=S)c1cccc(-c2cn(CCCC(F)(F)F)c3cc(CN4CCOCC4)ccc23)c1] | 461.17 | 462.1817 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| | $IC_{50} < 20\ \mu M$ | | |
| 115 | 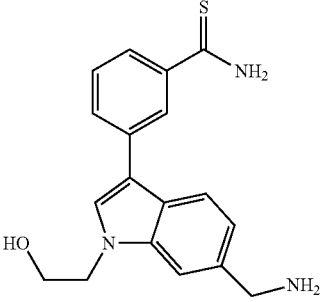 [SMILES: NCc1ccc2c(-c3cccc(C(N)=S)c3)cn(CCO)c2c1] | 325.12 | 326.1325 |
| 116 | 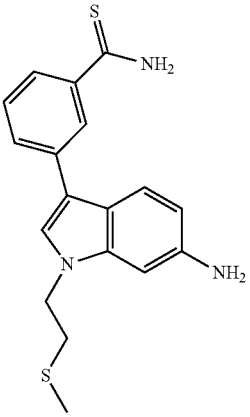 [SMILES: CSCCn1cc(-c2cccc(C(N)=S)c2)c2ccc(N)cc21] | 341.11 | 342.1095 |
| 117 | 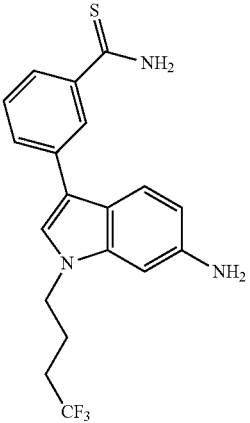 [SMILES: NC(=S)c1cccc(-c2cn(CCCC(F)(F)F)c3cc(N)ccc23)c1] | 377.12 | 378.1245 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 118 | 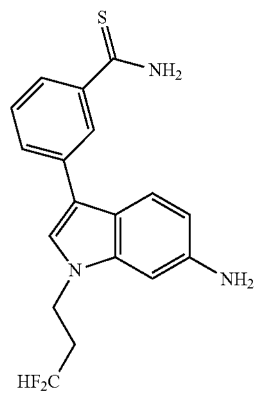 | 345.11 | 346.1184 |
| 119 | 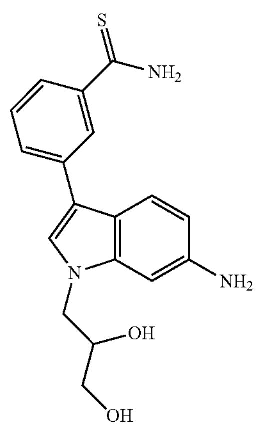 [SMILES: NC(=S)c1cccc(-c2cn(CC(O)CO)c3cc(N)ccc23)c1] | 341.12 | 342.1270 |
| 120 | 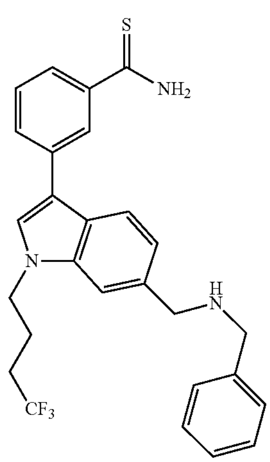 [SMILES: NC(=S)c1cccc(-c2cn(CCCC(F)(F)F)c3cc(CNCc4ccccc4)ccc23)c1] | 481.18 | 482.1872 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 121 | 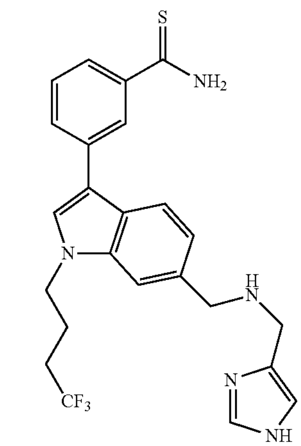 [SMILES: NC(=S)c1cccc(-c2cn(CCCC(F)(F)F)c3cc(CNCc4c[nH]cn4)ccc23)c1] | 471.17 | 472.1777 |
| 122 | 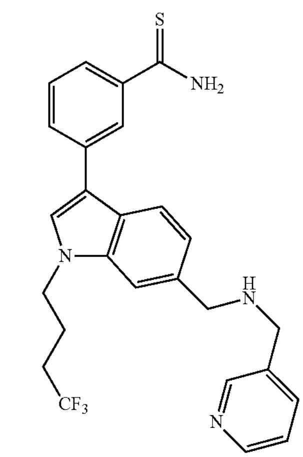 [SMILES: NC(=S)c1cccc(-c2cn(CCCC(F)(F)F)c3cc(CNCc4cccnc4)ccc23)c1] | 482.17 | 483.1825 |
| 123 | 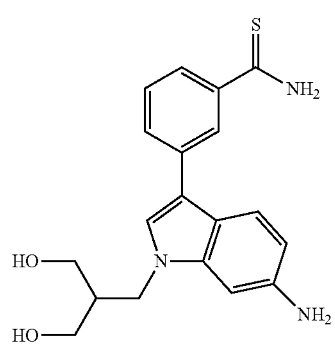 [SMILES: NC(=S)c1cccc(-c2cn(CC(CO)CO)c3cc(N)ccc23)c1] | 355.14 | 356.1423 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 124 | 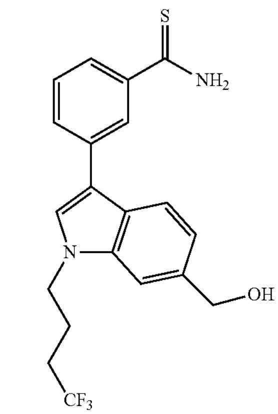 [SMILES: NC(=S)c1cccc(-c2cn(CCCC(F)(F)F)c3cc(CO)ccc23)c1] | 392.11 | 393.1241 |
| 125 | 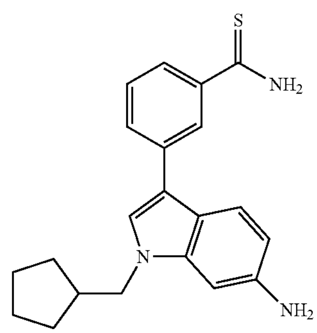 [SMILES: NC(=S)c1cccc(-c2cn(CC3CCCC3)c3cc(N)ccc23)c1] | 349.16 | 350.1685 |
| 126 | 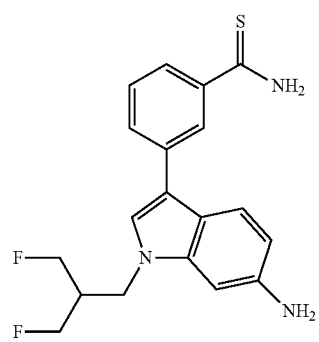 [SMILES: NC(=S)c1cccc(-c2cn(CC(CF)CF)c3cc(N)ccc23)c1] | 359.13 | 360.1341 |
| 127 | 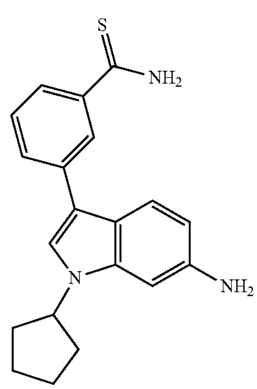 [SMILES: NC(=S)c1cccc(-c2cn(C3CCCC3)c3cc(N)ccc23)c1] | 335.14 | 336.1529 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 128 | 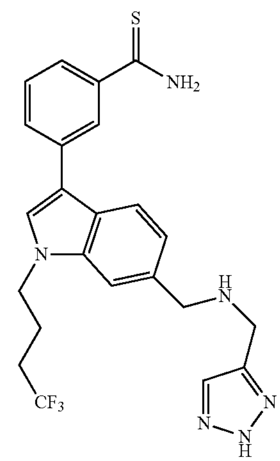 [SMILES: NC(=S)c1cccc(-c2cn(CCCC(F)(F)F)c3cc(CNCc4cn[nH]n4)ccc23)c1] | 472.16 | 473.1727 |
| 129 | 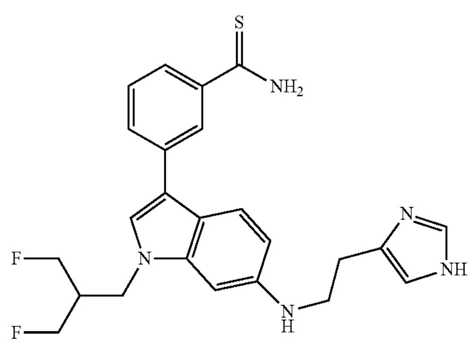 [SMILES: NC(=S)c1cccc(-c2cn(CC(CF)CF)c3cc(NCCc4c[nH]cn4)ccc23)c1] | 453.18 | 454.1869 |
| 130 | 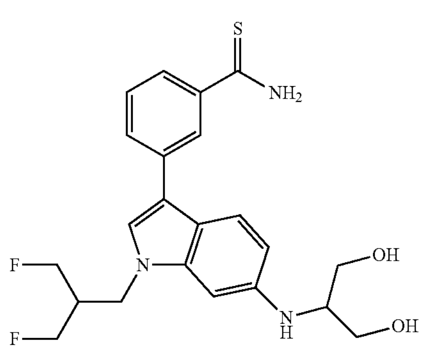 [SMILES: NC(=S)c1cccc(-c2cn(CC(CF)CF)c3cc(NC(CO)CO)ccc23)c1] | 433.16 | 434.1705 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 131 | | 360.11 | 361.1175. |
| 136 | | 401.14 | |
| 137 | | 452.15 | |
| 138 | 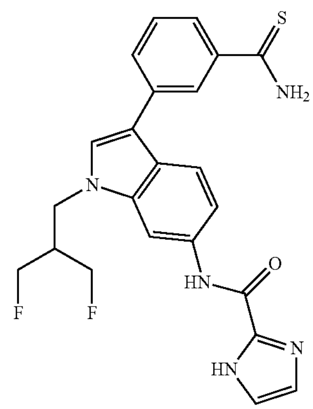 [SMILES: NC(=S)c1cccc(-c2cn(CC(CF)CF)c3cc(NC(=O)c4ncc[nH]4)ccc23)c1] | 453.51 | |
| 140 | 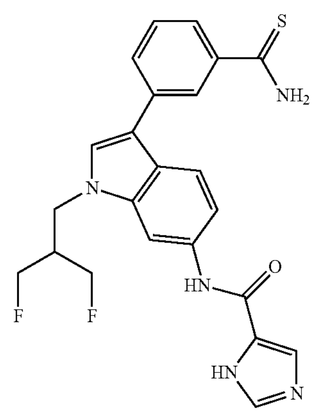 [SMILES: NC(=S)c1cccc(-c2cn(CC(CF)CF)c3cc(NC(=O)c4cnc[nH]4)ccc23)c1] | 453.51 | |
| 141 | 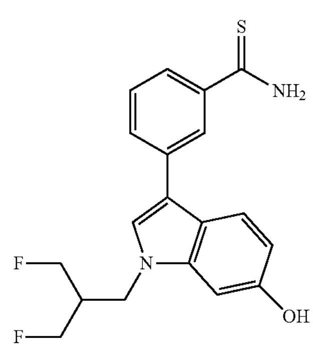 [SMILES: NC(=S)c1cccc(-c2cn(CC(CF)CF)c3cc(O)ccc23)c1] | 360.11 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 142 | 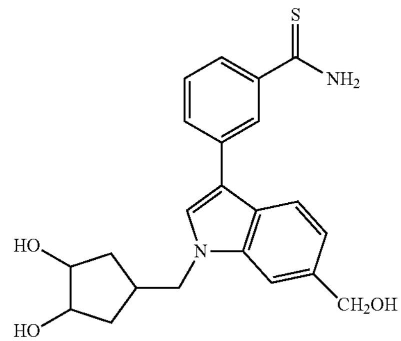 [SMILES: NC(=S)c1cccc(-c2cn(CC3CC(O)C(O)C3)c3cc(CO)ccc23)c1] | 396.15 | |
| 143 | 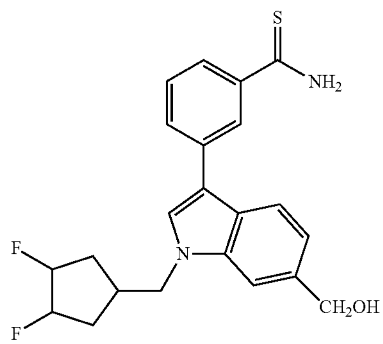 [SMILES: NC(=S)c1cccc(-c2cn(CC3CC(F)C(F)C3)c3cc(CO)ccc23)c1] | 400.14 | |
| 144 | 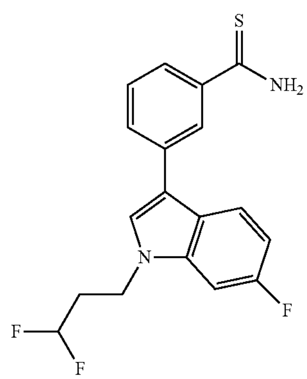 [SMILES: NC(=S)c1cccc(-c2cn(CCC(F)F)c3cc(F)ccc23)c1] | 362.11 | |
| 145 | 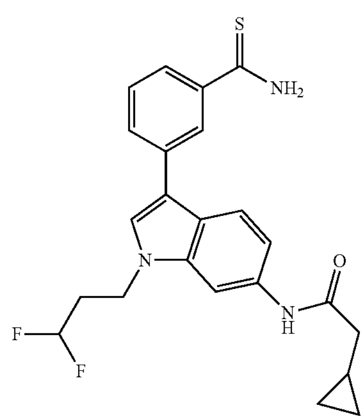 [SMILES: NC(=S)c1cccc(-c2cn(CCC(F)F)c3cc(NC(=O)CC4CC4)ccc23)c1] | 427.15 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 146 | 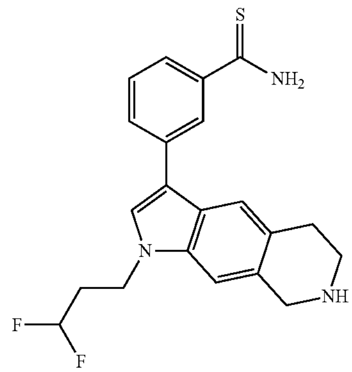 [SMILES: NC(=S)c1cccc(-c2cn(CCC(F)F)c3cc4c(cc23)CCNC4)c1] | 385.15 | |
| 147 | 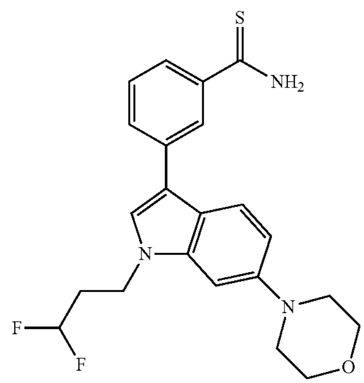 [SMILES: NC(=S)c1cccc(-c2cn(CCC(F)F)c3cc(N4CCOCC4)ccc23)c1] | 415.15 | |
| 148 | 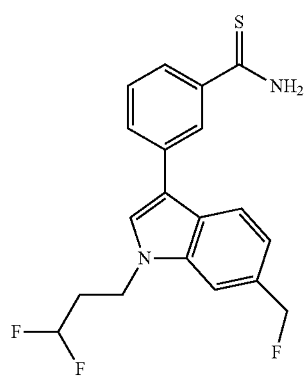 [SMILES: NC(=S)c1cccc(-c2cn(CCC(F)F)c3cc(CF)ccc23)c1] | 362.11 | |
| 149 | 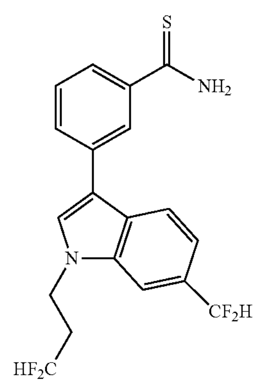 | 380.10 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 150 | 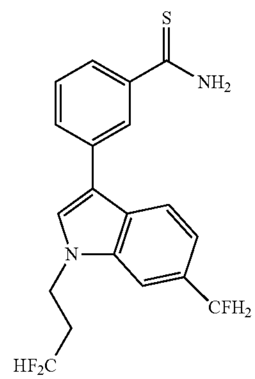 | | 362.11 |
| 151 | 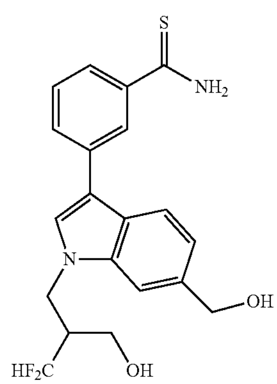 | | 390.12 |
| 152 | 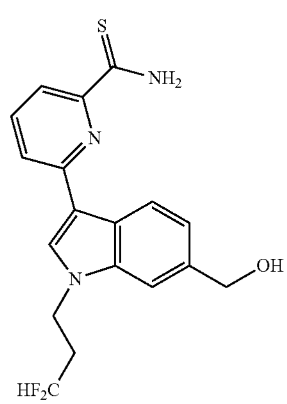 | | 361.11 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | [MH]+ found (Da) |
|---|---|---|---|
| 153 | 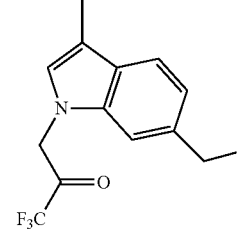 | 392.40 | |
| 154 | 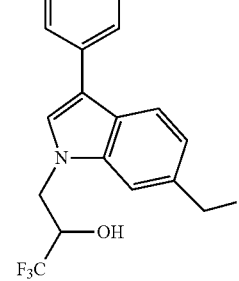 | 394.10 | |
| 155 | 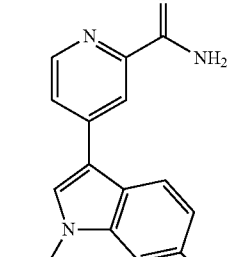 | 361.41 | |
| 156 | 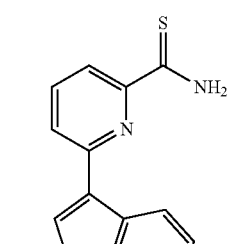 | 361.41 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M_w calc. (Da) | [MH]+ found (Da) |
|---|---|---|---|
| 157 | 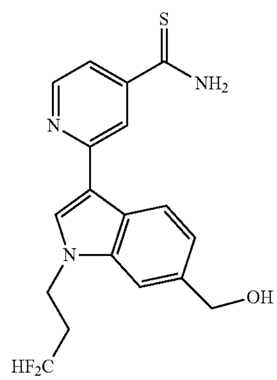 | 361.41 | |
| 158 | 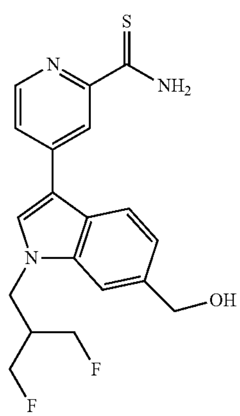 [SMILES: NC(=S)c1cc(-c2cn(CC(CF)CF)c3cc(CO)ccc23)ccn1] | 375.12 | |
| 159 | 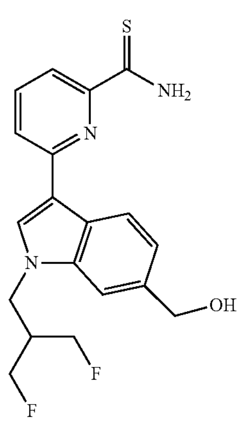 [SMILES: NC(=S)c1cccc(-c2cn(CC(CF)CF)c3cc(CO)ccc23)n1] | 375.12 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 160 | 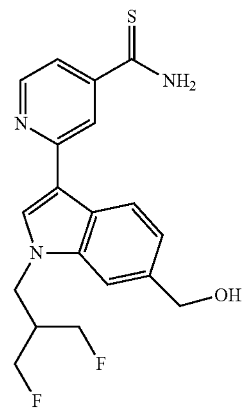 [SMILES: NC(=S)c1ccnc(-c2cn(CC(CF)CF)c3cc(CO)ccc23)c1] | | 375.12 |
| 161 | 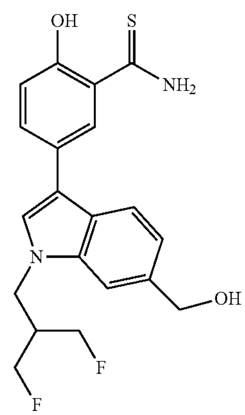 [SMILES: NC(=S)c1cc(-c2cn(CC(CF)CF)c3cc(CO)ccc23)ccc1O] | | 390.12 |
| 162 | 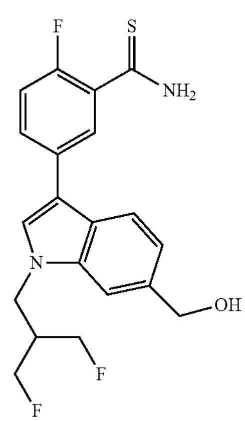 [SMILES: NC(=S)c1cc(-c2cn(CC(CF)CF)c3cc(CO)ccc23)ccc1F] | | 392.44 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 163 | 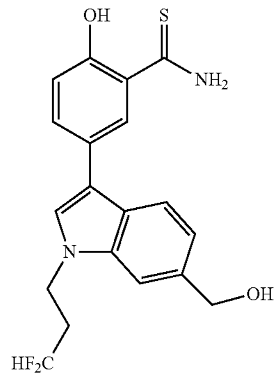 | 376.11 | |
| 164 | 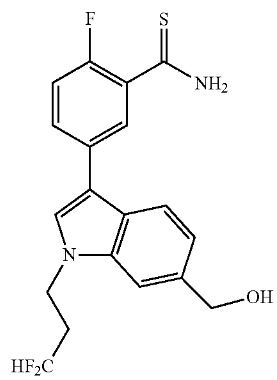 | 378.10 | |
| 165 | 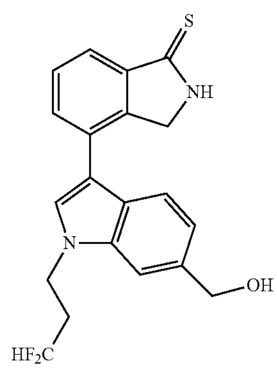 | 372.43 | |
| 166 | 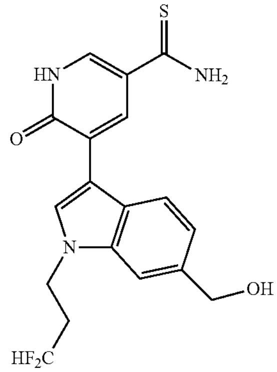 | 377.41 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 167 | 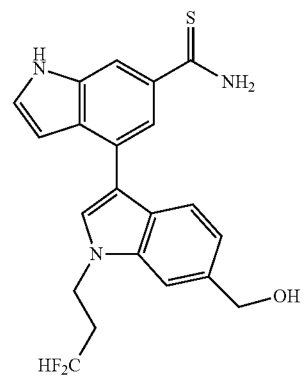 | 399.46 | |
| 168 | 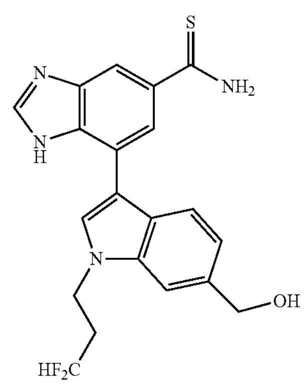 | 400.45 | |
| 169 | 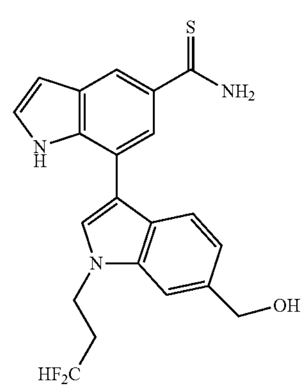 | 399.46 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 170 | 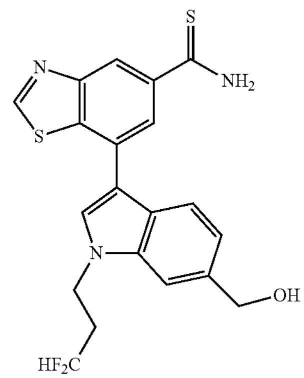 | 417.49 | |
| 171 | 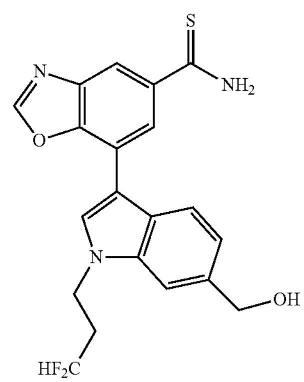 | 401.43 | |
| 172 | 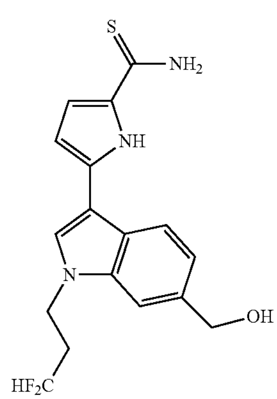 | 349.40 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 173 | 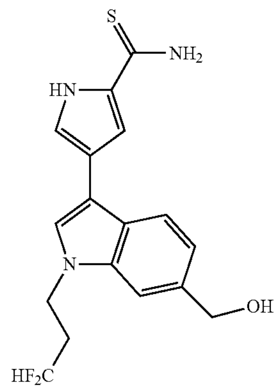 | 349.40 | |
| 174 | 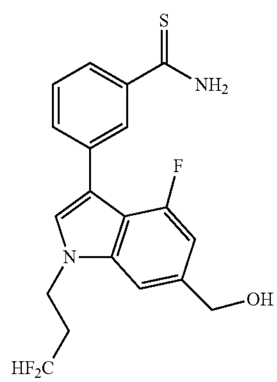 | 378.41 | |
| 175 | 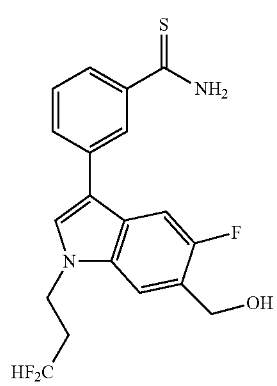 | 378.41 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 176 | 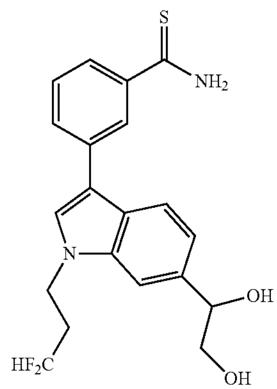 | 390.45 | |
| 177 | 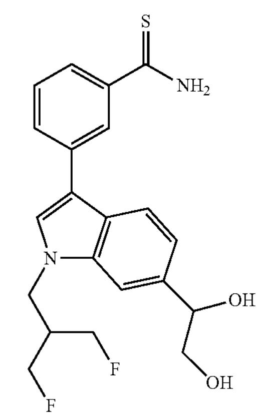 [SMILES: NC(=S)c1cccc(-c2cn(CC(CF)CF)c3cc(C(O)CO)ccc23)c1] | 404.48 | |
| 178 | 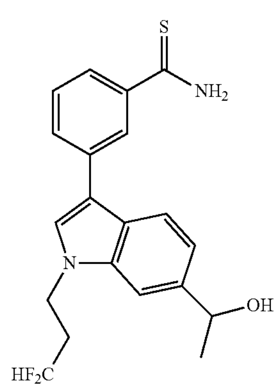 | 374.45 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 179 | 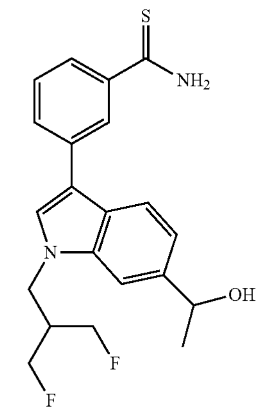 [SMILES: CC(O)c1ccc2c(-c3cccc(C(N)=S)c3)cn(CC(CF)CF)c2c1] | 388.48 | |
| 180 | 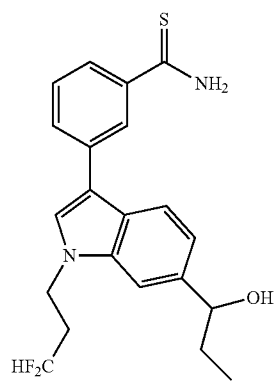 | 388.48 | |
| 181 | 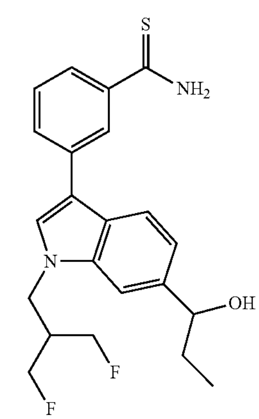 [SMILES: CCC(O)c1ccc2c(-c3cccc(C(N)=S)c3)cn(CC(CF)CF)c2c1] | 416.53 | |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | [MH]+ found (Da) |
|---|---|---|---|
| 182 | 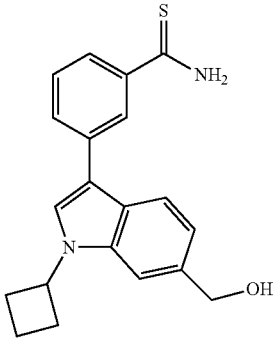 [SMILES: NC(=S)c1cccc(-c2cn(C3CCC3)c3cc(CO)ccc23)c1] | 336.45 | |
| 183 | 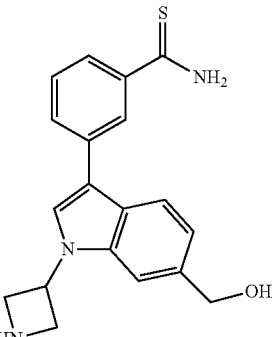 | 337.44 | |
| 184 | 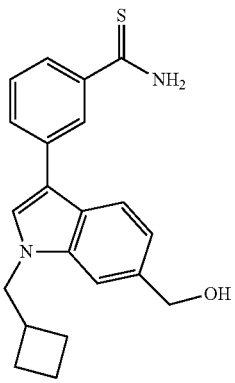 [SMILES: NC(=S)c1cccc(-c2cn(CC3CCC3)c3cc(CO)ccc23)c1] | 350.48 | |
| 185 | 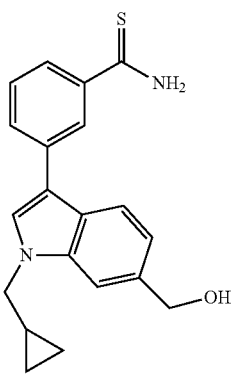 [SMILES: NC(=S)c1cccc(-c2cn(CC3CC3)c3cc(CO)ccc23)c1] | 336.45 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 186 | 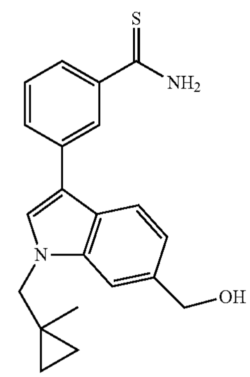 [SMILES: CC1(Cn2cc(-c3cccc(C(N)=S)c3)c3ccc(CO)cc32)CC1] | 350.15 | |
| 187 | 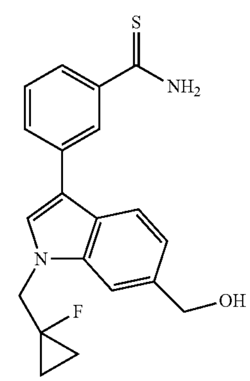 [SMILES: NC(=S)c1cccc(-c2cn(CC3(F)CC3)c3cc(CO)ccc23)c1] | 354.44 | |
| 188 | 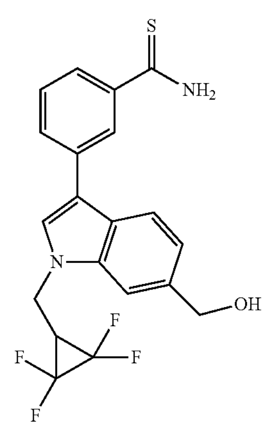 [SMILES: NC(=S)c1cccc(-c2cn(CC3C(F)(F)C3(F)F)c3cc(CO)ccc23)c1] | 408.41 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 189 | 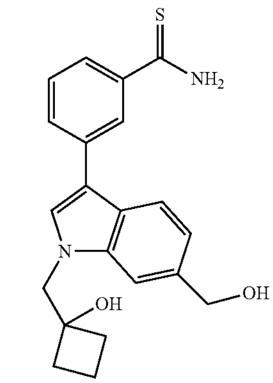 [SMILES: NC(=S)c1cccc(-c2cn(CC3(O)CCC3)c3cc(CO)ccc23)c1] | 366.48 | |
| 190 | 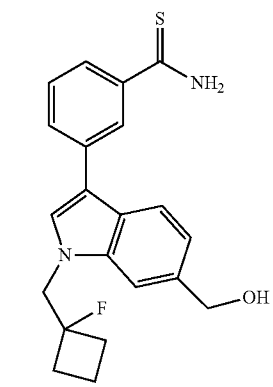 [SMILES: NC(=S)c1cccc(-c2cn(CC3(F)CCC3)c3cc(CO)ccc23)c1] | 368.47 | |
| 191 | 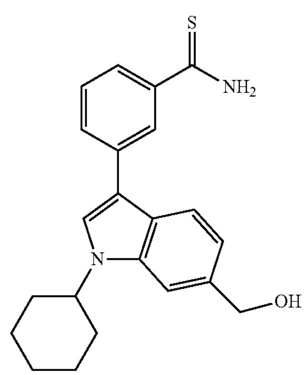 [SMILES: NC(=S)c1cccc(-c2cn(C3CCCCC3)c3cc(CO)ccc23)c1] | 364.51 | |
| 192 | 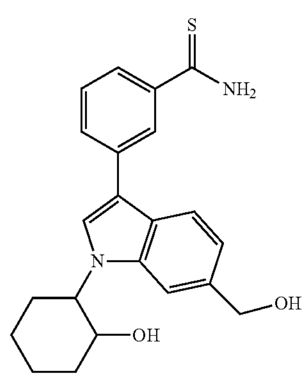 [SMILES: NC(=S)c1cccc(-c2cn(C3CCCCC3O)c3cc(CO)ccc23)c1] | 380.51 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 193 | 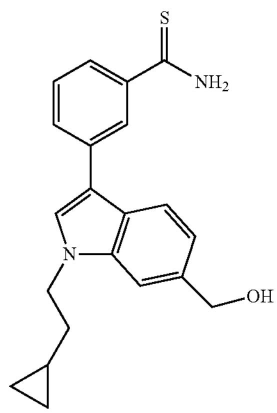 [SMILES: NC(=S)c1cccc(-c2cn(CCC3CC3)c3cc(CO)ccc23)c1] | 350.48 | |
| 194 | 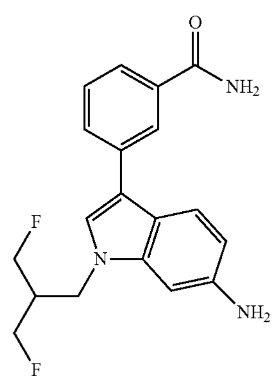 [SMILES: NC(=O)c1cccc(-c2cn(CC(CF)CF)c3cc(N)ccc23)c1] | 343.15 | 344.1567 |
| 195 | 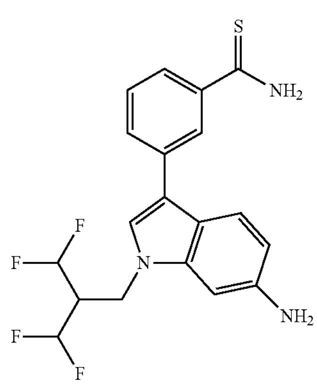 [SMILES: NC(=S)c1cccc(-c2cn(CC(C(F)F)C(F)F)c3cc(N)ccc23)c1] | 395.11 | |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 196 | 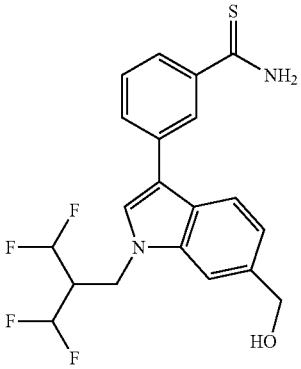 [SMILES: NC(=S)c1cccc(-c2cn(CC(C(F)F)C(F)F)c3cc(CO)ccc23)c1] | 410.11 | |
| 197 | 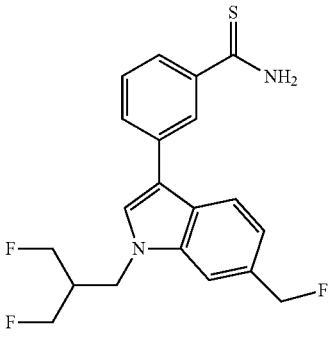 [SMILES: NC(=S)c1cccc(-c2cn(CC(CF)CF)c3cc(CF)ccc23)c1] | 376.12 | |
| 198 | 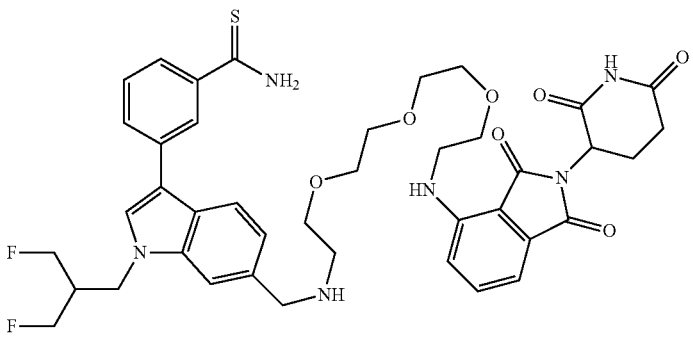 [SMILES: NC(=S)c1cccc(-c2cn(CC(CF)CF)c3cc(CNCCOCCOCCOCCNc4cccc5c4C(=O)N(C4CCC(=O)NC4=O)C5=O)ccc23)c1] | 804.31 | |
| 199 | 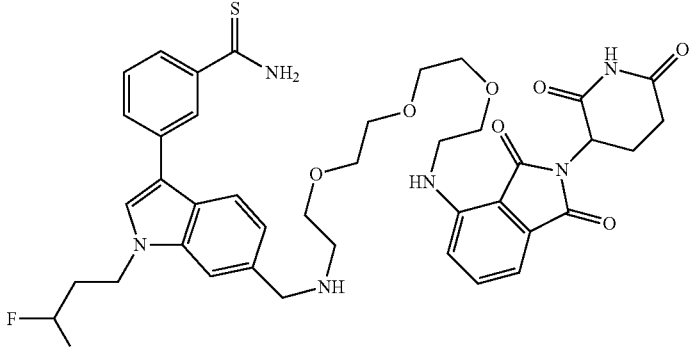 | 790.30 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M_w calc. (Da) | [MH]+ found (Da) |
|---|---|---|---|
| 200 | 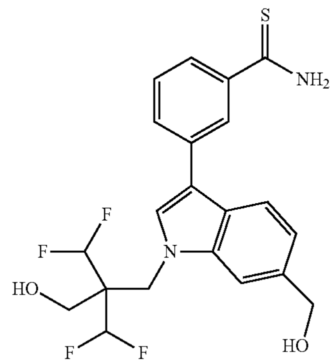 [SMILES: NC(=S)c1cccc(-c2cn(CC(CO)(C(F)F)C(F)F)c3cc(CO)ccc23)c1] | 440.1 | |
| 201 | 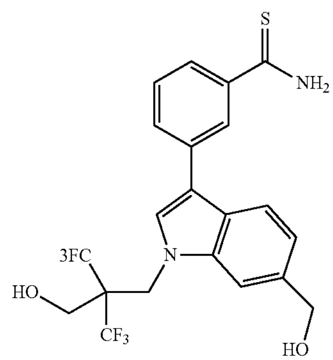 | 476.4 | |
| 202 | 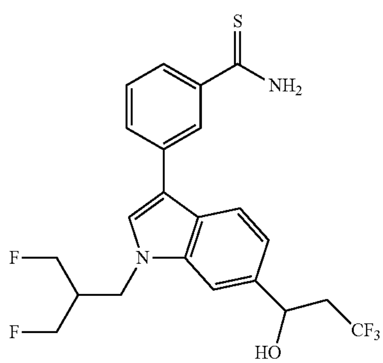 [SMILES: NC(=S)c1cccc(-c2cn(CC(CF)CF)c3cc(C(O)CC(F)(F)F)ccc23)c1] | 456.5 | |
| 203 | 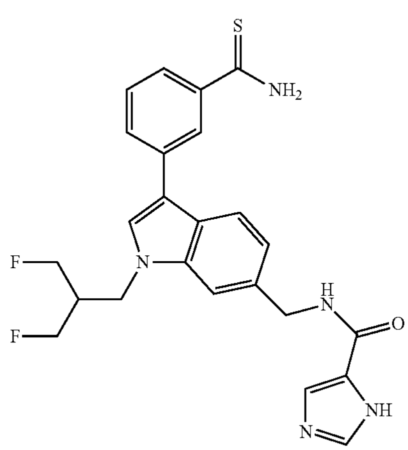 [SMILES: NC(=S)c1cccc(-c2cn(CC(CF)CF)c3cc(CNC(=O)c4cnc[nH]4)ccc23)c1] | 467.5 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 204 | 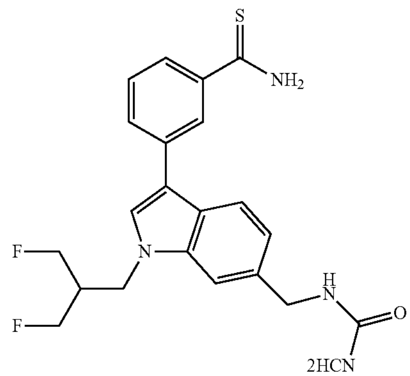 | | 416.5 |
| 205 | 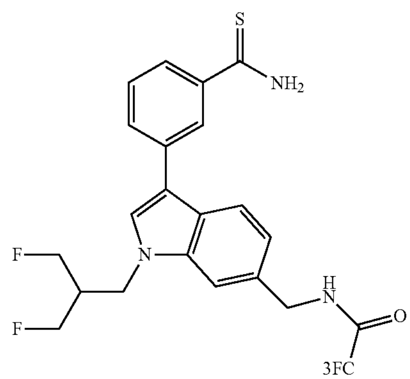 | | 469.5 |
| 206 | 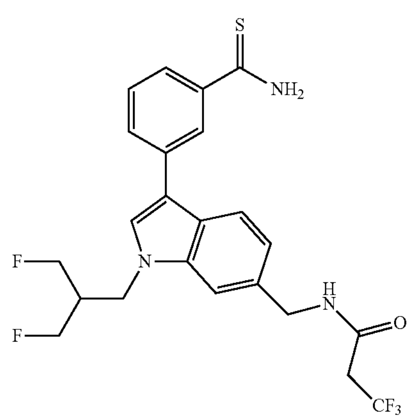 [SMILES: NC(=S)c1cccc(-c2cn(CC(CF)CF)c3cc(CNC(=O)CC(F)(F)F)ccc23)c1] | | 483.5 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 207 | 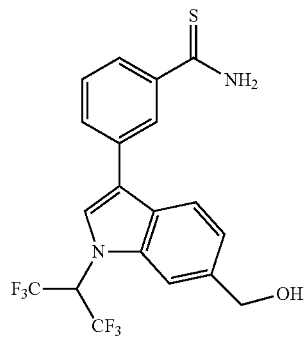 [SMILES: NC(=S)c1cccc(-c2cn(C(C(F)(F)F)C(F)(F)F)c3cc(CO)ccc23)c1] | 432.38 | |
| 208 | 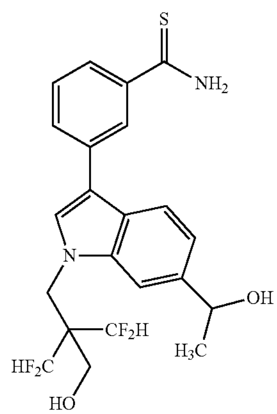 | 490.46 | |
| 209 | 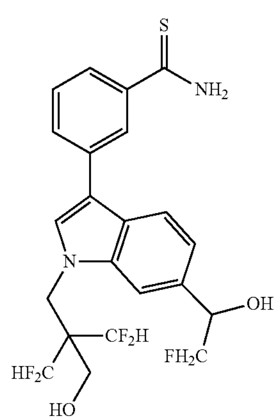 | 472.47 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 210 | 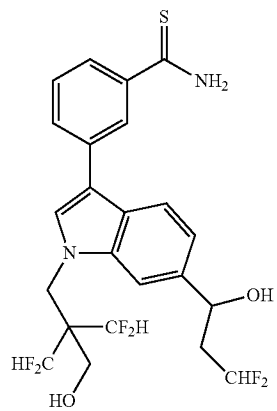 | 504.49 | |
| 211 | 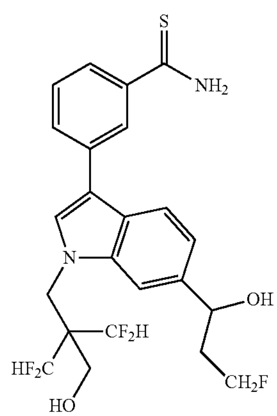 | 486.50 | |
| 212 | 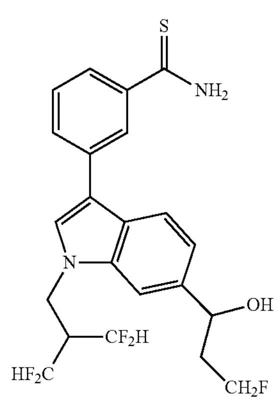 | 456.48 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 213 | 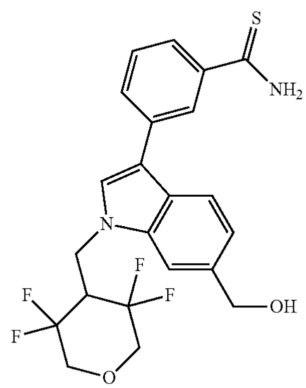 [SMILES: NC(=S)c1cccc(-c2cn(CC3C(F)(F)COCC3(F)F)c3cc(CO)ccc23)c1] | 452.12 | |
| 214 | 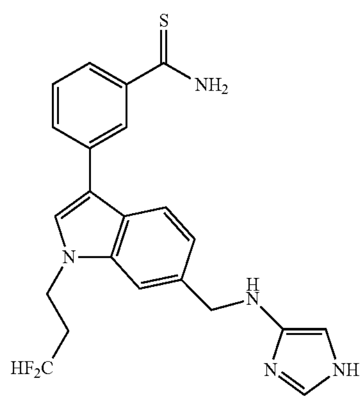 | 425.50 | |
| 215 | 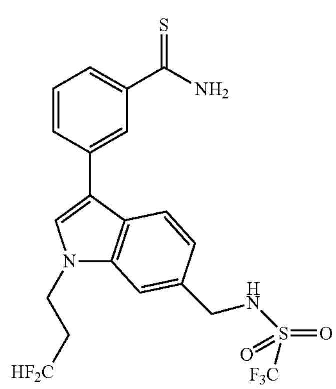 | 491.50 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 216 | 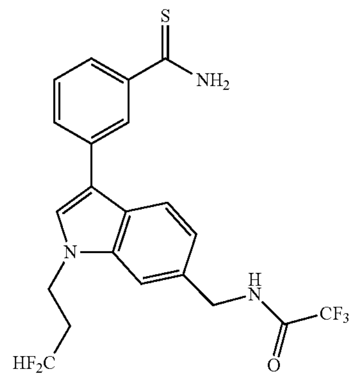 | 455.45 | |
| 217 | 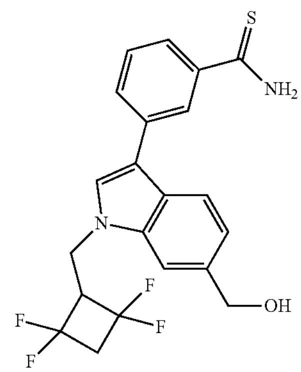 [SMILES: NC(=S)c1cccc(-c2cn(CC3C(F)(F)CC3(F)F)c3cc(CO)ccc23)c1] | 422.44 | |
| 218 | 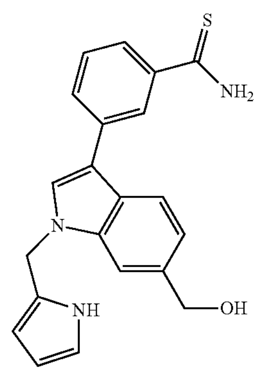 [SMILES: NC(=S)c1cccc(-c2cn(Cc3ccc[nH]3)c3cc(CO)ccc23)c1] | 361.46 | |
| 219 | 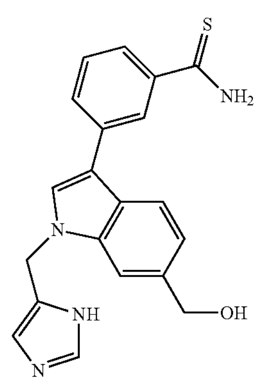 [SMILES: NC(=S)c1cccc(-c2cn(Cc3cnc[nH]3)c3cc(CO)ccc23)c1] | 362.45 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]$^+$ found (Da) |
|---|---|---|---|
| 220 | 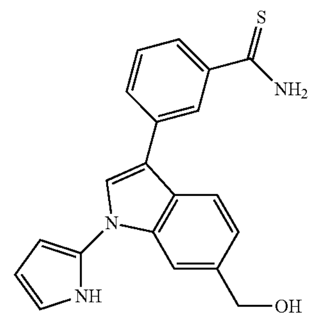 [SMILES: NC(=S)c1cccc(-c2cn(-c3ccc[nH]3)c3cc(CO)ccc23)c1] | 347.44 | |
| 221 | 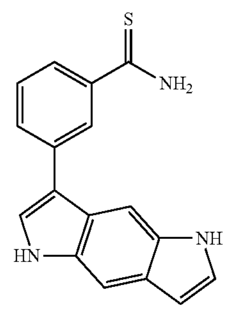 [SMILES: NC(=S)c1cccc(-c2c[nH]c3cc4cc[nH]c4cc23)c1] | 291.37 | |
| 222 | 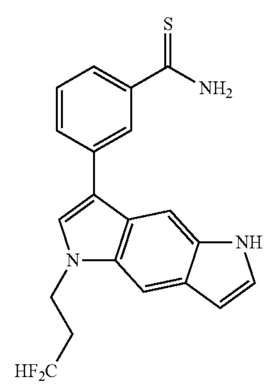 | 369.43 | |
| 223 | 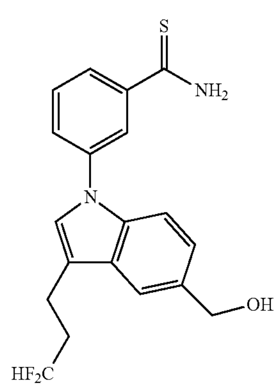 | 360.42 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 224 | 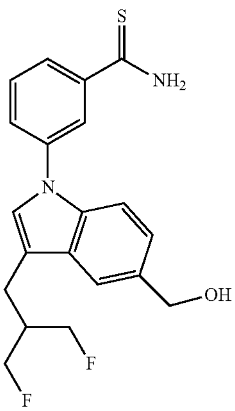 [SMILES: NC(=S)c1cccc(-n2cc(CC(CF)CF)c3cc(CO)ccc32)c1] | 374.45 | |
| 225 | 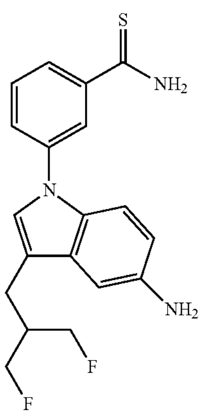 [SMILES: NC(=S)c1cccc(-n2cc(CC(CF)CF)c3cc(N)ccc32)c1] | 359.44 | |
| 226 | 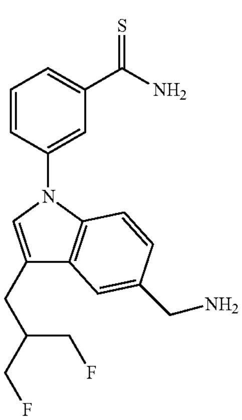 [SMILES: NCc1ccc2c(c1)c(CC(CF)CF)cn2-c1cccc(C(N)=S)c1] | 373.47 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 227 | 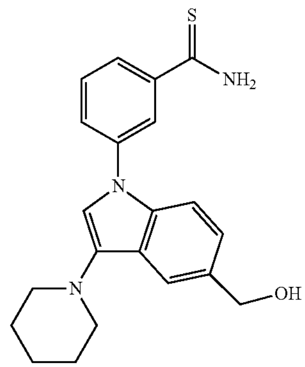 [SMILES: NC(=S)c1cccc(-n2cc(N3CCCCC3)c3cc(CO)ccc32)c1] | 365.50 | |
| 228 | 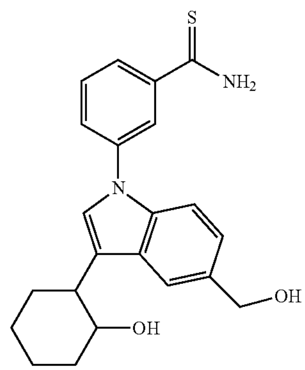 [SMILES: NC(=S)c1cccc(-n2cc(C3CCCCC3O)c3cc(CO)ccc32)c1] | 380.51 | |
| 229 | 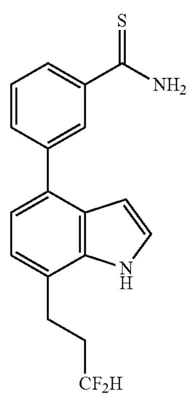 [SMILES: NC(=S)c1cccc(-c2ccc(CCC(F)F)c3[nH]ccc23)c1] | 330.40 | |
| 230 | 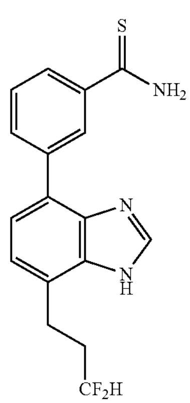 [SMILES: NC(=S)c1cccc(-c2ccc(CCC(F)F)c3[nH]cnc23)c1] | 331.38 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]$^+$ found (Da) |
|---|---|---|---|
| 231 | 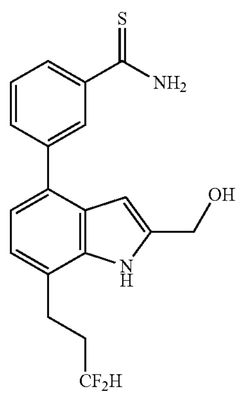 [SMILES: NC(=S)c1cccc(-c2ccc(CCC(F)F)c3[nH]c(CO)cc23)c1] | 360.42 | |
| 232 | 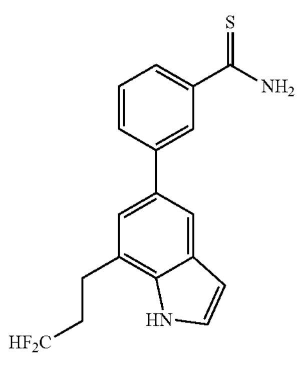 | 330.40 | |
| 233 | 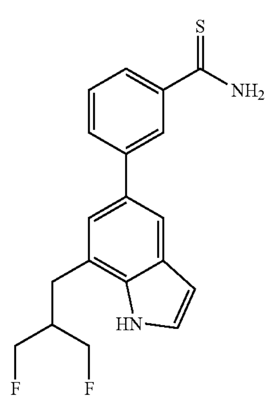 [SMILES: NC(=S)c1cccc(-c2cc(CC(CF)CF)c3[nH]ccc3c2)c1] | 344.42 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 234 | 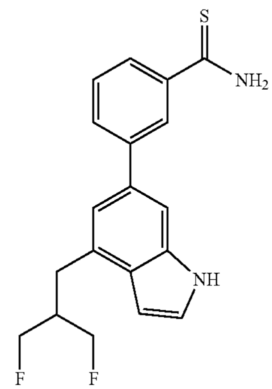 [SMILES: NC(=S)c1cccc(-c2cc(CC(CF)CF)c3cc[nH]c3c2)c1] | 344.42 | |
| 235 | 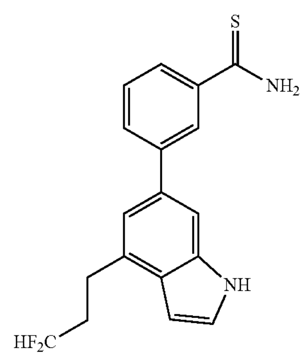 | 330.40 | |
| 236 | 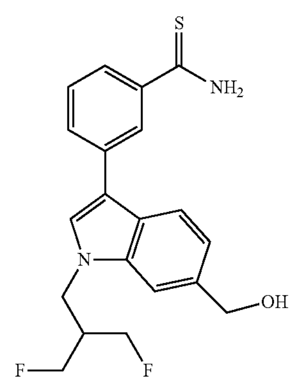 [SMILES: NC(=S)c1cccc(-c2cn(CC(CF)CF)c3cc(CO)ccc23)c1] | 375.13 | 375.1335 |
| 237 | 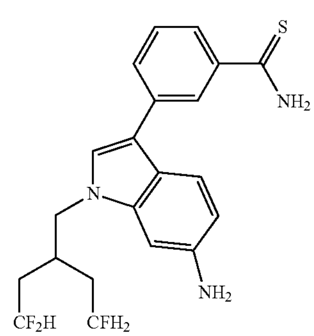 | 405.48 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 238 | 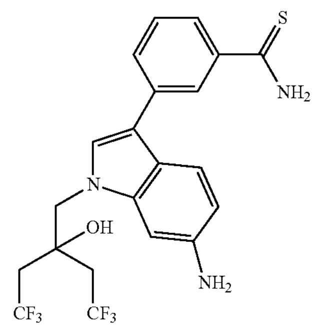 [SMILES: NC(=S)c1cccc(-c2cn(CC(O)(CC(F)(F)F)CC(F)(F)F)c3cc(N)ccc23)c1] | 475.45 | |
| 239 | 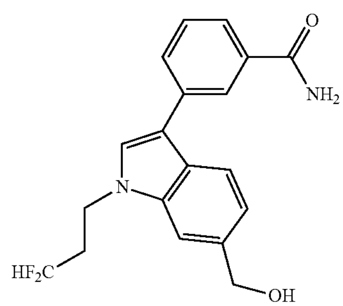 | | |
| 240 | 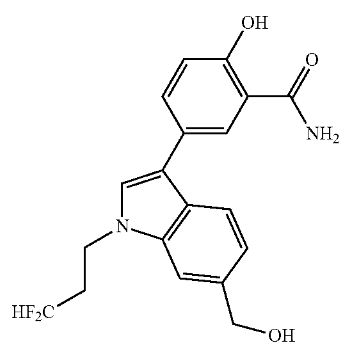 | 360.36 | |
| 241 | 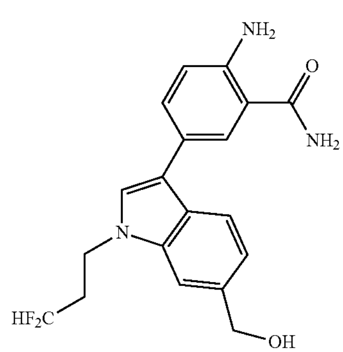 | 359.38 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 242 | 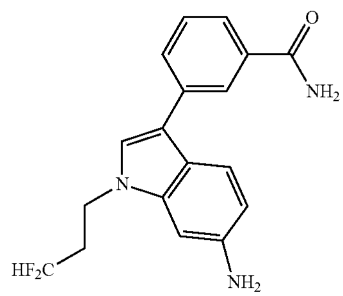 | 329.35 | |
| 243 | 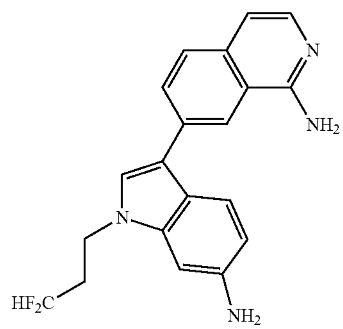 | 352.39 | |
| 244 | 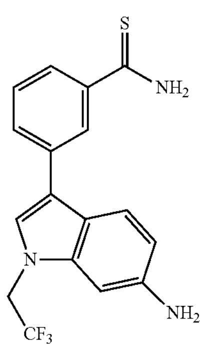 [SMILES: NC(=S)c1cccc(-c2cn(CC(F)(F)F)c3cc(N)ccc23)c1] | 349.38 | 350.0936 |
| 245 | 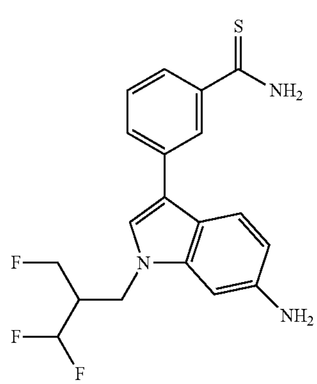 [SMILES: NC(=S)c1cccc(-c2cn(CC(CF)C(F)F)c3cc(N)ccc23)c1] | 377.43 | 378.1249 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 246 | 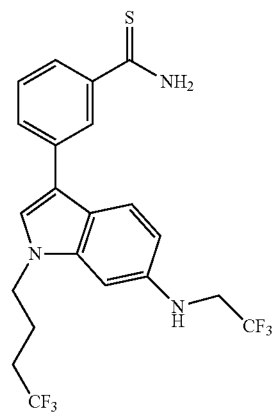 [SMILES: NC(=S)c1cccc(-c2cn(CCCC(F)(F)F)c3cc(NCC(F)(F)F)ccc23)c1] | 459.45 | 460.1281 |
| 248 | 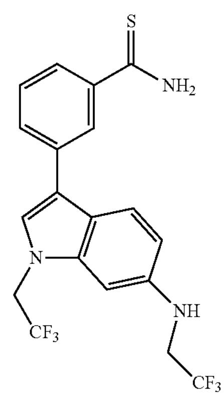 [SMILES: NC(=S)c1cccc(-c2cn(CC(F)(F)F)c3cc(NCC(F)(F)F)ccc23)c1] | 431.40 | 432.0970 |
| 251 | 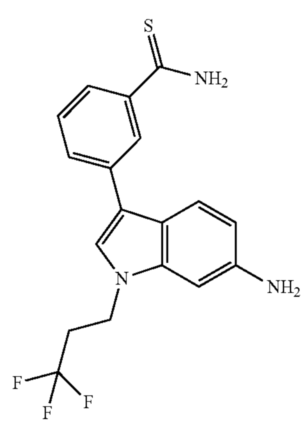 [SMILES: NC(=S)c1cccc(-c2cn(CCC(F)(F)F)c3cc(N)ccc23)c1] | 363.40 | 364.1092 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 252 | 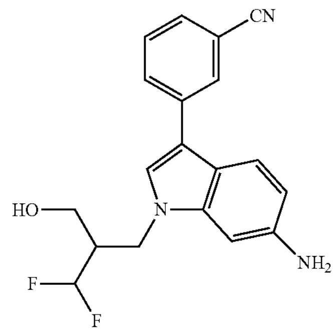 [SMILES: N#Cc1cccc(-c2cn(CC(CO)C(F)F)c3cc(N)ccc23)c1] | 341.36 | 342.1415 |
| 253 | 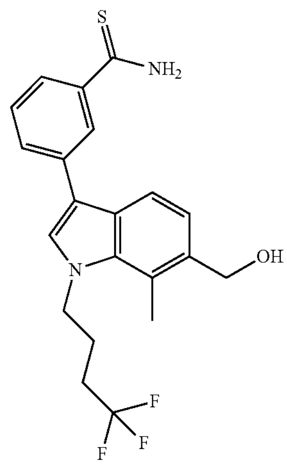 [SMILES: Cc1c(CO)ccc2c(-c3cccc(C(N)=S)c3)cn(CCCC(F)(F)F)c12] | 406.47 | 407.1396 |
| 256 | 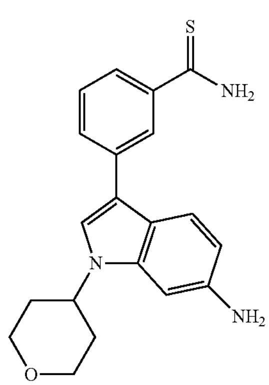 [SMILES: NC(=S)c1cccc(-c2cn(C3CCOCC3)c3cc(N)ccc23)c1] | 351.47 | 352.1478 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 257 | 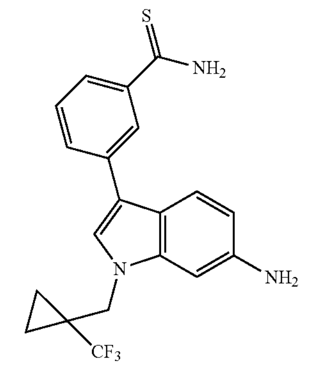 [SMILES: NC(=S)c1cccc(-c2cn(CC3(C(F)(F)F)CC3)c3cc(N)ccc23)c1] | 389.44 | 390.1249 |
| 258 | 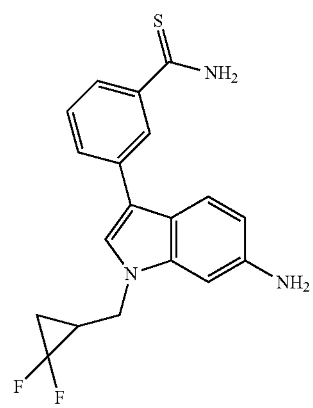 [SMILES: NC(=S)c1cccc(-c2cn(CC3CC3(F)F)c3cc(N)ccc23)c1] | 357.42 | 358.1187 |
| 259 | 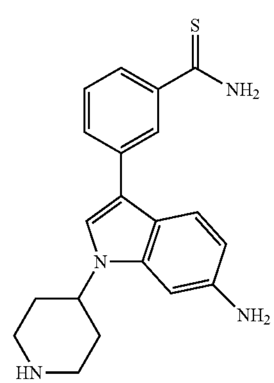 [SMILES: NC(=S)c1cccc(-c2cn(C3CCNCC3)c3cc(N)ccc23)c1] | 350.48 | 351.1635 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 260 | 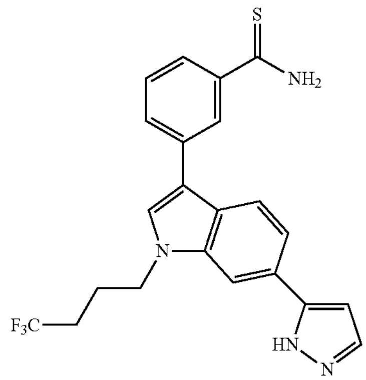 [SMILES: NC(=S)c1cccc(-c2cn(CCCC(F)(F)F)c3cc(-c4ccn[nH]4)ccc23)c1] | 428.48 | 429.15 |
| 261 | 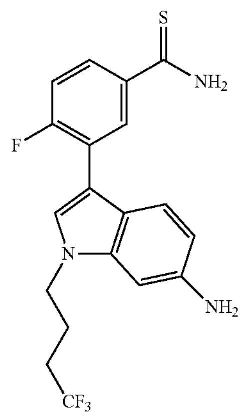 [SMILES: NC(=S)c1ccc(F)c(-c2cn(CCCC(F)(F)F)c3cc(N)ccc23)c1] | 395.42 | 396.1154 |
| 263 | 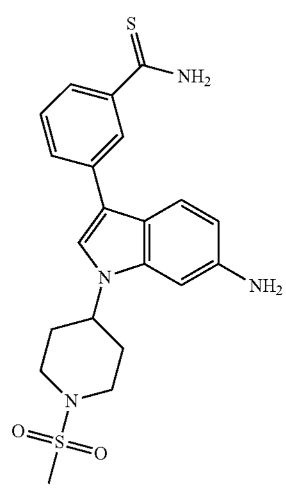 [SMILES: CS(=O)(=O)N1CCC(n2cc(-c3cccc(C(N)=S)c3)c3ccc(N)cc32)CC1] | 428.57 | 429.1414 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 265 | 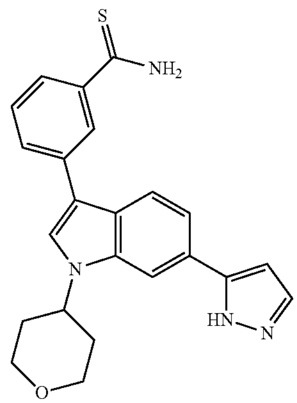 [SMILES: NC(=S)c1cccc(-c2cn(C3CCOCC3)c3cc(-c4ccn[nH]4)ccc23)c1] | 402.52 | 403.1585 |
| 266 | 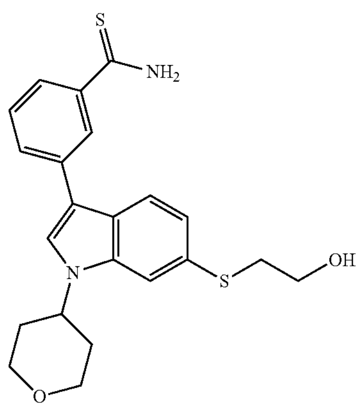 [SMILES: NC(=S)c1cccc(-c2cn(C3CCOCC3)c3cc(SCCO)ccc23)c1] | 412.57 | 413.1350 |
| 267 | 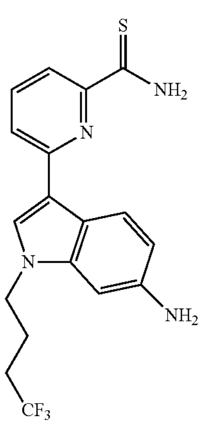 [SMILES: NC(=S)c1cccc(-c2cn(CCCC(F)(F)F)c3cc(N)ccc23)n1] | 378.42 | 379.1197 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 268 | | 429.56 | 430.1365 |
| 270 | | 365.50 | 366.1633 |
| 271 | | 464.61 | 465.1524 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 272 | 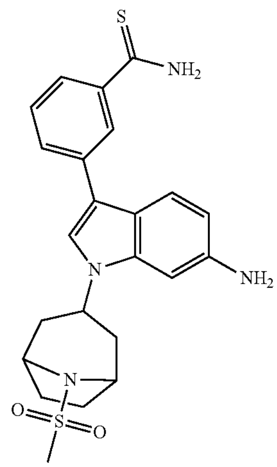 [SMILES: CS(=O)(=O)N1C2CCC1CC(n1cc(-c3cccc(C(N)=S)c3)c3ccc(N)cc31)C2] | 454.61 | 455.1571 |
| 273 | 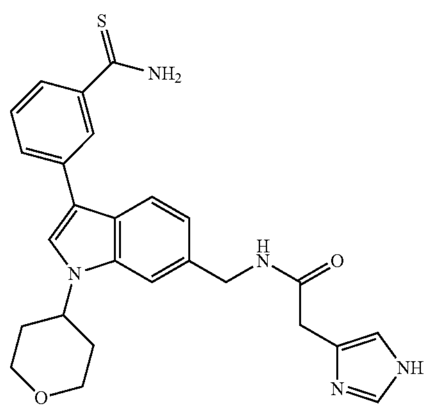 [SMILES: NC(=S)c1cccc(-c2cn(C3CCOCC3)c3cc(CNC(=O)Cc4c[nH]cn4)ccc23)c1] | 473.60 | 474.1958 |
| 274 | 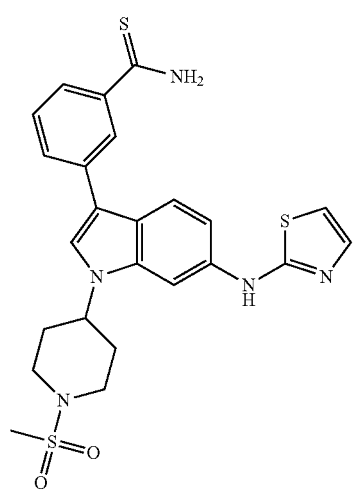 [SMILES: CS(=O)(=O)N1CCC(n2cc(-c3cccc(C(N)=S)c3)c3ccc(Nc4nccs4)cc32)CC1] | 511.68 | 512.1239 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 276 | 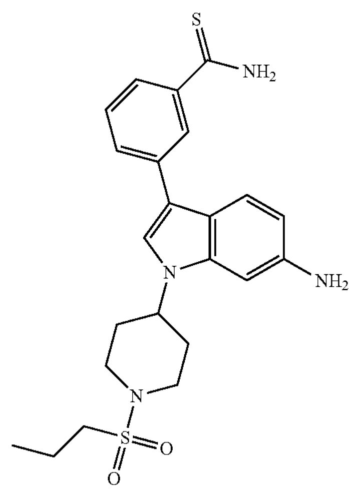 [SMILES: CCCS(=O)(=O)N1CCC(n2cc(-c3cccc(C(N)=S)c3)c3ccc(N)cc32)CC1] | 456.62 | 457.1722 |
| 277 | 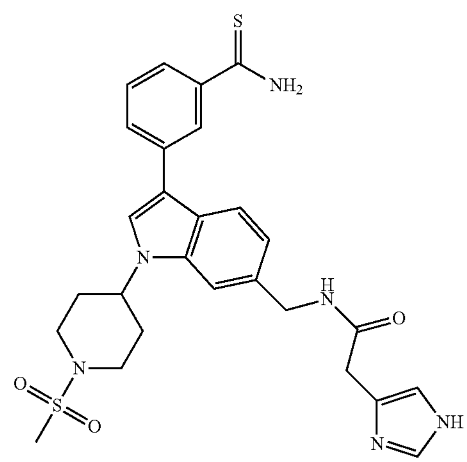 [SMILES: CS(=O)(=O)N1CCC(n2cc(-c3cccc(C(N)=S)c3)c3ccc(CNC(=O)Cc4c[nH]cn4)cc32)CC1] | 550.70 | 551.1895 |
| 278 | 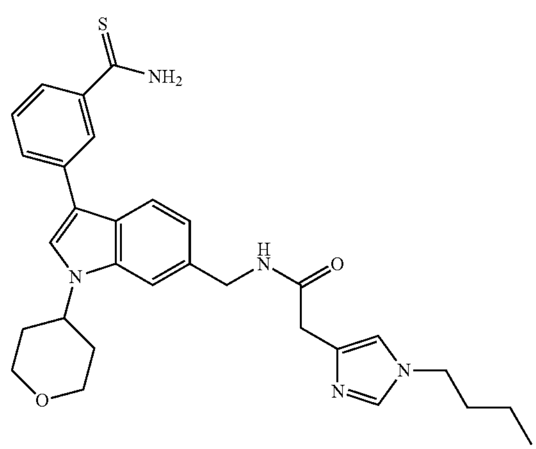 [SMILES: CCCCn1cnc(CC(=O)NCc2ccc3c(-c4cccc(C(N)=S)c4)cn(C4CCOCC4)c3c2)c1] | 529.70 | 530.2586 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M_w calc. (Da) | [MH]+ found (Da) |
|---|---|---|---|
| 279 | 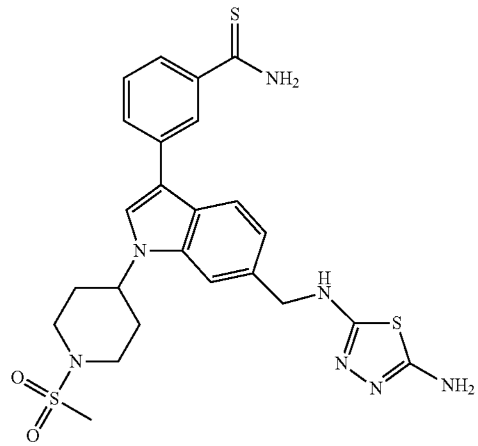 [SMILES: CS(=O)(=O)N1CCC(n2cc(-c3cccc(C(N)=S)c3)c3ccc(CNc4nnc(N)s4)cc32)CC1] | 541.71 | 542.1462 |
| 280 | 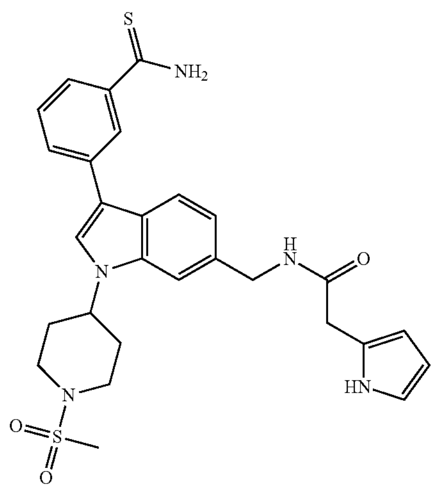 [SMILES: CS(=O)(=O)N1CCC(n2cc(-c3cccc(C(N)=S)c3)c3ccc(CNC(=O)Cc4ccc[nH]4)cc32)CC1] | 549.71 | 550.1936 |
| 281 | 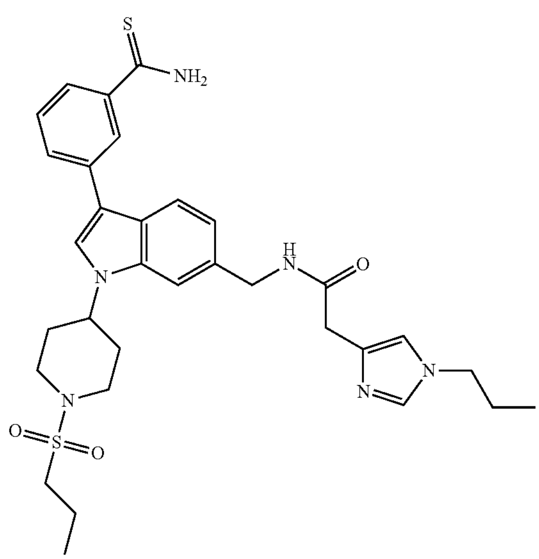 [SMILES: CCCn1cnc(CC(=O)NCc2ccc3c(-c4cccc(C(N)=S)c4)cn(C4CCN(S(=O)(=O)CCC)CC4)c3c2)c1] | 620.83 | |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 282 | 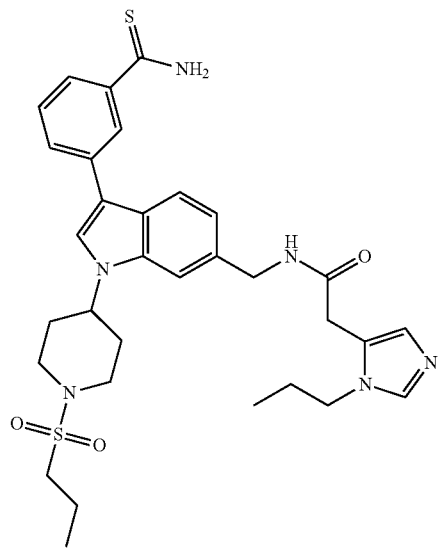 [SMILES: CCCn1cncc1CC(=O)NCc1ccc2c(-c3cccc(C(N)=S)c3)cn(C3CCN(S(=O)(=O)CCC)CC3)c2c1] | 620.83 | |
| 283 | 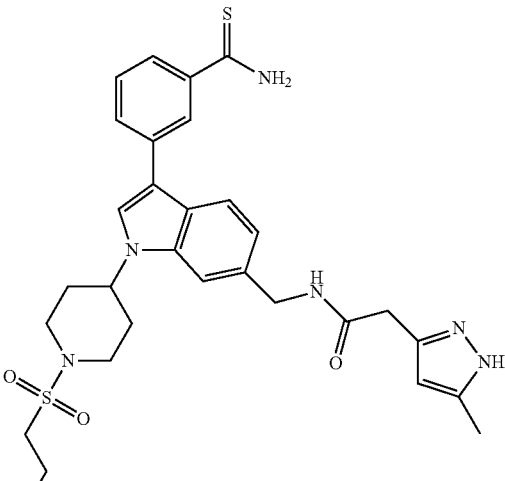 | 592.78 | |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 284 | 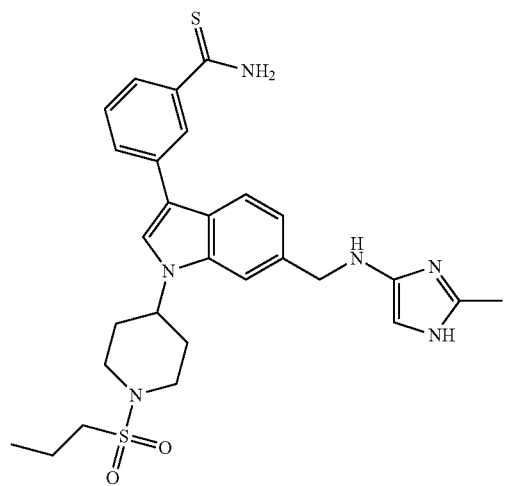 [SMILES: CCCS(=O)(=O)N1CCC(n2cc(-c3cccc(C(N)=S)c3)c3ccc(CNc4c[nH]c(C)n4)cc32)CC1] | 550.74 | |
| 285 | 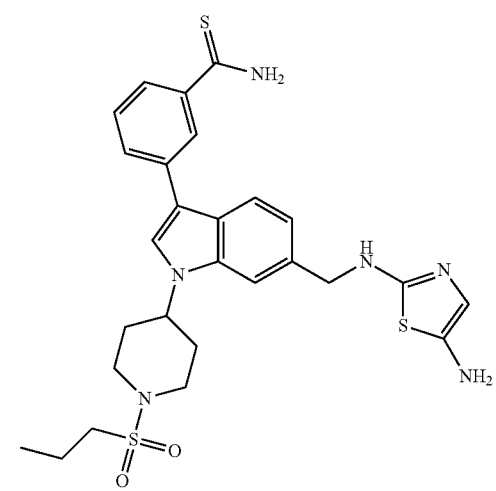 [SMILES: CCCS(=O)(=O)N1CCC(n2cc(-c3cccc(C(N)=S)c3)c3ccc(CNc4ncc(N)s4)cc32)CC1] | 568.77 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]$^+$ found (Da) |
|---|---|---|---|
| 286 | 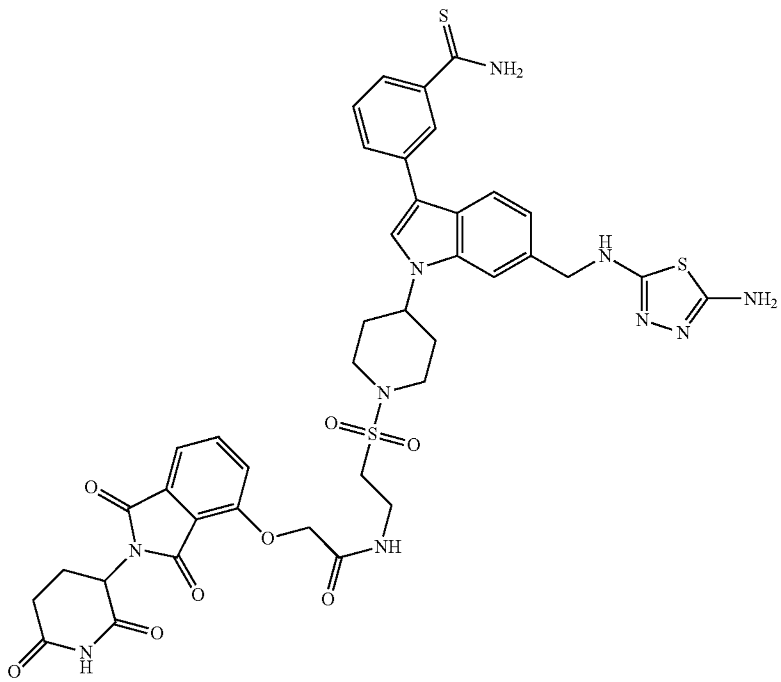 [SMILES: NC(=S)c1cccc(-c2cn(C3CCN(S(=O)(=O)CCNC(=O)COc4cccc5c4C(=O)N(C4CCC(=O)NC4=O)C5=O)CC3)c3cc(CNc4nnc(N)s4)ccc23)c1] | | 885.00 |
| 287 | 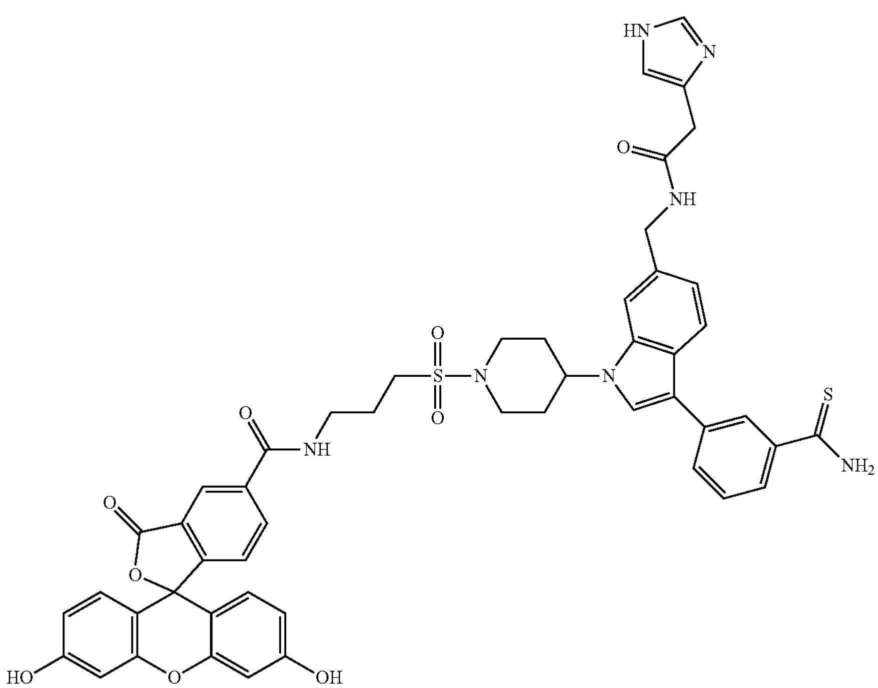 [SMILES: NC(=S)c1cccc(-c2cn(C3CCN(S(=O)(=O)CCCNC(=O)c4ccc5c(c4)C(=O)OC54c5ccc(O)cc5Oc5cc(O)ccc54)CC3)c3cc(CNC(=O)Cc4c[nH]cn4)ccc23)c1] | | 952.07 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | [MH]+ found (Da) |
|---|---|---|---|
| 288 | 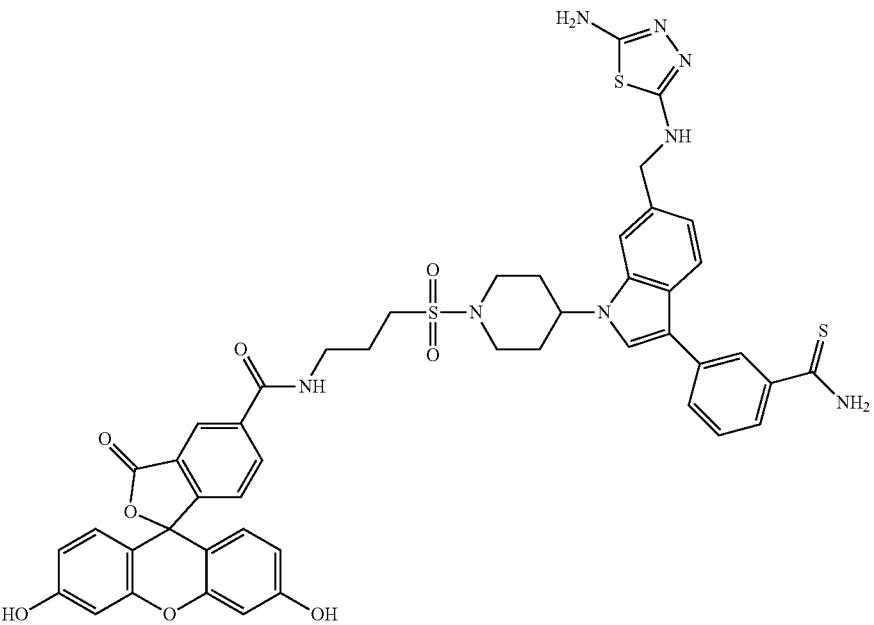 [SMILES: NC(=S)c1cccc(-c2cn(C3CCN(S(=O)(=O)CCCNC(=O)c4ccc5c(c4)C(=O)OC54c5ccc(O)cc5Oc5cc(O)ccc54)CC3)c3cc(CNc4nnc(N)s4)ccc23)c1] | 943.08 | |
| 289 | 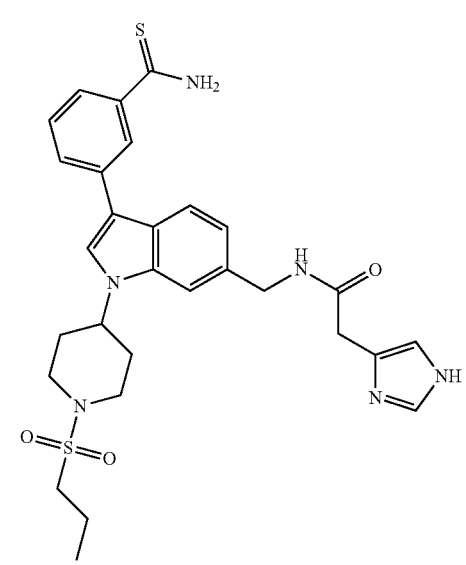 [SMILES: CCCS(=O)(=O)N1CCC(n2cc(-c3cccc(C(N)=S)c3)c3ccc(CNC(=O)Cc4c[nH]cn4)cc32)CC1] | 578.75 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 290 | 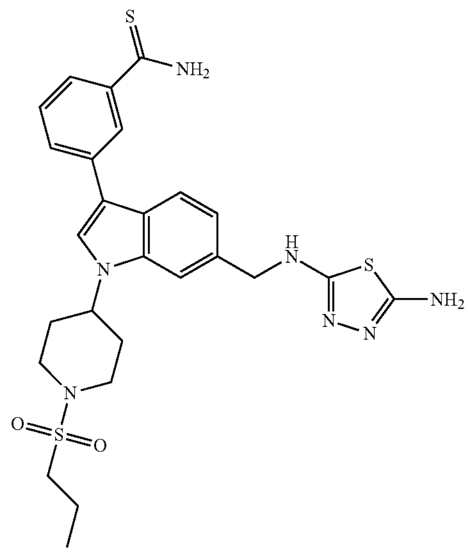 [SMILES: CCCS(=O)(=O)N1CCC(n2cc(-c3cccc(C(N)=S)c3)c3ccc(CNc4nnc(N)s4)cc32)CC1] | 569.76 | |
| 291 | 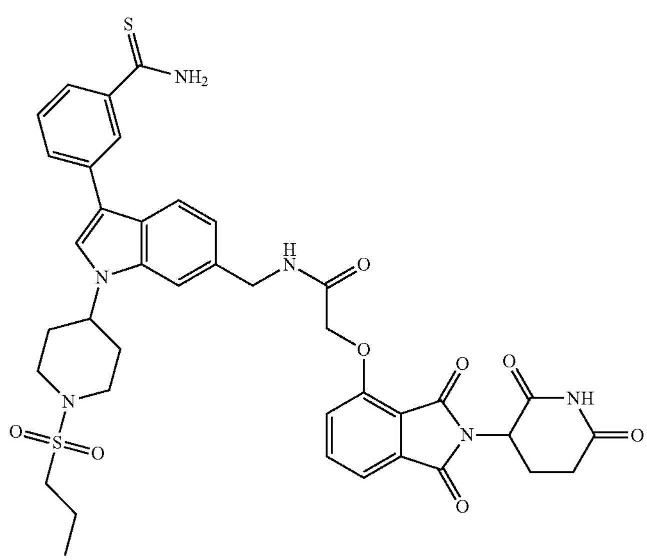 [SMILES: CCCS(=O)(=O)N1CCC(n2cc(-c3cccc(C(N)=S)c3)c3ccc(CNC(=O)COc4cccc5c4C(=O)N(C4CCC(=O)NC4=O)C5=O)cc32)CC1] | 784.90 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 292 | 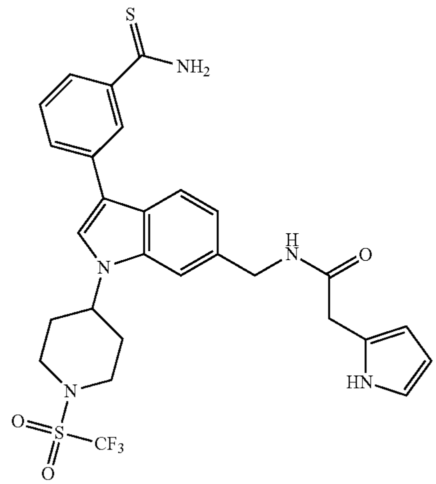 [SMILES: NC(=S)c1cccc(-c2cn(C3CCN(S(=O)(=O)C(F)(F)F)CC3)c3cc(CNC(=O)Cc4ccc[nH]4)ccc23)c1] | | 603.16 |
| 293 | 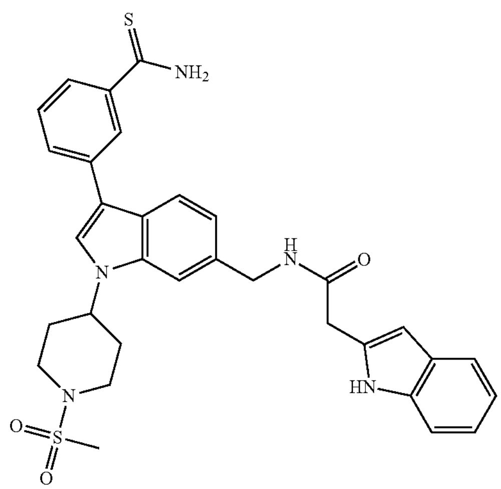 [SMILES: CS(=O)(=O)N1CCC(n2cc(-c3cccc(C(N)=S)c3)c3ccc(CNC(=O)Cc4cc5ccccc5[nH]4)cc32)CC1] | | 599.20 |
| 294 | 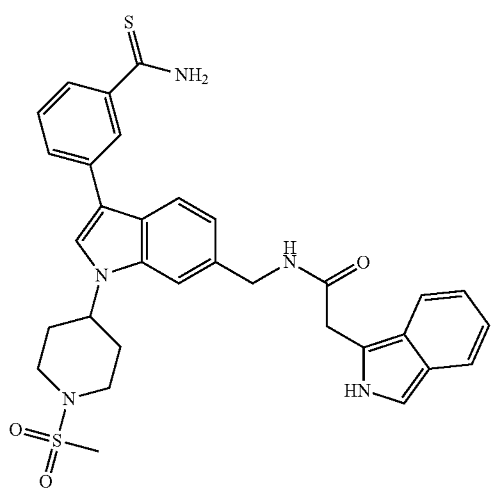 [SMILES: CS(=O)(=O)N1CCC(n2cc(-c3cccc(C(N)=S)c3)c3ccc(CNC(=O)Cc4[nH]cc5ccccc45)cc32)CC1] | | 599.20 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 295 | 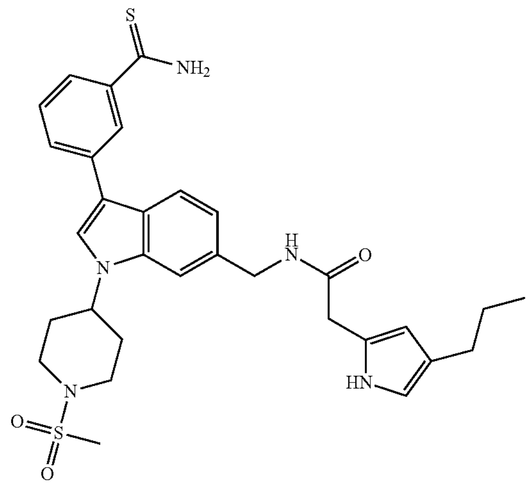 [SMILES: CCCc1c[nH]c(CC(=O)NCc2ccc3c(-c4cccc(C(N)=S)c4)cn(C4CCN(S(C)(=O)=O)CC4)c3c2)c1] | 591.79 | |
| 296 | 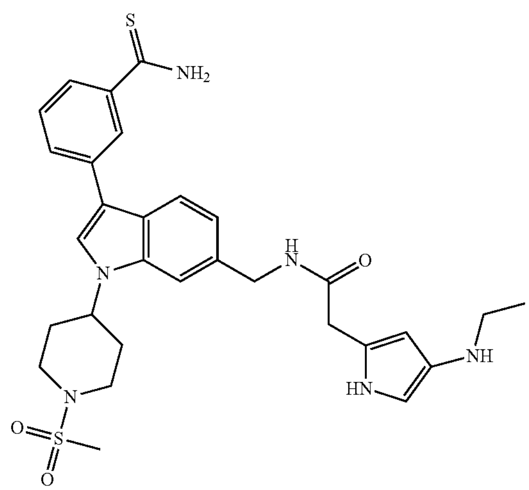 [SMILES: CCNc1c[nH]c(CC(=O)NCc2ccc3c(-c4cccc(C(N)=S)c4)cn(C4CCN(S(C)(=O)=O)CC4)c3c2)c1] | 592.23 | |
| 297 | 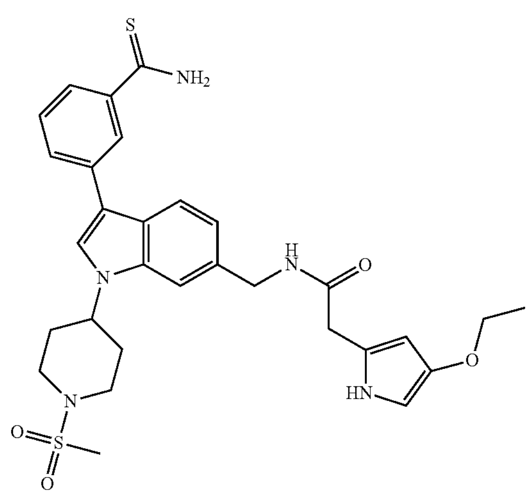 [SMILES: CCOc1c[nH]c(CC(=O)NCc2ccc3c(-c4cccc(C(N)=S)c4)cn(C4CCN(S(C)(=O)=O)CC4)c3c2)c1] | 593.21 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 298 | 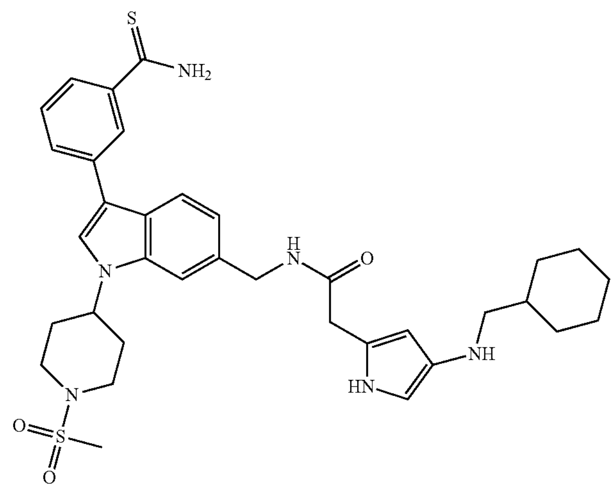 [SMILES: CS(=O)(=O)N1CCC(n2cc(-c3cccc(C(N)=S)c3)c3ccc(CNC(=O)Cc4cc(NCC5CCCCC5)c[nH]4)cc32)CC1] | 660.29 | |
| 299 | 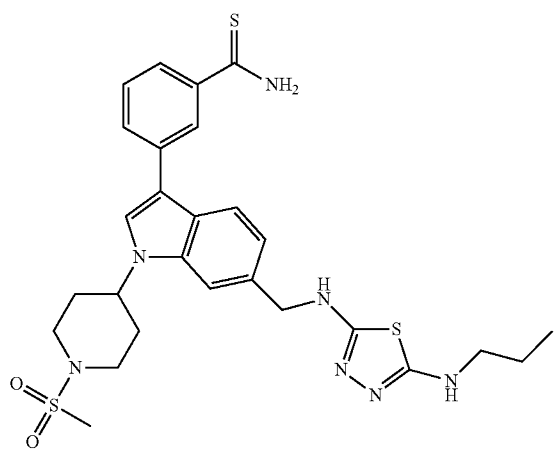 [SMILES: CCCNc1nnc(NCc2ccc3c(-c4cccc(C(N)=S)c4)cn(C4CCN(S(C)(=O)=O)CC4)c3c2)s1] | 583.19 | |
| 300 | 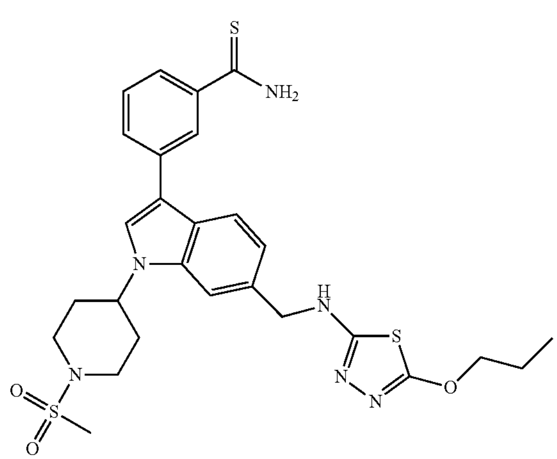 [SMILES: CCCOc1nnc(NCc2ccc3c(-c4cccc(C(N)=S)c4)cn(C4CCN(S(C)(=O)=O)CC4)c3c2)s1] | 584.17 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M$_w$ calc. (Da) | [MH]$^+$ found (Da) |
|---|---|---|---|
| 301 | 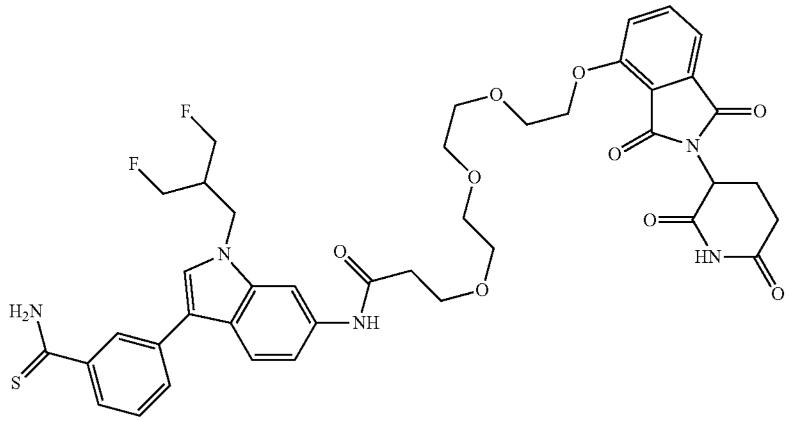 [SMILES: NC(=S)c1cccc(-c2cn(CC(CF)CF)c3cc(NC(=O)CCOCCOCCOCCOc4cccc5c4C(=O)N(C4CCC(=O)NC4=O)C5=O)ccc23)c1] | 819.27 | 820.2812 |
| 302 | 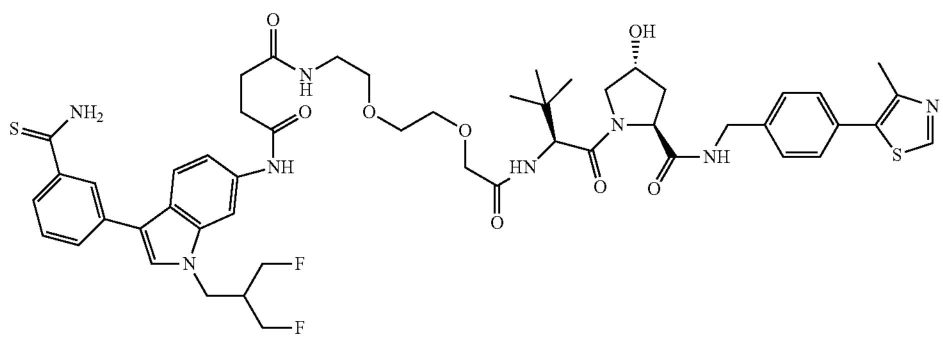 [SMILES: Cc1ncsc1-c1ccc(CNC(=O)[C@@H]2C[C@@H](O)CN2C(=O)[C@@H](NC(=O)COCCOCCNC(=O)CCC(=O)Nc2ccc3c(-c4cccc(C(N)=S)c4)cn(CC(CF)CF)c3c2)C(C)(C)C)cc1] | 1016.41 | 1017.4168 |
| 303 | 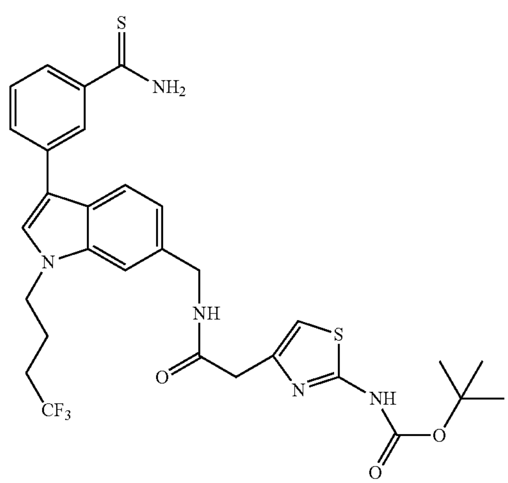 [SMILES: CC(C)(C)OC(=O)Nc1nc(CC(=O)NCc2ccc3c(-c4cccc(C(N)=S)c4)cn(CCCC(F)(F)F)c3c2)cs1] | 631.73 | 632.1969 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | M_w calc. (Da) | [MH]+ found (Da) |
|---|---|---|---|
| 304 | 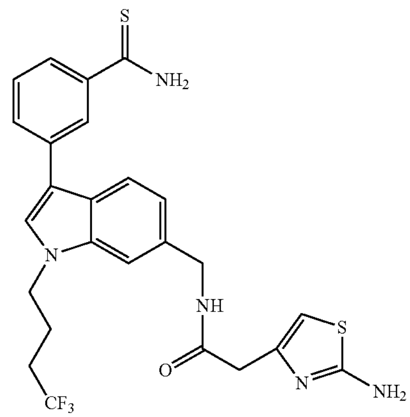 [SMILES: NC(=S)c1cccc(-c2cn(CCCC(F)(F)F)c3cc(CNC(=O)Cc4csc(N)n4)ccc23)c1] | 531.62 | 532.1447 |
| 305 | 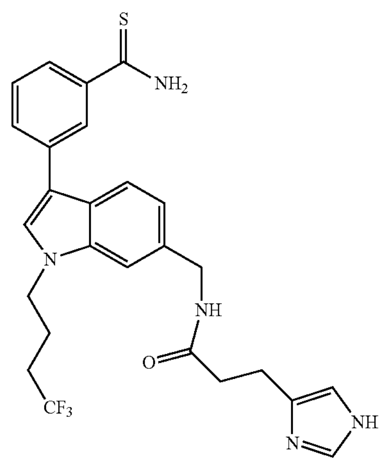 [SMILES: NC(=S)c1cccc(-c2cn(CCCC(F)(F)F)c3cc(CNC(=O)CCc4c[nH]cn4)ccc23)c1] | 513.58 | 514.1890 |
| 306 | 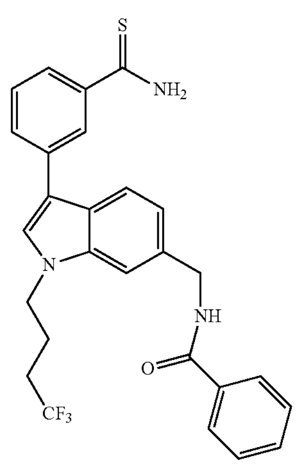 [SMILES: NC(=S)c1cccc(-c2cn(CCCC(F)(F)F)c3cc(CNC(=O)c4ccccc4)ccc23)c1] | 495.56 | 496.1660 |

TABLE 6-continued
Exemplary compounds of Formulas (I), (I-A), (I-B), (I-C), (I-D), (I-E), (I-F), (I-G), (I-H), (I-I) and/or (I-J).
| Number | Structure | $M_w$ calc. (Da) | $[MH]^+$ found (Da) |
|---|---|---|---|
| 307 | 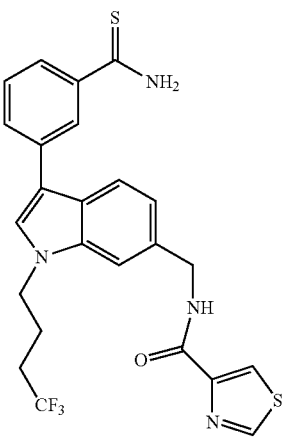 [SMILES: NC(=S)c1cccc(-c2cn(CCCC(F)(F)F)c3cc(CNC(=O)c4cscn4)ccc23)c1] | 502.57 | 503.1172 |
| 308 | 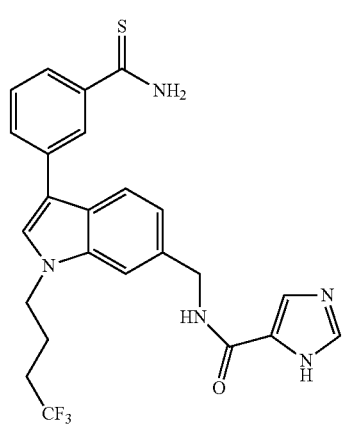 [SMILES: NC(=S)c1cccc(-c2cn(CCCC(F)(F)F)c3cc(CNC(=O)c4cnc[nH]4)ccc23)c1] | 485.53 | 486.1570 |
| 309 | 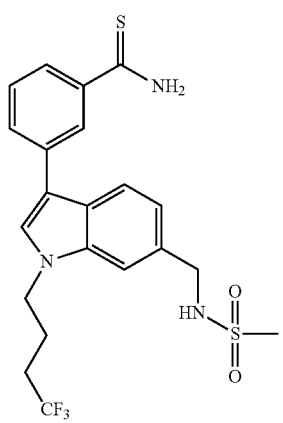 [SMILES: CS(=O)(=O)NCc1ccc2c(-c3cccc(C(N)=S)c3)cn(CCCC(F)(F)F)c2c1] | 469.54 | 470.1175 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 310 | 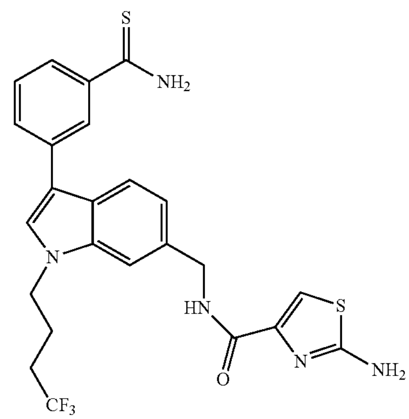 [SMILES: NC(=S)c1cccc(-c2cn(CCCC(F)(F)F)c3cc(CNC(=O)c4csc(N)n4)ccc23)c1] | 517.59 | 518.1298 |
| 311 | 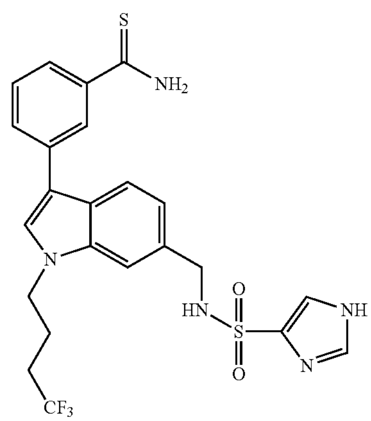 [SMILES: NC(=S)c1cccc(-c2cn(CCCC(F)(F)F)c3cc(CNS(=O)(=O)c4c[nH]cn4)ccc23)c1] | 521.58 | 522.1245 |
| 312 | 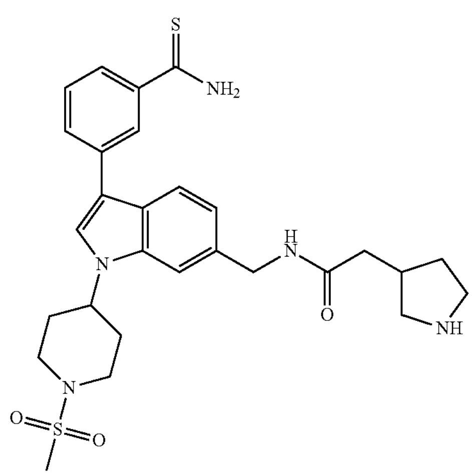 [SMILES: CS(=O)(=O)N1CCC(n2cc(-c3cccc(C(N)=S)c3)c3ccc(CNC(=O)CC4CCNC4)cc32)CC1] | 553.74 | 554.2259 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | [MH]+ found (Da) |
|---|---|---|---|
| 313 | 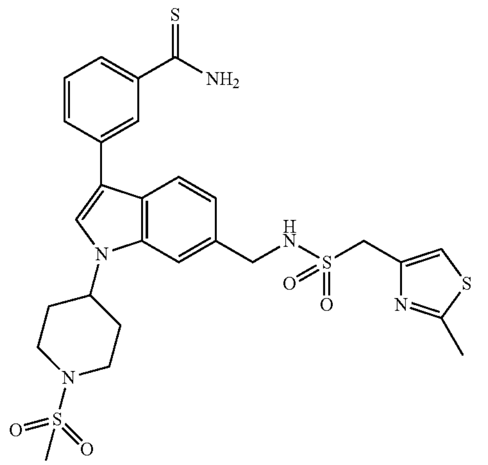 [SMILES: Cc1nc(CS(=O)(=O)NCc2ccc3c(-c4cccc(C(N)=S)c4)cn(C4CCN(S(C)(=O)=O)CC4)c3c2)cs1] | | 617.82 |
| 314 | 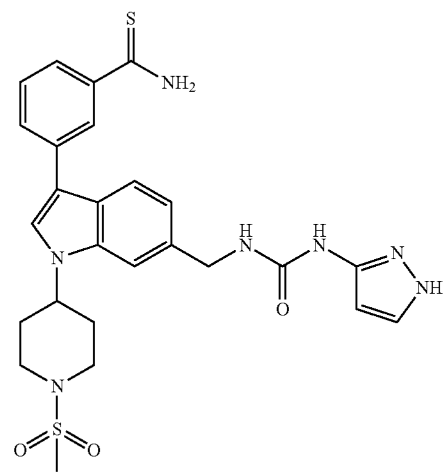 [SMILES: CS(=O)(=O)N1CCC(n2cc(-c3cccc(C(N)=S)c3)c3ccc(CNC(=O)Nc4cc[nH]n4)cc32)CC1] | | 551.68 |
| 315 | 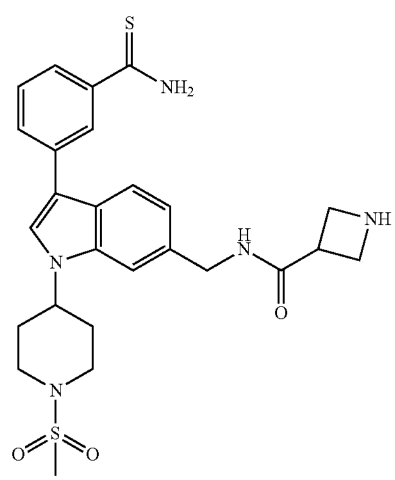 [SMILES: CS(=O)(=O)N1CCC(n2cc(-c3cccc(C(N)=S)c3)c3ccc(CNC(=O)C4CNC4)cc32)CC1] | | 525.69 |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 316 | 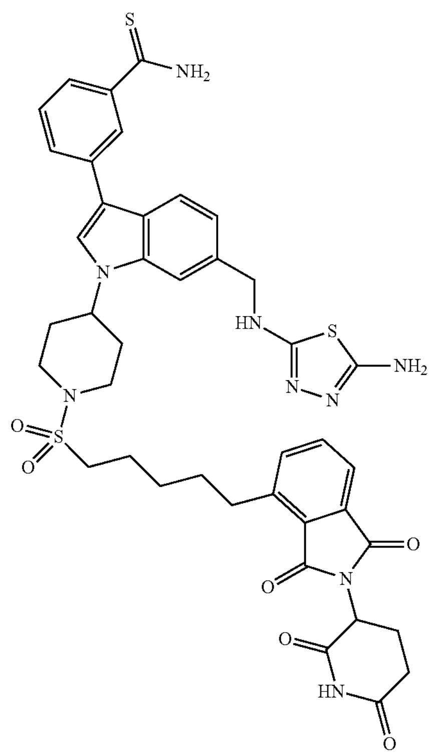 [SMILES: NC(=S)c1cccc(-c2cn(C3CCN(S(=O)(=O)CCCCCc4cccc5c4C(=O)N(C4CCC(=O)NC4=O)C5=O)CC3)c3cc(CNc4nnc(N)s4)ccc23)c1] | 853.25 | |
| 317 | 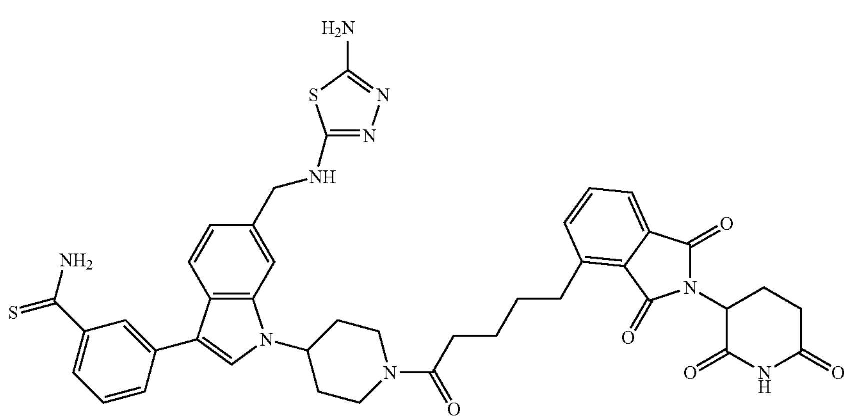 [SMILES: NC(=S)c1cccc(-c2cn(C3CCN(C(=O)CCCCc4cccc5c4C(=O)N(C4CCC(=O)NC4=O)C5=O)CC3)c3cc(CNc4nnc(N)s4)ccc23)c1] | 803.27 | |

TABLE 6-continued

Exemplary compounds of Formulas (I), (I-A), (I-B), (I-C), (I-D), (I-E), (I-F), (I-G), (I-H), (I-I) and/or (I-J).

| Number | Structure | $M_w$ calc. (Da) | $[MH]^+$ found (Da) |
|---|---|---|---|
| 318 | 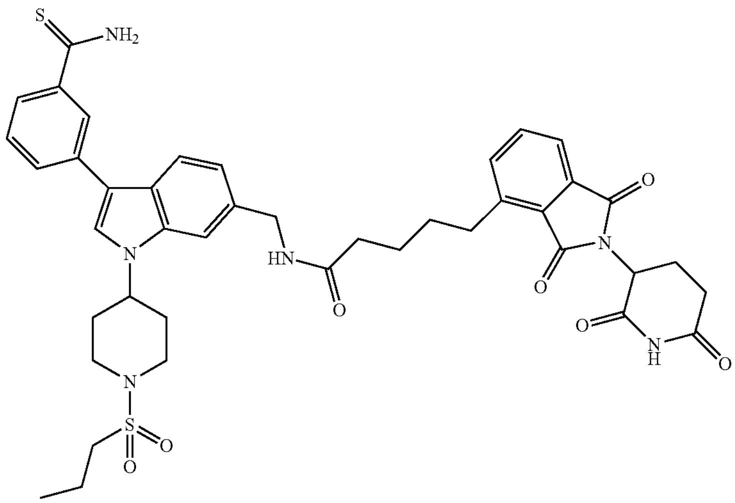 [SMILES: CCCS(=O)(=O)N1CCC(n2cc(-c3cccc(C(N)=S)c3)c3ccc(CNC(=O)CCCCc4cccc5c4C(=O)N(C4CCC(=O)NC4=O)C5=O)cc32)CC1] | 810.27 | |

In some embodiments, the substituents and functional groups of the compounds of Table 6 may be recombined within the Formulas (I), (I-A), (I-B), (I-C), (I-D), (I-E), (I-F), (I-G), (I-H), (I-I), and (I-J) to yield compounds within the scope herein.

A compound of any one of Formulas (I), (I-A), (I-B), (I-C), (I-D), (I-E), (I-F), (I-G), (I-H), (I-I), and (I-J) may be selected from compounds 319 to 324 listed in Table 7. Compounds of Formulas (I), (I-A), (I-B), (I-C), (I-D), (I-E), (I-F), (I-G), (I-H), (I-I) and/or (I-J) that are not listed in Table 7 are also within the scope herein.

TABLE 7

Exemplary compounds of Formulas (I), (I-A), (I-B), (I-C), (I-D), (I-E), (I-F), (I-G), (I-H), (I-I) and/or (I-J).

| 319 | | 592.23 | |
|---|---|---|---|

TABLE 7-continued
Exemplary compounds of Formulas (I), (I-A), (I-B), (I-C), (I-D), (I-E), (I-F), (I-G), (I-H), (I-I) and/or (I-J).
| 320 | 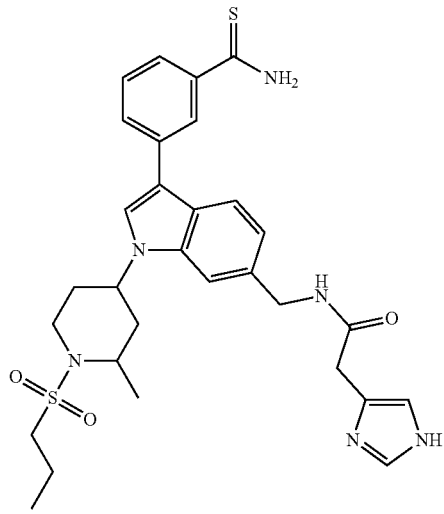 [SMILES: CCCS(=O)(=O)N1CCC(n2cc(-c3cccc(C(N)=S)c3)c3ccc(CNC(=O)Cc4c[nH]cn4)cc32)CC1C] | 592.23 |
| 321 | 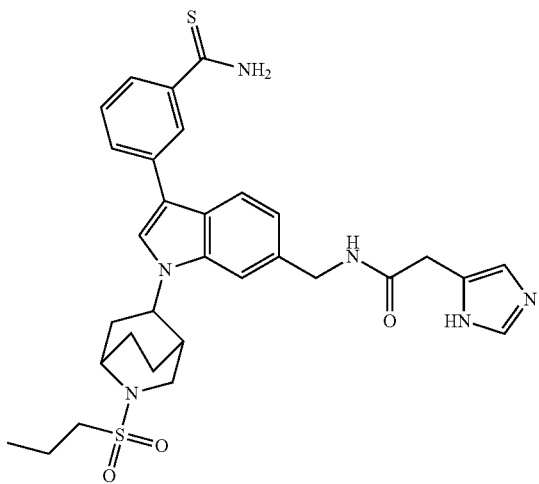 [SMILES: CCCS(=O)(=O)N1CC2CCC1CC2n1cc(-c2cccc(C(N)=S)c2)c2ccc(CNC(=O)Cc3cnc[nH]3)cc21] | 604.23 |
| 322 | 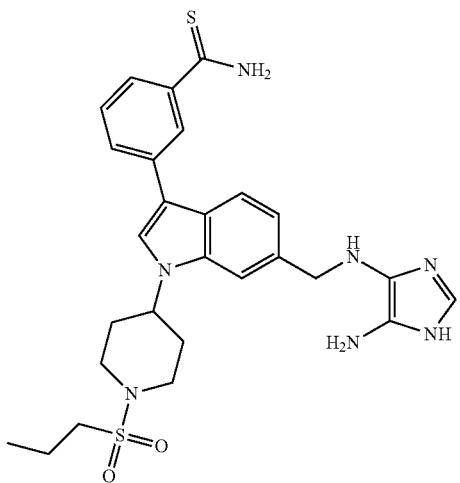 [SMILES: CCCS(=O)(=O)N1CCC(n2cc(-c3cccc(C(N)=S)c3)c3ccc(CNc4nc[nH]c4N)cc32)CC1] | 551.73 |

TABLE 7-continued

Exemplary compounds of Formulas (I), (I-A), (I-B), (I-C), (I-D), (I-E), (I-F), (I-G), (I-H), (I-I) and/or (I-J).

| 323 | 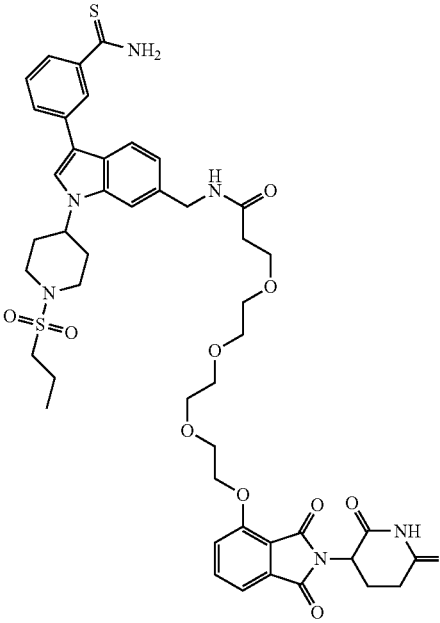 | 930.09 |
| 324 | 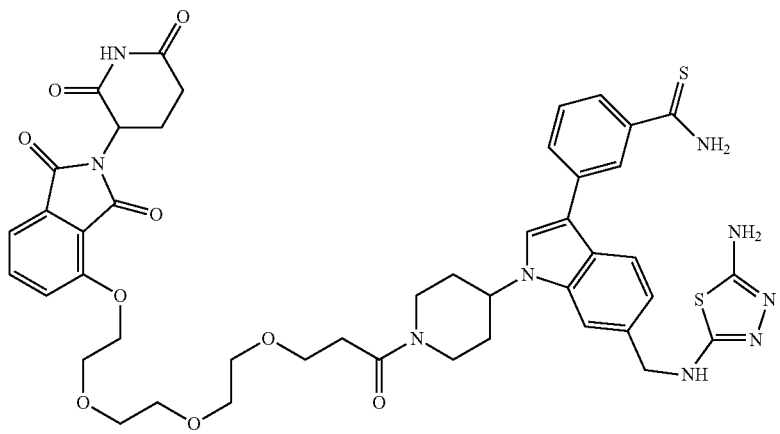 [SMILES: NC(=S)c1cccc(-c2cn(C3CCN(C(=O)CCOCCOCCOCCOc4cccc5c4C(=O)N(C4CCC(=O)NC4=O)C5=O)CC3)c3cc(CNc4nnc(N)s4)ccc23)c1] | 923.31  924.30 |

In some embodiments, the substituents and functional groups of the compounds of Table 7 may be recombined within the Formulas (I), (I-A), (I-B), (I-C), (I-D), (I-E), (I-F), (I-G), (I-H), (I-I), and (I-J) to yield compounds within the scope herein.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some embodiments, compounds may exist as tautomers. All tautomers are included within the formulas described herein.

Unless specified otherwise, divalent variables or groups described herein may be attached in the orientation in which they are depicted or they may be attached in the reverse orientation.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, etc. The solvated forms of the compounds presented herein are also considered to be disclosed herein.

In some embodiments, compounds or salts described herein may be prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry*, Vol. 41, 395-407, 2006).

The compounds described herein may be labeled isotopically (e.g. with a radioisotope) or by other means, including, but not limited to, the use of chromophores or fluorescent moieties, bioluminescent labels, photoactivatable or chemiluminescent labels, affinity labels (e.g. biotin), degradation tags (e.g. thalidomide conjugates (e.g., compounds 198, 199, etc.), VHL ligand conjugates (e.g., compound 302), etc.).

Compounds and salts described herein include isotopically-labeled compounds. In general, isotopically-labeled compounds are identical to those recited in the various formulae and structures presented herein, but for the fact that one or more atoms are replaced by an atom having an atomic mass or mass number different from the atomic mass or mass number most common in nature. Examples of isotopes that can be incorporated into the present compounds include isotopes of hydrogen, carbon, nitrogen, oxygen, fluorine and chlorine, for example, $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of any one of Formulas (I), (I-A), (I-B), (I-C), (I-D), (I-E), (I-F), (I-G), (I-H), (I-I), and (I-J), with any suitable substituents and functional groups disclosed herein, are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Pharmaceutical Compositions

In certain embodiments, compounds or salts of any one of Formulas (I), (I-A), (I-B), (I-C), (I-D), (I-E), (I-F), (I-G), (I-H), (I-I), and (I-J), with any suitable substituents and functional groups disclosed herein, are combined with one or more additional agents to form pharmaceutical compositions. Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound or salt of any one of Formulas (I), (I-A), (I-B), (I-C), (I-D), (I-E), (I-F), (I-G), (I-H), (I-I), and (I-J), with any suitable substituents and functional groups disclosed herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds or salts of any one of Formulas (I), (I-A), (I-B), (I-C), (I-D), (I-E), (I-F), (I-G), (I-H), (I-I), and (I-J), with any suitable substituents and functional groups disclosed herein, can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of any one of Formulas (I), (I-A), (I-B), (I-C), (I-D), (I-E), (I-F), (I-G), (I-H), (I-I), and (I-J), with any suitable substituents and functional groups disclosed herein, can be formulated into any suitable dosage form, including but not limited to, aqueous oral dispersions, liquids, gels, syrups, elixirs, slurries, suspensions, aerosols, fast melt formulations, effervescent formulations, lyophilized formulations, tablets, powders, pills, dragees, and capsules.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of any one of Formulas (I), (I-A), (I-B), (I-C), (I-D), (I-E), (I-F), (I-G), (I-H), (I-I), and (I-J), with any suitable substituents and functional groups disclosed herein, as an active ingredient in free-acid or free-base form, or in a pharmaceutically acceptable salt form.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipients with one or more of the compounds or salts of any one of Formulas (I), (I-A), (I-B), (I-C), (I-D), (I-E), (I-F), (I-G), (I-H), (I-I), and (I-J), with any suitable substituents and functional groups disclosed herein, optionally grinding the resulting mixture, and processing the mixture of granules, after adding suitable auxiliaries, if desired, to obtain tablets, pills, or capsules.

Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound or salt of any one of Formulas (I), (I-A), (I-B), (I-C), (I-D), (I-E), (I-F), (I-G), (I-H), (I-I), and (I-J), with any suitable substituents and functional groups disclosed herein, with one or more pharmaceutical excipients to form a bulk blend composition. When referring to these bulk blend compositions as homogeneous, it is meant that the particles of the compound or salt of any one of Formulas (I), (I-A), (I-B), (I-C), (I-D), (I-E), (I-F), (I-G), (I-H), (I-I), and (I-J), with any suitable substituents and functional groups disclosed herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound of any one of Formulas (I), (I-A), (I-B), (I-C), (I-D), (I-E), (I-F), (I-G), (I-H), (I-I), and (I-J), with any suitable substituents and functional groups disclosed herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound or salt of any one of Formulas (I), (I-A), (I-B), (I-C), (I-D), (I-E), (I-F), (I-G), (I-H), (I-I), and (I-J), with any suitable substituents and functional groups disclosed herein, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound or salt of any one of Formulas (I), (I-A), (I-B), (I-C), (I-D), (I-E), (I-F), (I-G), (I-H), (I-I), and (I-J), with any suitable substituents and functional groups disclosed herein, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound or salt of any one of Formulas (I), (I-A), (I-B), (I-C), (I-D), (I-E), (I-F), (I-G), (I-H), (I-I), and (I-J), with any suitable substituents and functional groups disclosed herein, are solid dispersions. Methods of producing such solid dispersions include, but are not limited to, for example, U.S. Pat. Nos. 4,343,789, 5,340,591, 5,456, 923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

In some embodiments, pharmaceutical formulations are provided that include particles of the compounds or salt of any one of Formulas (I), (I-A), (I-B), (I-C), (I-D), (I-E), (I-F), (I-G), (I-H), (I-I), and (I-J), with any suitable substituents and functional groups disclosed herein, and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960, 563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391, 452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229, 447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound or salt of any one of Formulas (I), (I-A), (I-B), (I-C), (I-D), (I-E), (I-F), (I-G), (I-H), (I-I), and (I-J), with any suitable substituents and functional groups disclosed herein; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, or the like. In suppository forms of the compositions, a low-melting wax such as, but not limited to, a mixture of fatty acid glycerides, optionally in combination with cocoa butter is first melted.

Generally, an agent, such as a compound of any one of Formulas (I), (I-A), (I-B), (I-C), (I-D), (I-E), (I-F), (I-G), (I-H), (I-I), and (I-J), with any suitable substituents and functional groups disclosed herein, is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

In some embodiments, the compositions described herein are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non-aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self-emulsifying solids and self-emulsifying semisolids.

The pharmaceutical and/or therapeutic formulations, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Dosing and administration regimes are tailored by the clinician, or others skilled in the pharmacological arts, based upon well-known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone. Dosing may be once per day or multiple times per day for one or more consecutive days.

Methods of Treatment

The present disclosure provides compounds and methods for inhibiting the activity of ASH1L. In certain embodiments, the disclosure provides compounds that bind to and/or inhibit ASH1L activity.

Inhibition of ASH1L activity may be assessed and demonstrated by a wide variety of ways known in the art. Non-limiting examples include measure (a) a direct decrease in ASH1L activity; (b) a decrease in cell proliferation and/or cell viability; (c) an increase in cell differentiation; (d) a decrease in the levels of downstream targets of ASH1L activity; and (e) decrease in tumor volume and/or tumor volume growth rate. Kits and commercially available assays can be utilized for determining one or more of the above.

The disclosure provides compounds and methods for treating a subject suffering from a disease, comprising administering a compound or salt described herein, for example, a compound or salt of any of Formulas (I), (I-A), (I-B), (I-C), (I-D), (I-E), (I-F), (I-G), (I-H), (I-I), and (I-J), with any suitable substituents and functional groups disclosed herein, to the subject. In certain embodiments, the disease is selected from a disease associated with ASH1L expression (e.g., aberrant expression, overexpression, etc.) and/or activity (e.g., cancer). In certain embodiments, the disease is mediated by ASH1L activity and/or expression (e.g., aberrant expression, overexpression, etc.). In certain embodiments, the disease is leukemia, hematologic malignancies, solid tumor cancer, glioma, other cancers, muscular dystrophy, liver fibrosis, etc.

In some embodiments, the disclosure provides a method for treating cancer in a subject, comprising administering a compound or salt described herein, for example, a compound or salt of any of Formulas (I), (I-A), (I-B), (I-C), (I-D), (I-E), (I-F), (I-G), (I-H), (I-I), and (I-J), with any suitable substituents and functional groups disclosed herein, to the subject. In some embodiments, the cancer is mediated by a ASH1L expression (e.g., aberrant expression, overexpression, etc.) and/or activity. In certain embodiments, the cancer is leukemia, breast cancer, prostate cancer, pancreatic cancer, lung cancer, thyroid cancer, liver cancer, skin cancer, or a brain tumor.

In certain embodiments, the disclosure provides method of treating a disease in a subject, wherein the method comprises determining if the subject has an ASH1l-mediated condition (e.g., cancer) and administering to the subject a therapeutically effective dose of a compound or salt described herein, for example, a compound or salt of any one of Formulas (I), (I-A), (I-B), (I-C), (I-D), (I-E), (I-F), (I-G), (I-H), (I-I), and (I-J), with any suitable substituents and functional groups disclosed herein.

In some embodiments, ASH1L expression (e.g., aberrant expression, overexpression, etc.) and/or activity has been identified in hematological malignancies, e.g., cancers that affect blood, bone marrow and/or lymph nodes. Accordingly, certain embodiments are directed to administration of a compound or salt described herein, for example, a compound or salt of any of any one of Formulas (I), (I-A), (I-B), (I-C), (I-D), (I-E), (I-F), (I-G), (I-H), (I-I), and (I-J), with any suitable substituents and functional groups disclosed herein, to a subject with a hematological malignancy. Such malignancies include, but are not limited to, leukemias and lymphomas. For example, the presently disclosed compounds can be used for treatment of diseases such as ALL, AML, Chronic lymphocytic leukemia (CLL), small lymphocytic lymphoma (SLL), Chronic myelogenous leukemia (CML), Acute monocytic leukemia (AMoL), hairy cell leukemia, and/or other leukemias. In certain embodiments, the compounds or salts of the disclosure can be used for treatment of lymphomas such as all subtypes of Hodgkins lymphoma or non-Hodgkins lymphoma.

Determining whether a tumor or cancer expresses (e.g., overexpresses, aberrantly expresses, etc.) ASH1L can be undertaken by assessing the nucleotide sequence encoding ASH1L or by assessing the amino acid sequence of ASH1L. Methods for detecting an ASH1L nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. Methods for detecting an ASH1L protein are known by those of skill in the art. These methods include, but are not limited to, detection using a binding agent, e.g., an antibody, specific for ASH1L, protein electrophoresis and Western blotting, and direct peptide sequencing.

Methods for determining whether a tumor or cancer expresses (e.g., overexpresses, aberrantly expresses, etc.) ASH1L or is mediated by ASH1L activity can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

In certain embodiments, the disclosure provides a method of inhibiting ASH1L activity in a sample, comprising administering the compound or salt described herein to said sample comprising ASH1L.

The disclosure provides methods for treating a disease by administering a compound or salt of any one of Formulas (I), (I-A), (I-B), (I-C), (I-D), (I-E), (I-F), (I-G), (I-H), (I-I), and (I-J), with any suitable substituents and functional groups disclosed herein, to a subject suffering from the disease, wherein the compound binds ASH1L and/or inhibits ASH1L activity. In certain embodiments, the compound covalently binds to ASH1L. In certain embodiments, the compound noncovalently binds to ASH1L.

The disclosure also relates to a method of treating a hyperproliferative disorder in a mammal that comprises administering to the mammal a therapeutically effective amount of a compound or salt of any one of Formulas (I), (I-A), (I-B), (I-C), (I-D), (I-E), (I-F), (I-G), (I-H), (I-I), and (I-J), with any suitable substituents and functional groups disclosed herein. In some embodiments, the method relates to the treatment of cancer such as acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some cases, the method relates to the treatment of leukemia, hematologic malignancy, solid tumor cancer, prostate cancer, e.g., castration-resistant prostate cancer, breast cancer, Ewing's sarcoma, bone sarcoma, primary bone sarcoma, T-cell prolymphocyte leukemia, glioma, glioblastoma, liver cancer, e.g., hepatocellular carcinoma, or diabetes.

Subjects that can be treated with compounds of the invention, or pharmaceutically acceptable salt, ester, prodrug, solvate, tautomer, stereoisomer, isotopologue, hydrate or derivative of the compounds, according to the methods of this invention include, for example, subjects that have been diagnosed as having acute myeloid leukemia, acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, leukemia, hematologic malignancy, solid tumor cancer, prostate cancer, castration-resistant prostate cancer, breast cancer, Ewing's sarcoma, bone sarcoma, primary bone sarcoma, T-cell prolymphocyte leukemia, glioma, glioblastoma, hepatocellular carcinoma, liver cancer, or diabetes. In some embodiments subjects that are treated with the compounds of the invention include subjects that have been diagnosed as having a non-cancerous hyperproliferative disorder such as benign hyperplasia of the skin, e.g., psoriasis, restenosis, or prostate, e.g., benign prostatic hypertrophy (BPH).

The invention further provides methods of inhibiting ASH1L activity, by contacting the ASH1L with an effective amount of a compound or salt of any one of Formulas (I), (I-A), (I-B), (I-C), (I-D), (I-E), (I-F), (I-G), (I-H), (I-I), and (I-J), with any suitable substituents and functional groups disclosed herein (e.g., by contacting a cell, tissue, or organ that expresses ASH1L). In some embodiments, the invention provides methods of inhibiting ASH1L activity in subject including but not limited to rodents and mammals, e.g., humans, by administering into the subject an effective amount of a compound or salt of any one of Formulas (I), (I-A), (I-B), (I-C), (I-D), (I-E), (I-F), (I-G), (I-H), (I-I), and (I-J), with any suitable substituents and functional groups disclosed herein. In some embodiments, the percentage inhibition exceeds 25%, 30%, 40%, 50%, 60%, 70%, 80%, or 90%.

In some embodiments, the disclosure provides methods of inhibiting ASH1L activity in a cell by contacting the cell with an amount of a compound of the invention sufficient to inhibit the activity. In some embodiments, the invention provides methods of inhibiting ASH1L activity in a tissue by contacting the tissue with an amount of a compound or salt of any one of Formulas (I), (I-A), (I-B), (I-C), (I-D), (I-E), (I-F), (I-G), (I-H), (I-I), and (I-J), with any suitable substituents and functional groups disclosed herein, sufficient to inhibit the ASH1L activity in the tissue. In some embodiments, the invention provides methods of inhibiting ASH1L activity in an organism (e.g., mammal, human, etc.) by contacting the organism with an amount of a compound or salt of any one of Formulas (I), (I-A), (I-B), (I-C), (I-D), (I-E), (I-F), (I-G), (I-H), (I-I), and (I-J), with any suitable substituents and functional groups disclosed herein, sufficient to inhibit the i ASH1L activity in the organism.

The compositions containing the compounds or salts thereof described herein can be administered for prophylactic and/or therapeutic treatments. In therapeutic applications, the compositions are administered to a patient already suffering from a disease, in an amount sufficient to cure or at least partially arrest the symptoms of the disease. Amounts effective for this use will depend on the severity and course of the disease, previous therapy, the patient's health status, weight, and response to the drugs, and the judgment of the treating clinician.

In prophylactic applications, compositions containing the compounds or salts thereof described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating clinician.

In the case wherein the patient's condition does not improve, upon the clinician's discretion the administration of the compounds may be administered chronically, that is, for an extended period of time, including throughout the duration of the patient's life in order to ameliorate or otherwise control or limit the symptoms of the patient's disease.

In the case wherein the patient's status does improve, upon the clinician's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Therapies

Provided herein are methods for combination therapies in which an agent known to modulate other pathways, or other components of the same pathway, or even overlapping sets of target enzymes are used in combination with a compound or salt of any one of Formulas (I), (I-A), (I-B), (I-C), (I-D), (I-E), (I-F), (I-G), (I-H), (I-I), and (I-J), with any suitable substituents and functional groups disclosed herein. In one aspect, such therapy includes but is not limited to the combination of one or more compounds of the invention with chemotherapeutic agents, targeted agents, therapeutic antibodies, and radiation treatment, to provide a synergistic or additive therapeutic effect.

In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound or salt of any one of Formulas (I), (I-A), (I-B), (I-C), (I-D), (I-E), (I-F), (I-G), (I-H), (I-I), and (I-J), with any suitable substituents and functional groups disclosed herein, is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis and judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the clinician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound or salt of any one of Formulas (I), (I-A), (I-B), (I-C), (I-D), (I-E), (I-F), (I-G), (I-H), (I-I), and (I-J), with any suitable substituents and functional groups disclosed herein, may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease, and the timing of administering the composition containing a compound can vary. Thus, for example, the compounds can be used as a prophylactic and can be administered continuously to subjects with a propensity to develop conditions or diseases in order to prevent the occurrence of the disease. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Particularly when the compounds and pharmaceutical compositions herein are used for treating cancer, they may be co-administered with one or more chemotherapeutics. Many chemotherapeutics are presently known in the art and can be used in combination with the compounds herein. In some embodiments, the chemotherapeutic is selected from the group consisting of mitotic inhibitors, alkylating agents, anti-metabolites, intercalating antibiotics, growth factor inhibitors, cell cycle inhibitors, enzyme inhibitors, topoisomerase inhibitors, protein-protein interaction inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylomithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Embodiments herein further relate to methods for using a compound or salt of any of Formulas (I), (I-A), (I-B), (I-C), (I-D), (I-E), (I-F), (I-G), (I-H), (I-I), and (I-J), with any suitable substituents and functional groups disclosed herein, or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Rec-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions herein are also used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Other suitable therapeutic agents for coadministration with compounds herein also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, (3-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated for co-administration with compounds and compositions herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated for co-administration with compounds and compositions herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound herein are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein may be used in combination with the agents disclosed herein or other suitable agents, depending on the condition being treated. Hence, in some embodiments the one or more compounds herein will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

In some embodiments, a compound described herein is co-administered with another therapeutic agent effective in treating leukemia and/or other cancers. In some embodiments, a compound described herein is co-administered with one or more therapeutic agents approved for the treatment of Acute Lymphoblastic Leukemia (ALL), for example: ABITREXATE (Methotrexate), ADRIAMYCIN PFS (Doxorubicin Hydrochloride), ADRIAMYCIN RDF (Doxorubicin Hydrochloride), ARRANON (Nelarabine), Asparaginase *Erwinia chrysanthemi*, CERUBIDINE (Daunorubicin Hydrochloride), CLAFEN (Cyclophosphamide), CLOFARABINE, CLOFAREX (Clofarabine), CLOLAR (Clofarabine), Cyclophosphamide, Cytarabine, CYTOSAR-U (Cytarabine), CYTOXAN (Cyclophosphamide), Dasatinib, Daunorubicin Hydrochloride, Doxorubicin Hydrochloride, Erwinaze (Asparaginase *Erwinia Chrysanthemi*), FOLEX (Methotrexate), FOLEX PFS (Methotrexate), GLEEVEC (Imatinib Mesylate), ICLUSIG (Ponatinib Hydrochloride), Imatinib Mesylate, MARQIBO (Vincristine Sulfate Liposome), Methotrexate, METHOTREXATE LPF (Methorexate), MEXATE (Methotrexate), MEXATE-AQ (Methotrexate), Nelarabine, NEOSAR (Cyclophosphamide), ONCASPAR (Pegaspargase), Pegaspargase, Ponatinib Hydrochloride, RUBIDOMYCIN (Daunorubicin Hydrochloride), SPRYCEL (Dasatinib), TARABINE PFS (Cytarabine), VINCASAR PFS (Vincristine Sulfate), Vincristine Sulfate, etc.

In some embodiments, a compound described herein is co-administered with one or more therapeutic agents approved for the treatment of Acute Myeloid Leukemia (AML), for example: ADRIAMYCIN PFS (Doxorubicin Hydrochloride), ADRIAMYCIN RDF (Doxorubicin Hydrochloride), Arsenic Trioxide, CERUBIDINE (Daunorubicin Hydrochloride), CLAFEN (Cyclophosphamide), Cyclophosphamide, Cytarabine, CYTOSAR-U (Cytarabine), CYTOXAN (Cyclophosphamide), Daunorubicin Hydrochloride, Doxorubicin Hydrochloride, NEOSAR (Cyclophosphamide), RUBIDOMYCIN (Daunorubicin Hydrochloride), TARABINE PFS (Cytarabine), TRISENOX (Arsenic Trioxide), VINCASAR PFS (Vincristine Sulfate), Vincristine Sulfate, etc.

In some embodiments, a compound described herein is co-administered with one or more therapeutic agents approved for the treatment of Chronic Lymphocytic Leukemia (CLL), for example: Alemtuzumab, AMBOCHLORIN (Chlorambucil), AMBOCLORIN (Chlorambucil), ARZERRA (Ofatumumab), Bendamustine Hydrochloride, CAMPATH (Alemtuzumab), CHLORAMBUCILCLAFEN (Cyclophosphamide), Cyclophosphamide, CYTOXAN (Cyclophosphamide), FLUDARA (Fludarabine Phosphate), Fludarabine Phosphate, LEUKERAN (Chlorambucil), INDOLIZIN (Chlorambucil), NEOSAR (Cyclophosphamide), Ofatumumab, TREANDA (Bendamustine Hydrochloride), etc.

In some embodiments, a compound described herein is co-administered with one or more therapeutic agents approved for the treatment of Chronic Myelogenous Leukemia (CML), for example: BOSULIF (Bosutinib), Bosutinib, CLAFEN (Cyclophosphamide), Cyclophosphamide, Cytarabine, CYTOSAR-U (Cytarabine), CYTOXAN (Cyclophosphamide), Dasatinib, GLEEVEC (Imatinib Mesylate), ICLUSIG (Ponatinib Hydrochloride), Imatinib Mesylate, NEOSAR (Cyclophosphamide), Nilotinib, Omacetaxine Mepesuccinate, Ponatinib Hydrochloride, SPRYCEL (Dasatinib), SYNRIBO (Omacetaxine Mepesuccinate), TARABINE PFS (Cytarabine), TASIGNA (Nilotinib), etc.

In some embodiments, a compound described herein is co-administered with one or more therapeutic agents approved for the treatment of Meningeal Leukemia, for example: CYTARABINE, CYTOSAR-U (Cytarabine), TARABINE PFS (Cytarabine), etc.

In some embodiments, a compound described herein is co-administered with one or more alkylating agents (e.g., for the treatment of cancer) selected from, for example, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

In some embodiments, a compound described herein is co-administered with one or more anti-metabolites (e.g., for the treatment of cancer) selected from, for example, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflomithine, ethynylcytidine, cytosine arabinoside, hydroxyurea, melphalan, nelarabine, nolatrexed, ocfosf [iota]te, disodium premetrexed, pentostatin, pelitrexol, raltitrexed, triapine, trimetrexate, vidarabine, vincristine, and vinorelbine; In some embodiments, a compound described herein is co-administered with one or more hormonal therapy agents (e.g., for the treatment of cancer) selected from, for example, exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel; In some embodiments, a compound described herein is co-administered with one or more cytotoxic topoisomerase inhibiting agents (e.g., for the treatment of cancer) selected from, for example, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, etc.

In some embodiments, a compound described herein is co-administered with one or more anti-angiogenic compounds (e.g., for the treatment of cancer) selected from, for example, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

In some embodiments, a compound described herein is co-administered with one or more antibodies (e.g., for the treatment of cancer) selected from, for example, trastuzumab, cetuximab, bevacizumab, rituximab, ticilimumab, ipilimumab, lumiliximab, catumaxomab, atacicept, oregovomab, and alemtuzumab.

In some embodiments, a compound described herein is co-administered with one or more VEGF inhibitors (e.g., for the treatment of cancer) selected from, for example, sorafenib, DAST, bevacizumab, sunitinib, recentin, axitinib, aflibercept, telatinib, brivanib alaninate, vatalanib, pazopanib, and ranibizumab.

In some embodiments, a compound described herein is co-administered with one or more EGFR inhibitors (e.g., for the treatment of cancer) selected from, for example, cetuximab, panitumumab, vectibix, gefitinib, erlotinib, and Zactima.

In some embodiments, a compound described herein is co-administered with one or more HER2 inhibitors (e.g., for the treatment of cancer) selected from, for example, lapatinib, tratuzumab, and pertuzumab; CDK inhibitor is selected from roscovitine and flavopiridol;

In some embodiments, a compound described herein is co-administered with one or more proteasome inhibitors (e.g., for the treatment of cancer) selected from, for example, bortezomib and carfilzomib.

In some embodiments, a compound described herein is co-administered with one or more serine/threonine kinase inhibitors (e.g., for the treatment of cancer), for example, MEK inhibitors and Raf inhibitors such as sorafenib.

In some embodiments, a compound described herein is co-administered with one or more tyrosine kinase inhibitors (e.g., for the treatment of cancer) selected from, for example, dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab.

In some embodiments, a compound described herein is co-administered with one or more androgen receptor antagonists (e.g., for the treatment of cancer) selected from, for example, nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide.

In some embodiments, a compound described herein is co-administered with one or more aromatase inhibitors (e.g., for the treatment of cancer) selected from, for example, anastrozole, letrozole, testolactone, exemestane, aminoglutethimide, and formestane.

In some embodiments, a compound described herein is co-administered with one or more other anti-cancer agents including, e.g., alitretinoin, ampligen, atrasentan bexarotene, borte-zomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin. In a preferred embodiment, the compounds of the present disclosure may be used in combination with chemotherapy (e.g., cytotoxic agents), anti-hormones and/or targeted therapies such as other kinase inhibitors, mTOR inhibitors and angiogenesis inhibitors.

In embodiments in which the compounds and pharmaceutical compositions herein are used for the treatment or prevention of non-cancer diseases and/or conditions, the compounds and pharmaceutical compositions herein may be co-administered with therapeutics and/or therapies known in the field to be appropriate for the treatment of such diseases and/or conditions.

Kits

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes a compound or salt of any of Formulas (I), (I-A), (I-B), (I-C), (I-D), (I-E), (I-F), (I-G), (I-H), (I-I), and (I-J), with any suitable substituents and functional groups disclosed herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

EXPERIMENTAL

The examples and preparations provided below further illustrate and exemplify the compounds provided herein and methods of preparing such compounds. It is to be understood that the scope of the present invention is not limited in any way by the scope of the following examples and preparations.

I. Chemical Syntheses

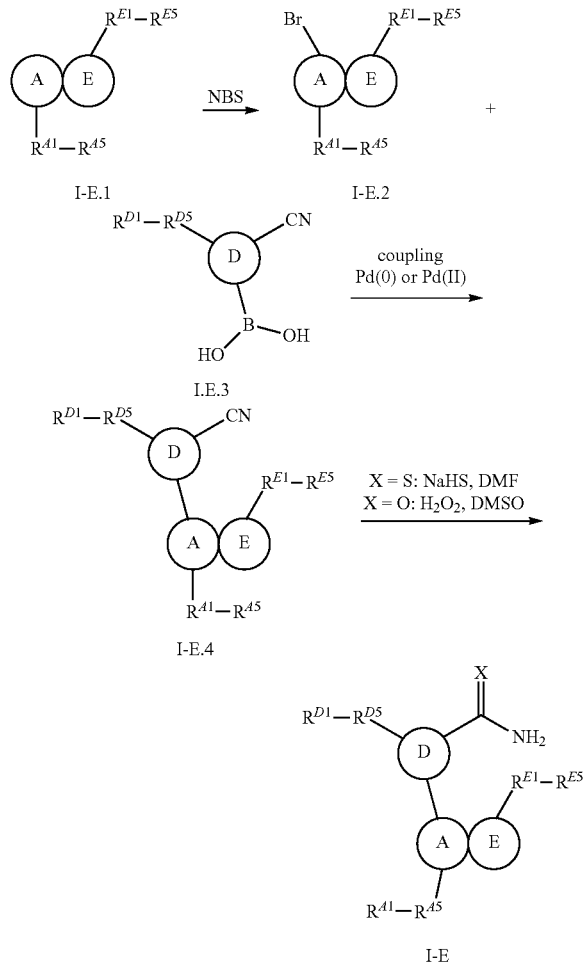

The first step of the general procedure for synthesis of compounds with Formula I-E is the introduction of halogen atom (i.e. bromine) as a substituent in the ring A. For selected compounds commercially available starting materials with bromine were used as I-E.2. Compound I-E.2 is then coupled with I-E.3, which contains a boronic acid (or boronic ester) moiety suitable for coupling reaction catalyzed by palladium complexes. Substituents $R^{A1}$-$R^{A5}$, $R^{D1}$-$R^{D5}$, $R^{E1}$-$R^{E5}$ can be optionally modified as illustrated in examples 2-7. After appropriate modifications, structure I-E.4 is further transformed to a thioamide or an amide I-E. Thioamides (X=S) are afforded by treatment I-E.4 with sodium hydrosulfide whereas amides (X=O) are obtained by treatment with hydrogen peroxide.

Example 1. Synthesis of 3-(1H-indol-4-yl)benzothioamide (81)

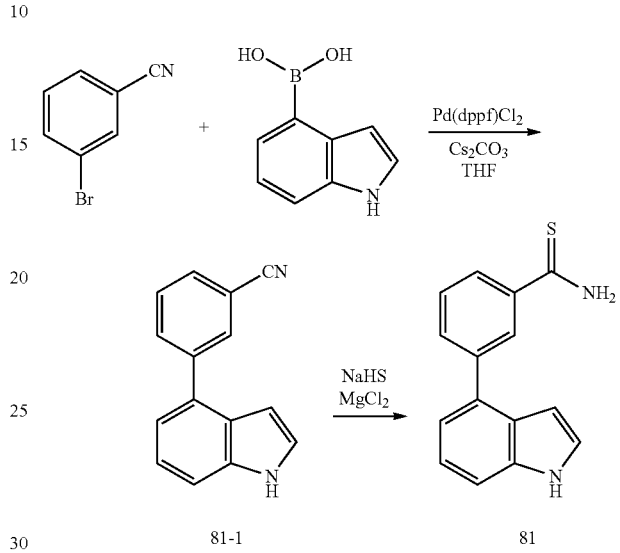

3-(1H-indol-4-yl)benzonitrile (81-1)

3-bromobenzonitrile(46 mg, 0.25 mmol) and (1H-indol-4-yl)boronic acid (60 mg, 0.37 mmol) was dissolved in THF (20 mL) and water (2 mL). Pd(dppf)Cl$_2$ (80 mg) was added along with cesium carbonate (300 mg). Mixture was refluxed for 30 min. THF was evaporated and crude product was purified using column chromatography (silica gel, hexane, ethyl acetate). 156 mg of compound were isolated (71% yield). $^1$H NMR (600 MHz, CDCl$_3$) δ ppm 6.61-6.68 (m, 1H) 7.16 (dd, J=7.3, 0.7 Hz, 1H) 7.27-7.33 (m, 2H) 7.46 (d, J=8.4 Hz, 1H) 7.55-7.60 (m, 1H) 7.65 (dt, J=7.7, 1.3 Hz, 1H) 7.93 (dt, J=7.7, 1.5 Hz, 1H) 7.98 (d, J=1.47 Hz, 1H) 8.38 (br. s., 1H); $^{13}$C NMR (150 MHz, CDCl$_3$) δ 111.3, 112.6, 119.1, 119.9, 122.4, 125.1, 125.9, 129.3, 130.4, 131.9, 132.2, 133.1, 136.3, 142.6;

3-(1H-indol-4-yl)benzothioamide (81)

3-(1H-indol-4-yl)benzonitrile (40 mg, 0.2 mmol) was dissolved in ethanol (2 mL) and NaHS was added (100 mg, 1.8 mmol). The mixture was stirred overnight. Solvent was evaporated and compound was purified using column chromatography (silica gel, hexane, ethyl acetate). 42 mg of material was obtained (94% yield). $^1$H NMR (600 MHz, ACETONITRILE-d$_3$) δ ppm 6.65-6.71 (m, 1H) 7.16-7.32 (m, 2H) 7.35-7.41 (m, 1H) 7.47-7.62 (m, 2H) 7.84-7.91-7.98 (m, 2H) 8.20 (br. s., 1H) 8.21-8.24 (m, 1H) 8.37 (br. s., 1H) 9.49-9.54 (m, 1H); $^{13}$C NMR (150 MHz, CDCl$_3$) δ 100.13, 113.8, 118.9, 121.5, 125, 125.5, 126.7, 128.2, 131.2, 132.3, 136.2, 139.5, 140.9, 202.1; HRMS (ESI) calculated for [M+H]+ 252.07, found: 253.0795.

Example 2. Synthesis of 3-(6-(hydroxymethyl)-1-(4,4,4-trifluorobutyl)-1H-indol-3-yl)benzothioamide (124)

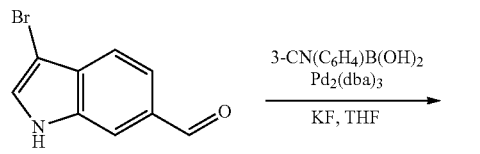

124-1

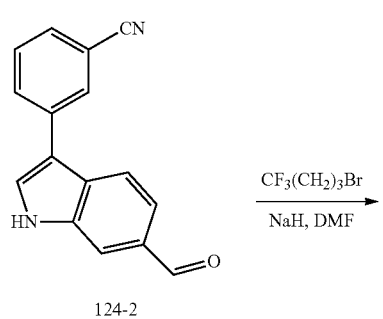

124-2

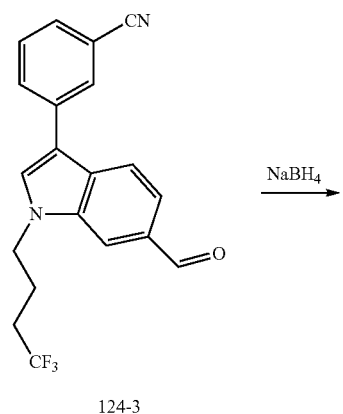

124-3

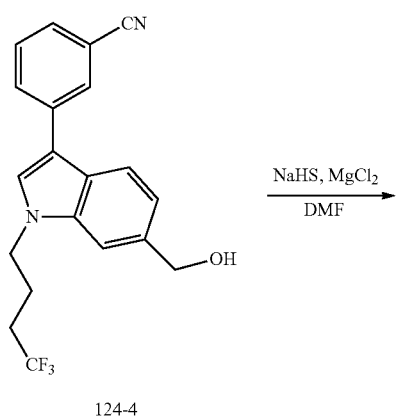

124-4

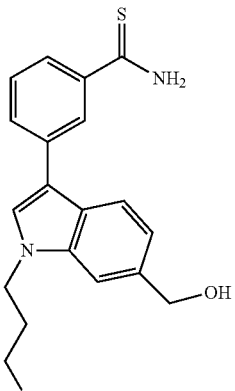

124

3-bromo-1H-indole-6-carbaldehyde (124-1)

At −20° C., to a DMF solution (20 mL) of 1H-indole-6-carbaldehyde (2.0 g, 13.8 mmol) was added a DMF solution (15 mL) of NBS (2.9 g, 15.2 mmol) over 20 min. The mixture was stirred and slowly warmed to rt over 5 h. The DMF was removed in vacuo, and the residue was purified by flash chromatography on silica gel with hexanes and ethyl acetate (0-50%) to give Compound 124-1 (2.9 g, 94%). $^1$H NMR (400 MHz, CD$_3$OD) δ 9.99 (s, 1H), 7.98 (s, 1H), 7.67 (dd, J=8.0, 1.3 Hz, 1H), 7.59 (m, 2H).

3-(6-formyl-1H-indol-3-yl)benzonitrile (124-2)

Under N$_2$ atmosphere, 3-Bromo-1H-indole-6-carbaldehyde (0.95 g, 4.26 mmol), (3-cyanophenyl)boronic acid (1.26 g, 8.57 mmol), tris(dibenzylideneacetone) dipalladium (O) (0.58 g, 0.63 mmol), tri-tert-butylphosphonium tetrafluoroborate (0.37 g, 1.27 mmol), anhydrous KF (0.74 g, 12.83 mmol), and anhydrous THF (24 mL) were mixed and stirred at 40° C. overnight. The mixture was cooled down to room temperature, filtered through celite and washed by ethyl acetate (100 mL). The filtrate was concentrated in vacuo, and the residue was purified by flash chromatography on silica gel with hexanes and ethyl acetate (0-60%) to give compound 124-2 (0.76 g, 72%). $^1$H NMR (400 MHz, CD$_3$OD) δ 10.0 (s, 1H), 8.02 (m, 4H), 7.91 (m, 1H), 7.72 (dd, J=8.0, 1.3 Hz, 1H), 7.62 (m, 2H).

3-(6-formyl-1-(4,4,4-trifluorobutyl)-1H-indol-3-yl)benzonitrile (124-3)

To an anhydrous DMF solution (11 mL) of 3-(6-Formyl-1H-indol-3-yl)benzonitrile (0.70 g, 2.85 mmol) at 0° C. under N$_2$ atmosphere was added NaH (0.22 g, 9.20 mmol) and stirred for 30 min. 4-Bromo-1,1,1-trifluorobutane (490 uL, 4.00 mmol) was added into the above mixture via syringe, and resulting mixture was stirred and gradually warmed to rt over 2 h. The mixture was worked up by ethyl acetate (40 mL) and water (10 mL, three times). The ethyl acetate layer was concentrated in vacuo and residue was purified by flash chromatography on silica gel with hexanes and ethyl acetate (0-40%) to give compound 124-3 (0.98 g, 97%). $^1$H NMR (400 MHz, CD$_3$CN) δ 10.1 (s, 1H), 7.94 (m, 2H), 7.85 (m, 2H), 7.71 (dd, J=8.0, 1.3 Hz, 1H), 7.55 (m, 3H), 4.35 (t, J=6.4 Hz, 2H), 2.20 (m, 4H).

3-(6-(hydroxymethyl)-1-(4,4,4-trifluorobutyl)-1H-indol-3-yl)benzonitrile (124-4)

At 0° C., to a methanol solution (5 mL) of 3-(6-formyl-1-(4,4,4-trifluorobutyl)-1H-indol-3-yl)benzonitrile (30 mg, 0.084 mmol) was added NaBH₄ (10 mg, 0.26 mmol), and stirred for 1 h. The methanol was removed in vacuo and residue was worked up by ethyl acetate (30 mL) and water (8 mL, three times). The ethyl acetate layer was concentrated in vacuo, and the residue was purified by flash chromatography on silica gel with hexanes and ethyl acetate (0-40%) to give compound 124-4 (25 mg, 84%). $^1$H NMR (400 MHz, CDCl₃) δ 7.84 (m, 1H), 7.80 (m, 2H), 7.47 (m, 2H), 7.37 (s, 1H), 7.19 (m, 1H), 7.16 (d, J=8.0 Hz, 1H), 4.80 (s, 2H), 4.21 (t, J=4.0 Hz, 2H), 2.09 (m, 4H). LCMS (ESI) calculated for [M-OH]⁺ 341, found 341.

3-(6-(hydroxymethyl)-1-(4,4,4-trifluorobutyl)-1H-indol-3-yl)benzothioamide (124)

3-(6-Formyl-1-(4,4,4-trifluorobutyl)-1H-indol-3-yl)benzonitrile (25 mg, 0.070 mmol), NaHS (78 mg, 1.40 mmol), MgCl₂ (130 mg, 1.40 mmol) and anhydrous DMF (4 mL) were mixed and stirred at rt for 3 h. The mixture was worked up by ethyl acetate (40 mL) and saturated NaHCO₃ solution (8 mL, ×3), and the ethyl acetate layer was concentrated in vacuo to give crude residue which was purified by flash chromatography on silica gel with DCM and methanol containing 5% of NH₄OH (methanol: 0-5%) to give compound 124 (15 mg, 55%). $^1$H NMR (600 MHz, CDCl₃) δ 8.18 (m, 1H), 7.91 (d, J=8.0 Hz, 1H), 7.80 (d, J=8.0 Hz, 1H), 7.71 (d, J=8.0 Hz, 1H), 7.48 (s, 1H), 7.42 (s, 1H), 7.33 (s, 1H), 7.21 (d, J=4.0 Hz, 1H), 4.28 (t, J=4.0 Hz, 2H), 2.18 (m, 4H). $^{13}$C NMR (150 MHz, CDCl₃) δ 204.1, 139.9, 136.8, 135.8, 135.7, 130.6, 124.9 (q, J=276 Hz), 120.0, 116.4, 108.1, 65.9, 45.0, 31.1 (q, J=28.5 Hz), 22.9 (q, J=3.0 Hz). HRMS (ESI) calculated for [M+H]⁺ 393.1243, found 393.1241.

Example 3. Synthesis of 3-(6-amino-1-(3-fluoro-2-(fluoromethyl)propyl)-1H-indol-3-yl)benzothioamide (126)

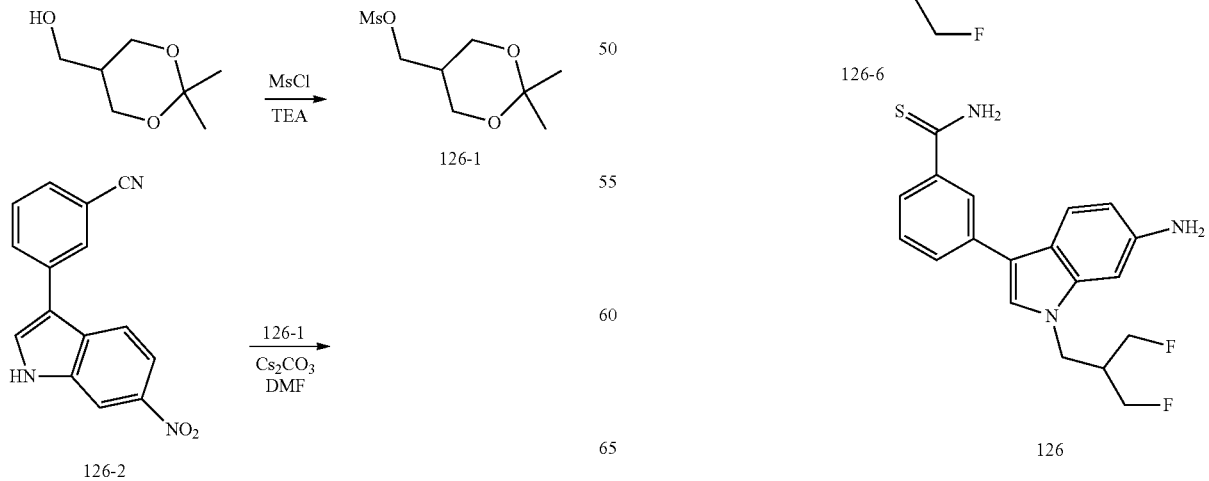

(2,2-dimethyl-1,3-dioxan-5-yl)methyl methanesulfonate (126-1)

(2,2-Dimethyl-1,3-dioxan-5-yl)methanol (50 mg, 0.34 mmol) was dissolved in DCM (0.4 mL). The mixture was cooled in to −78° C. Triethylamine (143 µL, 1 mmol) and methanesulfonyl chloride (32 µL, 0.4 mmol) were added sequentially. The reaction mixture stirred at −78° C.→0° C. After 3 hours, the reaction mixture was transferred to a separatory funnel, diluted with DCM, and washed with sodium bicarbonate. The organic layer was dried over sodium sulfate, filtered, and concentrated. $^1$H NMR (600 MHz, Acetone-$d_6$) δ ppm 1.35 (d, J=2.5 Hz, 3H) 1.42 (d, J=2.9 Hz, 3H) 2.03 (td, J=7.2, 3.3 Hz, 1H) 3.14 (d, J=3.3 Hz, 3H) 3.74-3.83 (m, 2H) 4.04-4.15 (m, 2H) 4.39 (dd, J=7.2, 3.1 Hz, 2H);

3-(6-nitro-1H-indol-3-yl)benzonitrile (126-2)

(3-cyanophenyl)boronic acid (805 mg, 5.5 mmol), 3-bromo-6-nitro-1H-indole (660 mg, 2.7 mmol) Pd$_2$(dba)$_3$ (512 mg 0.6 mmol), tri-t-butyl phosphonium tetrafluorborate (157 mg, 0.5 mmol) and KF (477 mg, 8.2 mmol) were combined in THF. The mixture was degassed. The reaction was kept under an argon atmosphere and heated to 40° C. The reaction mixture cooled to room temperature and was filtered through a celite pad, which was washed with ethyl acetate (60 mL). The filtrate was concentrated to yield a dark red solid. Purified by column chromatography. $^1$H NMR (600 MHz, ACETONITRILE-$d_3$) δ ppm 7.63-7.71 (m, 2H) 7.93-7.96 (m, 1H) 7.99-8.05 (m, 2H) 8.05-8.09 (m, 2H) 8.47-8.50 (m, 1H) 10.00-10.40 (bs, 1H);

3-(1-((2,2-dimethyl-1,3-dioxan-5-yl)methyl)-6-nitro-1H-indol-3-yl)benzonitrile (126-3)

3-(6-nitro-1H-indol-3-yl)benzonitrile (540 mg) and cesium carbonate were combined in dry DMF (4 mL). The dark red reaction mixture stirred at room temperature for several minutes. Then suspension of mesylate 126-1 in DMF (3 mL) was added. The flask stirred under argon, and was heated to 60° C. Water was added and compound was extracted by ethyl acetate. Water phase was extracted 2 times with ethyl acetate and combined organic phases were dried over sodium sulfate. After evaporation, crude compound was purified using column chromatography (silica gel, hexane-ethyl acetate). 470 mg (50%) of yellow solid was obtained $^1$H NMR (600 MHz, CDCl$_3$) δ ppm 1.51 (s, 3H) 1.55 (s, 3H) 2.06-2.13 (m, 1H) 3.59 (d, J=11.4 Hz, 2H) 4.13 (dd, J=12.3, 2.8 Hz, 2H) 4.61 (d, J=8.4 Hz, 2H) 7.55-7.67 (m, 3H) 7.86 (d, J=7.7 Hz, 1H) 7.88-7.95 (m, 2H) 8.12 (dd, J=8.8, 2.2 Hz, 1H) 8.46 (d, J=1.5 Hz, 1H); $^{13}$C NMR (150 MHz, CDCl$_3$) δ ppm 19.6, 28.3, 34.8, 46.1, 61.0, 98.9, 107.2, 113.3, 116.1, 116.1, 118.7, 119.6, 129.8, 130.1, 130.2, 130.8, 131.6, 132.0, 135.4, 135.8, 143.7;

3-(1-(3-hydroxy-2-(hydroxymethyl)propyl)-6-nitro-1H-indol-3-yl)benzonitrile (126-4)

3-(1-((2,2-dimethyl-1,3-dioxan-5-yl)methyl)-6-nitro-1H-indol-3-yl)benzonitrile (350 mg, 0.9 mmol) was dissolved in THF (4.5 mL) and 3M HCl (aq, 0.6 mL) was added. The reaction mixture stirred at room temperature for 1.5 hrs. The mixture was concentrated to remove THF, diluted with water and extracted with several portions of ethyl acetate. The combined organic layers were dried over sodium sulfate, filtered, and concentrated to yield a bright orange solid (280 mg, 89% yield). $^1$H NMR (600 MHz, ACETONITRILE-$d_3$) δ ppm 2.23 (td, J=12.0, 6.1 Hz, 1H) 2.96 (br. s., 2H) 3.51-3.63 (m, 4H) 4.45 (d, J=7.0 Hz, 2H) 7.62-7.72 (m, 2H) 7.96 (m, 1H) 7.99-8.11 (m, 4H) 8.60 (d, J=1.8 Hz, 1H); $^{13}$C NMR (150 MHz, ACETONITRILE-$d_3$) δ ppm 45.5, 46.2, 61.7, 109.1, 114.2, 116.4, 116.7, 120.2, 120.8, 131.1, 131.2, 131.8, 132.9, 135.3, 136.9, 137.4, 144.7;

3-(1-(3-fluoro-2-(fluoromethyl)propyl)-6-nitro-1H-indol-3-yl)benzonitrile (126-5)

To a solution of TEA·HF (93 uL, 0.57 mmol) in dry DCM (0.9 mL), Xtalfluor E (97 mg, 0.42 mmol) was added at 0° C. Then the solution of 3-(1-(3-hydroxy-2-(hydroxymethyl)propyl)-6-nitro-1H-indol-3-yl)benzonitrile (50 mg, 014 mmol) in DCM (0.5 mL) was added dropwise at 0° C. The mixture was stirred for 30 min at 0° C. and 2h at room temperature. Reaction was then quenched with sat. NaHCO$_3$ and water phase was extracted with DCM and organic phase was dried over sodium sulfate. Volatiles were evaporated and the residue was purified by column chromatography (silica gel, hexane-ethyl acetate) resulting in 29 mg of the product (57% yield). $^1$H NMR (600 MHz, DMSO-$d_6$) δ ppm 2.71-2.87 (m, 1H) 4.45-4.52 (m, 1H) 4.53-4.59 (m, 4H) 4.60-4.66 (m, 1H) 7.68-7.73 (m, 1H) 7.78 (d, J=7.7 Hz, 1H) 8.05 (dd, J=8.8, 1.8 Hz, 1H) 8.09 (d, J=8.1 Hz, 1H) 8.13-8.19 (m, 2H) 8.37 (m, 1H) 8.66 (d, J=1.8 Hz, 1H);

3-(6-amino-1-(3-fluoro-2-(fluoromethyl)propyl)-1H-indol-3-yl)benzonitrile (126-6)

To a solution of 3-(1-(3-fluoro-2-(fluoromethyl)propyl)-6-nitro-1H-indol-3-yl)benzonitrile (29 mg, 0.082 mmol) in acetone (1.6 m) water was added (320 uL) followed by ammonium chloride (176 mg) and zinc powder (106 mg). The mixture was stirred for 60 min. Acetone was evaporated, the residue was partitioned between ethyl acetate and conc. ammonia solution. Mixture was filtered through celite and organic phase was dried over MgSO4 and evaporated. Compound was used without further purification for the next step. LR-MS calcd for: [M+H+AcCN]$^+$: 367, found 367.10.

3-(6-amino-1-(3-fluoro-2-(fluoromethyl)propyl)-1H-indol-3-yl)benzothioamide (126)

To a solution of 3-(6-amino-1-(3-fluoro-2-(fluoromethyl)propyl)-1H-indol-3-yl)benzonitrile (23 mg, 0.072 mmol) in DMF (0.2 mL) sodium hydrosulfite (60 mg, 1 mmol) and magnesium chloride (101 mg, 0.5 mmol) were added at RT. Mixture was stirred for 2h. Water was added (0.4 mL) and product was extracted by ethyl acetate (3×5 mL). Organic phase was dried over sodium sulfate and evaporated. Yellow residue was purified using column chromatography (silica gel, hexane-ethyl acetate) affording 10 mg (39%) of thioamide. $^1$H NMR (600 MHz, DMSO-$d_6$) δ ppm 2.50-2.64 (m, 1H) 4.10 (d, J=7.7 Hz, 2H) 4.35-4.53 (m, 4H) 4.88 (s, 2H) 6.48 (dd, J=8.6, 1.7 Hz, 1H) 6.54 (d, J=1.1 Hz, 1H) 7.33-7.39 (m, 2H) 7.53 (d, J=8.4 Hz, 1H) 7.62 (d, J=8.1 Hz, 1H) 7.66 (d, J=8.1 Hz, 1H) 8.05 (m, 1H) 9.47 (br. s., 1H) 9.81 (br. s., 1H); $^{13}$C NMR (150 MHz, DMSO-$d_6$) δ ppm 40.7 (J=18 Hz), 42.2, 80.7, 81.8, 93.4, 110.7, 115.0, 117.0, 119.8, 124.0, 124.2, 124.9, 128.3, 128.6, 135.4, 138.6, 140.1, 144.8, 200.6 HR-MS [ESI, M+H$^+$] calcd for: C$_{19}$H$_{19}$F$_2$N$_3$S: 360.1346, found: 360.1341.

Example 4. Synthesis of 3-(6-amino-1-cyclopentyl-1H-indol-3-yl)benzothioamide (127)

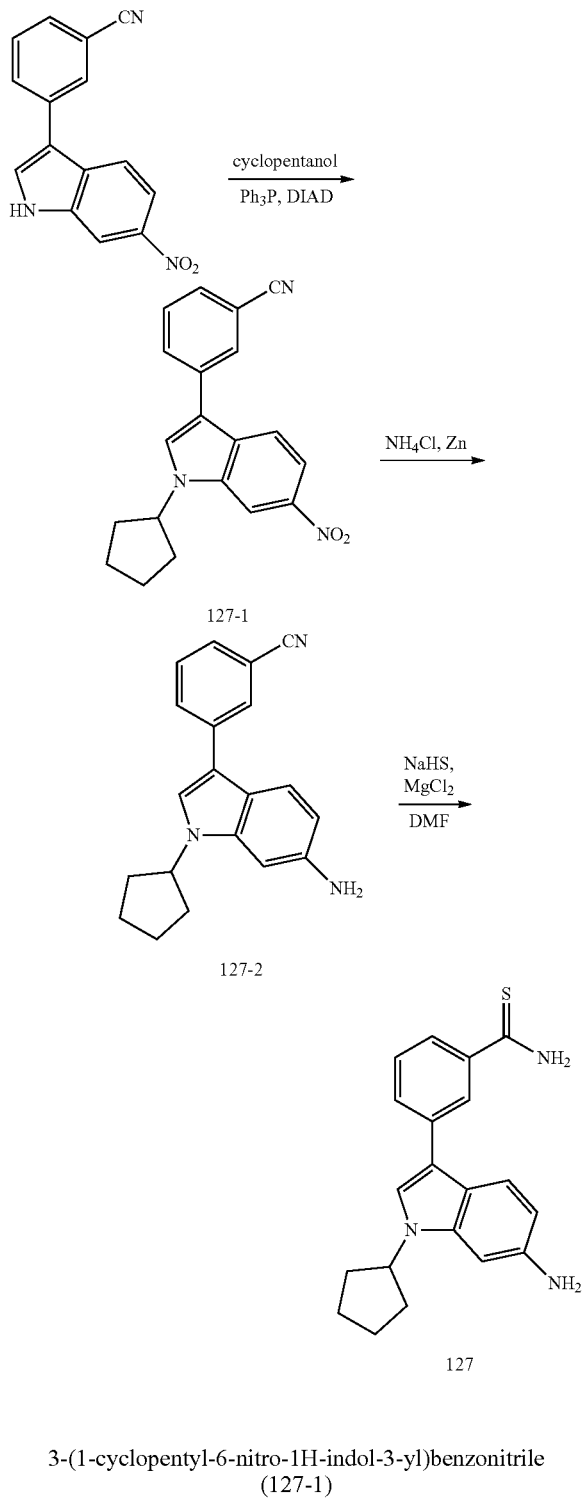

3-(1-cyclopentyl-6-nitro-1H-indol-3-yl)benzonitrile (127-1)

Under N₂ atmosphere, to a suspension of 3-(6-nitro-1H-indol-3-yl)benzonitrile (50 mg, 0.19 mmol), Ph₃P (90 mg, 0.34 mmol), cyclopentanol (36 uL, 0.34 mmol) and anhydrous DCM (3 mL) was added dropwise an anhydrous DCM (0.1 mL) solution of DIAD (90 uL, 0.34 mmol) at 0° C. over 15 min. The mixture was slowly warmed to rt and kept stirring overnight. The mixture was purified by flash chromatography on silica gel with hexanes and ethyl acetate (ethyl acetate: 0-50%) to give compound 127-1 (52 mg, 83%). LCMS (ESI) calculated for [M+H]⁺ 332, found 332.

3-(6-amino-1-cyclopentyl-1H-indol-3-yl)benzonitrile (127-2)

3-(1-cyclopentyl-6-nitro-1H-indol-3-yl)benzonitrile (50 mg, 0.14 mmol), Zn (200 mg, 3.2 mmol), NH₄Cl (200 mg, 3.8 mmol), acetone (8 mL) and water (1.5 mL) were mixed into a round bottom flask and stirred at rt for 2 h. The mixture was worked up by ethyl acetate (40 mL) and saturated NaHCO₃ (10 mL, two times). Ethyl acetate layer was concentrated in vacuo, and residue was purified by flash chromatography on silica gel with DCM and methanol containing 5% of NH₄OH (methanol: 0-15%) to give compound 127-2 (33 mg, 76%). ¹H NMR (600 MHz, CD₃OD) δ 7.94 (m, 2H), 7.63 (d, J=6.0 Hz, 1H), 7.52 (m, 2H), 7.44 (m, 1H), 6.87 (d, J=6.0 Hz, 1H), 6.72 (d, J=6.0 Hz, 1H), 4.74 (m, 1H), 2.23 (m, 2H), 1.95 (m, 4H), 1.95 (m, 2H). LCMS (ESI) calculated for [M+H]⁺ 302, found 302.

3-(6-amino-1-cyclopentyl-1H-indol-3-yl)benzothioamide (127)

3-(6-amino-1-cyclopentyl-1H-indol-3-yl)benzonitrile (30 mg, 0.1 mmol), NaHS (200 mg, 3.6 mmol), MgCl₂ (200 mg, 2.1 mmol) and anhydrous DMF (5 mL) were mixed and stirred at rt for 3 h. The mixture was worked up by ethyl acetate (40 mL) and saturated NaHCO₃ solution (8 mL, ×3), and the ethyl acetate layer was concentrated in vacuo to give crude residue which was purified by flash chromatography on silica gel with DCM and methanol containing 5% of NH₄OH (methanol: 0-5%) to give compound 127 (19 mg, 56%). 1H NMR (600 MHz, CD₃OD) δ 8.20 (s, 1H), 7.78 (d, J=6.0 Hz, 1H), 7.71 (m, 2H), 7.42 (t, J=6.0 Hz, 2H), 6.93 (s, 1H), 6.74 (d, J=6.0 Hz, 1H), 4.80 (m, 1H), 2.23 (m, 2H), 1.95 (m, 4H), 1.95 (m, 2H). ¹³C NMR (150 MHz, CD₃OD) δ 204.1, 142.6, 141.7, 139.9, 137.7, 134.5, 130.6, 130.2, 129.9, 126.9, 124.8, 122.4, 121.2, 116.9, 112.8, 58.1, 33.3, 30.6, 27.7. HRMS (ESI) calculated for [M+H]⁺ 336.1529, found 336.1529.

Example 5. Synthesis of 3-(6-amino-1-(3-fluoro-2-(fluoromethyl)propyl)-1H-indol-3-yl)benzamide (194)

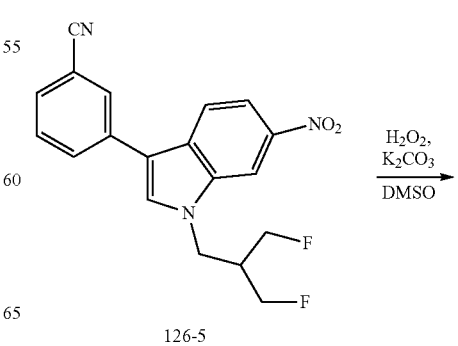

126-5

315

-continued

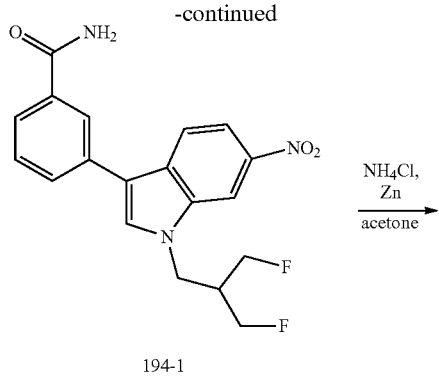

194-1

194

3-(6-amino-1-(3-fluoro-2-(fluoromethyl)propyl)-1H-indol-3-yl)benzamide (194)

To a stirred solution of 3-(6-amino-1-(3-fluoro-2-(fluoromethyl)propyl)-1H-indol-3-yl)benzonitrile (15 mg, 0.04 mmol). and potassium carbonate (15 mg) in DMSO, hydrogen peroxide (30%, 15 uL) was added at 0° C. The solid mixture was allowed to warm to room temperature. After 20 min water was added and extracted with ethyl acetate. Organic phase was dried over sodium sulfate, evaporated and purified on a column (silica gel, hexane-ethyl acetate). Crude product 194.1 was dissolved in acetone (0.8 mL) and water (0.15 mL) was added. Ammonium chloride (86 mg) and zinc powder (52 mg) were then added and the mixture was stirred for 40 min at room temperature. Mixture was filtered through Celite, washed with ethyl acetate. Organic phase was dried over sodium sulfate and evaporated. Compound was purified using column chromatography (silica gel, hexane-ethyl acetate). 10 mg of colorless oil was obtained (76% yield). $^1$H NMR (600 MHz, ACETONITRILE-d$_3$) δ ppm 2.56-2.73 (m, 1H) 4.20 (d, J=7.7 Hz, 2H) 4.39-4.64 (m, 4H) 6.01 (bs, 1H) 6.56-6.65 (m, 1H) 6.68-6.75 (m, 1H) 6.83 (bs, 1H) 7.31 (m, 1H) 7.46-7.54 (m, 1H) 7.63-7.72 (m, 2H) 7.78-7.86 (m, 1H) 8.02-8.09 (m, 1H); $^{13}$C NMR (150 MHz, CDCl$_3$, HSQC) δ ppm 40.4, 41.7, 80.2, 81.3, 93.8, 110.2, 119.6, 123.7, 123.7, 124.8, 128.2, 129.0; HR-MS [ESI, M+H$^+$] calcd for: C$_{19}$H$_{20}$F$_2$N$_3$O: 344.1574, found: 344.1567.

316

Example 6. Synthesis of 3-(1-(3-fluoro-2-(fluoromethyl)propyl)-6-(hydroxymethyl)-1H-indol-3-yl)benzothioamide (236)

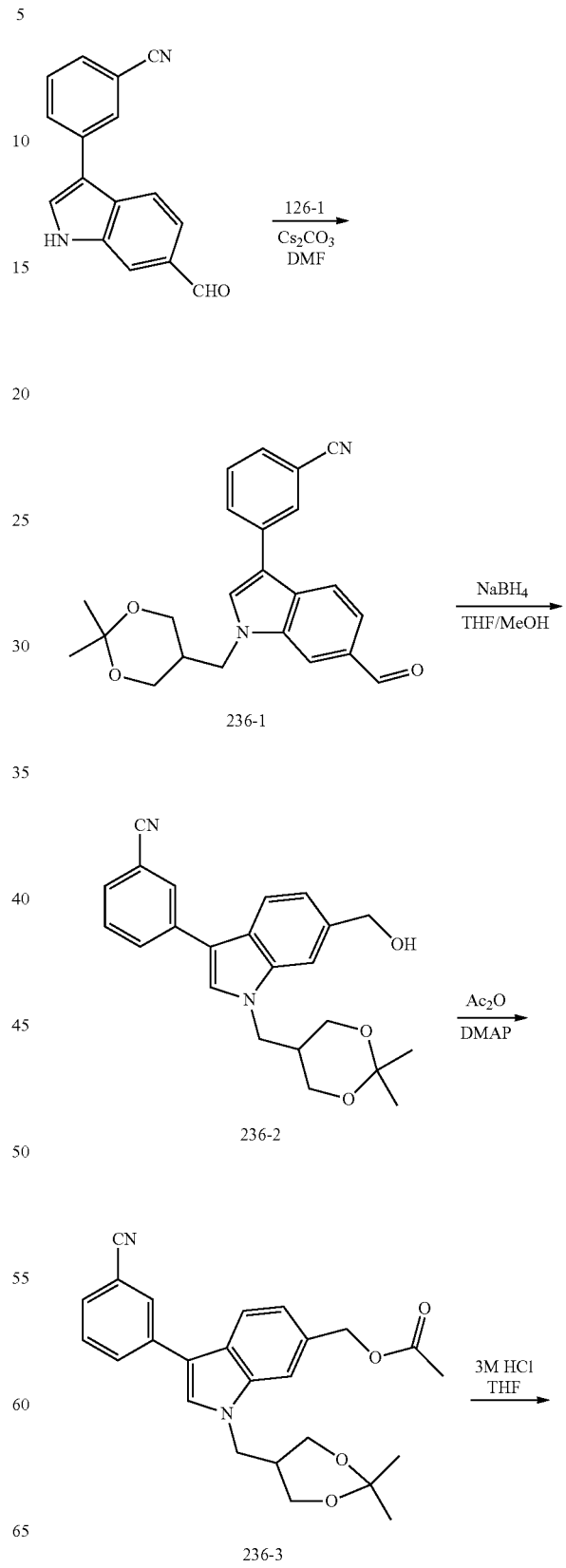

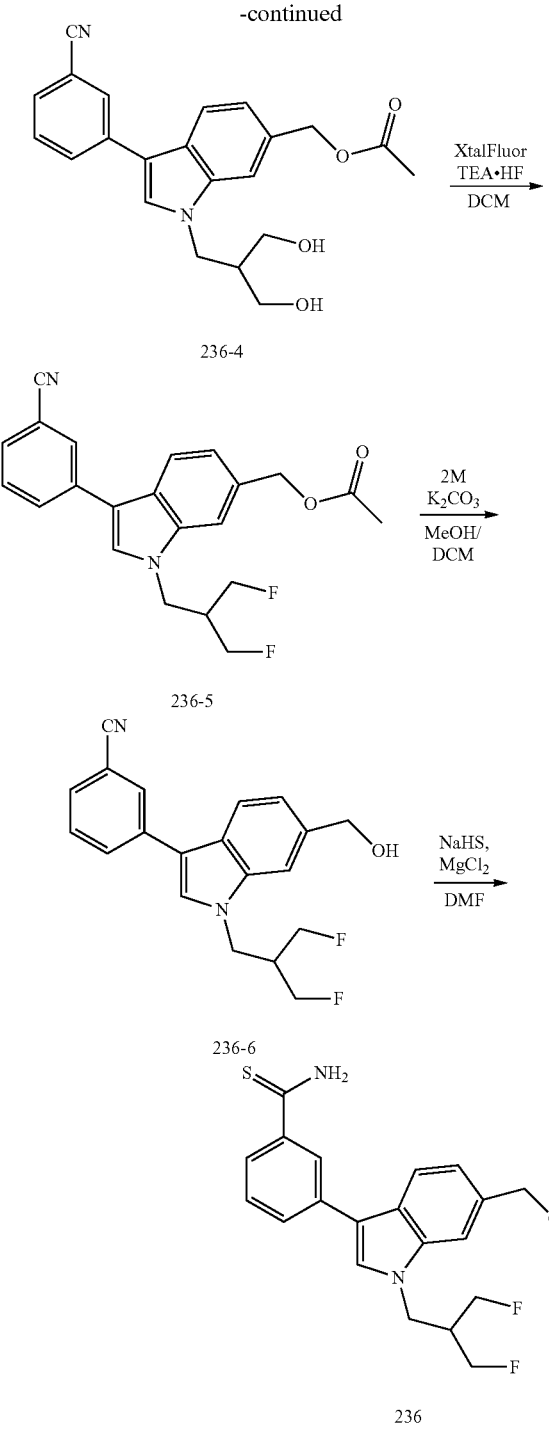

3-(1-((2,2-dimethyl-1,3-dioxan-5-yl)methyl)-6-formyl-1H-indol-3-yl)benzonitrile (236-1)

3-(6-formyl-1H-indol-3-yl)benzonitrile (150 mg, 0.6 mmol), (2,2-dimethyl-1,3-dioxan-5-yl)methyl methanesulfonate (125-1) (204 mg 0.9 mmol) and cesium carbonate (596 mg, 1.8 mmol) were stirred in DMF (0.6 mL) for 18h at 60° C. Water was added and compound was extracted by ethyl acetate. Water phase was extracted 2 times with ethyl acetate and combined organic phases were dried over sodium sulfate. After evaporation, crude compound was purified using column chromatography (silica gel, hexane-ethyl acetate). 50 mg (33%) of yellow solid was obtained. $^1$H NMR (600 MHz, CDCl$_3$) δ ppm 1.50 (s, 3H) 1.53 (s, 3H) 2.08-2.14 (m, 1H) 3.59-3.65 (m, 2H) 4.07-4.13 (m, 2H) 4.59 (d, J=8.1 Hz, 2H) 7.53-7.62 (m, 3H) 7.76 (dd, J=8.2, 0.9 Hz, 1H) 7.88 (d, J=7.7 Hz, 1H) 7.92 (m, 1H) 7.98 (d, J=8.1 Hz, 1H) 8.01-8.05 (m, 2H) 10.11 (s, 1H);

3-(3-cyanophenyl)-1-((2,2-dimethyl-1,3-dioxan-5-yl)methyl)-1H-indol-6-yl)methyl acetate (236-3)

To a stirred solution of 3-(1-((2,2-dimethyl-1,3-dioxan-5-yl)methyl)-6-formyl-1H-indol-3-yl)benzonitrile (110 mg, 0.29 mmol) in MeOH/THF (6 mL. 1:1 v/v) sodium borohydride (16 mg, 0.44 mmol) was added at 0° C. Mixture was stirred for additional 30 min at 0° C. Solvents were evaporated and water was added followed by ethyl acetate. Organic phase was dried over sodium sulfate and solvent was evaporated. Residue was then dissolved in DCM (2 mL) and triethyl amine was added (76 μL, 0.58 mmol) followed by acetic anhydride (56 μL, 0.58 mmol). Mixture was stirred for 2h at room temperature and solvent was evaporated. Crude mixture was purified using column chromatography (silica gel, hexane-ethyl acetate). 104 mg (85%) of colorless oil was obtained. $^1$H NMR (600 MHz, CDCl$_3$) δ ppm 1.49 (s, 3H) 1.52 (s, 3H) 2.06-2.11 (m, 1H) 2.11-2.14 (m, 3H) 3.62 (dd, J=12.1, 1.8 Hz, 2H) 4.02-4.16 (m, 2H) 4.48 (d, J=8.1 Hz, 2H) 5.26 (s, 2H) 7.25 (d, J=8.1 Hz, 1H) 7.39 (m, 1H) 7.45 (m, 1H) 7.51-7.57 (m, 2H) 7.87 (d, J=8.4 Hz, 2H) 7.91 (m, 1H); $^{13}$C NMR (150 MHz, CDCl$_3$) δ ppm 20.1, 21.2, 27.8, 34.7, 45.8, 61.3, 67.0, 98.5, 98.7, 110.5, 112.9, 115.0, 119.1, 119.7, 121.5, 125.8, 127.6, 129.2, 129.6, 130.5, 131.4, 136.7, 136.9, 171.0;

(3-(3-cyanophenyl)-1-(3-hydroxy-2-(hydroxymethyl)propyl)-1H-indol-6-yl)methyl acetate (236-4)

To a solution of 3-(3-cyanophenyl)-1-((2,2-dimethyl-1,3-dioxan-5-yl)methyl)-1H-indol-6-yl)methyl acetate (40 mg, 0.096 mmol) in THF (0.4 mL) HCl (3M, aq. 64 uL) was added and the mixture was stirred for 15 min. THF was evaporated and residue was partitioned between acetyl acetate and water. Water phase was extracted with additional ethyl acetate. Combined organic layers were dried over sodium sulfate and evaporated. Used for the next step without further purification.

(3-(3-cyanophenyl)-1-(3-fluoro-2-(fluoromethyl)propyl)-1H-indol-6-yl)methyl acetate (236-5)

To a solution of TEA·HF (33 uL, 0.2 mmol) in dry DCM (0.3 mL), Xtalfluor E (35 mg, 0.15 mmol) was added at 0° C. Then the solution of (3-(3-cyanophenyl)-1-(3-hydroxy-2-(hydroxymethyl)propyl)-1H-indol-6-yl)methyl acetate (19 mg, 0.05 mmol) in DCM (0.5 mL) was added dropwise at 0° C. The mixture was stirred for 30 min at 0° C. and 4h at room temperature. Reaction was then quenched with sat. NaHCO$_3$ and water phase was extracted with DCM and organic phase was dried over sodium sulfate. Volatiles were evaporated and the residue was purified by column chromatography (silica gel, hexane-ethyl acetate) resulting 10 mg of the product (55% yield). $^1$H $^1$H NMR (600 MHz, CDCl$_3$) δ ppm 2.14 (s, 3H) 2.59-2.75 (m, 1H) 4.39 (d, J=7.3 Hz, 2H) 4.45-4.53 (m, 2H) 4.53-4.61 (m, 2H) 5.28 (s, 2H) 7.28 (m, 1H) 7.37 (m, 1H) 7.45 (m, 1H) 7.53-7.60 (m, 2H) 7.86-7.91 (m, 2H) 7.92 (m, 1H)$^{13}$C NMR (150 MHz, CDCl$_3$) δ ppm 21.0, 41.7 (J=18 Hz), 42.9, 66.9, 80.2, 81.3, 110.0, 113.0, 115.6, 119.0, 121.7, 125.8, 127.2, 129.4, 129.6, 130.5, 131.4, 136.4, 136.9, 170.9;

3-(1-(3-fluoro-2-(fluoromethyl)propyl)-6-(hydroxymethyl)-1H-indol-3-yl)benzothioamide (236, SKA-174)

To a solution of (3-(3-cyanophenyl)-1-(3-fluoro-2-(fluoromethyl)propyl)-1H-indol-6-yl)methyl acetate(10 mg, 0.026 mmol) in MeOH:DCM (2:1 v/v) 2M solution of potassium carbonate (26.5 uL) was added and the mixture was sonicated for 60 min. Volatiles were evaporated and the residue was dissolved in DCM, dried over sodium sulfate and evaporated. DMF was added (100 uL) followed by sodium hydrosulfide (50 mg) and magnesium chloride (100 mg). After 30 min water was added and extracted with ethyl acetate. Organic phase was dried over sodium sulfate and purified using prep. TLC (silica gel, hexane:ethyl acetate 1:1 v/v). $^1$H NMR (600 MHz, AcCN-$d_3$) δ ppm 2.66-2.80 (m, 1H) 4.39 (d, J=7.7 Hz, 2H) 4.46-4.67 (m, 4H) 4.75 (d, J=5.1 Hz, 2H) 7.19-7.24 (m, 1H) 7.52 (s, 2H) 7.59 (s, 1H) 7.77-7.82 (m, 1H) 7.86-7.90 (m, 1H) 7.92-7.99 (m, 1H) 8.11-8.19 (m, 1H) 8.20-8.23 (m, 1H) 8.31-8.42 (m, 1H); $^{13}$C NMR (150 MHz, AcCN-$d_3$) δ ppm 41.7, 42.7, 44.2, 65.8, 82.2, 83.3, 109.7, 117.1, 120.9, 121.3, 125.9, 126.4, 126.8, 128.6, 130.1, 131.2, 136.9, 138.1, 138.7, 141.6, 204.1; HR-MS [ESI, M+H$^+$] calcd for: $C_{20}H_{21}F_2N_2OS$: 375.1343, found: 375.1335.

Example 7. Synthesis of 3-(1-(3,3-difluoropropyl)-6-(hydroxymethyl)-1H-indol-3-yl)benzothioamide (131)

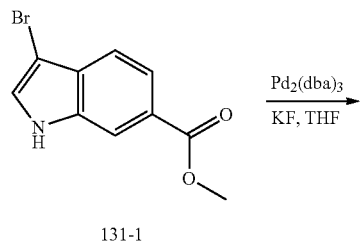

131-1

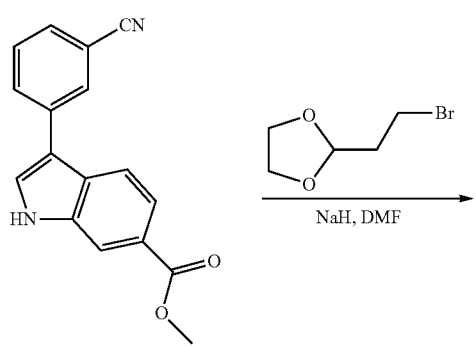

131-2

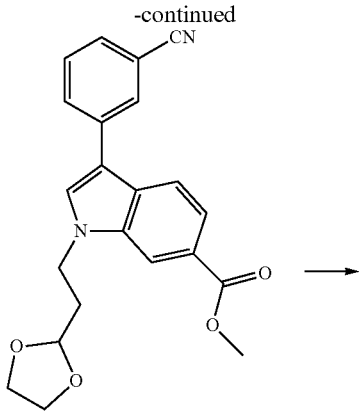

131-3

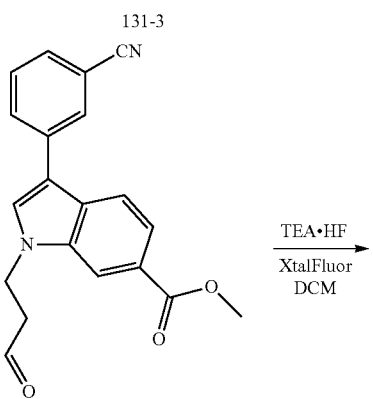

131-4

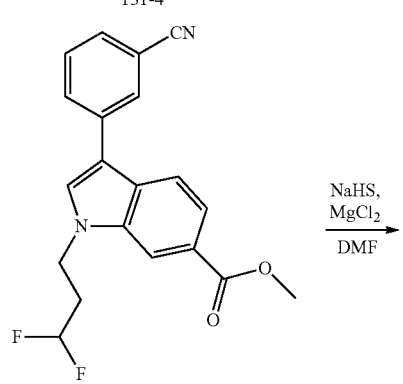

131-5

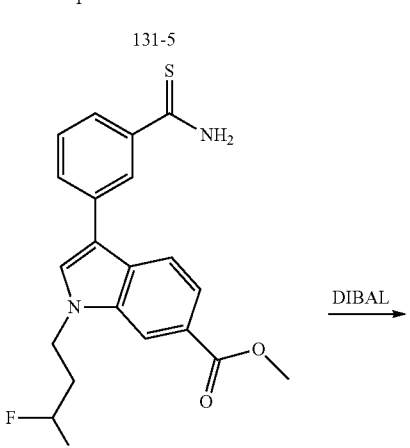

131-6

-continued

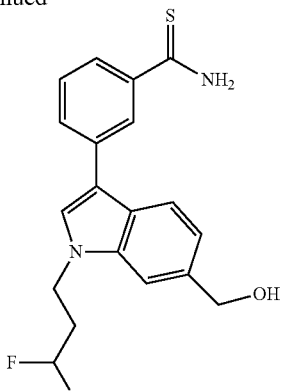

131

3-bromo-1H-indole-6-carboxylate (131-1)

Under N₂ atmosphere, to an anhydrous DMF solution (10 mL) of methyl 1H-indole-6-carboxylate (1.00 g, 5.71 mmol) was added dropwise an anhydrous DMF (10 mL) solution of NBS (1.04 g, 5.84 mmol) at −60° C. over 20 min, and stirred and slowly warmed to rt in 3 h. The reaction mixture was worked up by ethyl acetate (100 mL) and water (20 mL, ×3), and ethyl acetate layer was concentrated in vacuo and residue was purified by flash chromatography on silica gel with hexanes and ethyl acetate (EA: 0-40%) to give product (1.41 g, 98%). ¹H NMR (600 MHz, CD₃OD) δ 8.15 (s, 1H), 7.80 (d, J=6.0 Hz, 1H), 7.50 (m, 2H), 3.94 (s, 3H).

Methyl 3-(3-cyanophenyl)-1H-indole-6-carboxylate (131-2)

Under N₂ atmosphere, methyl 3-bromo-1H-indole-6-carboxylate (1.12 g, 4.43 mmol), (3-cyanophenyl)boronic acid (1.30 g, 8.84 mmol), tris(dibenzylideneacetone) dipalladium (O) (608 mg, 0.66 mmol), tri-tert-butylphosphonium tetrafluoroborate (385 mg, 1.32 mmol), anhydrous KF (769 mg, 13.30 mmol), and anhydrous THF (20 mL) were mixed and stirred at 40° C. overnight. The mixture was cooled down to rt, filtered through celite and washed by ethyl acetate (100 mL). The filtrate was concentrated in vacuo, and the residue was purified by flash chromatography on silica gel with hexanes and ethyl acetate (0-60%) to give product (1.05 g, 86%). ¹H NMR (600 MHz, CD₃OD) δ 8.20 (S, 1H), 8.02 (brs, 2H), 7.93 (d, J=12.0 Hz, 1H), 7.84 (m, 2H), 7.62 (m, 2H), 3.95 (s, 3H).

Methyl 1-(2-(1,3-dioxolan-2-yl)ethyl)-3-(3-cyanophenyl)-1H-indole-6-carboxylate (131-3)

To an anhydrous DMF solution (2.0 mL) of methyl 3-(3-cyanophenyl)-1H-indole-6-carboxylate (100 mg, 0.36 mmol) at 0° C. under N₂ atmosphere was added NaH (40 mg, 1.67 mmol) and stirred for 30 min. 2-(2-Bromoethyl)-1,3-dioxolane (126 uL, 1.08 mmol) was added into the above mixture via syringe, and resulting mixture was stirred and gradually warmed to rt over 2 h. The mixture was worked up by ethyl acetate (40 mL) and water (10 mL, ×3). The ethyl acetate layer was concentrated in vacuo and residue was purified by flash chromatography on silica gel with hexanes and ethyl acetate (0-50%) to give product (120 mg, 89%). ¹H NMR (600 MHz, CD₃OD) δ 8.24 (s, 1H), 8.06 (s, 1H), 8.01 (m, 2H), 7.86 (d, J=6.0 Hz, 1H), 7.83 (s, 1H), 7.64 (m, 2H), 4.92 (t, J=6.0 Hz, 1H), 4.45 (t, J=6.0 Hz, 2H), 3.98 (m, 2H), 3.95 (s, 3H), 3.86 (m, 2H), 2.24 (m, 2H).

Methyl 3-(3-cyanophenyl)-1-(3-oxopropyl)-1H-indole-6-carboxylate (131-4)

Methyl 1-(2-(1,3-dioxolan-2-yl)ethyl)-3-(3-cyanophenyl)-1H-indole-6-carboxylate (120 mg, 0.32 mmol), THF (8 mL) and aqueous HCl (3.5 M, 2 mL) were mixed and stirred at 0° C. until no progress by TLC analysis. THF was removed by air blowing and remaining mixture was extracted with EA (25 mL). EA layer was dried over Na₂SO₄, filtered and concentrated in vacuo to give product (100 mg, 94%).

Methyl 3-(3-cyanophenyl)-1-(3,3-difluoropropyl)-1H-indole-6-carboxylate (131-5)

To a DCM solution (4 mL) of Et₃N 3HF (120 uL, 0.74 mmol), XtalFluor-E (130 mg, 0.57 mmol) was added methyl 3-(3-cyanophenyl)-1-(3-oxopropyl)-1H-indole-6-carboxylate (100 mg, 0.30 mmol) and stirred at 0° C. for 1 h, then gradually warmed to rt overnight. The DCM was removed in vacuo, and the residue was worked up by ethyl acetate (25 mL) and saturated Na₂HCO₃ (8 mL, ×2). Ethyl acetate layer was concentrated in vacuo and residue was purified by flash chromatography on silica gel with hexanes and ethyl acetate (0-40%) to give title compound (30 mg, 28%) which contain some impurity. ¹H NMR (600 MHz, CD₃OD) δ 8.23 (s, 1H), 8.03 (s, 1H), 7.98 (m, 2H), 7.80 (m, 2H), 7.64 (m, 2H), 6.03 (tt, J=60.0, 6.0 Hz, 1H), 4.49 (t, J=6.0 Hz, 2H), 2.48 (m, 2H).

Methyl 3-(3-carbamothioylphenyl)-1-(3,3-difluoropropyl)-1H-indole-6-carboxylate (131-6)

Methyl 3-(3-cyanophenyl)-1-(3,3-difluoropropyl)-1H-indole-6-carboxylate (30 mg, 0.08 mmol), NaHS (230 mg, 4.1 mmol), MgCl₂ (220 mg, 2.3 mmol) and anhydrous DMF (2.5 mL) were mixed and stirred at rt for 3 h. The mixture was worked up by ethyl acetate (40 mL) and saturated NaHCO₃ solution (10 mL, ×3). The ethyl acetate layer was dried over Na₂SO₄, filtered and concentrated in vacuo to give title compound (25 mg, 81%). ¹H NMR (600 MHz, CD₃OD) δ 8.11 (d, J=12.0 Hz, 2H), 7.98 (s, 1H), 7.80 (m, 4H), 7.45 (d, J=6.0 Hz, 1H), 5.98 (tt, J=60.0, 6.0 Hz, 1H), 4.47 (t, J=6.0 Hz, 2H), 2.43 (m, 2H).

3-(1-(3,3-difluoropropyl)-6-(hydroxymethyl)-1H-indol-3-yl)benzothioamide (131)

To an anhydrous THF solution (2.0 mL) of methyl 3-(3-carbamothioylphenyl)-1-(3,3-difluoropropyl)-1H-indole-6-carboxylate (25 mg, 0.06 mmol) was added a THF solution of DIBAL (1 M, 0.55 mL, 0.55 mmol) at −78° C. under N₂ atmosphere, and stirred and gradually warmed to rt over 2 h. The mixture was worked up by ethyl acetate (15 mL) and aqueous HCl (1M, 10 mL), and Ethyl acetate layer was concentrated and purified by flash chromatography on silica gel with hexanes and ethyl acetate (EA: 0-80%) to give product (10 mg, 46%). ¹H NMR (600 MHz, CD₃OD) δ 8.26 (s, 1H), 7.93 (d, J=12.0 Hz, 1H), 7.82 (d, J=6.0 Hz, 1H), 7.75 (d, J=6.0 Hz, 1H), 7.59 (m, 1H), 7.51 (m, 1H), 7.47 (t, J=6.0 Hz, 1H), 7.21 (d, J=12.0 Hz, 1H), 5.95 (tt, J=60.0, 6.0 Hz, 1H), 4.47 (t, J=6.0 Hz, 2H), 2.43 (m, 2H). ¹³C NMR (150 MHz, CD₃OD) δ 204.5, 141.8, 138.3, 137.1, 130.9, 129.5, 127.5, 127.3, 126.9, 125.1, 121.1, 120.8, 117.5, 117.4 (t, J=237.0 Hz), 65.9, 40.8 (t, J=6.0 Hz), 35.8 (t, J=21.0 Hz). HRMS (ESI) calculated for [M+H]$^+$ 361.1181, found 361.1175.

II. Experimental Procedures

Protein Purification

ASH1L SET protein was expressed as MOCR fusion proteins in *E. coli* BL21(DE3) T1R cells at 22° C. Transformed cells were lysed in buffer A containing 50 mM Tris (pH 7.5), 500 mM NaCl, 1 mM tris(2-carboxyethyl)phosphine (TCEP), and 20 mM imidazole. Cell debris was pelleted by centrifugation, and the supernatant was loaded on a column packed with nickel-nitrilotriacetic acid beads. The column was washed with buffer A and protein eluted with a 100 mL linear gradient up to buffer A containing 500 mM imidazole. The MOCR tag was cleaved with tobacco etch virus (TEV) protease during overnight dialysis against 50 mM Tris (pH 7.5), 100 mM NaCl, and 1 mM TCEP. Cleaved ASH1L was isolated from MOCR by repeating the nickel column purification and collecting ASH1L in the flow-through and low-imidazole fractions. ASH1L was further purified by gel filtration chromatography using a Superdex-75 column running in buffer B containing 50 mM Tris (pH 7.5), 100 mM NaCl, and 1 mM TCEP. ASH1L SET-PHD and SET-BAH proteins were purified similarly, with the following differences. Expression was performed at 18° C.; cleavage with TEV and the second nickel column were omitted to maintain protein stability, and gel filtration was performed on a Superdex-200 column.

ASH1L Histone Methyltransferase Assay (KMTase Assay)

Chicken mono/dinucleosomes (HMT-35-179), chicken oligo nucleosomes (HMT-35-177), and HeLa nucleosomes (HMT-35-123) were purchased from Reaction Biology. For testing compounds, ASH1L SET-BAH construct (amino acids 2069-2833) at 0.25 μM was incubated with 0.7 μM SAM, 0.2 μM chicken mono/dinucleosomes, and the compound in a concentration range from 500 to 0.2 μM in HMTase buffer (50 mM Tris (pH 8.5), 25 mM NaCl, 2 mM MgCl$_2$, and 1 mM DTT) in a total volume of 15 μl for 1 hr at 30° C. The reactions were stopped by spotting 5 μL of the reaction mixture on P81 cellulose squares (Reaction Biology). The P81 squares were dried for 45 min and washed five times with 50 mM sodium bicarbonate (pH 9.0), 10 min per wash. The P81 squares were then dried for 1 h, added to 10 mL of Ultima Gold scintillation cocktail (PerkinElmer), and analyzed using a Beckman scintillation counter.

Isothermal Titration Calorimetry

ASH1L SET was extensively dialyzed at 4° C. against ITC buffer (50 mM sodium phosphate pH 7.5, 50 mM NaCl, 1 mM TCEP). Compound 126 was dissolved in DMSO and diluted with ITC buffer to final concentrations of 0.1 mM in 5% DMSO. The protein solution was adjusted to 5% DMSO final concentration. Both protein and compound solutions were adjusted to 50 μM SAM, to maintain ASH1L stability. The titrations were performed using a VP-ITC titration calorimetric system (MicroCal) at 25° C. The calorimetric cell, containing ASH1L (10 μM) was titrated with the compounds (0.1 mM) injected in 10 μl volumes. Data was analyzed using Origin 7.0 (OriginLab) to obtain thermodynamic parameters.

Cell Viability Assays

MA9 (MLL-AF9 transformed), HM2 (Hoxa9/Meis1 transformed) murine bone marrow cells (BMC), MV4;11 and MOL13 human leukemia cells were plated at 1×10$^5$ cells/ml in 24-well plates, treated with 0.25% DMSO or compounds and cultured at 37° C. for 12 days. Every four days, the volume corresponding to 1×10$^5$ cells of DMSO-treated cells was spun down and resuspended in fresh media with fresh compound. At day 0 and each four day interval, 100 μl aliquots of the cell suspension were transferred to 96-well plates in quadruplicates. The quadruplicate samples were incubated for 4 days at 37° C., and then an MTT cell proliferation assay kit (Roche) was used to measure viable cells. Absorbance was read at 570 nm using a PHERAstar (BMG) microplate reader.

Quantitative RT-PCR

Total RNA was extracted from cells using the RNeasy mini kit (QIAGEN), and then 100-2000 ng of total RNA was reverse transcribed using the High Capacity cDNA Reverse Transcription Kit (Applied Biosystems) according to the manufacturer's protocol. Real-time PCR was performed using a CFX96 Real-Time PCR Detection System (Biorad). TaqMan Gene Expression Master Mix and TaqMan Gene Expression Assays for mouse Gapdh (Mm99999915), mouse Ash1l (Mm00467322), mouse Hoxa7 (Mm00657963), mouse Hoxa9 (Mm00439364), mouse Hoxa10 (Mm00433966), mouse Meis1 (Mm00487664), and mouse B-actin (Mm00607939) were purchased from Thermo Fisher. Relative quantification of each gene transcript was carried out using the $\Delta\Delta C_t$ method as described in the Biorad Real-Time PCR Applications Guide.

Cytospin/Wrigtht-Giemsa Staining

1×10$^5$ MA9 mouse BMCs treated with compounds were harvested and placed in a Shandon EZ Single Cytofunnel (Thermo Fisher). Samples were centrifuged at 600 rpm for 5 min. The slides were air dried before staining with a Hema-3 kit (Thermo Fisher).

Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above by their number/letter, are herein incorporated by reference in their entireties.

1. Li Zhu, Qin Li2, Stephen H. K. Wong, Min Huang, Brianna J. Klein, Jinfeng Shen, Larissa Ikenouye, Masayuki Onishi, Dominik Schneidawind, Corina Buechele, Loren Hansen, Jesús Duque-Afonso, Fangfang Zhu, Gloria Mas Martin, Or Gozani, Ravindra Majeti, Tatiana G. Kutateladze, and Michael L. Cleary, (2016), ASH1L Links Histone H3 Lysine 36 di-methylation to MLL Leukemia. Cancer Discovery, in press.
2. Colamaio, M., Puca, F., Ragozzino, E., Gemei, M., Decaussin-Petrucci, M., Aiello, C., Bastos, A. U., Federico, A., Chiappetta, G., Vecchio, L. Del, Torregrossa, L., Battista, S., and Fusco, A. (2014) miR-142-3p downregulation contributes to thyroid follicular tumorigenesis by targeting ASH1L and MLL1. J. Clin. Endocrinol. Metab. 100, E59-E69.
3. Liu, L., Kimball, S., Liu, H., Holowatyj, A., and Yang, Z.-Q. (2014) Genetic alterations of histone lysine methyltransferases and their significance in breast cancer. Oncotarget. 6, 2466-2482.

4. Fujimoto, A., Furuta, M., Totoki, Y., Tsunoda, T., Kato, M., Shiraishi, Y., Tanaka, H., Taniguchi, H., Kawakami, Y., Ueno, M., Gotoh, K., Ariizumi, S., Wardell, C. P., Hayami, S., Nakamura, T., Aikata, H., Arihiro, K., Boroevich, K. A., Abe, T., Nakano, K., Maejima, K., Sasaki-Oku, A., Ohsawa, A., Shibuya, T., Nakamura, H., Hama, N., Hosoda, F., Arai, Y., Ohashi, S., Urushidate, T., Nagae, G., Yamamoto, S., Ueda, H., Tatsuno, K., Ojima, H., Hiraoka, N., Okusaka, T., Kubo, M., Marubashi, S., Yamada, T., Hirano, S., Yamamoto, M., Ohdan, H., Shimada, K., Ishikawa, O., Yamaue, H., Chayama, K., Miyano, S., Aburatani, H., Shibata, T., and Nakagawa, H. (2016) Whole-genome mutational landscape and characterization of noncoding and structural mutations in liver cancer. Nat. Genet. 10.1038/ng.3547.
5. Jones, M., Chase, J., Brinkmeier, M., Xu, J., Weinberg, D. N., Schira, J., Friedman, A., Malek, S., Grembecka, J., Cierpicki, T., Dou, Y., Camper, S. A., and Maillard, I. (2015) Ash1l controls quiescence and self-renewal potential in hematopoietic stem cells. J. Clin. Invest. 125, 2007-2020.
6. Tanaka, Y., Kawahashi, K., Katagiri, Z. I., Nakayama, Y., Mahajan, M., and Kioussis, D. (2011) Dual function of histone H3 lysine 36 methyltransferase ASH1 in regulation of hox gene expression. PLoS One. 6, e28171.
7. Kanellopoulou, C., Gilpatrick, T., Kilaru, G., Burr, P., Nguyen, C. K., Morawski, A., Lenardo, M. J., and Muljo, S. A. (2015) Reprogramming of Polycomb-Mediated Gene Silencing in Embryonic Stem Cells by the miR-290 Family and the Methyltransferase Ash1l. Stem cell reports. 10.1016/j.stemcr.2015.10.001.
8. Miyazaki, H., Higashimoto, K., Yada, Y., Endo, T. a., Sharif, J., Komori, T., Matsuda, M., Koseki, Y., Nakayama, M., Soejima, H., Handa, H., Koseki, H., Hirose, S., and Nishioka, K. (2013) Ash1l Methylates Lys36 of Histone H3 Independently of Transcriptional Elongation to Counteract Polycomb Silencing. PLoS Genet. 9, e1003897.
9. Shah, N., and Sukumar, S. (2010) The Hox genes and their roles in oncogenesis. Nat. Rev. Cancer. 10, 361-371.
10. Andreeff, M., Ruvolo, V., Gadgil, S., Zeng, C., Coombes, K., Chen, W., Komblau, S., Barón, A. E., and Drabkin, H. A. (2008) HOX expression patterns identify a common signature for favorable AML. Leukemia. 22, 2041-7.
11. Faber, J., Krivtsov, A. V, Stubbs, M. C., Wright, R., Davis, T. N., van den Heuvel-Eibrink, M., Zwaan, C. M., Kung, A. L., and Armstrong, S. A. (2009) HOXA9 is required for survival in human MLL-rearranged acute leukemias. Blood. 113, 2375-85.
12. Kroon, E., Krosl, J., Thorsteinsdottir, U., Baban, S., Buchberg, A. M., and Sauvageau, G. (1998) Hoxa9 transforms primary bone marrow cells through specific collaboration with Meis1a but not Pbx1b. EMBO J. 17, 3714-25.
13. Cabianca, D. S., Casa, V., Bodega, B., Xynos, A., Ginelli, E., Tanaka, Y., and Gabellini, D. (2012) A long ncRNA links copy number variation to a polycomb/trithorax epigenetic switch in FSHD muscular dystrophy. Cell. 149, 819-31.
14. Perugorria, M. J., Wilson, C. L., Zeybel, M., Walsh, M., Amin, S., Robinson, S., White, S. A., Burt, A. D., Oakley, F., Tsukamoto, H., Mann, D. A., and Mann, J. (2012) Histone methyltransferase ASH1 orchestrates fibrogenic gene transcription during myofibroblast transdifferentiation. Hepatology. 56, 1129-1139.

The invention claimed is:
1. A composition comprising a compound of the formula:

or a salt thereof;
wherein X is S;
wherein each of (A), (D), and (E) are aryl or heteroaryl;
wherein each of $X^1$-$X^4$ are independently selected from C and N;
wherein each of $X^5$-$X^9$ are independently selected from C, N, S, and O, when present on a 5-member ring;
wherein each of $X^5$-$X^9$ are independently selected from C and N, when present on a 6-member ring; and
wherein any of the $R^{D1-D4}$, $R^{A1-A3}$, and $R^{E1-E4}$ substituents, when present, are of one of Formulas (IIa-IIq):

—J;  Formula (IIa)

—J—(Q);  Formula (IIb)

—J$^1$—(Q)—J$^2$;  Formula (IIc)

—J$^1$—(Q$^1$)—J$^2$—(Q$^2$);  Formula (IId)

—J$^1$—(Q$^1$)—J$^2$—(Q$^2$)—J$^3$;  Formula (IIe)

—J$^1$—J$^2$;  Formula (IIf)

—J$^1$—J$^2$—J$^3$;  Formula (IIg)

—J$^1$—J$^2$—(Q$^1$);  Formula (IIh)

—J$^1$—J$^2$—(Q$^1$)—J$^3$;  Formula (IIi)

—J$^1$—J$^2$—(Q$^1$)—J$^3$—J$^4$;  and  Formula (IIj)

-continued

Formula (IIk)

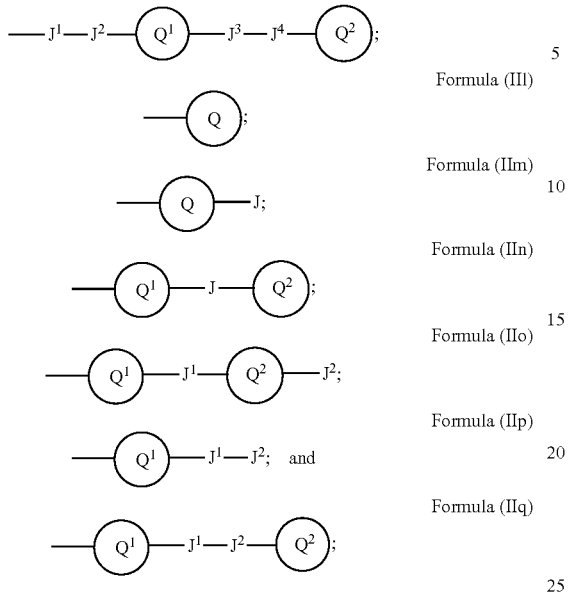

Formula (III)

Formula (IIm)

Formula (IIn)

Formula (IIo)

Formula (IIp)

Formula (IIq)

wherein one of J, $Q^1$, or $J^1$, when present, is linked to one of the D, A, or E rings, wherein each J, $J^1$, $J^2$, $J^3$, and $J^4$, when present, are independently selected from the group consisting of: a covalent bond, H, $alkyl_{1-15}$, $alkenyl_{1-6}$, $alkynyl_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}$ $(CH_2)_{1-6}$, $(CH_2)_{0-6}NH_2$, $(CH_2)_{0-6}SO_2$ $(CH_2)_{1-6}$, $(CH_2)_{0-6}NHSO_2$ $(CH_2)_{1-6}$, $(CH_2)_{0-6}$ $SO_2$ $NH_2$, halogen, haloalkyl, dihaloalkyl, trihaloalkyl, alkyl with 1-3 halogens at two or more positons along the alkyl, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH$ $(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}$ $S(CH_2)_{1-5}OH$, $(CH_2)_{0-6}O(CH_2)_{1-6}S$ $(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}$ $S(CH_2)_{1-5}OH$, $(CH_2)_{0-6}S(CH_2)_{1-6}$ $S(CH_2)_{1-5}NH_2$, $(CH_2)_{0-6}NH$ $(CH_2)_{1-6}NH(CH_2)_{1-5}OH$, $(CH_2)_{0-6}NH(CH_2)_{1-6}NH$ $(CH_2)_{1-5}NH_2$, $(CH_2)_{0-6}NH(CH_2)_{1-6}NH(CH_2)_{1-5}SH$, $(CH_2)_{0-6}NH(CH_2)_{1-6}O(CH_2)_{1-5}OH$, $(CH_2)_{0-6}NH$ $(CH_2)_{1-6}O(CH_2)_{1-5}NH_2$, $(CH_2)_{0-6}NH(CH_2)_{1-6}$ $O(CH_2)_{1-5}SH$, $(CH_2)_{0-6}NH(CH_2)_{1-6}S(CH_2)_{1-5}OH$, $(CH_2)_{0-6}NH(CH_2)_{1-6}$ $S(CH_2)_{1-5}NH_2$, $(CH_2)_{0-6}NH$ $(CH_2)_{1-6}S(CH_2)_{1-5}SH$, $(CH_2)_{0-3}C(O)O(CH_2)_{0-3}$, $(CH_2)_{0-3}C(S)O(CH_2)_{0-3}$, $(CH_2)_{0-3}C(O)S(CH_2)_{0-3}$, $(CH_2)_{0-3}C(S)S(CH_2)_{0-3}$, $(CH_2)_{0-3}C(O)NH(CH_2)_{0-3}$, $(CH_2)_{0-3}C(S)NH(CH_2)_{0-3}$, $(CH_2)_{0-3}NHC(O)(CH_2)_{0-3}$, $(CH_2)_{0-3}NHC(S)(CH_2)_{0-3}$, $(CH_2)_{0-3}OC(O)(CH_2)_{0-3}$, $(CH_2)_{0-3}OC(S)(CH_2)_{0-3}$, $(CH_2)_{0-3}SC(O)(CH_2)_{0-3}$, $(CH_2)_{0-3}SC(S)(CH_2)_{0-3}(CH_2)_{0-3}NHC(O)NH(CH_2)_{0-3}$, $(CH_2)_{0-3}NHC(S)NH(CH_2)_{0-3}$, $(CH_2)_{0-3}OC(O)NH$ $(CH_2)_{0-3}(CH_2)_{0-3}OC(S)NH(CH_2)_{0-3}$, $(CH_2)_{0-3}SC(O)$ $NH(CH_2)_{0-3}$, $(CH_2)_{0-3}SC$ $(S)NH(CH_2)_{0-3}$ $(CH_2)_{0-3}NHC(O)O(CH_2)_{0-3}$, $(CH_2)_{0-3}NHC(S)$ $O(CH_2)_{0-3}$, $(CH_2)_{0-3}OC(O)O(CH_2)_{0-3}$, $(CH_2)_{0-3}OC(S)$ $O(CH_2)_{0-3}$, $(CH_2)_{0-3}SC(O)O(CH_2)_{0-3}$, $(CH_2)_{0-3}SC$ $(S)O(CH_2)_{0-3}$, $(CH_2)_{0-3}NHC(O)S(CH_2)_{0-3}$, $(CH_2)_{0-3}NHC(S)S(CH_2)_{0-3}$, $(CH_2)_{0-3}OC(O)S(CH_2)_{0-3}$, $(CH_2)_{0-3}OC(S)S(CH_2)_{0-3}$, $(CH_2)_{0-3}SC(O)S(CH_2)_{0-3}$, $(CH_2)_{0-3}SC$ $(S)S(CH_2)_{0-3}$, $(CH_2O)_{1-6}$, and trimethyl methane;

wherein each Q, $Q^1$, and $Q^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine, thiadiazole, aziridine, thiirane, oxirane, oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, pepierazine, morpholine, thiomorpholine, dioxane, dithiane, trioxane, thithiane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, and cycloheptyl;

wherein each Q, $Q^1$, and $Q^2$, when present, may display one or more additional J groups at any position on the Q ring;

wherein $R^{D1-D4}$, when present are not alkoxy groups;

wherein at least one $R^{E1-E4}$, when present, is not H;

wherein any alkyl or alkylene groups above may be straight or branched;

wherein any alkyl or alkylene groups above may additionally comprise OH, =O, $NH_2$, CN, dihaloalkyl, trihaloalkyl, or halogen substituents at one or more carbons;

wherein the number of hydrogens on terminal positions of the groups above may be adjusted if the group is linked to an additional group or if the group is terminal.

2. A pharmaceutical composition comprising the composition of claim 1 and a pharmaceutically acceptable carrier.

3. The pharmaceutical composition of claim 2, wherein the pharmaceutical composition is formulated for oral administration.

4. The pharmaceutical composition of claim 2, wherein the pharmaceutical composition is formulated for injection.

5. A method of inhibiting the activity of ASH1L, comprising contacting ASH1L with an effective amount of the composition of claim 1.

6. The method of claim 5, wherein the step of contacting comprises contacting a cell that expresses ASH1L.

7. A method of treating cancer, comprising administering to a subject a pharmaceutical composition of claim 2 in an amount effective to inhibit the activity of ASH1 L.

8. The method of claim 7, wherein the cancer comprises leukemia, hematologic malignancy, solid tumor cancer, breast cancer, prostate cancer, liver cancer or thyroid cancer.

9. The method of claim 8, wherein cancer comprises AML, ALL, Mixed Lineage Leukemia or a leukemia with Partial Tandem Duplication of MLL.

10. A method of treating a disorder mediated by chromosomal rearrangement on chromosome 11q23 in a subject in need thereof, the method comprising: administering to the subject a therapeutically effective amount of a compound of claim 1.

11. The method of claim 7, wherein the pharmaceutical composition is co-administered with an additional therapeutic.

12. The method of claim 7, wherein the subject is a human.

13. A compound selected from the group consisting of:

Compound 40

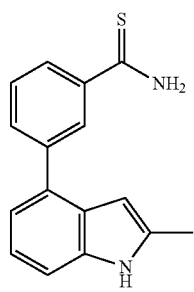

Compound 42

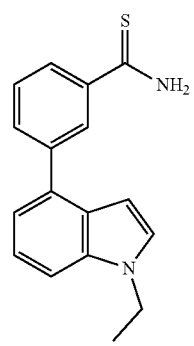

Compound 48

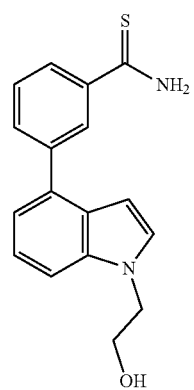

Compound 49

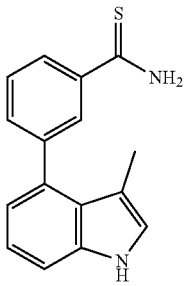

Compound 50

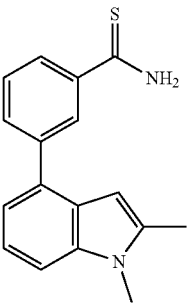

Compound 52

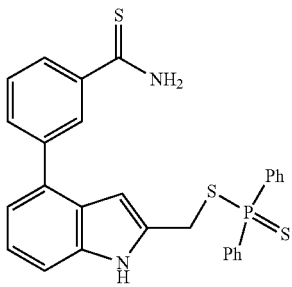

Compound 54

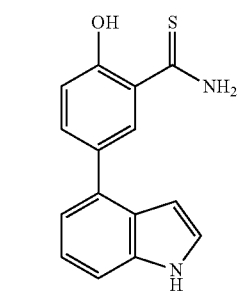

Compound 55

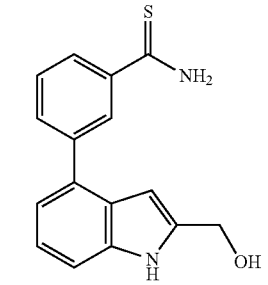

Compound 61
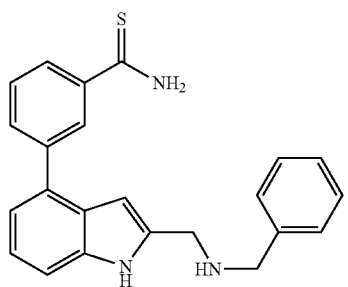
Compound 63
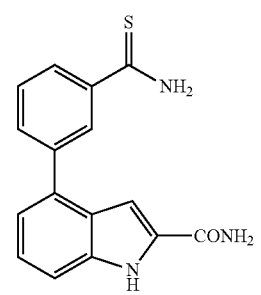
Compound 67
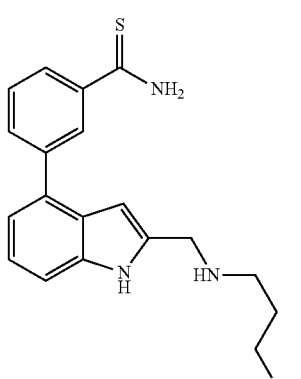
Compound 68
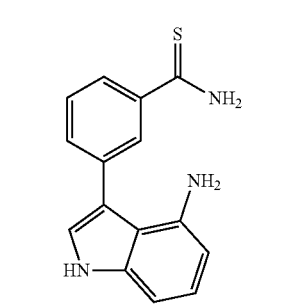
Compound 69
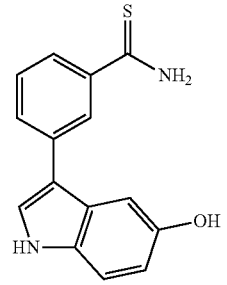
Compound 70
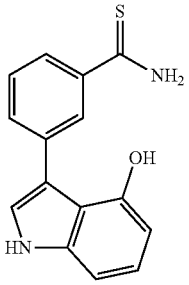
Compound 76
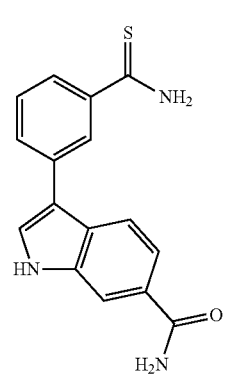
Compound 80
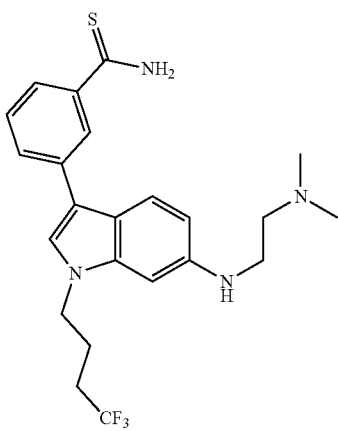
Compound 249
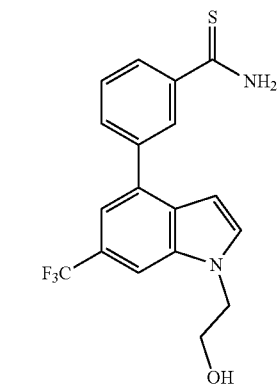

Compound 250
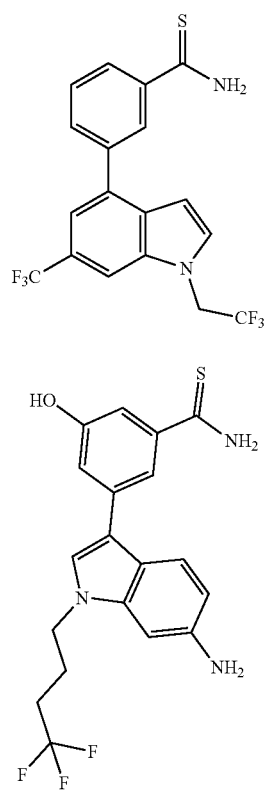
Compound 254
Compound 264
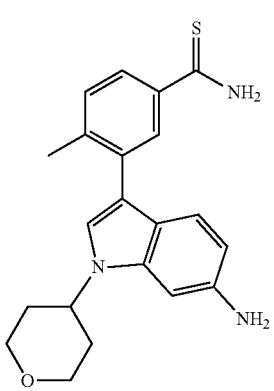
Compound 269
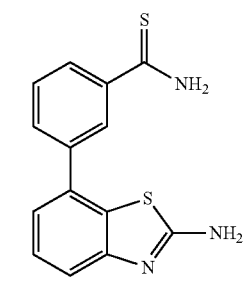
Compound 275
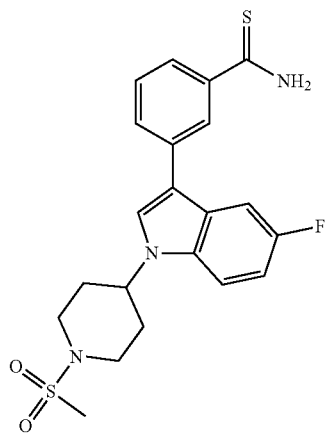
Compound 82
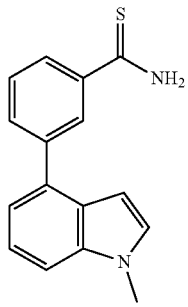
Compound 83
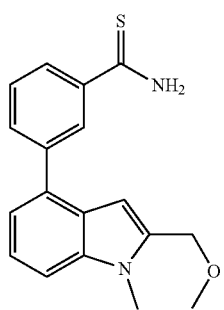
Compound 84
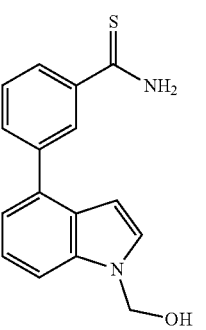

Compound 85
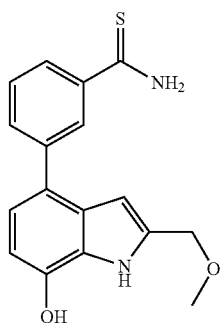
Compound 86
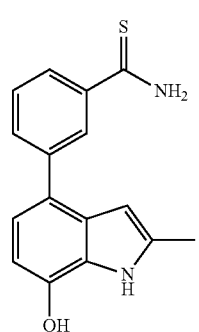
Compound 91
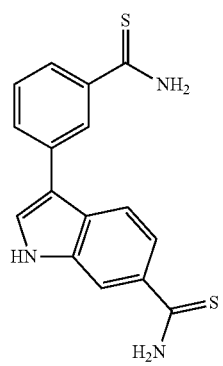
Compound 92
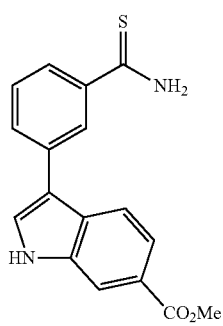
Compound 93
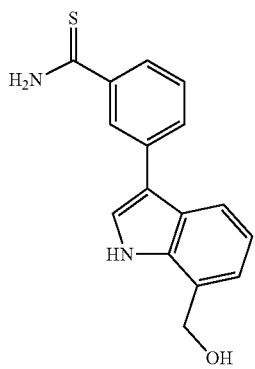
Compound 94
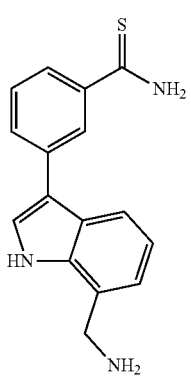
Compound 95
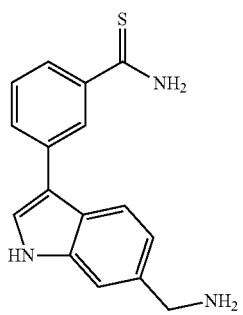
Compound 99
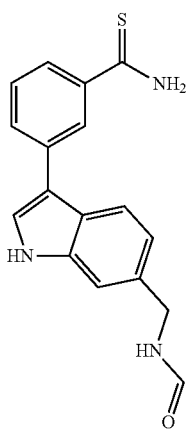

Compound 100
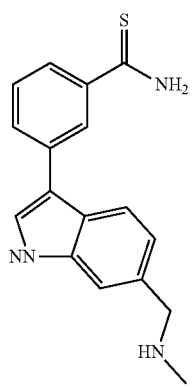
Compound 101
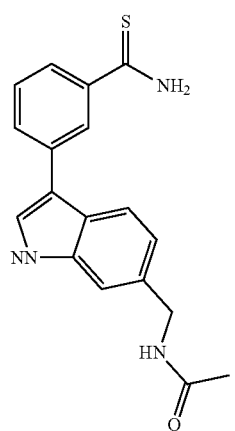
Compound 102
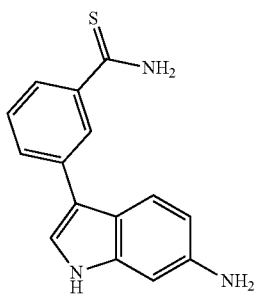
Compound 105
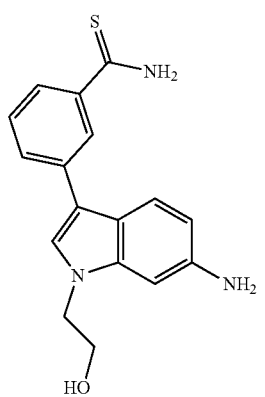
Compound 106
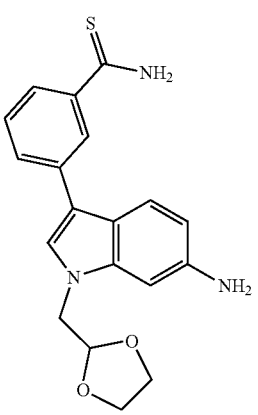
Compound 107
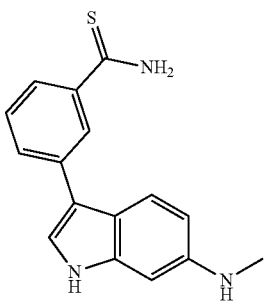
Compound 108
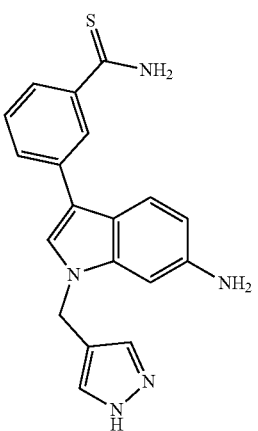
Compound 109
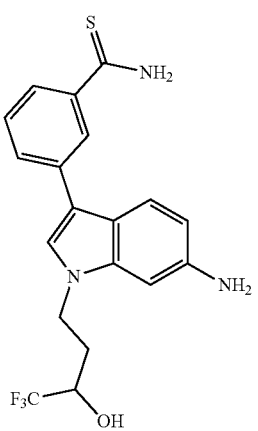

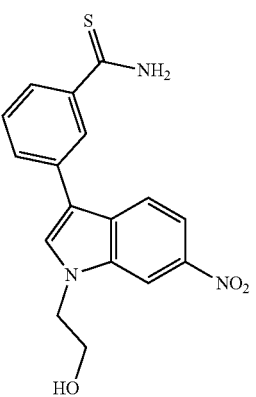
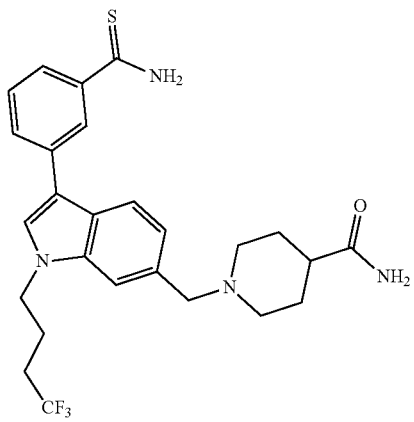

Compound 117
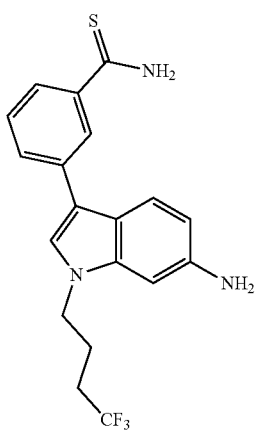
Compound 118
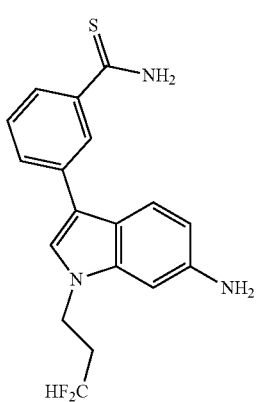
Compound 119
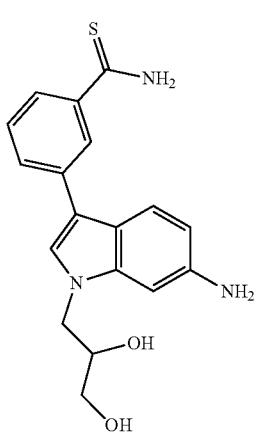
Compound 120
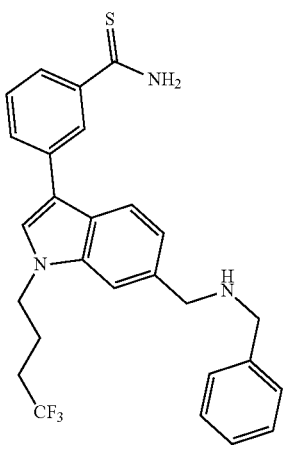
Compound 121
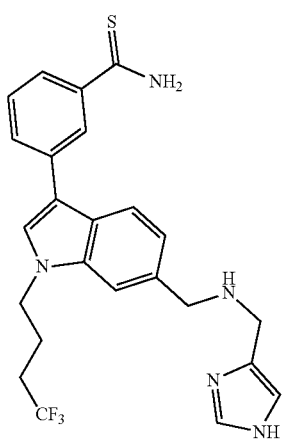
Compound 122
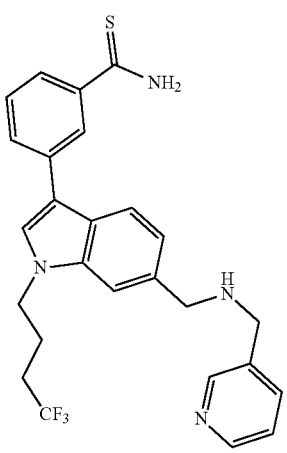
Compound 123
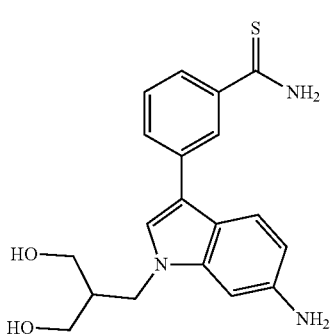

Compound 124
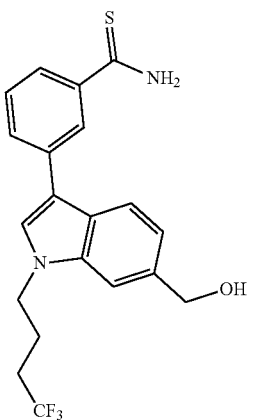
Compound 128
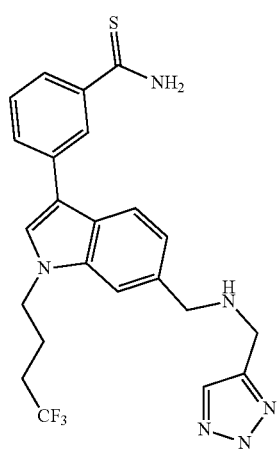
Compound 125
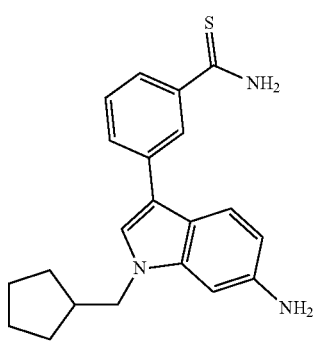
Compound 129
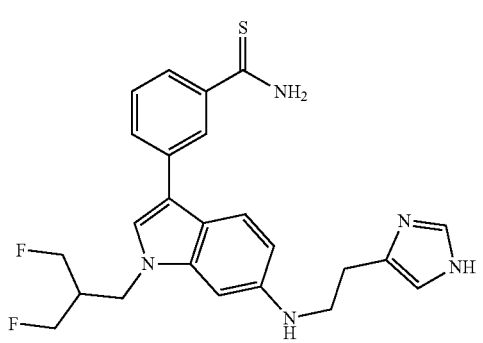
Compound 126
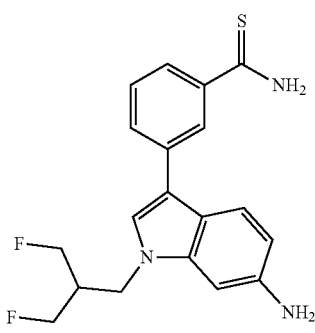
Compound 130
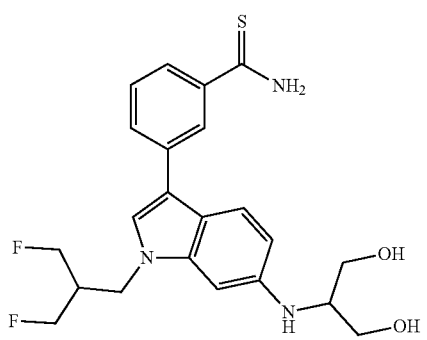
Compound 127
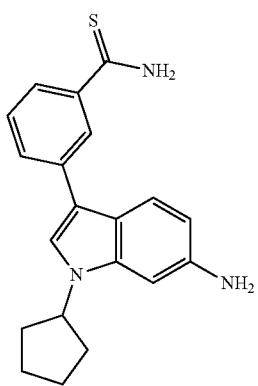
Compound 131
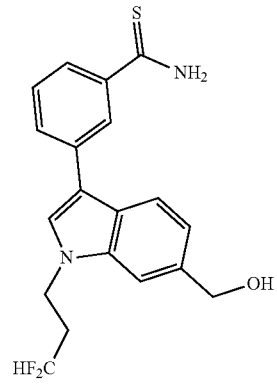

Compound 136, Compound 137, Compound 138, Compound 140, Compound 141, Compound 142, Compound 143, Compound 144

Compound 145
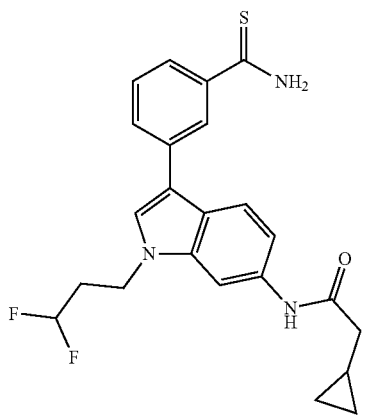
Compound 147
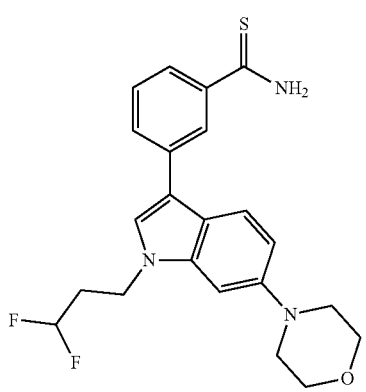
Compound 148
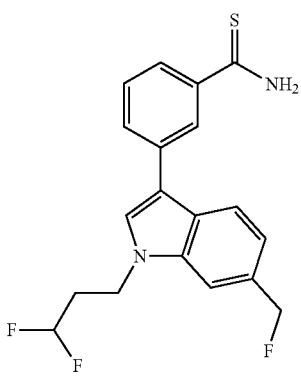
Compound 149
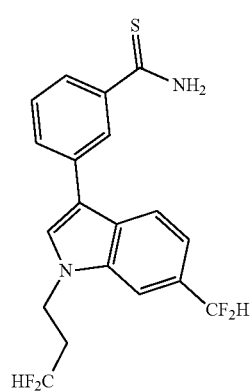
Compound 150
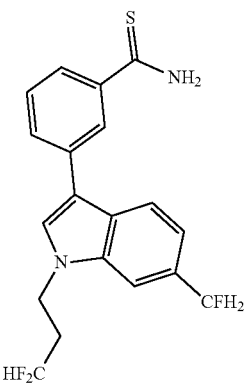
Compound 151
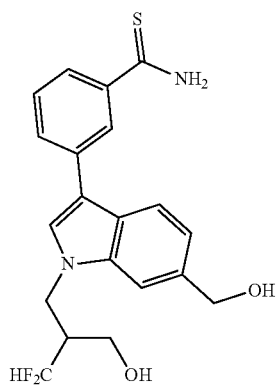
Compound 152
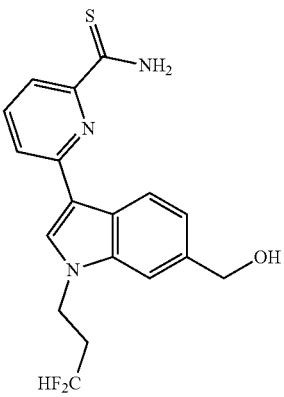
Compound 153
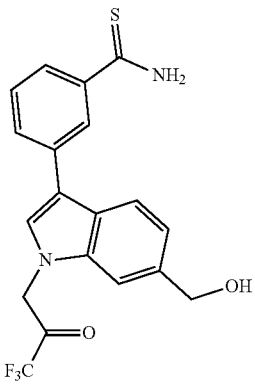

-continued
Compound 154
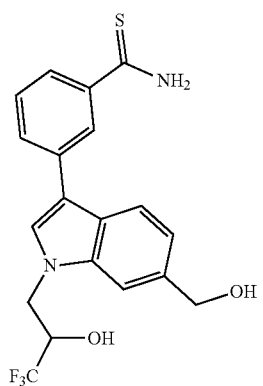
Compound 155
Compound 156
Compound 157
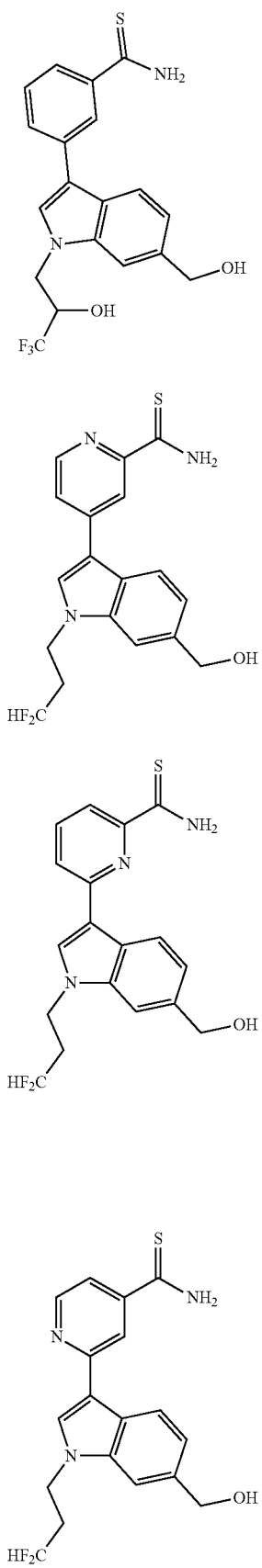
-continued
Compound 158
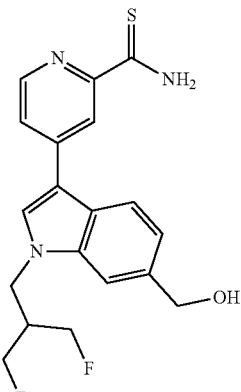
Compound 159
Compound 160
Compound 161
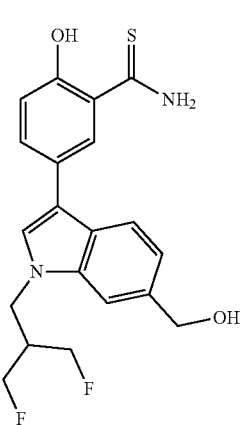

-continued
Compound 162
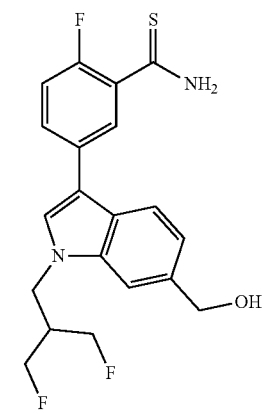
Compound 163
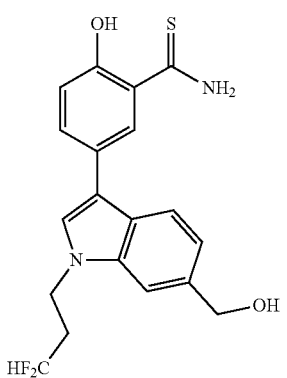
Compound 164
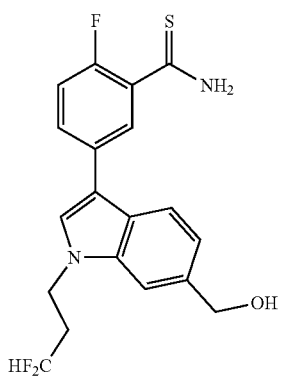
Compound 166
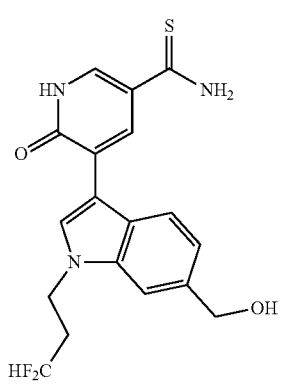
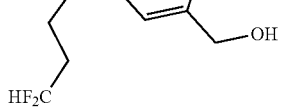
-continued
Compound 174
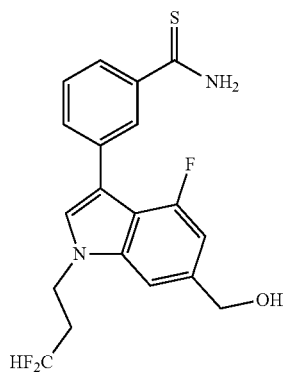
Compound 175
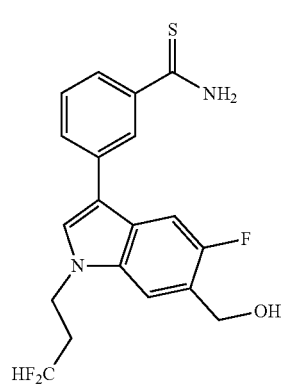
Compound 176
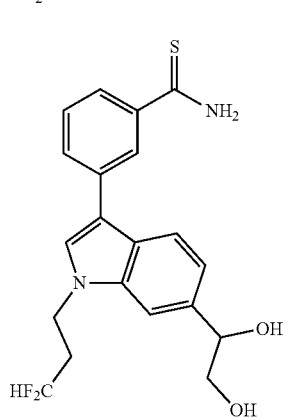
Compound 177
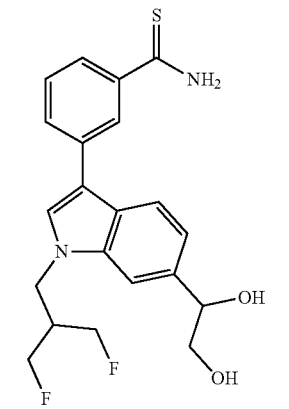

-continued
Compound 178
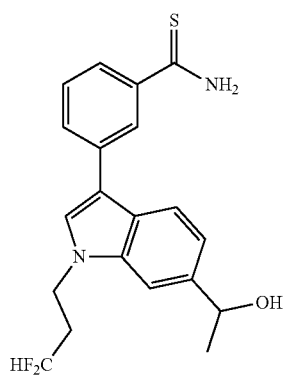
Compound 179
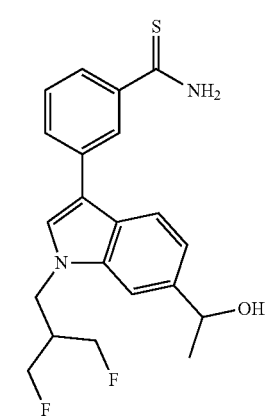
Compound 180
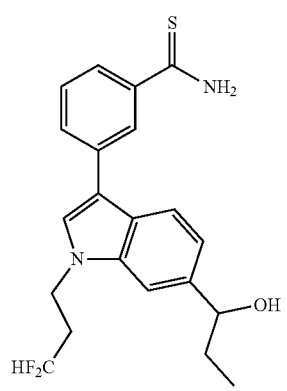
Compound 181
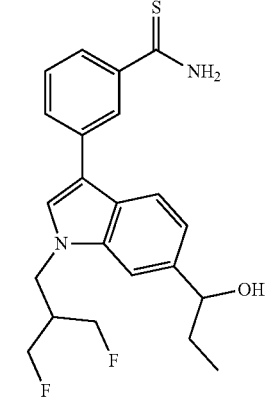
-continued
Compound 182
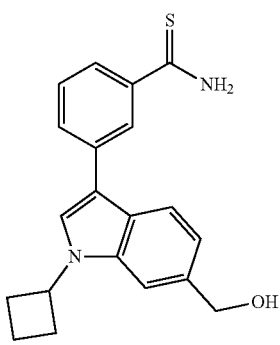
Compound 183
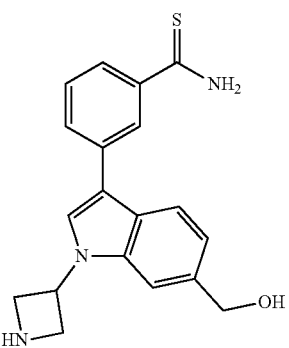
Compound 184
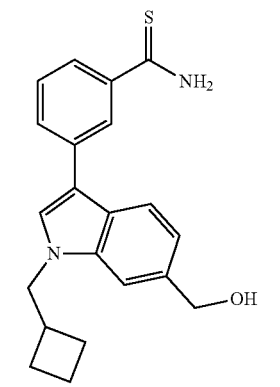
Compound 185

Compound 186
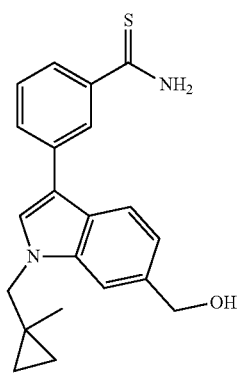
Compound 187
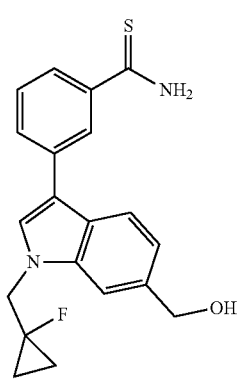
Compound 188
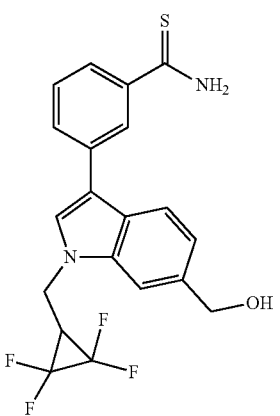
Compound 189
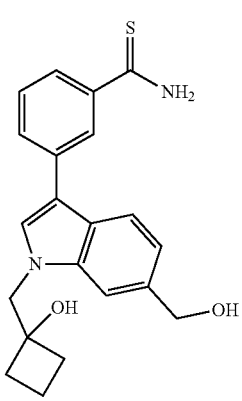
Compound 190
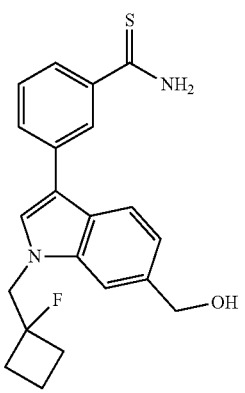
Compound 191
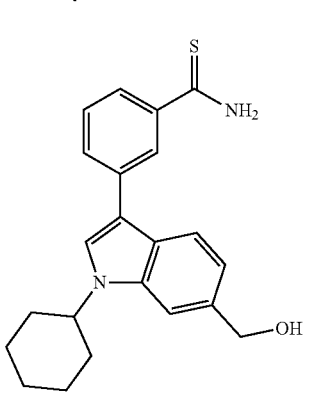
Compound 192
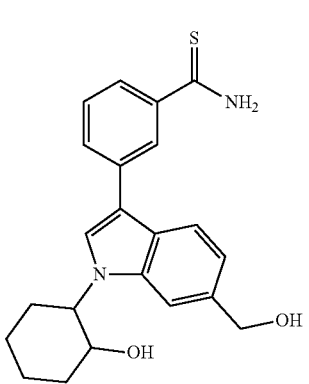
Compound 193
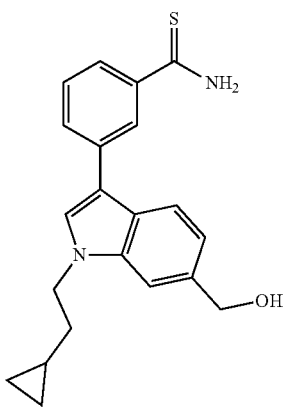

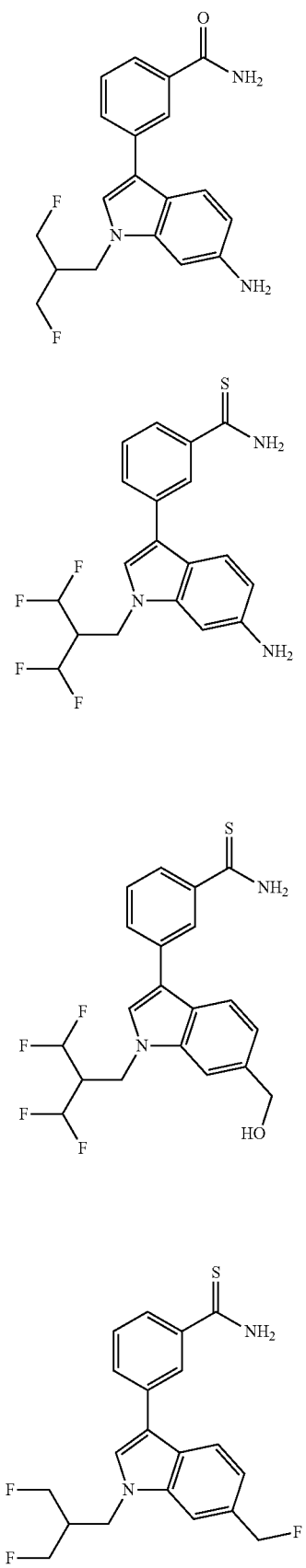

Compound 204
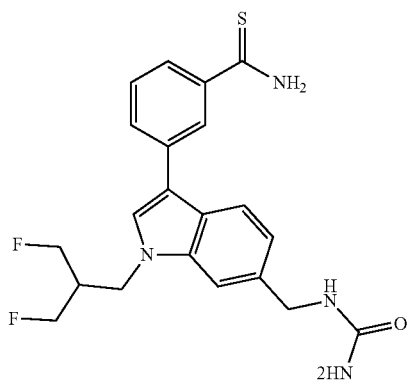
Compound 205
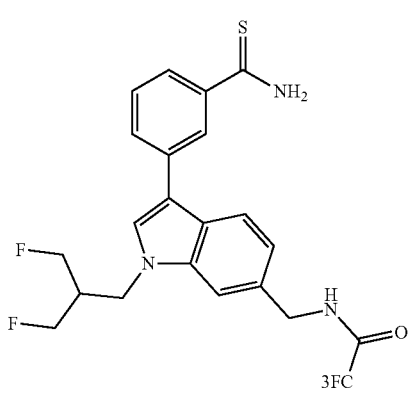
Compound 206
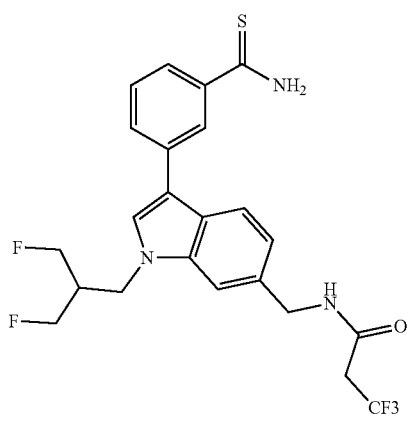
Compound 207
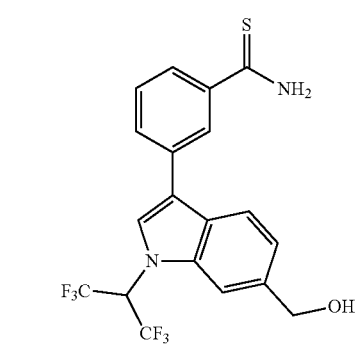
Compound 208
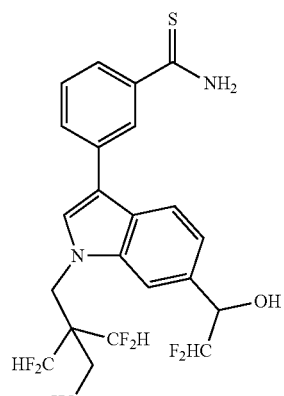
Compound 209
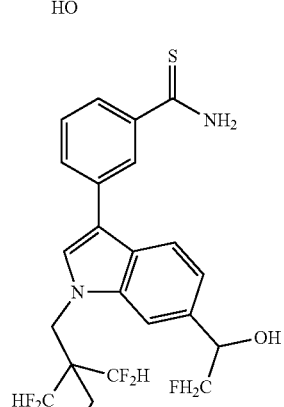
Compound 210
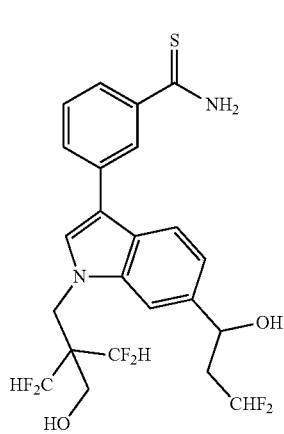
Compound 211
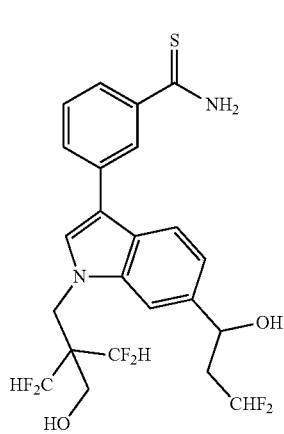

Compound 212
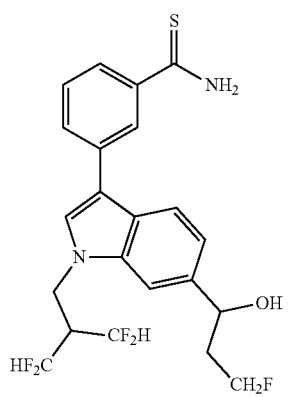
Compound 213
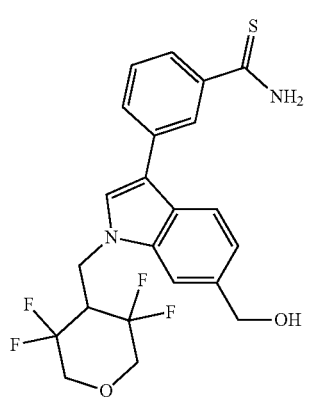
Compound 214
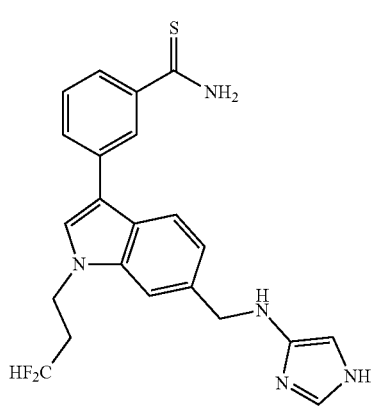
Compound 215
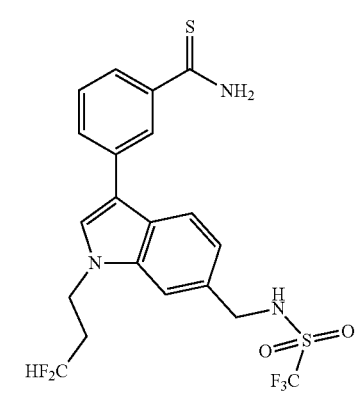
Compound 216
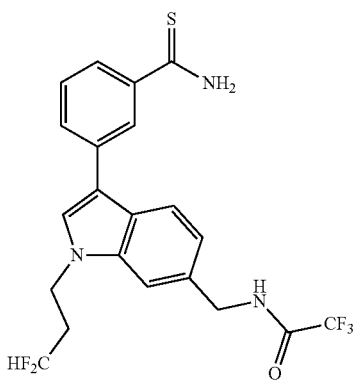
Compound 217
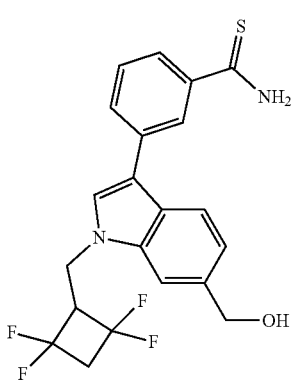
Compound 218
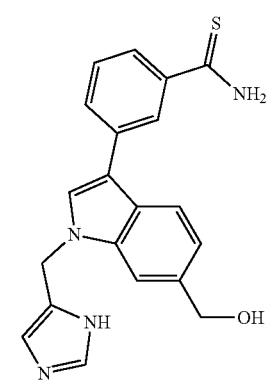
Compound 219
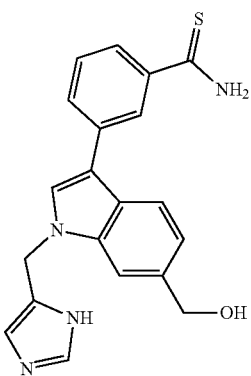

Compound 220
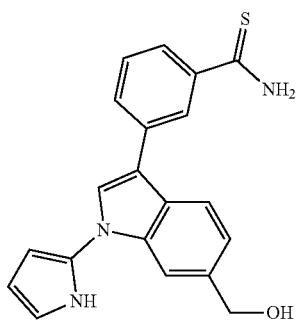
Compound 231
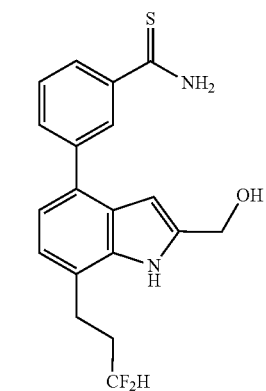
Compound 236
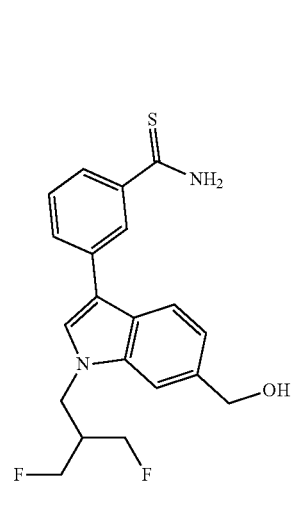
Compound 237
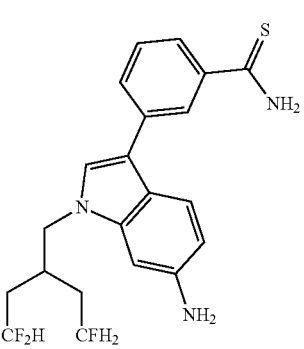
Compound 238
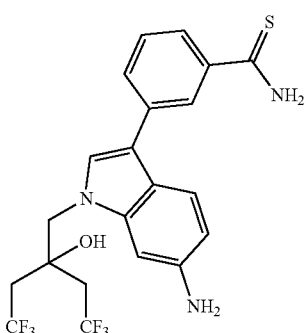
Compound 239
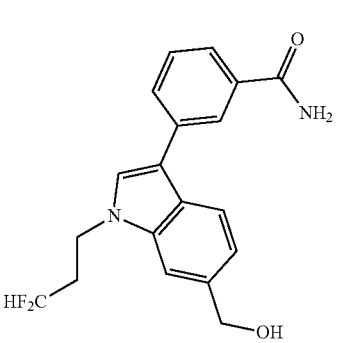
Compound 240
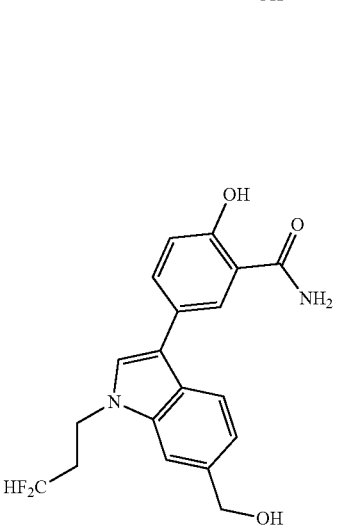
Compound 241
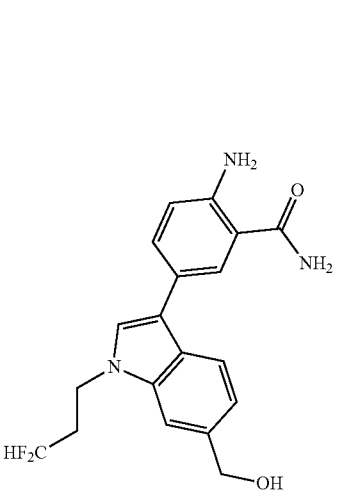

-continued
Compound 242
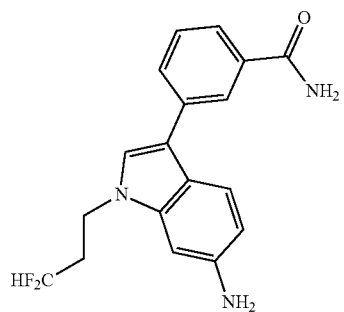
Compound 244
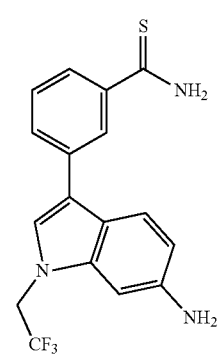
Compound 245
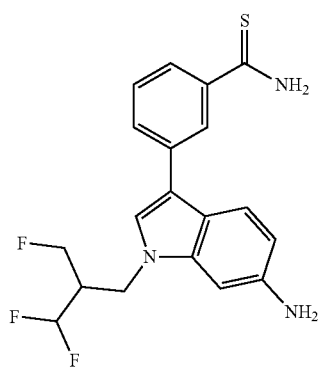
Compound 246
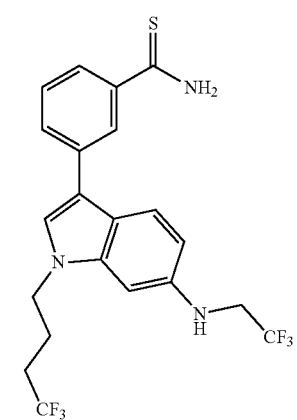
-continued
Compound 248
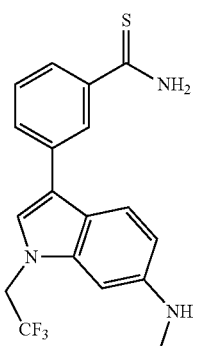
Compound 251
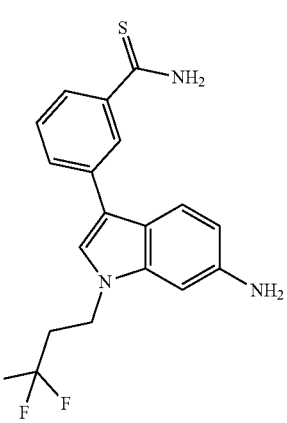
Compound 253
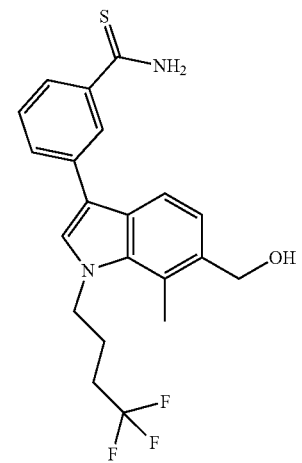
Compound 256
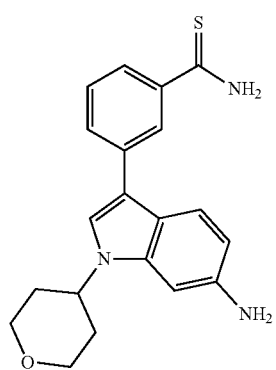

Compound 257
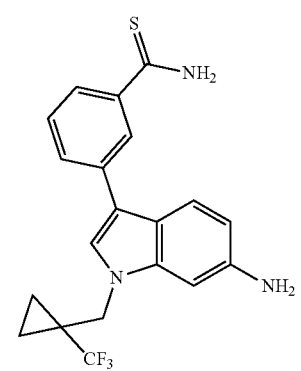
Compound 258
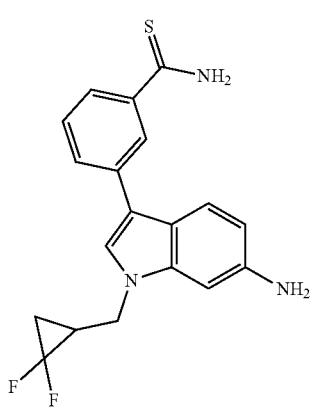
Compound 259
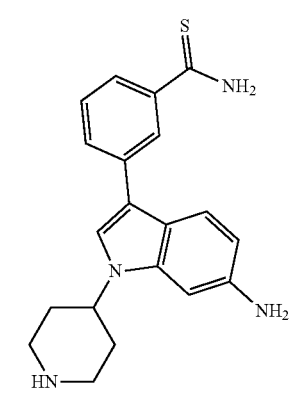
Compound 260
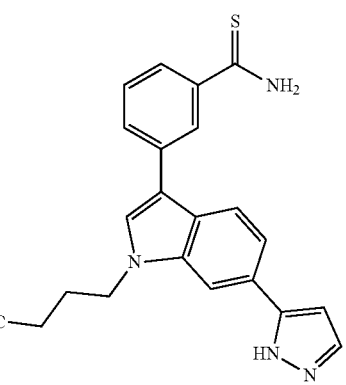
Compound 261
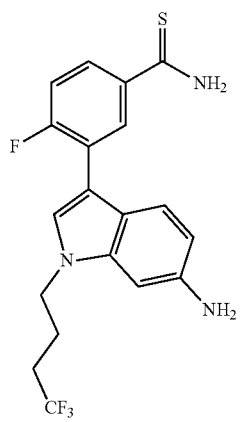
Compound 263
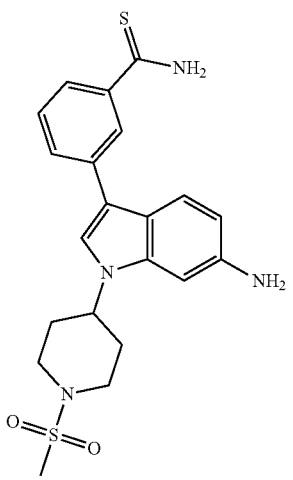
Compound 265
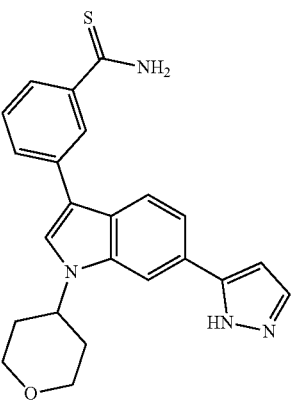

-continued
Compound 266
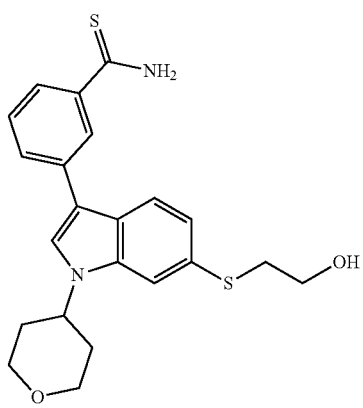
Compound 267
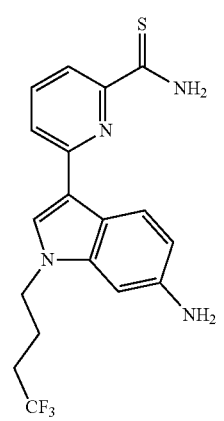
Compound 268
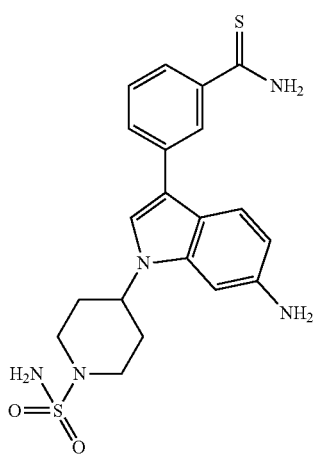
Compound 270
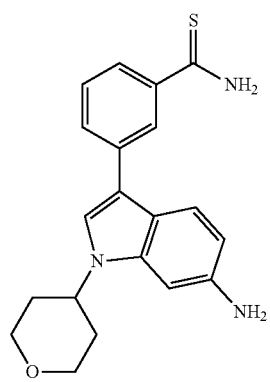
-continued
Compound 271
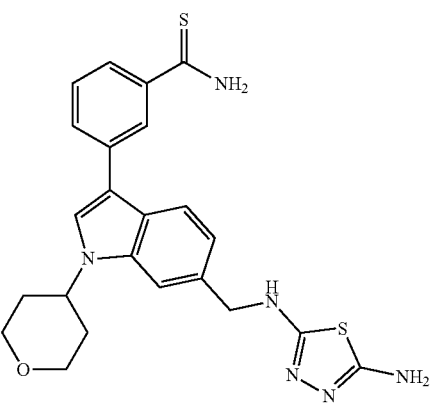
Compound 272
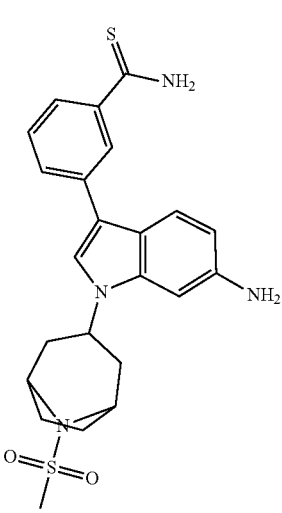
Compound 273
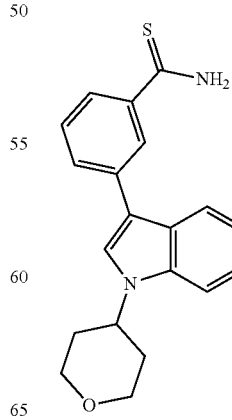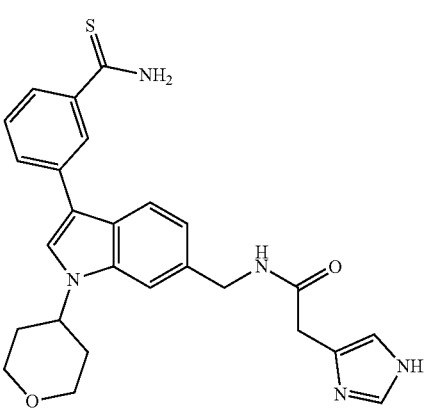

Compound 274
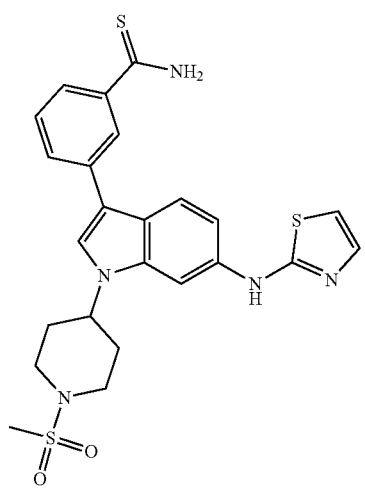
Compound 278
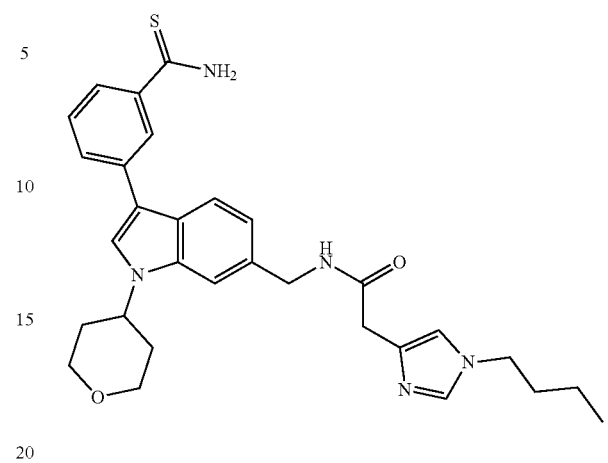
Compound 276
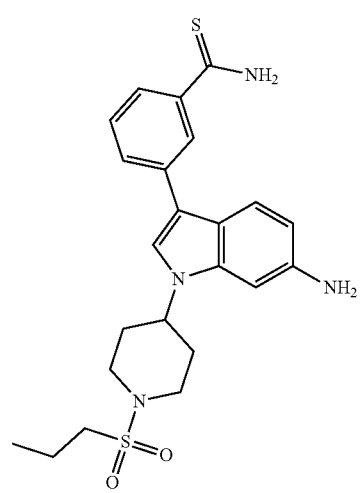
Compound 279
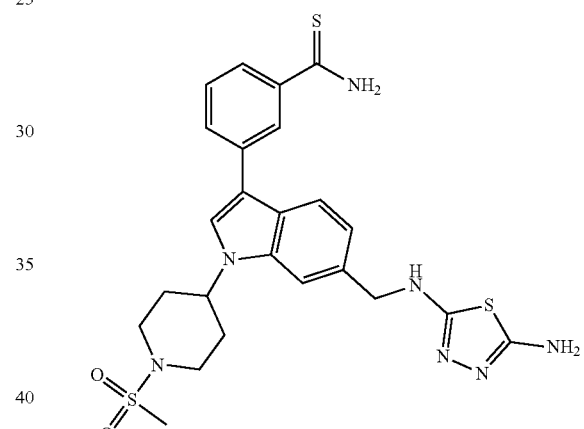
Compound 277
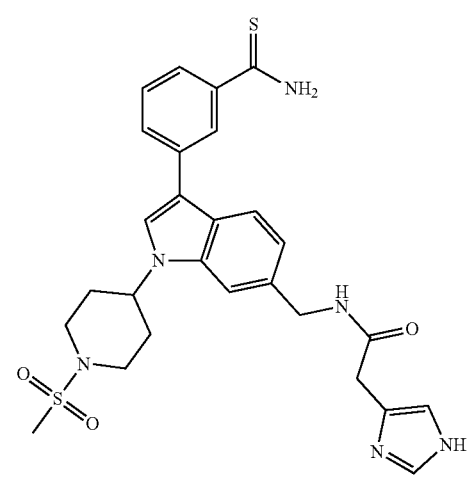
Compound 280
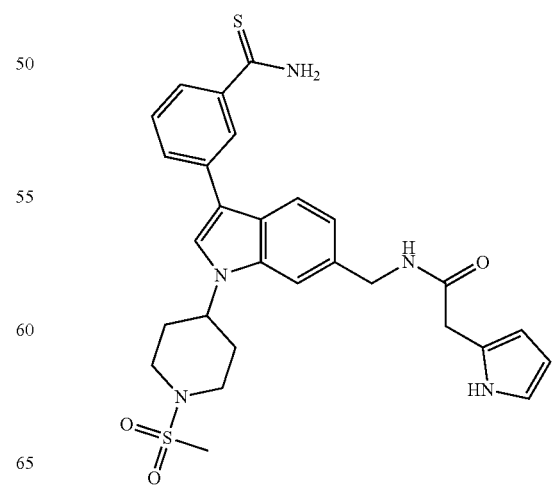

Compound 281
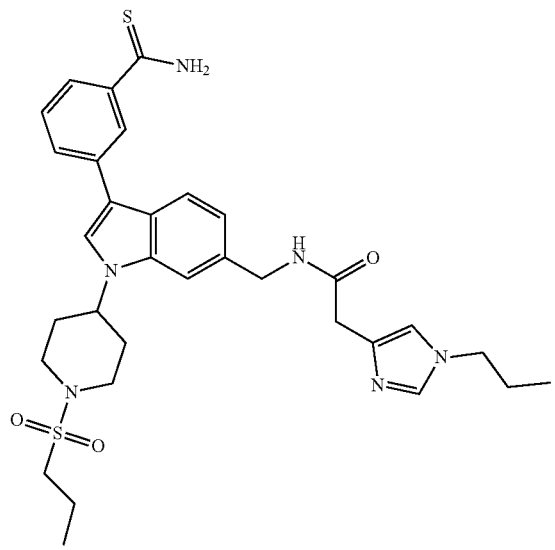
Compound 282
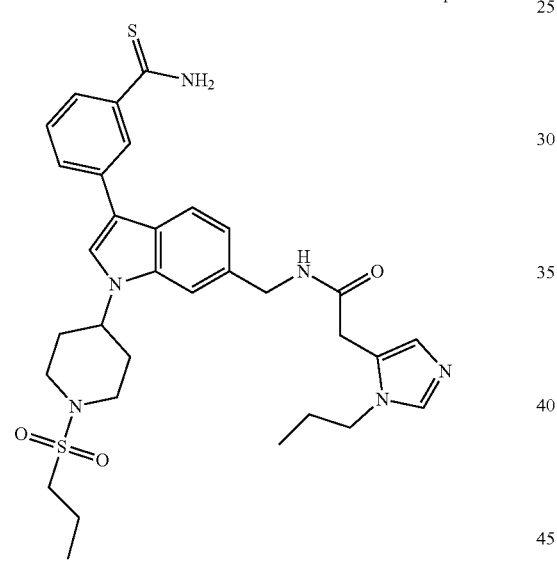
Compound 283
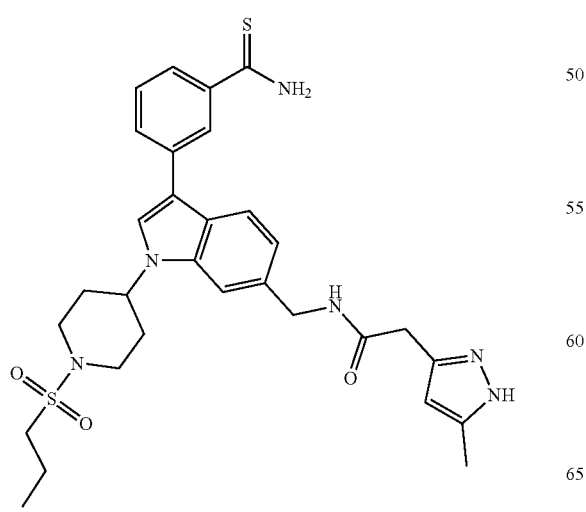
Compound 284
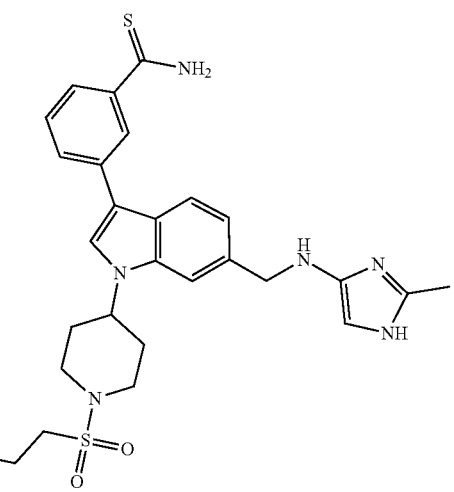
Compound 285
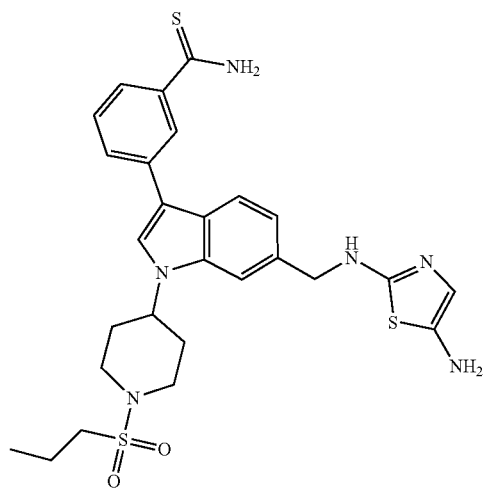
Compound 289
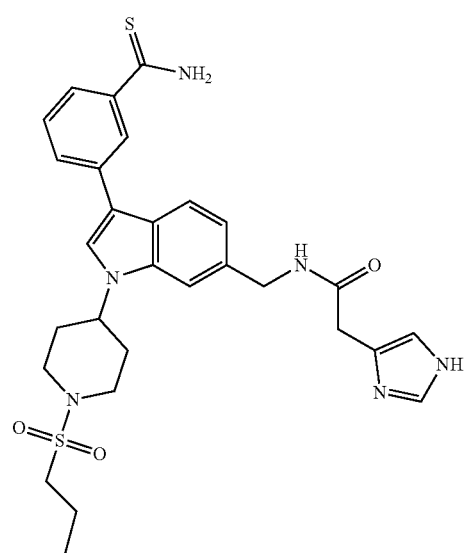

Compound 290
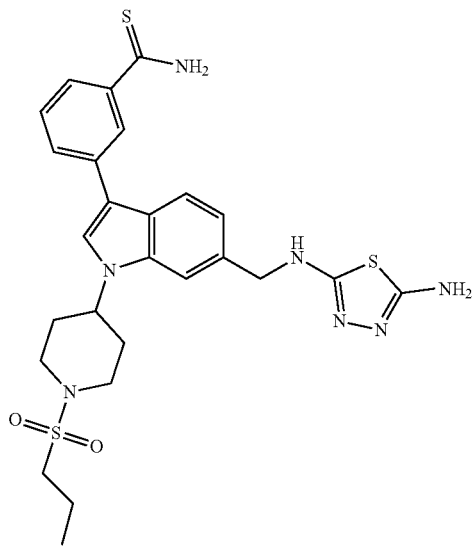
Compound 294
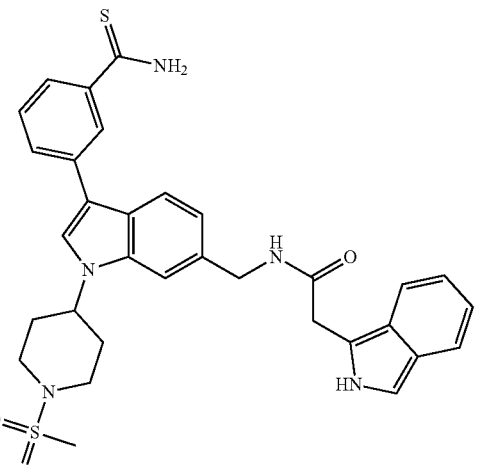
Compound 292
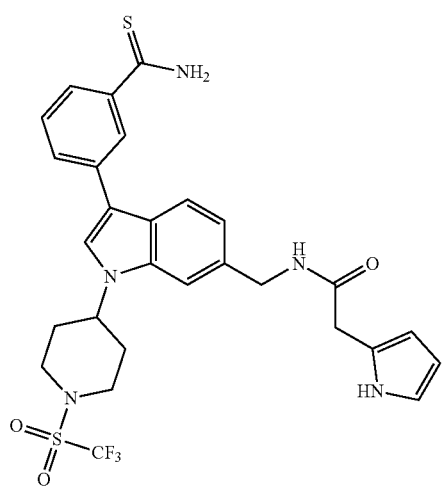
Compound 295
Compound 293
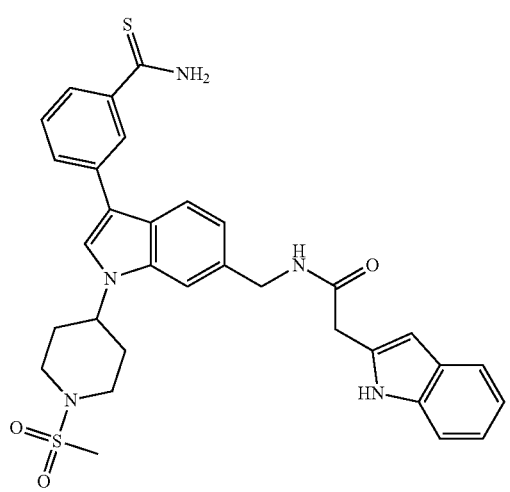
Compound 296
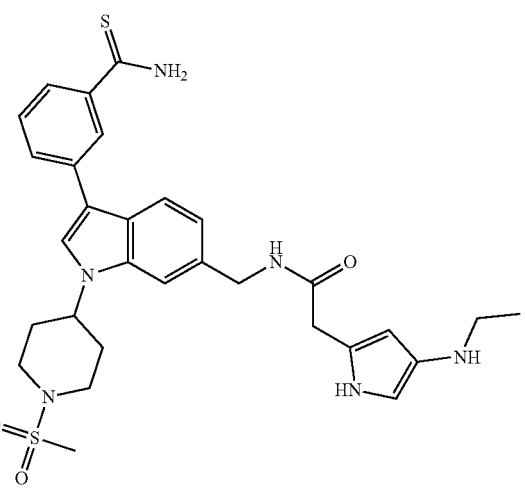

Compound 297
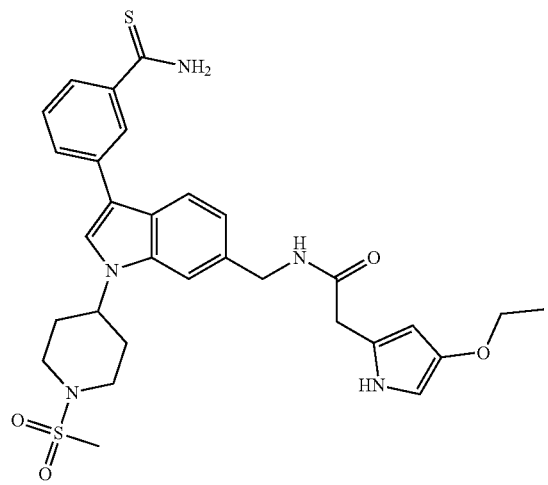
Compound 298
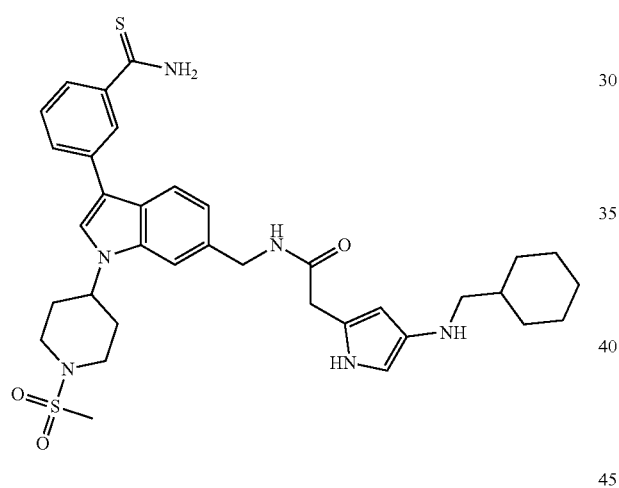
Compound 299
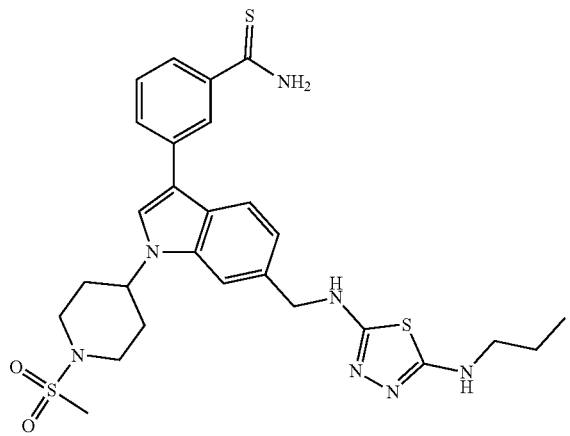
Compound 300
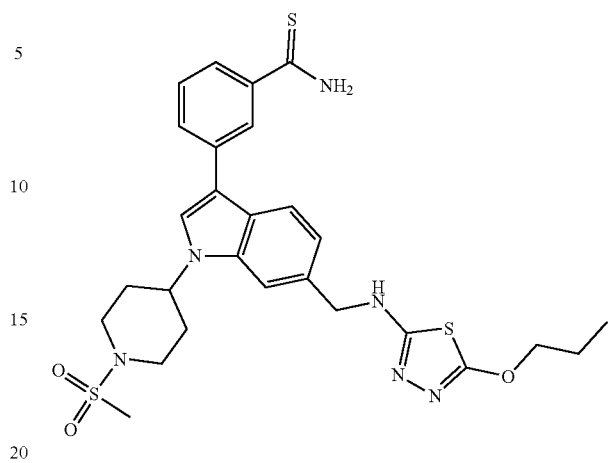
Compound 303
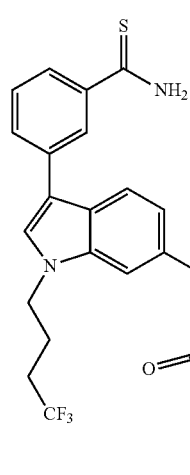
Compound 304
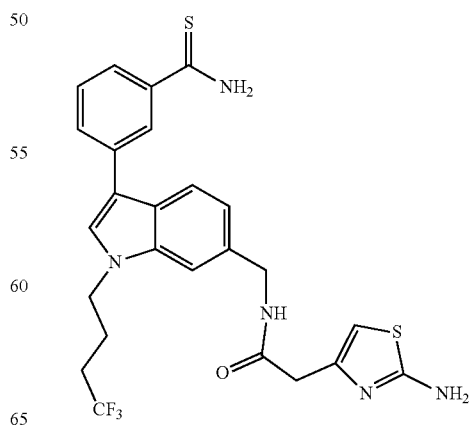

Compound 305
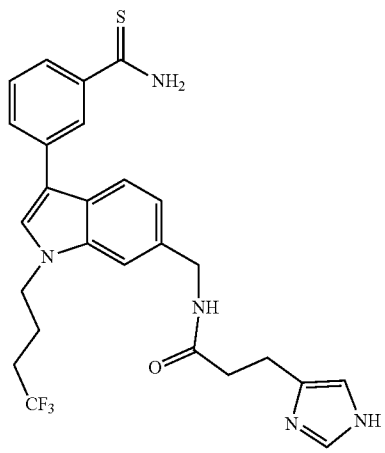
Compound 306
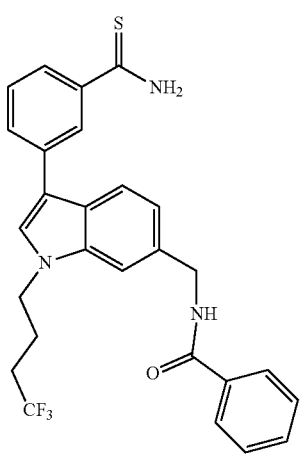
Compound 307
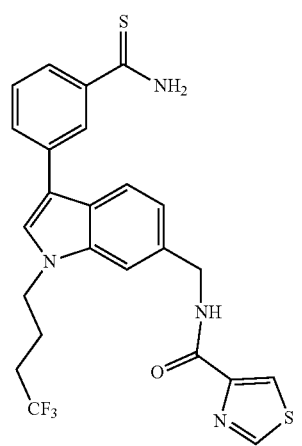
Compound 308
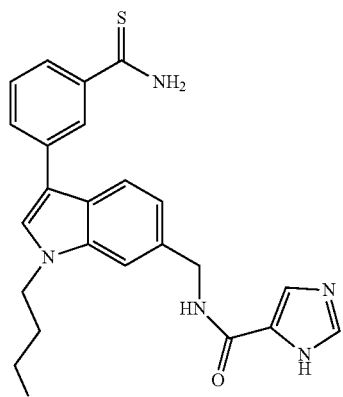
Compound 309
Compound 310

Compound 311
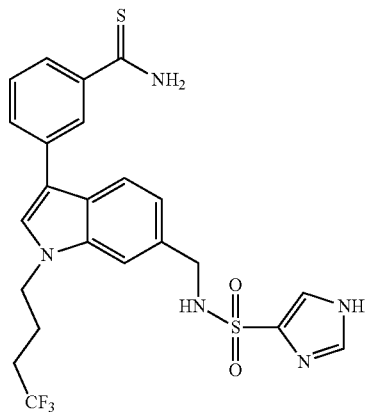
Compound 312
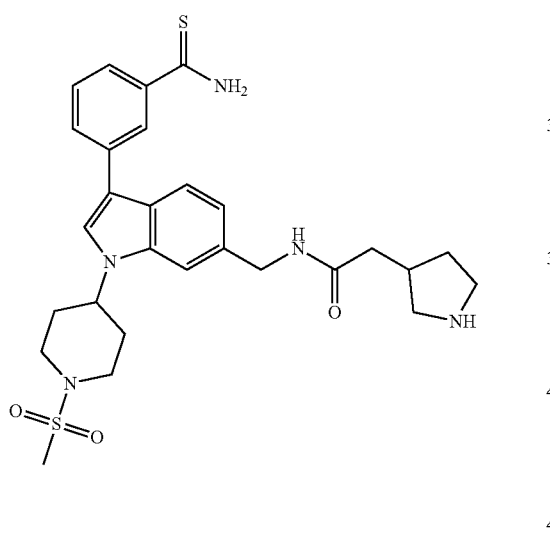
Compound 313
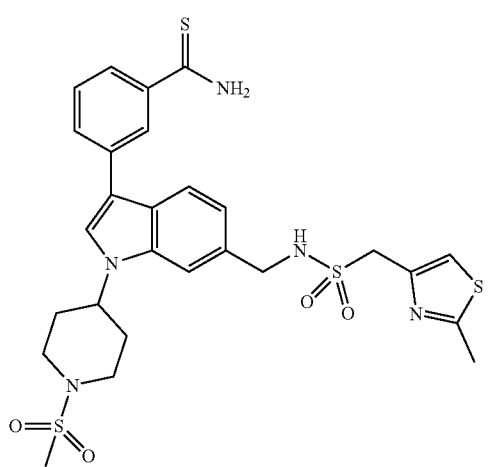
Compound 314
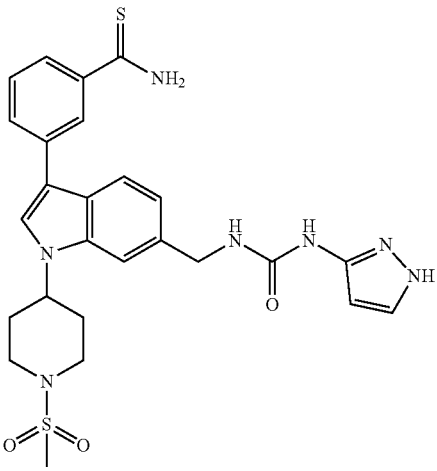
Compound 315
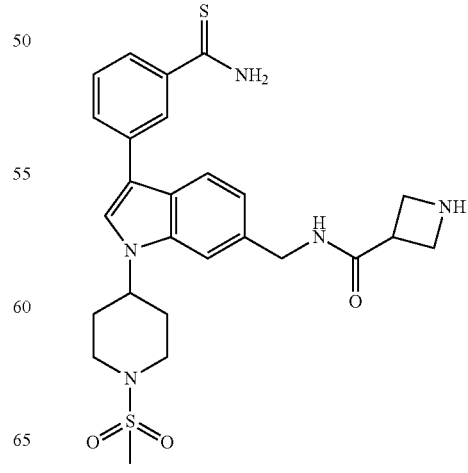

Compound 319
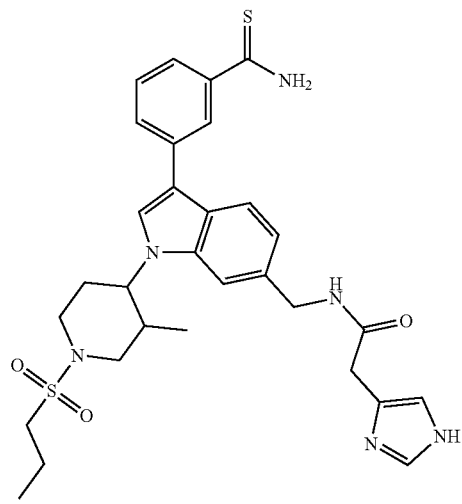
Compound 320
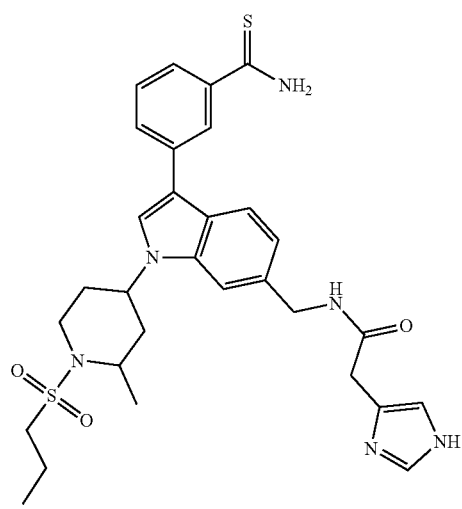
Compound 321
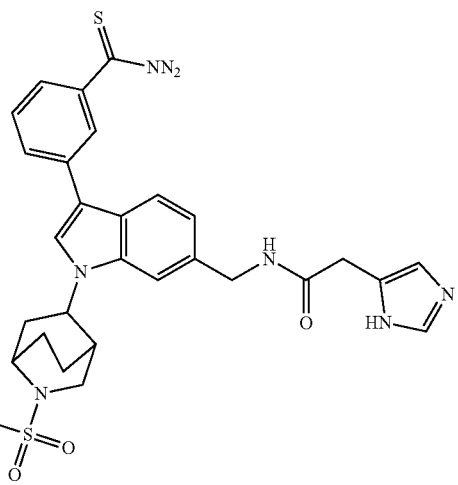
Compound 322
* * * * *